(12) United States Patent
Thormann et al.

(10) Patent No.: US 9,499,535 B2
(45) Date of Patent: Nov. 22, 2016

(54) KINASE INHIBITORS

(75) Inventors: Michael Thormann, Martinsried (DE);
Andreas Treml, Martinsried (DE);
Michael Almstetter, Martinsried (DE);
Roland Koestler, Martinsried (DE);
Nasser Yehia, Martinsried (DE)

(73) Assignee: ORIGENIS GMBH, Martinsried (DE)

( * ) Notice: Subject to any disclaimer, the term of this patent is extended or adjusted under 35 U.S.C. 154(b) by 702 days.

(21) Appl. No.: 13/506,509

(22) Filed: Apr. 23, 2012

(65) Prior Publication Data
US 2012/0329785 A1 Dec. 27, 2012

Related U.S. Application Data

(60) Provisional application No. 61/517,581, filed on Apr. 21, 2011.

(51) Int. Cl.
| | |
|---|---|
| *A61K 31/55* | (2006.01) |
| *A61K 31/54* | (2006.01) |
| *A61K 31/535* | (2006.01) |
| *C07D 471/04* | (2006.01) |

(52) U.S. Cl.
CPC .................. *C07D 471/04* (2013.01)

(58) Field of Classification Search
CPC  C07D 201/02; C07D 203/02; C07D 205/08; C07D 207/20; C07D 207/26; C07D 207/38; C07D 209/04; C07D 209/10; C07D 209/56; C07D 209/90
USPC ............. 514/217, 220, 222.8, 229.8
See application file for complete search history.

(56) References Cited

U.S. PATENT DOCUMENTS

| | | | |
|---|---|---|---|
| 6,531,475 B1 | 3/2003 | Haddach et al. | 514/250 |
| 2006/0094707 A1 | 5/2006 | Chaturvedula et al. | 514/212.02 |

FOREIGN PATENT DOCUMENTS

| | | |
|---|---|---|
| CA | 1148159 | 6/1983 |
| EP | 2013/003147 | 12/2013 |

(Continued)

OTHER PUBLICATIONS

Database Registry [Online] Chemical Abstracts Service, Columbus, Ohio: XP-002658260 retrieved from Registry Database Accession No. 304872-03-5, 2012.

(Continued)

*Primary Examiner* — San-Ming Hui
(74) *Attorney, Agent, or Firm* — Licata & Tyrrell P.C.

(57) ABSTRACT

The present invention relates to novel compounds of formula (I)

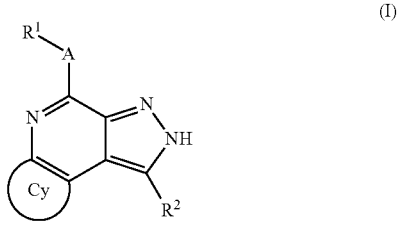

that are capable of inhibiting one or more kinases, especially SYK (Spleen Tyrosine Kinase), LRRK2 (Leucine-rich repeat kinase 2) and/or MYLK (Myosin light chain kinase) or mutants thereof. The compounds find applications in the treatment of a variety of diseases.

14 Claims, 1 Drawing Sheet

(56) References Cited

FOREIGN PATENT DOCUMENTS

| | | |
|---|---|---|
| JP | 2008519074 | 6/2008 |
| JP | 2010143829 | 7/2010 |
| WO | WO 98/29413 A1 | 7/1998 |
| WO | WO 02/074774 A1 | 9/2002 |
| WO | WO 2005/079195 A2 | 9/2005 |
| WO | WO 2006/107851 | 10/2006 |
| WO | WO2006107771 A2 | 10/2006 |
| WO | WO 2008/144253 A1 | 11/2008 |
| WO | WO 2009/152133 A1 | 12/2009 |
| WO | WO 2009/155527 A2 | 12/2009 |
| WO | WO 2010/030785 A2 | 3/2010 |
| WO | WO 2010/106333 A1 | 9/2010 |
| WO | WO 2011/068881 A1 | 6/2011 |
| WO | WO 2011/068899 A1 | 6/2011 |
| WO | WO 2011/112731 A2 | 9/2011 |
| WO | WO 2012/143143 A1 | 10/2012 |

OTHER PUBLICATIONS

Database Registry. [Online] Chemical Abstracts Service, Columbus, Ohio: XP-002658261 retrieved from Registry Database Accession No. 327100-02-7, 2012.

Database Registry [Online] Chemical Abstracts Service, Columbus, Ohio: XP-002658262 retrieved from Registry Database Accession No. 368839-23-0, 2012.

Database Registry [Online] Chemical Abstracts Service, Columbus, Ohio: XP-002658263 retrieved from Registry Database Accession No. 382610-70-0, 2012.

Database Registry [Online] Chemical Abstracts Service, Columbus, Ohio: XP-002658264 retrieved from Registry Database Accession No. 383161-12-4, 2012.

European Search Report from EP11003373.5, Sep. 26, 2011, PCT.

International Search Report and Written Opinion from PCT/EP2012/001736, Apr. 23, 2012, PCT.

Database Columbus, Database Registry [Online] Chemical Abstracts Service, Ohio: XP-002658260 retrieved from Registry Accession No. 304879-41-2.

Colotta et al. "Synthesis and Structure-Activity Relationships of a New Set of 2-Arylpyrazolo[3,4- c]quinoline Derivatives as Adenosine Receptor Antagonists" Journal of Medicinal Chemistry 2000 43:3118-3124 [XP002717138].

Lenzi et al. "Synthesis, Structure-Affinity Relationships, and Molecular Modeling Studies of Novel Pyrazolo[3,4-c]quinoline Derivatives as Adenosine Receptor Antagonists" Bioorganic & Medicinal Chemistry 2011 19:3757-3768 [XP028378041].

Nagarajan, K. and Shah, R. K. "Condensed Heterotricycles: Synthesis of Pyrazolo[3,4-c]quinoline Derivatives" Indian Journal of Chemistry 1992 31B:316-321 [XP009174674].

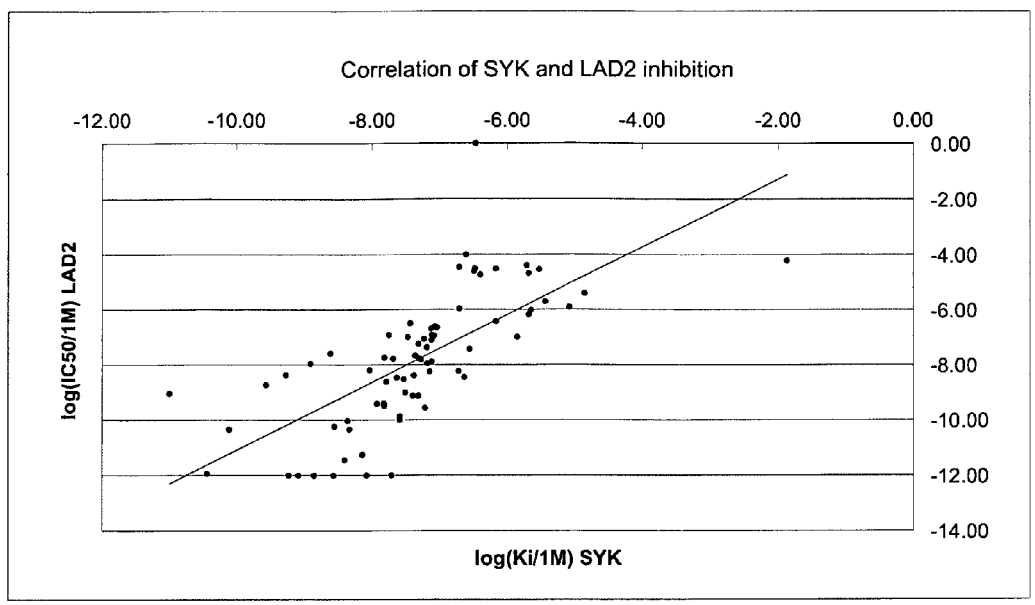

KINASE INHIBITORS

INTRODUCTION

This application claims benefit of priority to U.S. Provisional Application 61/517,581 filed Apr. 21, 2011, the contents of which are incorporated herein by reference in their entirety. The present invention relates to novel compounds that are capable of inhibiting one or more kinases, especially SYK (Spleen Tyrosine Kinase), LRRK2 (Leucine-rich repeat kinase 2) and/or MYLK (Myosin light chain kinase) or mutants thereof. The compounds find applications in the treatment of a variety of diseases. These diseases include autoimmune diseases, inflammatory diseases, bone diseases, metabolic diseases, neurological and neurodegenerative diseases, cancer, cardiovascular diseases, allergies, asthma, alzheimer's disease, parkinson's disease, skin disorders, eye diseases, infectious diseases and hormone-related diseases.

BACKGROUND OF THE INVENTION

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994), EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, alzheimer's disease, parkinson's disease skin disorders, infectious diseases and hormone-related diseases. As a consequence, there has been substantial effort in medicinal chemistry to find inhibitors of protein kinases for use as therapeutic agents.

SYK—Spleen Tyrosine Kinase

Syk is known to play an essential role in adaptive immune response and immune cell signaling. Recent findings impressively demonstrate a variety of further biological functions as cellular adhesion, innate immune recognition, osteoclast maturation, platelet activation and vascular development (Moscai, A. et al., Nat Rev Immunol, 10:387-402, 2010). Syk associates with a variety of receptors of immune cells (mast cells, B cells, macrophages and neutrophils) and non-immune cells (osteoclasts, breast cancer cells) and orchestrates various different cellular processes including cytokine production, bone resorption and phagocytosis. Due to the interaction with immunoreceptors and G-coupled receptors Syk not only functions as a protein kinase but also as a true protein adaptor and therefore became a central paradigm in immune cell signaling.

Immunoreceptor tyrosine activation motif (ITAM)-mediated signaling has emerged as a primary event in signaling pathways responsible for human pathologies. ITAM-mediated and hemITAM-mediated signaling is responsible for relaying activation signals initiated at classical immune receptors such as T-cell receptors, B-cell receptors, Fc receptors in immune cells and at GPVI and FcgammaRIIa in platelets to downstream intracellular molecules such as Syk and ZAP-70 (Underhill, D. M and Goodridge, H. S., Trends Immunol., 28:66-73, 2007) but also furthermore with hemITAM-containing factors as CLEC7A and other C-type lectins.

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either Syk or ZAP-70 interact.

Syk, along with Zap-70, is a member of the Syk family of protein tyrosine kinases. The interaction of Syk or ZAP-70 with diphosphorylated ITAM sequences induces a conformation change in the kinases that allows for tyrosine phosphorylation of the kinase itself. Phosphorylated Syk family members activate a multitude of downstream signaling pathway proteins which include Src homology 2 (SH2) domains. Direct binding partners of Syk are VAV family members, phospholipase C gamma (PLCgamma, PLCgamma 2), phosphoinositide 3-kinases (PI3Ks), SH2 domain-containing leukocyte protein family members (SLP-76 or SLP-65). Other signaling intermediates are p38, Janus kinase (JNK), RAS homologue (RHO) family, Ca++, diacylglycerol DAG, TEC family, caspase-recruitment domain—B cell lymphoma 10—mucosa-associated lymphoid tissue lymphoma translocation protein 1 (CARD-BCL-10-MALT1) complex, protein tyrosine kinase 2 (PYK2), nuclear factor of activated T cells (NFAT), protein kinase C (PKC), RAS guanyl-releasing protein (RASGRP), extracellular signal-regulated kinase (ERK), AKT, NLR family, pyrin domain-containing 3 (NLRP3) inflammasome, NLR family and nuclear factor kappaB (NFkappaB) and factors in the canonical and non-canonical signaling pathways. These contribute to a variety of cellular responses as cytoskelletal changes, ROS production, differentiation, proliferation, survival of cells and cytokine release.

Syk as a key mediator of immunoreceptor and non immuno receptor signaling in a host of inflammatory cells is identified as a key player in the pathogenesis of a variety of diseases and disorders attributed to dysfunctional signaling including autoimmune diseases such as rheumatoid arthritis, systemic lupus, multiple sclerosis, hemolytic anemia, immune-thrombocytopenia purpura, and heparin-induced thrombocytopenia, functional gastrointestinal disorders, asthma, allergic disorders, anaphylactic shock and arteriosclerosis (Riccaboni, M. et al., DDT, 15:517-529, 2010). Interestingly, many of the above mentioned diseases are thought to occur through crosslinking of Fc receptors by antibodies which, via Syk, activate a signaling cascade in mast, basophil and other immune cells that result in the release of cell mediators responsible for inflammatory reactions. The release of mediators and the production of cytokines in IgE stimulation-dependent allergic and inflammatory reactions from mast cells and basophiles can be controlled by inhibiting the kinase activity of Syk (Rossi, A. B. et al., J Allergy Clin Immunol., 118:749-755, 2006). In immune-thrombocytopenia, antibody bound platelets are cleared by the spleen by an Fc receptor/ITAM/Syk-mediated process (Crow, A. R. et al., Blood, 106:abstract 2165, 2005). Drug-induced thrombocytopenia, caused by heparin-platelet factor 4 immune complexes that activate platelet FcgammaRIIa, also involve Syk signaling downstream of receptor engagement (Reilly, M. P., Blood, 98:2442-2447, 2001).

Syk has also been shown to mediate signaling by classes of receptors that do not contain conventional ITAM motifs as integrins and lectins (Kerrigan, A. M. et al., Immunol. Rev., 234:335-352, 2010). Furthermore Syk plays an important role in pathogen recognition like fungi, bacteria and viruses (Hughes, C. E., et al., Blood, 115:2947-2955, 2010; Geijtenbeek, T. B. et al., Nat Rev Immunol, 9:465-479, 2009) The mechanism of Syk activation by integrins-mediated Platelet agonists induce inside-out integrin signaling resulting in fibrinogen binding and platelet aggregation. This initiates outside-in signaling which produces further stimulation of platelets. Syk is activated during both phases of integrin signaling, and inhibition of Syk is shown to inhibit platelet adhesion to immobilized proteins (Law, D. A. et al., Blood, 93:2645-2652, 1999). Release of arachidonic acid and serotonin and platelet aggregation induced by collagen are markedly inhibited in platelets derived from Syk deficient mouse (Poole, A. et al., EMBO J., 16:2333-2341, 1997). Thus Syk inhibitors may also possess anticoagulation action.

Because of the role Syk plays in Ig-induced platelet activations, it is of interest in arteriosclerosis and restenosis. Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. A serious shortcoming of intravascular procedures is that, in a significant number of treated individuals, some or all of the treated vessels restenose (i.e., re-narrow). While the exact hormonal and cellular processes promoting restenosis have not been determined, restenosis is thought to be due in part to mechanical injury to the walls of the blood vessels caused by the balloon catheter or other intravascular device. In response to this injury, adhering platelets, infiltrating macrophages, leukocytes, or the smooth muscle cells themselves release cell-derived growth factors such as platelet-derived growth factor (PDGF), with subsequent proliferation and migration of medial smooth muscle cells (SMCs) through the internal elastic lamina to the area of the vessel intima. Further proliferation and hyperplasia of intimal SMCs and, most significantly, production of large amounts of extracellular matrix over a period of three to six months results in the filling in and narrowing of the vascular space sufficient to significantly obstruct blood flow.

In addition to the role Syk plays in Ig-induced platelet activations, Syk plays a very important role in collagen-mediated signaling. The primary adhesive protein responsible for platelet adhesion and activation is collagen. Collagen is a filamentous protein contained within the fibrotic caps of atheromas which becomes exposed to blood during plaque rupture. Collagen functions initially by binding von Willebrand factor which tethers platelets through binding platelet membrane GPIb. Collagen functions secondarily by engaging the two collagen receptors on platelets, GPVI and integrin alpha2beta1. GPVI exists in platelet membranes as a complex with FcRgamma, an interaction required for the expression of GPVI. Activation of FcgammaRIIa on platelets results in platelet shape change, secretion and thrombosis. Signaling by the GPVI/FcRgamma complex is initiated by tyrosine phosphorylation of the ITAM domain of FCRgamma followed by the recruitment of Syk. Activation of GPVI leads to induction of multiple platelet functions including: activation of integrins alpha2beta1 to achieve firm platelet adhesion, and GP IIb-IIIa which mediates platelet aggregation and thrombosis growth; platelet secretion, allowing for the delivery of inflammatory proteins such as CD40L, RANTES and TGFbeta to the vessel wall; and the expression of P-selectin which allows for the recruitment of leukocytes. Therefore, it is believed that Syk inhibitors can inhibit thrombotic events mediated by platelet adhesion, activation and aggregation.

It has been reported that the tyrosine phosphorylation of intracellular protein (activation) induced by stimulation of a receptor for IgG antibody, FcgammaR, and the phagocytosis mediated by FcgammaR are considerably inhibited in macrophages derived from Syk deficient mouse (Crowley, M. T. et al., J. Exp. Med., 186:1027-1039, 1997). This suggests that Syk has a markedly important role in the FcgammaR-mediated phagocytosis of macrophages.

It has also been reported that an antisense oligonucleotide of Syk suppresses the apoptosis inhibition of eosinophils induced by GM-CSF (Yousefi, S. et al., J. E. Med., 183: 1407-1414, 1996), showing that Syk is essential for the life extending signal of eosinophils caused by GM-CSF and the like. Since life extension of eosinophils is closely related to the transition of diseases into a chronic state in allergic disorders, such as asthma, Syk inhibitors can also serve as therapeutic agents for chronic eosinophilic inflammation.

Syk is important for the activation of B-cells via a B-cell antigen receptor and is involved in the phosphatidylinositol metabolism and increase in the intracellular calcium concentration caused by the antigen receptor stimulation (Hutchcroft, J E. et al., J. Biol. Chem., 267:8613-8619, 1992; and Takata, M. et al., EMBO J., 13:1341-1349, 1994). Thus, Syk inhibitors may be used to control the function of B-cells and are, therefore, expected to serve as therapeutic agents for antibody-related diseases.

Syk binds to a T-cell antigen receptor, quickly undergoes tyrosine phosphorylation through crosslinking of the receptor and synergistically acts upon intracellular signals mediated by Src tyrosine kinases such as Lck (Couture, C. et al., Proc. Natl. Acad. Sci. USA, 91:5301-5305, 1994; and Couture, C. et al., Mol. Cell. Biol., 14:5249-5258, 1994). Syk is present in mature T-cell populations, such as intraepithelial gammadelta T-cells and naive alphabeta T-cells, and has been reported to be capable of phosphorylation of multiple components of the TCR signaling cascade (Latour, S. et. al., Mol Cell Biol., 17:4434-4441, 1997). As a consequence, Syk inhibitors may serve as agents for inhibiting cellular immunity mediated by T-cell antigen receptor.

Recent comparative genomic hybridization studies have identified Syk as another gene important in the pathogenesis of Mantle Cell Lymphoma (MCL) (Chen, R. et al. Journal of Clinical Oncology, 2007 ASCO Annual Meeting Proceedings (Post-Meeting Edition), Vol 25, No 18S (June 20 Supplement), 2007: 8056). MCL represents 5-10% of all non-Hodgkins lymphomas and it is a difficult form of lymphoma to treat. It has the worst prognosis among the B cell lymphomas with median survival of three years. It has been reported that Syk is overexpressed in MCL (Rinaldi, A, et. al, Br. J. Haematol, 2006; 132:303-316) and that Syk mediates mTOR (mammalian target of Rapamycin) survival signals in follicular, mantel cell, Burkitt's, and diffuse large B-cell non-Hodgkin's lymphomas (Leseux, L., et. al, Blood, 2006; 108:4156-4162).

Several lines of evidence suggest that many B-cell lymphomas depend upon B-cell receptor (BCR)-mediated survival signals. BCR signaling induces receptor oligomerization and phosphorylation of Igalpha and beta immunoreceptor tyrosine-based activated motifs by SRC family kinases. ITAM phosphorylation results in the recruitment and activation of Syk that initiates downstream events and amplifies the original BCR signal. Given the role of tonic BCR signaling in normal B cell and Syk-dependent survival of non-Hodgkins lymphoma cell lines in vitro (Chen, L., et. al, Blood, 2006; 108:3428-3433), Syk inhibition is a promising rational treatment target for certain B-cell lymphomas and chronic lymphocytic leukemia (CLL) (Stefania Gobessi, Luca Laurenti, Pablo Longo, Laura Carsetti, Giuseppe Leone, Dimitar G. Efremov, Constitutive activation of the protein tyrosine kinase Syk in Chronic Lymphocytic Leukemia B-cells, Blood, 2007, 110, Abstract 1123). Recent data shows that administration of a multikinase inhibitor which inhibits Syk, may have significant clinical activity in CLL patients (Friedberg J W et al, Blood 2008; 112(11), Abstract 3).

The oncogenic potential of Syk has been described in a number of different settings. Clinically, Syk over-expression is reported in Mantle Cell Lymphoma (Rinaldi, A, et. al, Br. J. Haematol., 2006; 132:303-316) and the TEL-Syk fusion protein (Translocated ETS Leukemia) generated by a chromosomal translocation (t(9; 12)(q22; p12)) leads to increased Syk activity and is associated with myelodysplastic syndrome (Kuno, Y., et. al, Blood, 2001; 97:1050-1055). Leukemia is induced in mice by adoptively transferring bone marrow cells that express human TEL-Syk (Wossning, T., JEM, 2006; 203:2829-2840). Further, in mouse primary bone marrow cells, over-expression of Syk results in IL-7 independent growth in culture (Wossning, T., et. al, JEM, 2006; 203:2829-2840).

Interestingly, Syk signaling appears to be required for B-cell development and survival in humans and mouse. Inducible loss of the B-cell receptor (Lam, K., et. al, Cell, 1997; 90:1073-1083) or Igalpha (Kraus, M., et. al, Cell, 2004; 117:787-800) results in loss of peripheral B-cells in mice. Over-expression of the protein tyrosine phosphatase PTP-RO, which is known to negatively regulate Syk activity, inhibits proliferation and induces apoptosis in cell lines derived from non-Hodgkin's lymphomas (Chen, L., et. al, Blood, 2006; 108:3428-3433). Finally, B-cell lymphomas rarely exhibit loss of BCR expression, and anti-idiotype therapy rarely leads to resistance (Kuppers, R. Nat Rev Cancer, 2005; 5:251-262).

Engagement of the antigen-specific B cell receptor (BCR) activates multiple signaling pathways that ultimately regulate the cells activation status, promoting survival and clonal expansion. Signaling through the BCR is made possible by its association with two other members of the immunoglobulin super-family; Igalpha and Igbeta, each bearing an immuno-tyrosine based activation motif (ITAM) (Jumaa, Hendriks et al. Annu Rev Immunol 23: 415-45 (2005). The ITAM domain is directly phosphorylated by Src family kinases in response to BCR engagement. Syk docks with and phosphorylates the ITAM, a process that enhances its kinase activity, resulting in Syk autophosphorylation and tyrosine phosphorylation of multiple downstream substrates (Rolli, Gallwitz et al. Mol Cell 10(5): 1057-69 (2002). This signaling pathway is active in B cells beginning at the transition from pro- to pre-B cell stage of development, when the newly formed pre-BCR is expressed. In fact, B cell development arrests at the pro-B cell stage in Syk knockout mice (Cheng, Rowley et al. 1995; Turner, Mee et al. Nature 378(6554): 303-6 (1995). Inducible loss of the B cell receptor (Lam, Kuhn et al. Cell 90(6): 1073-83 (1997) or Igalpha (Kraus, Alimzhanov et al. Cell 117(6): 787-800 (2004) results in loss of peripheral B cells in mice. Human B cells also appear to require Syk for proliferation and survival. Over-expression of the protein tyrosine phosphatase PTP-RO, a negative regulator of Syk activity, inhibits proliferation and induces apoptosis in cell lines derived from non-Hodgkin's lymphomas (NHL) (Chen, Juszczynski et al. Blood 108(10): 3428-33 (2006). Knock down of Syk by siRNA in the NHL line SUDHL-4 led to a block in the G1/S transition of the cell cycle (Gururaj an, Dasu et al. J Immunol 178(1): 111-21 (2007). Together, these data suggest that Syk signaling is required for the development, proliferation, and even survival of human and mouse B cells.

Conversely, the oncogenic potential of Syk has been described in a number of different settings. Clinically, Syk over-expression is reported in Mantle Cell Lymphoma (Rinaldi, Kwee et al. Br J Haematol 132(3): 303-16 (2006) and the TEL-Syk fusion protein (Translocated ETS Leukemia) generated by a chromosomal translocation (t(9; 12) (q22; p12)) leads to increased Syk activity and is associated with myelodysplastic syndrome (Kuno, Abe et al. Blood 97(4): 1050-5 (2001). Leukemia is induced in mice by the adoptive transfer of bone marrow cells that express human TEL-Syk (Wossning, Herzog et al. J Exp Med 203(13): 2829-40 (2006). Further, in mouse primary bone marrow cells, over-expression of Syk results in IL-7 independent growth in culture (Wossning, Herzog et al. 2006). Consistently, Syk was reported to mediate mTOR (mammalian target of Rapamycin) survival signals in follicular, mantle cell, Burkitt's, and diffuse large B-cell NHL (Leseux, Hamdi et al. Blood 108(13): 4156-62 (2006). Additional recent studies also suggest that Syk-dependant survival signals may play a role in B-cell malignancies, including DLBCL, mantle cell lymphoma and follicular lymphoma (Gururajan, Jennings et al. 2006; Irish, Czerwinski et al. J Immunol 176(10): 5715-9 (2006)). Given the role of tonic BCR signaling in normal B cells and Syk-dependent survival of NHL cell lines in vitro, the specific inhibition of Syk may prove promising for the treatment of certain B-cell lymphomas.

Recently, R406 (Rigel Pharmaceuticals) was reported to inhibit ITAM signaling in response to various stimuli, including FcepsilonR1 and BCR induced Syk activation (Braselmann, Taylor et al. J Pharmacol Exp Ther 319(3): 998-1008 (2006). Interestingly, this ATP-competitive inhibitor of Syk was also active against Flt3, cKit, and JAK kinases, but not against Src kinsase (Braselmann, Taylor et al. 2006). Activating mutations to Flt3 are associated with AML and inhibition of this kinase is currently under clinical development (Burnett and Knapper Hematology Am Soc Hematol Educ Program 2007: 429-34 (2007). Over-activation of the tyrosine kinase cKit is also associated with hematologic malignancies, and a target for cancer therapy (Heinrich, Griffith et al. Blood 96(3): 925-32 (2000). Similarly, JAK3 signaling is implicated in leukemias and lymphomas, and is currently exploited as a potential therapeutic target (Heinrich, Griffith et al. 2000). Importantly, the multi-kinase inhibitory activity of R406 attenuates BCR signaling in lymphoma cell lines and primary human lymphoma samples, resulting in apoptosis of the former (Chen, Monti et al. Blood 111(4): 2230-7 (2008). Further, a phase II clinical trial reported favorable results by this compound in refractory NHL and chronic lymphocytic leukemia (Friedberg J W et al, Blood 2008; 112(11), Abstract 3). Although the precise mechanism of action is unclear for R406, the data suggest that inhibition of kinases that mediate survival signaling in lymphocytes is clinically beneficial.

Additional recent studies also suggest that Syk-dependant survival signals may play a role in B-cell malignancies, including DLBCL, mantle cell lymphoma and follicular lymphoma (see e.g., S. Linfengshen et al. Blood, February 2008; 111: 2230-2237; J. M. Irish et al. Blood, 2006; 108: 3135-3142; A. Renaldi et al. Brit J. Haematology, 2006; 132: 303-316; M. Guruoajan et al. J. Immunol, 2006; 176: 5715-5719; L. Laseux et al. Blood, 2006; 108: 4156-4162.

A recent publication summarizes the frequent finding of eye involvement with rheumatoid arthritis and other autoimmune diseases. Scleritis, episcleritis and keratoconjunctivitis sicca may represent the leading clinical manifestation of these autoimmune diseases. All components of the visual organ might be affected. Autoimmune reactions based on the patient's genetic predisposition are assumed to be of significance in pathogenesis of eye diseases.

This manifests Syk as relevant therapeutic target in occular diseases. (Feist, E., Pleyer, U., Z Rheumatol, 69: 403-410, 2010).

Furthermore SYK is also a relevant target in the treatment of fungal, viral and bacterial infections of the eye e.g. fungal keratitis. Dectin-1 mediated activation of p-Syk, and further factors as p-IkB or NFkB lead to the production of IL-1b and CXCL1/KC that are important for neutrophil and mononuclear cell recruitment to the corneal stroma. Leal, S. M., Cowden, S., Hsia, Y.-C., Ghannoum, M. A., Momany, M., & Pearlman, E. (2010). Distinct roles for Dectin-1 and TLR4 in the pathogenesis of *Aspergillus fumigatus* keratitis. PLoS Pathogens, 6.

In general recent evidence shows that SYK is an essential target for treatment of PRR and CLR mediated adaptive immune response. Kingeter, L. M., & Lin, X. (2012). C-type lectin receptor-induced NF-κB activation in innate immune and inflammatory responses. Cellular & molecular immunology, 9(2), 105-112. Drummond, R. A., Saijo, S., Iwakura, Y., & Brown, G. D. (2011). The role of Syk/CARD9 coupled C-type lectins in antifungal immunity. European journal of immunology, 41(2), 276-281. Lee, H.-M., Yuk, J.-M., Kim, K.-H., Jang, J., Kang, G., Park, J. B., Son, J.-W., et al. (2011). *Mycobacterium abscessus* activates the NLRP3 inflammasome via Dectin-1-Syk and p62/SQSTM1. Immunology and cell biology.

According to one embodiment, the present invention provides compounds that are capable of inhibiting one or more kinases, more particularly SYK and mutants thereof.

LRRK2—Leucine-Rich Repeat Kinase 2

There has been much interest raised by the discovery that different autosomal dominant point mutations within the gene encoding for LRRK2 predispose humans to develop late-onset Parkinson's disease (PD), with a clinical appearance indistinguishable from idiopathic PD (see Paisan-Ruiz, C, Jain, S., Evans, E. W., Gilks, W. P., Simon, J., van der Brug, M., Lopez de Munain, A., Aparicio, S., Gill A. M., Khan, N., Johnson, J., Martinez, J. R., Nicholl, D., Carrera, I. M., Pena, A. S., de Silva, R., Lees, A., Marti-Masso, J. F., Perez-Tur, J., Wood, N. W. and Singleton, A. B. (2004) Cloning of the gene containing mutations that cause PARK8-linked Parkinson's disease. Neuron. 44, 595-600; Mata, I. F., Wedemeyer, W. J., Farrer, M. J., Taylor, J. P. and Gallo, K. A. (2006) LRRK2 in Parkinson's disease: protein domains and functional insights. Trends Neurosci. 29, 286-293; Taylor, J. P., Mata, I. F. and Farrer, M. J. (2006) LRRK2: a common pathway for parkinsonism, pathogenesis and prevention? Trends MoI Med. 12, 76-82). The genetic analysis undertaken to date indicates that mutations in LRRK2 are relatively frequent, not only accounting for 5-10% of familial PD, but also being found in a significant proportion of sporadic PD cases (see Farrer, M., Stone, J., Mata, I. F., Lincoln, S., Kachergus, J., Hulihan, M., Strain, K. J. and Maraganore, D. M. (2005) LRRK2 mutations in Parkinson disease. Neurology. 65, 738-740; Zabetian, C. P., Samii, A., Mosley, A. D., Roberts, J. W., Leis, B. C, Yearout, D., Raskind, W. H. and Griffith, A. (2005) A clinic-based study of the LRRK2 gene in Parkinson disease yields new mutations. Neurology. 65, 741-744. Little is known about how LRRK2 is regulated in cells, what its physiological substrates are and how mutations cause or increase risk of PD.

Genomewide-wide association studies show a possible involvement in further neurodegenerative diseases like Alzheimer furthermore leprosy but also revealed a higher probability of cancer occurrence for carriers of LRRK2 mutants and may indicate an involvement of this kinase and mutants in cancer development. Inzelberg, et al. The LRRK2 G2019S mutation is associated with Parkinson disease and concomitant non-skin cancers. Neurology, 2012, 78, 781-786. Zhao, Y., Ho, P., Yih, Y., Chen, C., Lee, W. L., & Tan, E. K. (2011). LRRK2 variant associated with Alzheimer's disease. Neurobiology of aging, 32(11), 1990-1993. Lewis, P. A., & Manzoni, C. (2012). LRRK2 and Human Disease: A Complicated Question or a Question of Complexes? Science Signaling, 5(207).

An unexpected finding was the involvement of LRRK2 as a major susceptibility gene for Crohn's disease (CD) and other related inflammatory diseases. LRRK2 deficiency in mice confers enhanced susceptibility to experimental colitis. The complex nature of the multidomain LRRK2 protein makes it plausible that LRRK2 may also regulate different pathways in immune reactions through its involvement in NFAT1 regulation in participating in the NRON complex in immune cells. Liu, Z., & Lenardo, M. J. (2012) "The role of LRRK2 in inflammatory bowel disease", Cell research; "LRRK2 as a negative regulator of NFAT: implications for the pathogenesis of inflammatory bowel disease", Puja Vora, Dermot P B McGovern, Expert Review of Clinical Immunology, March 2012, Vol. 8, No. 3, Pages 227-229.

According to one embodiment, the present invention provides compounds that are capable of inhibiting one or more kinases, more particularly, LRRK, even more preferably LRRK2.

Myosin Light Chain Kinase (MLCK or MYLK)

Inhibitors of MYLK (or MLCK) are of interest in the treatment and/or prevention of any disorder where tissue barrier dysfunction or changes in cell motility are part of the disease mechanism or progression of pathophysiology. These include a large number of diseases in a variety of categories, including but not limited to skin disorders: including ichthyosis vulgaris, atopic dermatitis, psoriasis, eczema, allergic skin disease, and hypersensitivity reactions; intestinal disorders: including inflammatory bowel disease, Crohn's disease, ulcers, bacterial infections hemorrhagic shock, diarrhea, colitis, viral and alcoholic liver disease, pancreatitis; lung disorders: including acute lung injury after infection, mechanical ventilation-induced injury, sepsis, thrombin-induced lung injury, lung injury after reperfusion; interstitial cystitis of the bladder; coronary disease after ischemia-reperfusion injury, flow-induced injury, aortic aneurysm, hypertension; burn-induced injury; chorioretinal vascular disease; neurologic disorders: including multiple sclerosis, Alzheimer's disease, vascular dementia, traumatic brain injury, ALS, Parkinson's disease, stroke, meningoencephalitis, cerebral hemorrhage, Guillain-Barre syndrome, vasogenic brain edema, hypoxia-induced injury and blood brain barrier compromise after ethanol toxicity; and cancers, including metastatic cancers such as non-small cell lung cancers, pancreatic cancer, adenocarcinoma and prostate cancer. See, e.g., Behanna H A, Watterson D M and Ralay Ranaivo H (2006) Development of a novel bioavailable inhibitor of the calmodulin-regulated protein kinase MLCK: a lead compound that attenuates vascular leak. Biochim Biophys Acta 1763: 1266-1274; Behanna H A, Bergan R and Watterson D M (2007), unpublished observations; Bratcher J M and Korelitz B I (2006) Toxicity of infliximab in the course of Crohn's disease. Expert Opin Drug Saf 5: 9-16; Clayburgh D R, Shen L and Turner J R (2004) A porous defense: the leaky epithelial barrier in intestinal disease. Lab Invest 84: 282-291; Clayburgh D R, Barrett T A, Tang Y, Meddings J B, Van Eldik L J, Watterson D M, Clarke L L, Mrsny R J and Turner J R (2005) Epithelial myosin light chain kinase-dependent barrier dysfunction mediates T cell activation-induced diarrhea in vivo. J Clin Invest 115: 2702-2715; Demling R H (2005) The burn edema process: current concepts. J Burn Care Rehabil 26: 207-227; Dreyfuss D and Saumon G (1998) Ventilator-induced lung injury: lessons from experimental studies. Am J Respir Crit. Care Med 157: 294-323; Haorah J, Heilman D, Knipe B, Chrastil J, Leibhart J, Ghorpade A, Miller D W and Persidsky Y (2005) Ethanol-induced activation of myosin light chain kinase leads to dysfunction of tight junctions and blood-brain barrier compromise. Alcohol Clin Exp Res 29: 999-1009; Huang Q, Xu W, Ustinova E, Wu M, Childs E, Hunter F and Yuan S (2003) Myosin light chain kinase-dependent microvascular hyperpermeability in thermal injury. Shock 20: 363-368; Kaneko K, Satoh K, Masamune A, Satoh A and Shimosegawa T (2002) Myosin light chain kinase inhibitors can block invasion and adhesion of human pancreatic cancer cell lines. Pancreas 24: 34-41; Ma T Y, Boivin M A, Ye D, Pedram A and Said H M (2005) Mechanism of TNFalpha modulation of Caco-2 intestinal epithelial tight junction barrier: role of myosin light-chain kinase protein expression. Am J Physiol Gastrointest Liver Physiol 288: G422-G430; Minamiya Y, Nakagawa T, Saito H, Matsuzaki I, Taguchi K, Ito M and Ogawa J (2005) Increased expression of myosin light chain kinase mRNA is related to metastasis in non-small cell lung cancer. Tumour Biol 26: 153-157; Ralay Ranaivo H, Carusio N, Wangensteen R, Ohlmann P, Loichot C, Tesse A, Chalupsky K, Lobysheva I, Haiech J, Watterson D M and Andriantsitohaina R (2007) Protection against endotoxic shock as a consequence of reduced nitrosative stress in MLCK210-null mice. Am J Pathol 170:439-446; Reynoso R, Perrin R M, Breslin J W, Daines D A, Watson K D, Watterson D M, Wu M H and Yuan S A role for long chain myosin light chain kinase (MLCK-210) in microvascular hyperpermeability during severe burns. Shock, June 14 epub; Rossi J, Bayram M, Udelson J E, Lloyd-Jones D, Adams K F, Oconnor C M, Stough W G, Ouyang J, Shin D D, Orlandi C and Gheorghiade M (2007) Improvement in hyponatremia during hospitalization for worsening heart failure is associated with improved outcomes: insights from the Acute and Chronic Therapeutic Impact of a Vasopressin Antagonist in Chronic Heart Failure (ACTIV in CHF) trial. Acute Card Care 9:82-86; Scott K G, Meddings J B, Kirk D R, Lees-Miller S P and Buret A G (2002) Intestinal infection with *Giardia* spp. reduces epithelial barrier function in a myosin light chain kinase-dependent fashion. Gastroenterology 123: 1179-1190; Tohtong R, Phattarasakul K, Jiraviriyakul A and Sutthiphongchai T (2003) Dependence of metastatic cancer cell invasion on MLCK-catalyzed phosphorylation of myosin regulatory light chain. Prostate Cancer Prostatic Dis 6: 212-216; Yuan S Y (2002) Protein kinase signaling in the modulation of microvascular permeability. Vascul Pharmacol 39: 213-223; Yuan S Y, Wu M H, Ustinova E E, Guo M, Tinsley J H, De Lanerolle P and Xu W (2002) Myosin light chain phosphorylation in neutrophil-stimulated coronary microvascular leakage. Circ Res 90: 1214-1221; Zolotarevsky Y, Hecht G, Koutsouris A, Gonzalez D E, Quan C, Tom J, Mrsny R J and Turner J R (2002) A membrane-permeant peptide that inhibits MLC kinase restores barrier function in in vitro models of intestinal disease. Gastroenterology 123 (2002) 163-172. Role of myosin light chain kinase in regulation of basal blood pressure and maintenance of salt-induced hypertension. (2011). Role of myosin light chain kinase in regulation of basal blood pressure and maintenance of salt-induced hypertension. American journal of physiology. Heart and circulatory physiology, 301 (2).

According to one embodiment, the present invention provides compounds that are capable of inhibiting one or more kinases, especially MYLK (or MLCK).

STATEMENT OF INVENTION

The present invention provides one or more compounds of formula (I)

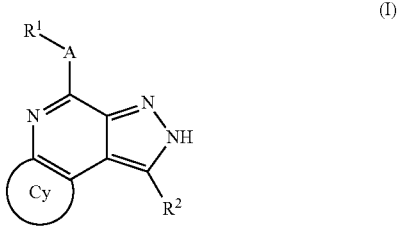

wherein

A is O, S, C=O, NR$^3$ or CR$^4$R$^5$ (especially NH);

Cy is an optionally substituted aryl, heteroaryl, cycloalkyl, heterocycloalkyl, alkylcycloalkyl, heteroalkylcycloalkyl, aralkyl or heteroaralkyl group;

R$^1$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

R$^2$ is a hydrogen atom, a halogen atom, NO$_2$, N$_3$, OH, SH, NH$_2$ or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

R$^3$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

R$^4$ is a hydrogen atom, NO$_2$, N$_3$, OH, SH, NH$_2$ or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group; and R$^5$ is a hydrogen atom, NO$_2$, N$_3$, OH, SH, NH$_2$ or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

or a pharmaceutically acceptable salt, ester, solvate or hydrate or a pharmaceutically acceptable formulation thereof.

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulfur atom (preferably by an oxygen, sulfur or nitrogen atom). The expression heteroalkyl furthermore refers to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy.

Preferably, a heteroalkyl group contains from 1 to 12 carbon atoms and from 1 to 4 hetero atoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) hetero atoms selected from oxygen, nitrogen and sulphur (especially oxygen and nitrogen). The term $C_1$-$C_6$ heteroalkyl refers to a heteroalkyl group containing from 1 to 6 carbon atoms and 1, 2 or 3 heteroatoms selected from O, S and/or N (especially O and/or N). The term $C_1$-$C_4$ heteroalkyl refers to a heteroalkyl group containing from 1 to 4 carbon atoms and 1, 2 or 3 heteroatoms selected from O, S and/or N (especially O and/or N). Furthermore, the term heteroalkyl refers to groups in which one or more hydrogen atoms have been replaced by a halogen atom (preferably F or Cl).

Examples of heteroalkyl groups are groups of formulae: $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$) $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a direct bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —CH$_2$CH$_2$OH, —CH$_2$OH, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, NH$_2$, =NH, N$_3$ or NO$_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom). A heterocycloalkyl group has preferably 1 or 2 ring(s) containing from 3 to 10 (especially 3, 4, 5, 6 or 7) ring atoms (preferably seccted from C, O, N and S). The expression heterocycloalkyl refers furthermore to groups in which one or more hydrogen atoms have been replaced by fluorine, chlorine, bromine or iodine atoms or by OH, =O, SH, =S, NH$_2$, =NH, N$_3$ or NO$_2$ groups. Examples are a piperidyl, prolinyl, imidazolidinyl, piperazinyl, morpholinyl, urotropinyl, pyrrolidinyl, tetrahydro-thiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom). A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and hetero-alkylheterocycloalkenyl, the cyclic groups being saturated or mono-, di- or tri-unsaturated.

The expression aryl refers to an aromatic group that contains one or more rings containing from 6 to 14 ring carbon atoms, preferably from 6 to 10 (especially 6) ring carbon atoms. The expression aryl refers furthermore to groups in which one or more hydrogen atoms have been replaced by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6 or 9 or 10) ring atoms, and contains one or more (preferably 1, 2, 3 or 4) oxygen, nitrogen, phosphorus or sulfur ring atoms (preferably O, S or N). The expression heteroaryl refers furthermore to groups in which one or more hydrogen atoms have been replaced by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms have been replaced by an oxygen, nitrogen, silicon, selenium, phosphorus, boron or sulfur atom (preferably oxygen, sulfur or nitrogen), that is to say to groups containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheterocycloalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups in which one or more hydrogen atoms of such groups have been replaced by fluorine, chlorine, bromine or iodine atoms or by OH, =O, SH, =S, $NH_2$, =NH, $N_3$ or $NO_2$ groups.

The expression "optionally substituted" especially refers to groups in which one, two, three or more hydrogen atoms may have been replaced by fluorine, chlorine, bromine or iodine atoms or by OH, =O, SH, =S, $NH_2$, =NH, $N_3$ or $NO_2$ groups. This expression refers furthermore to groups that may be substituted by one, two, three or more unsubstituted $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{18}$ heteroaralkyl groups. This expression refers furthermore especially to groups that may be substituted by one, two, three or more unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Preferred substituents are F, Cl, Br, OH, =O, $NH_2$, $C_{1-4}$ alkyl (e.g. methyl, ethyl, t-butyl), $NMe_2$, $CONH_2$, $CH_2NMe_2$, $NHSO_2Me$, $C(CH_3)_2CN$, COMe, OMe, SMe, COOMe, COOEt, $CH_2COOH$, $OCH_2COOH$, COOH, SOMe, $SO_2Me$, cyclopropyl, $SO_2NH_2$, $SO_2NHMe$, $SO_2CH_2CH_2OH$, $SF_5$, $SO_2NMe_2$, $OCF_3$, $SO_2CF_3$, COMe, CN or $CF_3$.

Especially preferred substituents are F, Cl, Br, Me, OMe, CN or $CF_3$.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Preferred are compounds of formula (I) wherein A is NH.

Further preferred are compounds of formula (I) wherein $R^2$ is H, F, Cl, $CH_3$, $CF_3$, $NO_2$, cyclopropyl, CN, $N_3$, OH, SH, OMe, SMe, NHMe, $NMe_2$ or $NH_2$.

Moreover preferred are compounds of formula (I) wherein $R^2$ is a hydrogen atom, a $NO_2$ group, a $CF_3$ group or a methyl group (especially H or $CH_3$; especially preferably H).

Especially preferred are compounds of formula (I) wherein A is NH and $R^2$ is H, $NO_2$, $CF_3$ or $CH_3$ (especially H or $CH_3$; especially preferably H).

Further preferred are compounds of formula (I) wherein Cy is an optionally substituted phenyl (or phenylene; or $C_6$ aryl) group or an optionally substituted heteroaryl (or heteroarylene) group having 5 or 6 ring atoms and 1, 2 or 3 heteroatoms selected from O, S and N. Preferably, these groups are unsubstituted or substituted by one or two of the following groups: $C_{1-6}$ alkyl, $C_{1-6}$ heteroalkyl and/or (a) halogen atom(s). Especially preferably, these groups are unsubstituted or substituted by one or two of the following groups: $CH_3$, $OCH_3$, COOMe, $OCH_2CH_3$, CN and/or a halogen atom like e.g. Br. Most preferably, these groups are unsubstituted or substituted by OMe, F or CN.

Moreover preferred are compounds of formula (I) wherein Cy is an optionally substituted phenyl group or an optionally substituted pyridyl group, an optionally substituted thiophenyl group or an optionally substituted isothiazole group. Preferably, these groups are unsubstituted or substituted by one or two of the following groups: $C_{1-6}$ alkyl, $C_{1-6}$ heteroalkyl and/or (a) halogen atom(s). Especially preferably, these groups are unsubstituted or substituted by one or two of the following groups: $CH_3$, $OCH_3$, $OCH_2CH_3$, COOMe, CN and/or a halogen atom like e.g. Br. Most preferably, these groups are unsubstituted or substituted by OMe, F or CN.

Further preferred are compounds of formula (I) wherein Cy is oxazole, thiazole, isoxazole, 1,2,5-thiadiazole, furan, thiophene, 1,2,3-thiadiazole, 1,2,5-oxadiazole, 1,2,3-oxadiazole, 1H-imidazole, 1H-1,2,4-triazole, 1H-pyrrole, 1H-1,2,3-triazole, 1H-tetrazole, 4H-1,2,4-triazole, 1H-pyrazole, 1,2,5-selenadiazole, 1,3-selenazole, selenophene, 2H-1,2,3-triazole, 1,3-dithiol-1-ium, benzene, pyrimidine, pyrazine, pyridine, pyridazine, 1,2,4-triazine, 1,2,3-triazine, 1,4-dithiine or a regioisomer thereof. These groups may be unsubstituted or substituted. Preferably, these groups are unsubstituted or substituted by one or two of the following groups: $C_{1-6}$ alkyl, $C_{1-6}$ heteroalkyl and/or a halogen atom. Especially preferably, these groups are unsubstituted or substituted by on or two of the following groups: $CH_3$, $OCH_3$, $OCH_2CH_3$, COOMe, CN and/or a halogen atom like e.g. Br. Most preferably, these groups are unsubstituted or substituted by OMe, F or CN.

Further preferred are compounds of formula (Ia):

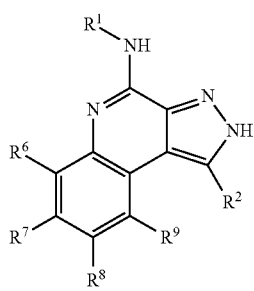

(Ia)

wherein $R^6$, $R^7$, $R^8$ and $R^9$ are independently selected from H, OH, $C_{1-6}$ alkyl, $C_{1-6}$ heteroalkyl and a halogen atom and wherein $R^1$ and $R^2$ are as defined above.

Preferably, $R^6$, $R^7$, $R^8$ and $R^9$ are independently selected from H, OH, $OCH_3$, CN and a halogen atom (like e.g. F, Cl, Br or I).

Especially preferably, $R^6$, $R^7$, $R^8$ and $R^9$ are independently selected from H, OH, CN, OMe, F, Cl, Br and I (e.g. H, OH, OMe, F, Cl, Br and I; preferably from H, F, OMe and CN; especially from H and $OCH_3$), wherein preferably 2, 3 or 4 of $R^6$, $R^7$, $R^8$ and $R^9$ are H.

Further preferably, one or two of $R^6$, $R^7$, $R^8$ and $R^9$ are F, CN or OMe (especially OMe) and the other of $R^6$, $R^7$, $R^8$ and $R^9$ are H.

Further preferred are compounds of formula (Ib):

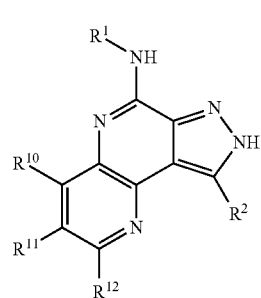

(Ib)

wherein $R^{10}$, $R^{11}$ and $R^{12}$ are independently selected from H, $C_{1-6}$ alkyl, $C_{1-6}$ heteroalkyl and a halogen atom and wherein $R^1$ and $R^2$ are as defined above.

Preferably, $R^{10}$, $R^{11}$ and $R^{12}$ are independently selected from H, $OCH_3$, CN and a halogen atom (like e.g. Br); especially preferably from H, F, CN and OMe.

Especially preferably, $R^{10}$, $R^{11}$ and $R^{12}$ are independently selected from H, F, CN and OMe (preferably H and $OCH_3$; especially H), wherein preferably 2 or 3 of $R^{10}$, $R^{11}$ and $R^{12}$ are H.

Further preferred are compounds of formula (Ic):

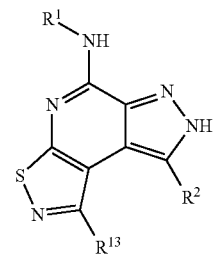

(Ic)

wherein $R^{13}$ is selected from H, $C_{1-6}$ alkyl, $C_{1-6}$ heteroalkyl and a halogen atom and wherein $R^1$ and $R^2$ are as defined above.

Preferably, $R^{13}$ is selected from H, $CH_3$, $OCH_3$, CN and a halogen atom (like e.g. Br).

Especially preferably, $R^{13}$ is methyl.

Moreover preferred are compounds of formula (Id):

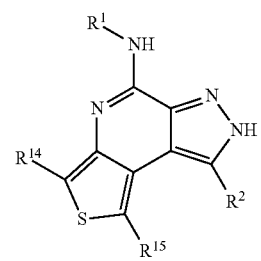

(Id)

wherein $R^{14}$ and $R^{15}$ are independently selected from H, $C_{1-6}$ alkyl, $C_{1-6}$ heteroalkyl and a halogen atom and wherein $R^1$ and $R^2$ are as defined above.

Preferably, $R^{14}$ is COOMe and $R^{15}$ is H.

Further preferred are compounds of formula (I), (Ia), (Ib), (Ic) and (Id) wherein $R^1$ is an aryl, heteroaryl, cycloalkyl, heterocycloalkyl, alkylcycloalkyl, heteroalkylcycloalkyl, aralkyl or heteroaralkyl group, all of which may optionally be substituted.

Further preferred are compounds of formula (I), (Ia), (Ib), (Ic) and (Id) wherein $R^1$ is an aryl, heteroaryl, $CH_2$-aryl or $CH_2$-heteroaryl group, all of which may optionally be substituted.

Moreover preferred are compounds of formula (I), (Ia), (Ib), (Ic) and (Id) wherein $R^1$ is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings (especially two annullated rings) and 9 to 20 (especially 9 or 10) ring atoms. Preferably, the heteroatoms are selected from S, O and N, especially from N and O. Further preferably, the number of heteroatoms is 1 to 6 (especially 1, 2, 3 or 4).

Especially preferably, $R^1$ is an optionally substituted phenyl group or an optionally substituted heteroaryl group having one ring containing 5 or 6 ring atoms. Preferably this phenyl or heteroaryl group is substituted by one or more (especially one) $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{10}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl group(s). Preferably, the heteroatoms are selected from S, O and N, especially from N and O. Especially preferably, the phenyl or heteroaryl group is substituted by one or more (especially one) $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl group(s). Preferably, the heteroatoms are selected from S, O and N, especially from N and O.

Further preferred are compounds of formula (I), (Ia), (Ib), (Ic) and (Id) wherein $R^1$ is a group of formula —$CH_2$—Ar wherein Ar is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings (especially two annullated rings) and 9 to 20 (especially 9 or 10) ring atoms. Preferably, the heteroatoms are selected from S, O and N, especially from N and O. Further preferably, the number of heteroatoms is 1 to 6 (especially 1, 2, 3 or 4).

Especially preferably, Ar is an optionally substituted phenyl group or an optionally substituted heteroaryl group having one ring containing 5 or 6 ring atoms. Preferably this phenyl or heteroaryl group is substituted by one or more (especially one) $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl group(s). Preferably, the heteroatoms are selected from S, O and N, especially from N and O. Especially preferably the phenyl or heteroaryl group is substituted by one or more (especially one) $C_1$-$C_8$ alkyl, $C_2$-$C_6$ alkenyl, $C_2$-$C_6$ alkynyl, $C_1$-$C_8$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_8$ heteroaryl, $C_7$-$C_{12}$ aralkyl or $C_2$-$C_{11}$ heteroaralkyl group(s). Preferably, the heteroatoms are selected from S, O and N, especially from N and O.

Further preferred, $R^1$ is a group of formula —$CH_2CH_2OCH_3$ or a 2-amino cyclohexyl group.

Further preferably, $R^1$ is a group of formula $X^1$-$L^1$-$Y^1$ or a group of formula $X^1$-$L^1$-$Y^1$-$L^2$-$Z^1$ wherein $X^1$ is an optionally substituted phenyl group or an optionally substituted heteroaryl group containing 5 or 6 ring atoms and 1, 2, 3 or 4 heteroatoms selected from O, S and N;

$L^1$ is a bond or a group of formula —$CH_2$—, —C(=O)—, —SO—, —$SO_2$—, —NH—C(=O)—, —C(=O)—NH—; —C(=O)—O—, —O—C(=O)—, —NH—C(=O)—O—, —O—C(=O)—NH—, —NH—$SO_2$—NH—, —$CH_2$—NH—$CH_2$—, —NH—$SO_2$—, —$SO_2$—NH— or —NH—C(=O)—NH— (preferably, $L^1$ is a bond or a group of formula —$CH_2$—, —C(=O)—, —$SO_2$— or —NH—C(=O)—NH—);

$Y^1$ is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N (preferably, $Y^1$ is an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N);

$L^2$ is a bond or a group of formula —$CH_2$—, —C(=O)—, —SO—, —$SO_2$—, —NH—C(=O)—, —C(=O)—NH—; —C(=O)—O—, —O—C(=O)—, —NH—C(=O)—O—, —O—C(=O)—NH—, —$CH_2$—NH—$CH_2$—, —NH—$SO_2$—, —$SO_2$—NH— or —NH—C(=O)—NH— (preferably, $L^2$ is a bond or a group of formula —$CH_2$—, —C(=O)—, —$SO_2$— or —NH—C(=O)—NH—; especially preferably, $L^2$ is a bond); and $Z^1$ is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N (preferably, $Z^1$ is an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N).

Especially preferably, $R^1$ is selected from the following groups:

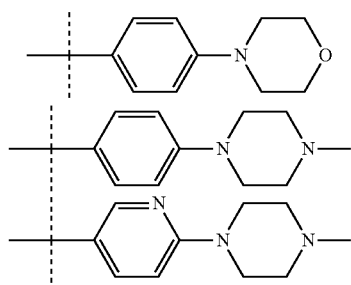

-continued
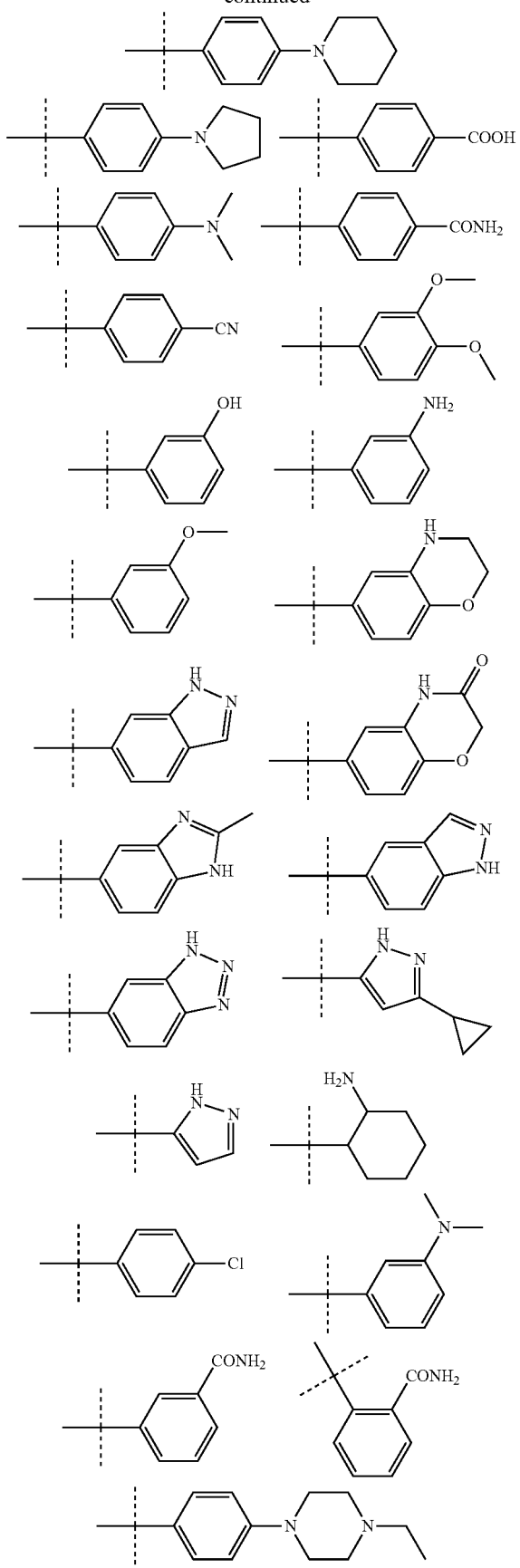
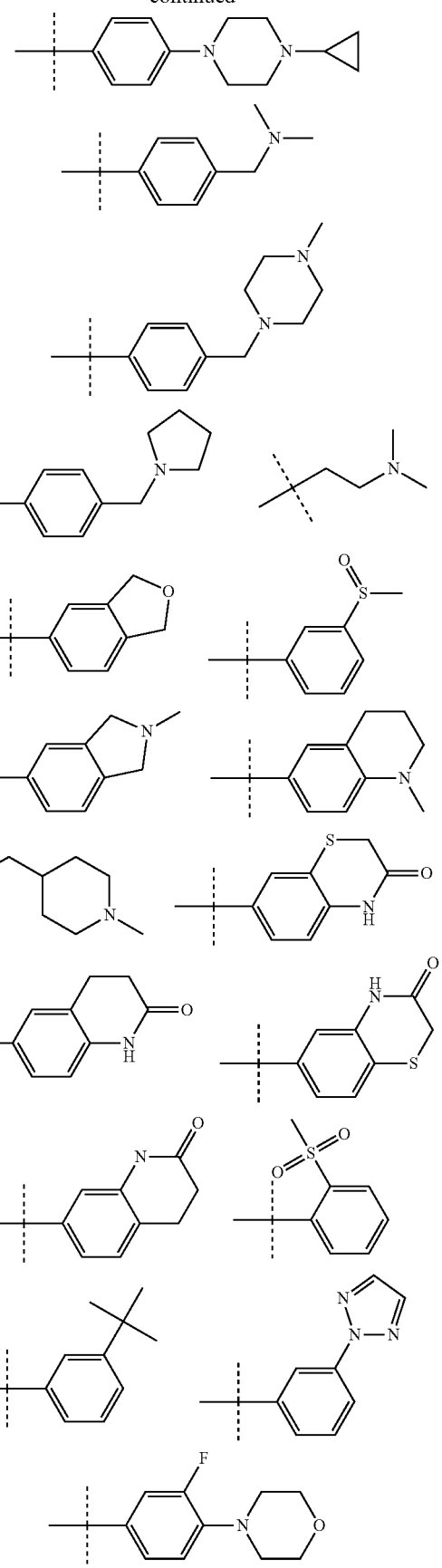

-continued
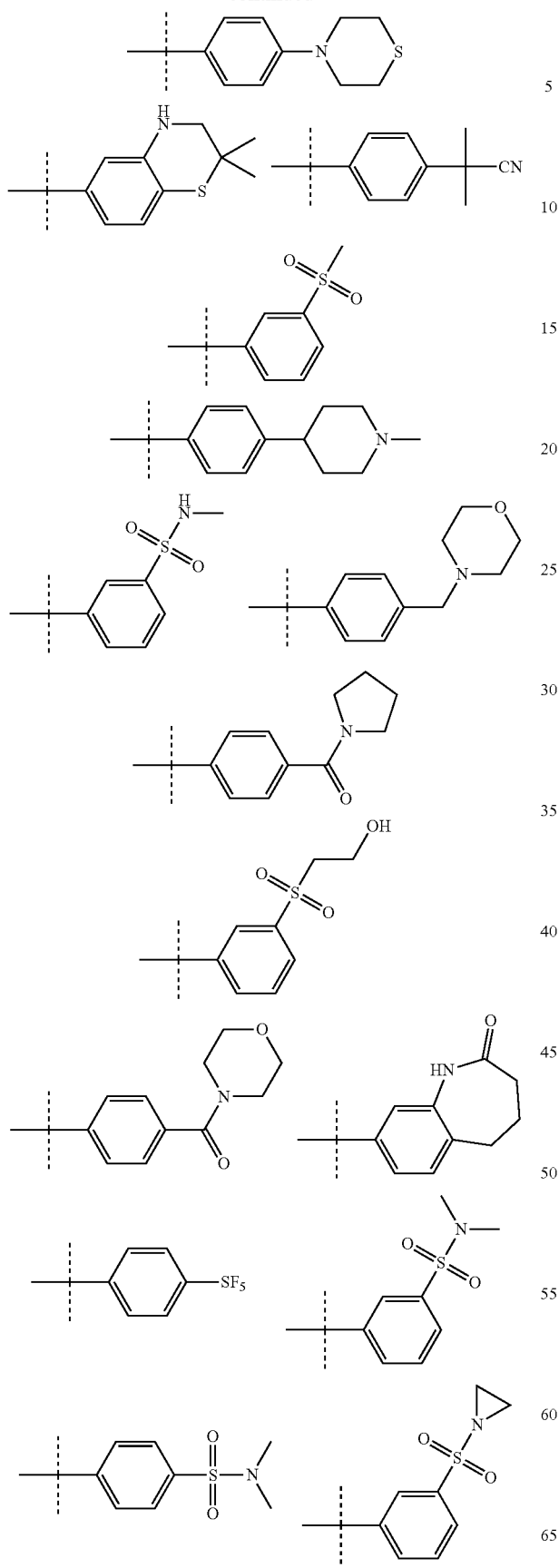
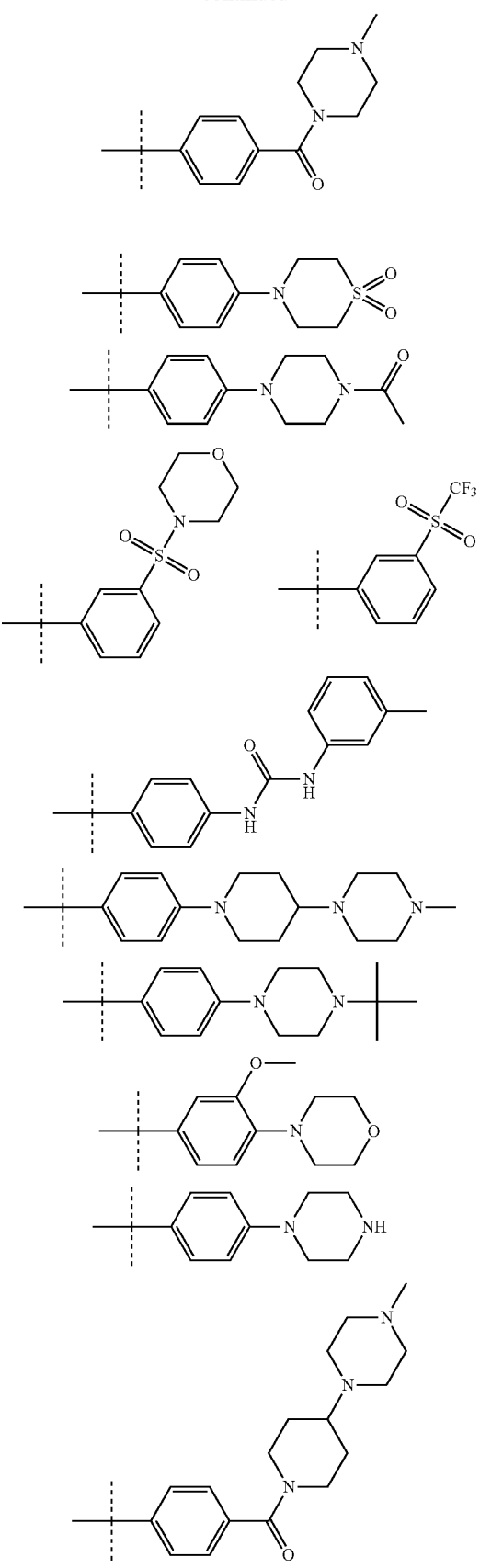

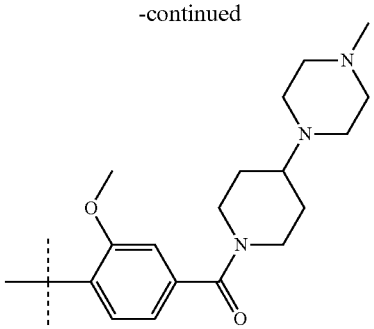

Especially preferred are compounds of formula (I), (Ia), (Ib), (Ic) and/or (Id) wherein, $R^1$ is derived from the following amines:

m-toluidine; 3-(trifluoromethyl)aniline; 3,4,5-trimethoxyaniline; 1H-indazol-5-amine; aniline; 1H-indazol-6-amine; 3-chloroaniline; 7-methyl-1H-indazol-5-amine; 2-methoxyethan-1-amine; thiophen-2-ylmethanamine; 6-methyl-1H-indazol-5-amine; 2H-indazol-6-amine; methyl 4-aminobenzoate; 1H-benzo[d]imidazol-5-amine; 2H-indazol-7-amine; (1-methyl-1H-pyrrol-2-yl)methanamine; benzo[d][1,3]dioxol-5-amine; pyridin-3-amine; 1-methyl-1H-indazol-6-amine; 6-methoxypyridin-3-amine; 4-(4-methylpiperazin-1-yl)aniline; 4-(4-methyl-1,4-diazepan-1-yl)aniline; pyridin-2-amine; 5-bromopyridin-2-amine; isoquinolin-3-amine; 4-methylpyridin-2-amine; 4,6-dimethylpyridin-2-amine; 1H-indazol-7-amine; benzene-1,3-diamine; 6-amino-2H-benzo[b][1,4]oxazin-3(4H)-one; 1H-benzo[d][1,2,3]triazol-5-amine; 3-aminobenzimidamide; 4-(piperidin-1-yl)aniline; N1,N1-dimethylbenzene-1,4-diamine; 3-aminobenzamide; 3,4-dimethoxyaniline; 4-morpholinoaniline; 2-methyl-1H-benzo[d]imidazol-6-amine; 4-aminobenzoic acid; 4-aminobenzamide; 4-aminobenzonitrile; 3-methoxyaniline; 4-methoxyaniline; 3-aminobenzonitrile; benzo[c][1,2,5]thiadiazol-5-amine; 3-aminopyridin-2(1H)-one; 2-ethoxyaniline; 1H-pyrazol-3-amine; 5-amino-1H-pyrazole-4-carboxamide; 2-phenoxyaniline; 3-phenoxyaniline; 5-amino-1H-benzo[d]imidazol-2(3H)-one; 1H-indol-5-amine; 4-(aminomethyl)aniline; 1H-indol-6-amine; N1,N1-dimethylbenzene-1,3-diamine; 3-phenyl-1H-pyrazol-5-amine; N1,N1-diethylbenzene-1,4-diamine; 4-(pyrrolidin-1-yl)aniline; 4H-1,2,4-triazole-3,5-diamine; 3-morpholinoaniline; 3-cyclobutyl-1H-pyrazol-5-amine; 4-(4,5-dihydro-1H-imidazol-2-yl)aniline; 4-(4-aminophenyl)morpholin-3-one; 2,2-dimethyl-3,4-dihydro-2H-benzo[b][1,4]thiazin-6-amine; 7-amino-3,4-dihydroquinolin-2(1H)-one; 6-amino-2H-benzo[b][1,4]thiazin-3(4H)-one; 5-(tert-butyl)-1H-pyrazol-3-amine; 3-methyl-1H-pyrazol-5-amine; 5-cyclopropyl-1H-pyrazol-3-amine; 4-(1H-tetrazol-5-yl)aniline; 2,3-dihydrobenzo[b][1,4]dioxin-6-amine; 4-(1-methylpiperidin-4-yl)aniline; 6-morpholinopyridin-3-amine; 4-(2-methoxyethoxy)aniline; 4-ethoxy-3-methoxyaniline; 1-(4-aminophenyl)pyrrolidin-2-one; 4-thiomorpholinoaniline; 5-aminobenzo[d]oxazol-2(3H)-one; 3,4-dihydro-2H-benzo[b][1,4]oxazin-6-amine; 7-aminoquinazolin-4-ol; 4-(4-aminophenyl)thiomorpholine 1,1-dioxide; 2-(4-aminophenyl)acetamide; 3-aminophenol; 3,4-diethoxyaniline; 6-amino-1H-benzo[d][1,3]oxazine-2,4-dione; 5-amino-2-methoxyphenol; 3-methoxy-N-methylaniline; N-(3-aminophenyl)acetamide; 1H-pyrazol-4-amine; 4-fluoro-3-methoxyaniline; 3-fluoro-4-methoxyaniline; 1-methyl-1H-benzo[d]imidazol-5-amine; 1-(3-aminophenyl)ethan-1-one; N-(4-aminophenyl)acetamide; 1H-pyrrolo[2,3-b]pyridin-6-amine; 3-aminobenzenesulfonamide; 4-aminobenzenesulfonamide; pyridine-2,6-diamine; 1,2,3-trimethyl-1H-indol-5-amine; pyrimidine-2,4-diamine; 5-(methylthio)-4H-1,2,4-triazol-3-amine; 5-cyclopropyl-4H-1,2,4-triazol-3-amine; N-(5-amino-2-methoxyphenyl)acetamide; 1H-benzo[d]imidazol-2-amine; 1H-imidazol-2-amine; 1-(4-aminophenyl)ethan-1-one; 4H-benzo[d][1,3]dioxin-6-amine; 1,3-dihydroisobenzofuran-5-amine; 1-methyl-1H-benzo[d]imidazol-6-amine; 4,5-dimethylthiazol-2-amine; 2-methyl-4-(4-methylpiperazin-1-yl)aniline; 6-methylpyridin-2-amine; 4-methylthiazol-2-amine; 4,5,6,7-tetrahydrobenzo[d]thiazol-2-amine; 4-phenoxyaniline; 2-methyl-1,2,3,4-tetrahydrobenzo[4,5]imidazo[1,2-a]pyrazin-8-amine; 4-(pyridin-4-ylmethyl)aniline; 4-aminobenzene-1,2-diol; 4-((1-methylpiperidin-4-yl)oxy)aniline; 1-(4-(4-aminophenyl)piperazin-1-yl)ethan-1-one; 6-(4-methylpiperazin-1-yl)pyridin-3-amine; N1,N1,2-trimethylbenzene-1,4-diamine; 4-(4-cyclopropylpiperazin-1-yl)aniline; ammonia; 3-fluoro-4-morpholinoaniline; 7-aminoquinoxalin-2(1H)-one; 3-methyl-4-(4-methylpiperazin-1-yl)aniline; 4-(piperazin-1-yl)aniline; 4-((dimethylamino)methyl)aniline; 2-fluoro-4-morpholinoaniline; 4-(4-ethylpiperazin-1-yl)aniline; 8-amino-4,5-dihydro-1H-benzo[b]azepin-2(3H)-one; 5-amino-1,3-dimethyl-1H-benzo[d]imidazol-2(3H)-one; 4-benzylaniline; 2-methyl-4-morpholinoaniline; N1-methyl-N1-(1-methylpiperidin-4-yl)benzene-1,4-diamine; 4-(2-morpholinoethyl)aniline; 3-chloro-4-(4-methylpiperazin-1-yl)aniline; 1,2,3,4-tetrahydroquinolin-7-amine; cyclohexane-1,2-diamine; pyridin-4-amine; 2-(4-aminophenyl)-N-(4-methoxyphenethyl)acetamide; 3-(piperazin-1-yl)aniline; 4-amino-N-(2-(diethylamino)ethyl)benzamide; 2-(4-methylpiperazin-1-yl)pyrimidin-5-amine; 7-amino-2H-benzo[b][1,4]oxazin-3(4H)-one; 3,4-dihydro-2H-benzo[b][1,4]oxazin-7-amine; 3-(4-methylpiperazin-1-yl)aniline; 3-(2-(piperazin-1-yl)ethoxy)aniline; 6-methyl-5,6,7,8-tetrahydro-1,6-naphthyridin-3-amine; (4-aminophenyl)(pyrrolidin-1-yl)methanone; (4-aminophenyl)(morpholino)methanone; 4-(pyrrolidin-1-ylmethyl)aniline; (4-aminophenyl)(4-methylpiperazin-1-yl)methanone; N2-(2-(dimethylamino)ethyl)pyrimidine-2,5-diamine; 4-(morpholinomethyl)aniline; 4-((4-methylpiperazin-1-yl)methyl)aniline; 4-(4-ethylpiperazin-1-yl)-3-fluoroaniline; 4-(2-(4-benzylpiperidin-1-yl)ethyl)aniline; 4-((4-benzylpiperidin-1-yl)methyl)aniline; p-toluidine; 6-(2-(dimethylamino)ethoxy)pyridin-3-amine; 2-methyl-1H-benzo[d]imidazol-5-amine; N2-(3-(dimethylamino)propyl)pyridine-2,5-diamine; N2-(2-(dimethylamino)ethyl)pyridine-2,5-diamine; 6-((1-methylpiperidin-4-yl)oxy)pyridin-3-amine; 4-(4-cyclopentylpiperazin-1-yl)aniline; 4-(4-isobutylpiperazin-1-yl)aniline; 4-(4-isopropylpiperazin-1-yl)aniline; 4-(4-(cyclopropylmethyl)piperazin-1-yl)aniline; 4-(4-(tert-butyl)piperazin-1-yl)aniline; 2-(4-(4-aminophenyl)piperazin-1-yl)acetic acid; 2-(4-amino-2-methoxyphenoxy)acetic acid; (4-aminophenyl)methanol; 4-(4-(2-(dimethylamino)ethyl)piperazin-1-yl)aniline; 2-(4-aminophenyl)acetic acid; 6-amino-2-naphthoic acid; 3-aminobenzoic acid; 4'-amino-[1,1'-biphenyl]-4-carboxylic acid; 1-(4-aminophenyl)-3-(m-tolyl)urea; 2-(4-aminophenoxy)acetic acid; 2-methylisoindolin-5-amine; (4-amino-3-methoxyphenyl)(4-(4-methylpiperazin-1-yl)piperidin-1-yl)methanone; 4-amino-N-(2-(dimethylamino)ethyl)-N-methylbenzamide; (4-aminophenyl)(2-(methoxymethyl)pyrrolidin-1-yl)methanone; (4-aminophenyl)(azetidin-1-yl)methanone; 4-amino-N,N-dimethylbenzamide; (4-aminophenyl)(4-methyl-1,4-diazepan-1-yl)methanone; 1-(4-aminobenzoyl)piperidin-4-one; (4-aminophenyl)(1,4-dioxa-8-azaspiro[4.5]decan-8-yl)

methanone; (4-aminophenyl)(3-(dimethylamino)pyrrolidin-1-yl)methanone; 1-methyl-1,2,3,4-tetrahydroquinolin-6-amine; 3-aminophenylsulphur pentafluoride; 4-fluoroaniline; 3,4-difluoroaniline; N-(4-aminophenyl)-2,2,2-trifluoroacetamide; 3-((6-amino-2H-benzo[b][1,4]oxazin-3-yl)amino)propan-1-ol; N3-phenethyl-2H-benzo[b][1,4]oxazine-3,6-diamine; 3,5-difluoroaniline; 3-fluoro-4-methylaniline; 3,4,5-trifluoroaniline; 4-nitroaniline; 3-methoxy-4-morpholinoaniline; 3-(methylsulfonyl)aniline; 2-(4-aminophenyl)-1,1,1,3,3,3-hexafluoropropan-2-ol; 4-(difluoromethoxy)-3-methoxyaniline; 3-fluoro-4-(trifluoromethyl)aniline; 3-fluoro-4-(trifluoromethoxy)aniline; 2,3-dimethoxyaniline; 2,4-dimethoxyaniline; 3,5-dimethoxyaniline; 4-amino-N,N-dimethylbenzenesulfonamide; 3-amino-N-cyclopropylbenzenesulfonamide; 4-(2H-1,2,3-triazol-2-yl)aniline; 3-(methylsulfinyl)aniline; 3-(2H-1,2,3-triazol-2-yl)aniline; 3-amino-N-methylbenzenesulfonamide; 3-(morpholinosulfonyl)aniline; 3-((trifluoromethyl)sulfonyl)aniline; 2-((3-aminophenyl)sulfonyl)ethan-1-ol; N-(4-aminophenyl)-4-fluorobenzamide; 4-morpholino-3-nitroaniline; 2,4-difluoroaniline; 2-aminobenzamide; 4-chloroaniline; N1,N1-dimethylethane-1,2-diamine; (1-methylpiperidin-4-yl)methanamine; 1-methyl-1,2,3,4-tetrahydroquinolin-7-amine; 2-(4-aminophenyl)-2-methylpropanenitrile; 4-aminophenylsulphur pentafluoride; 3-amino-N,N-dimethylbenzenesulfonamide; 2-(methylsulfonyl)aniline; 4-(4-(4-methylpiperazin-1-yl)piperidin-1-yl)aniline; 3-((dimethylamino)methyl)aniline; (4-aminophenyl)(4-(4-methylpiperazin-1-yl)piperidin-1-yl)methanone.

Furthermore preferably, $R^1$ can be derived from the following amines:

formamide; 2-aminoethan-1-ol; prop-2-yn-1-amine; N1-methylethane-1,2-diamine; 2-aminoacetonitrile; 3-aminopropan-1-ol; butan-1-amine; cyclopropanamine; propan-2-amine; 3-aminopropanenitrile; 4-aminobutan-1-ol; cyclobutanamine; 2-aminopropan-1-ol; acetamide; cyclopropylmethanamine; 5-aminopentan-1-ol; 2-aminoacetamide; isoxazol-3-amine; thiazol-2-amine; 3-aminopropane-1,2-diol; cyclopentanamine; piperidin-4-amine; piperidin-3-amine; pyrimidin-2-amine; 2-aminocyclopentanol; 3-aminopropanamide; tetrahydro-2H-pyran-4-amine; 2-methylpropan-2-amine; o-toluidine; 2,2,2-trifluoroethan-1-amine; phenylmethanamine; piperidin-4-ylmethanamine; 2-aminocyclohexanol; 4-aminobutanamide; piperidin-3-ylmethanamine; 1-methyl-1H-pyrazol-4-amine; 2-methoxyaniline; 2-chloroaniline; 2-aminopropanamide; 4-methylthiophen-2-amine; 2-phenylethan-1-amine; 1H-pyrazol-5-amine; 5-methylisoxazol-3-amine; 2-morpholinoethan-1-amine; 1-(aminomethyl)-N-methylcyclopropanamine; 1-methyl-1H-pyrrol-3-amine; 5-methylthiazol-2-amine; 5-methylthiophen-2-amine; 4-aminophenol; 3-fluoroaniline; 3,5-dimethylisoxazol-4-amine; 3-morpholinopropan-1-amine; 2-aminobutanamide; 4-iodoaniline; (3-aminophenyl)methanol; 2-aminothiazole-4-carbaldehyde; 3-bromoaniline; 2,6-dimethylaniline; 4-ethylaniline; 3-amino-2-methylphenol; 4-(methylthio)aniline; 3-ethylaniline; 1-phenylethan-1-amine; 2-(4-aminophenyl)ethan-1-ol; 5-aminonicotinaldehyde; 6-aminonicotinaldehyde; 4-aminobenzaldehyde; 3-aminobenzaldehyde; indolin-6-amine; 4-amino-2-methoxyphenol; 2-aminopyrimidine-5-carbaldehyde; 5-aminopyrazine-2-carbaldehyde; 5-aminopicolinaldehyde; 3-methoxy-4-methylaniline; 6-aminopyrazine-2-carbaldehyde; N1,6-dimethylbenzene-1,3-diamine; 5-methyl-1H-pyrazol-3-amine; 4-ethoxyaniline; 2,3-dihydrobenzofuran-5-amine; 3-ethoxyaniline; benzo[d]thiazol-5-amine; benzo[d]thiazol-6-amine; piperidine-3-carboxamide; imidazo[1,2-a]pyridin-6-amine; piperidine-4-carboxamide; benzo[d]thiazol-7-amine; benzo[d]isoxazol-5-amine; 4-methoxy-3-methylaniline; benzo[d]thiazol-2-amine; 4-vinylaniline; benzo[c][1,2,5]thiadiazol-4-amine; 1-aminocyclopropanecarboxamide; 2-phenylcyclopropanamine; 2-aminocyclopentanecarboxamide; 3-vinylaniline; (5-amino-2-methoxyphenyl)methanol; 2-(4-aminophenoxy)ethan-1-ol; 1,2,3,4-tetrahydroisoquinolin-6-amine; (4-amino-2-methoxyphenyl)methanol; 2-amino-4-methylpyrimidine-5-carbaldehyde; 6-amino-4-methylnicotinaldehyde; 2-isopropoxyaniline; 6-amino-2-methylnicotinaldehyde; 4-amino-2-methylphenol; 5-amino-2-methylphenol; 3-chloro-4-methoxyaniline; 3,5-dimethylaniline; N-(3-aminophenyl)formamide; 2-(3-aminophenoxy)ethan-1-ol; N-(6-aminopyridin-2-yl)formamide; 4-amino-2-fluorophenol; 5-amino-2-hydroxybenzonitrile; 4-amino-3-fluorophenol; N-(4-aminophenyl)formamide; 2,4-dimethylaniline; 3,4-dimethylaniline; 2-fluoro-5-methylaniline; 2,5-dimethylaniline; quinoxalin-6-amine; quinolin-6-amine; 2-amino-3-methylbutanamide; quinoxalin-5-amine; naphthalen-1-amine; naphthalen-2-amine; 4-fluoro-3-methylaniline; quinolin-5-amine; quinolin-8-amine; 2,6-dimethylpyrimidin-4-amine; 1-(4-aminophenyl)ethan-1-ol; 2,3,4,5-tetrahydrobenzo[b][1,4]oxazepin-7-amine; 3-methoxy-4-(methoxymethyl)aniline; 2-fluoro-4-methoxyaniline; 5-amino-6-methoxypyrazine-2-carbaldehyde; 2-amino-4-methoxypyrimidine-5-carbaldehyde; 6-amino-5-methoxynicotinaldehyde; 3-chloro-4-fluoroaniline; 4H-benzo[b][1,4]oxazin-6-amine; 4-isopropylaniline; 4-amino-2,5-dimethylphenol; 4-amino-2-chlorophenol; 4H-benzo[b][1,4]oxazin-7-amine; 3-(2-methoxyethoxy)aniline; 4-methoxy-2-methylaniline; 5-methoxy-2-methylaniline; 3-(2-(methylamino)ethoxy)aniline; 3-isopropylaniline; 4-amino-2,3-dimethylphenol; N-(5-amino-2-methylphenyl)formamide; 2-amino-4-methylpentanamide; 4-chloro-3-methylaniline; 3-aminocyclopentanecarboxamide; 2-chloro-5-fluoropyrimidin-4-amine; 3,4-dihydroquinolin-6-amine; 2-amino-4-methylpentanethioamide; 2-(isopentyloxy)aniline; 6-amino-5-methylnicotinaldehyde; 5-amino-6-methylpyrazine-2-carbaldehyde; 2-amino-6-methylpyrimidine-4-carbaldehyde; 2-methyl-2H-indazol-6-amine; 5-amino-6-methylpicolinaldehyde; 5-amino-4-methylpicolinaldehyde; 4-isopropoxyaniline; 1-methyl-1H-indazol-5-amine; 3,5-dichloroaniline; 3,4-dichloroaniline; [1,1'-biphenyl]-2-amine; 2,6-dimethoxypyridin-3-amine; 4-methoxy-3,5-dimethylaniline; 2-methyl-2H-indazol-5-amine; 3-(ethyl(hydroxy)amino)aniline; 3-isopropoxyaniline; N1-isopropylbenzene-1,3-diamine; 4-amino-5-chloro-2-methylphenol; 1-methyl-1H-indol-4-amine; 1H-indazol-4-amine; 1-methyl-1H-indazol-4-amine; 2-methyl-2H-indazol-4-amine; 1H-indol-4-amine; 1H-benzo[d]imidazol-6-amine; 1H-benzo[d][1,2,3]triazol-6-amine; 2-methylbenzo[d]thiazol-5-amine; 4-(methylsulfinyl)aniline; 1-methyl-1H-indol-5-amine; 3-(2-aminophenyl)propanamide; 2-((2-aminocyclohexyl)amino)acetic acid; (2,3,6-trifluorophenyl)methanamine; 5-bromo-2-chloropyrimidin-4-amine; 1-methyl-1H-indazol-7-amine; 1-methyl-1H-benzo[d]imidazol-4-amine; 2-methyl-2H-indazol-7-amine; 2-methylbenzo[d]oxazol-7-amine; 4-methyl-3,4-dihydro-2H-benzo[b][1,4]oxazin-7-amine; 4-methyl-3,4-dihydro-2H-benzo[b][1,4]oxazin-6-amine; 4-(4H-1,2,4-triazol-4-yl)aniline; 4-(1H-imidazol-1-yl)aniline; 4-(1H-pyrazol-1-yl)aniline; 5-aminoindolin-2-one; 6-aminoindolin-2-one; 3-methoxy-4-(2-methoxyethoxy)aniline; 3-(4-amino-2-methoxyphenoxy)propan-1-ol; 2-((4-aminophenyl)(methyl)amino)ethan-1-ol; 2-methyl-1,2,3,4-tetrahydroisoquinolin-6-amine; 4-amino-N-methylbenzamide; 3-amino-N-methylbenzamide; 1-(piperidin-4-yl)-1H-pyrazol-4-amine; 4-(oxazol-4-yl)aniline;

4-(pyrrolidin-3-yl)aniline; 2-(trifluoromethoxy)aniline; 3-chloro-4-methoxy-5-methylaniline; 2-((2-aminophenyl)imino)acetic acid; 3-(oxazol-5-yl)aniline; (5-aminobenzofuran-2-yl)methanol; 3,4,5-trimethylaniline; N-(5-amino-2-fluorophenyl)formamide; methyl 4-amino-1-methyl-1H-pyrrole-2-carboxylate; methyl 3-aminobenzoate; N-(3-amino-4-ethoxyphenyl)formamide; 2-((3-aminophenyl)amino)propan-1-ol; 2-methyl-2,3-dihydrobenzo[b][1,4]dioxin-6-amine; 4-(1H-1,2,4-triazol-1-yl)aniline; 3-(1H-pyrazol-1-yl)aniline; 2-amino-2-phenylacetamide; 4-(thiazol-4-yl)aniline; 1,2-dimethyl-1H-indol-4-amine; 4-(oxazol-5-yl)aniline; 1-ethyl-1H-indol-4-amine; 3-(thiazol-2-yl)aniline; 4-(1,2,3-thiadiazol-4-yl)aniline; 3-(isoxazol-3-yl)aniline; 4-(isoxazol-3-yl)aniline; 4-(isoxazol-5-yl)aniline; 4-(thiophen-2-yl)aniline; 3-(1H-tetrazol-1-yl)aniline; 4-(1H-tetrazol-1-yl)aniline; 3-(1H-imidazol-1-yl)aniline; 5-aminobenzofuran-2(3H)-one; 8-methylquinolin-4-amine; 2-amino-2-(pyridin-3-yl)acetamide; 1-phenyl-1H-pyrazol-4-amine; 1-phenyl-1H-pyrrol-3-amine; 3-(2H-tetrazol-2-yl)aniline; 3-(1H-1,2,4-triazol-1-yl)aniline; 3-(1H-1,2,3-triazol-1-yl)aniline; 4-(1H-1,2,3-triazol-1-yl)aniline; 3-(pyrrolidin-1-yl)aniline; 3-(1H-pyrrol-1-yl)aniline; 4-(1H-pyrrol-1-yl)aniline; 4-(1,3,4-oxadiazol-2-yl)aniline; 4-(thiazol-2-yl)aniline; 3-(thiazol-4-yl)aniline; 3-(oxazol-4-yl)aniline; 3-(thiazol-5-yl)aniline; 4-(thiazol-5-yl)aniline; 6-fluoronaphthalen-2-amine; methyl 2-((2-aminocyclohexyl)amino)acetate; 4-isobutoxyaniline; 2-methylquinolin-6-amine; 2-methylquinolin-8-amine; 3-methylcinnolin-5-amine; 2-(4-aminophenyl)propan-2-ol; 2-((4-aminophenyl)(ethyl)amino)ethan-1-ol; 4-(2-(dimethylamino)ethoxy)aniline; 4-(tetrahydro-2H-pyran-4-yl)aniline; 3-methoxy-4-((2-methoxyethoxy)methyl)aniline; N1-(2-methoxyethyl)-N1-methylbenzene-1,4-diamine; 4-isopropoxy-3-methoxyaniline; 4-amino-2-methoxybenzoic acid; 4-(piperidin-4-yl)aniline; 4-amino-N,2-dimethylbenzamide; 6-(tetrahydro-2H-pyran-4-yl)pyridin-3-amine; 6-(piperidin-4-yl)pyridin-3-amine; 4-(3-(dimethylamino)propyl)aniline; 4-(pyridin-3-yl)aniline; 4-(piperidin-3-yl)aniline; 2-ethyl-1,2,3,4-tetrahydroisoquinolin-6-amine; 3,5-dichloro-4-methoxyaniline; 4-amino-2-chloro-6-methylphenol; 3-(4-aminophenoxy)propane-1,2-diol; 3-(tert-butyl)aniline; 2-(5-amino-1H-indazol-1-yl)ethan-1-ol; 2-(6-amino-1H-indazol-1-yl)ethan-1-ol; 4-chloro-2,5-dimethoxyaniline; ethyl 3-aminobenzoate; 4-(tert-butyl)aniline; 4-chloro-3,5-dimethylaniline; N-(3-amino-5-chlorophenyl)formamide; 4-(trifluoromethyl)aniline; [1,1'-biphenyl]-3-amine; 6-amino-2H-chromen-2-one; 7-amino-2H-chromen-2-one; methyl 2-(4-aminophenyl)acetate; methyl 2-(3-aminophenyl)acetate; methyl 5-amino-2-hydroxybenzoate; methyl 4-amino-2-hydroxybenzoate; 5-amino-2-methoxybenzoic acid; 3-(2-(dimethylamino)ethoxy)aniline; 4-methyl-4H-benzo[b][1,4]oxazin-7-amine; 3-amino-4-isopropylphenol; 5-methyl-3-phenylisoxazol-4-amine; 3-(pyrimidin-2-yl)aniline; 3-(pyrimidin-5-yl)aniline; 2,3-dihydro-1H-pyrrolo[1,2-a]indol-8-amine; 4-(pyrimidin-2-yl)aniline; 3-(pyridin-3-yl)aniline; 4-(pyridin-2-yl)aniline; 6-methoxynaphthalen-2-amine; 2-methyl-2H-indol-4-amine; 4-chloronaphthalen-1-amine; 3-(pyridin-4-yl)aniline; 4-amino-2-methoxybenzamide; 3-(5-methyl-1H-tetrazol-1-yl)aniline; 2-fluoro-4-(1H-pyrazol-1-yl)aniline; 2-fluoro-4-(thiazol-4-yl)aniline; 4-(pyrimidin-5-yl)aniline; 3-(pyrazin-2-yl)aniline; 4-(pyrazin-2-yl)aniline; 3-(tetrahydro-2H-pyran-4-yl)aniline; 3-(pyridazin-4-yl)aniline; 4-(pyridazin-4-yl)aniline; 4-(pyridin-4-yl)aniline; 3-(pyridin-2-yl)aniline; [1,1'-biphenyl]-4-amine; 7-chloro-1H-indazol-6-amine; 6-bromonaphthalen-2-amine; 3-(1-methyl-1H-tetrazol-5-yl)aniline; 4-(4-methyl-4H-1,2,4-triazol-3-yl)aniline; 4-(1-methyl-1H-imidazol-2-yl)aniline; 3-(1-methyl-1H-imidazol-2-yl)aniline; 4-(2-methyl-1H-imidazol-1-yl)aniline; 3-(2-methyl-1H-imidazol-1-yl)aniline; 2-(4-aminophenyl)-2-methylpropan-1-ol; 1-(4-aminophenyl)azetidin-3-ol; 2-aminoquinazoline-6-carbaldehyde; 1-(4-aminophenyl)-2-methylpropan-2-ol; 2-(4-aminophenoxy)-N-methylacetamide; 4-(1,4-oxazepan-4-yl)aniline; 3-methoxy-4-(pyrrolidin-1-yl)aniline; 4-amino-N-propylbenzamide; 3-aminoquinoline-6-carbaldehyde; 4-((tetrahydrofuran-2-yl)methoxy)aniline; 4-((tetrahydro-2H-pyran-4-yl)oxy)aniline; 4-(pyridin-4-yloxy)aniline; 4-(3-fluoroazetidin-1-yl)aniline; 4-amino-N-(2-hydroxyethyl)benzamide; 1-(4-aminophenyl)cyclobutanol; 2-aminoquinoline-6-carbaldehyde; 4-(2-methoxypropan-2-yl)aniline; 2-((4-amino-2-methoxyphenyl)(methyl)amino)ethan-1-ol; 4-methoxy-3-(pyrrolidin-1-yl)aniline; 4-(3-methylazetidin-1-yl)aniline; 2,3-dimethyl-2H-indazol-6-amine; 4-(trifluoromethoxy)aniline; 3-methyl-1H-indazol-6-amine; 1-(2-morpholinoethyl)-1H-pyrazol-4-amine; 3-(trifluoromethoxy)aniline; 4-amino-N-ethoxybenzamide; 3-amino-N-propylbenzamide; 4-((2-methyl-1H-imidazol-1-yl)methyl)aniline; 3-(5-amino-1H-indazol-1-yl)propan-1-ol; 4-amino-2,6-dichlorophenol; 3-(6-amino-1H-indazol-1-yl)propan-1-ol; 2-((3-aminophenyl)imino)acetamide; methyl 5-amino-2-methoxybenzoate; ethyl 2-((2-aminophenyl)imino)acetate; 4-((trifluoromethyl)thio)aniline; 5-amino-2-hydroxybenzoic acid; 4-amino-2-hydroxybenzoic acid; 2-((3-aminophenyl)imino)acetic acid; 2,2'-((3-aminophenyl)azanediyl)bis(ethan-1-ol); 2,2-difluorobenzo[d][1,3]dioxol-5-amine; 2-((methylamino)methylene)-2,3-dihydrobenzofuran-5-amine; 3-aminophenyl ethylcarbamate; 1-(4-aminophenyl)-3-ethylurea; 1-(3-aminophenyl)-3-ethylurea; 6-amino-2-methyl-2H-benzo[b][1,4]oxazin-3(4H)-one; 4-methyl-[1,1'-biphenyl]-3-amine; 2-methyl-1H-indol-4-amine; 3-(4-aminopiperidin-1-yl)-3-oxopropanenitrile; 4-(pyridin-3-yloxy)aniline; 1-(3-aminophenyl)pyrrolidin-2-one; 4-(5,6-dihydro-4H-1,3-oxazin-2-yl)aniline; 4-(3,6-dihydro-2H-pyran-4-yl)aniline; 6-aminoquinoline-2-carbonitrile; 2-chloro-5-cyclopropylpyrimidin-4-amine; 3-(3-aminopiperidin-1-yl)-3-oxopropanenitrile; 3-((tetrahydro-2H-pyran-4-yl)oxy)aniline; 3-(3,6-dihydro-2H-pyran-4-yl)aniline; dibenzo[b,d]furan-2-amine; 3-methoxy-4-(oxazol-5-yl)aniline; 4-methoxy-3-(2H-1,2,3-triazol-2-yl)aniline; 1-(4-aminophenyl)pyrrolidin-3-ol; 1-(4-aminophenoxy)-2-methylpropan-2-ol; 4-((tetrahydro-2H-pyran-4-yl)methoxy)aniline; (4-(4-aminophenyl)morpholin-3-yl)methanol; 4-(2H-tetrazol-5-yl)aniline; 2-methoxy-N1-(2-methoxyethyl)-N1-methylbenzene-1,4-diamine; 4-(1-methoxy-2-methylpropan-2-yl)aniline; 5-amino-1-methyl-6-oxo-1,6-dihydropyridine-3-carbaldehyde; 2-((4-amino-2-ethoxyphenyl)(methyl)amino)ethan-1-ol; 4-(2-(pyrrolidin-1-yl)ethoxy)aniline; 4-(1-methyl-1H-pyrazol-4-yl)aniline; 4-(1H-imidazol-4-yl)aniline; 4-(methylsulfonyl)aniline; 2-methoxy-[1,1'-biphenyl]-4-amine; 4-(1-methylpyrrolidin-3-yl)aniline; 5-amino-2-methylisoindolin-1-one; 6-amino-2-methylisoindolin-1-one; 3-(2-(pyrrolidin-1-yl)ethoxy)aniline; 2-(2-methoxyethyl)-1,2,3,4-tetrahydroisoquinolin-6-amine; 4-methoxy-3-(trifluoromethyl)aniline; 2-((3-aminophenyl)imino)-N-methylacetamide; 3-(1H-tetrazol-5-yl)aniline; N-(4-aminophenyl)-N-methylacetamide; 3-(benzyloxy)aniline; 3-(1H-pyrazol-3-yl)aniline; 2-amino-7-oxabicyclo[4.2.0]octa-1,3,5-triene-8-carboxylic acid; (5-amino-1H-indol-2-yl)methanol; 6-methoxy-[1,1'-biphenyl]-3-amine; 4-methoxy-[1,1'-biphenyl]-3-amine; ethyl (4-amino-2-hydroxyphenyl)carbamate; 3-fluoro-4-(thiazol-4-yl)aniline; 3-fluoro-4-(1H-pyrazol-1-yl)aniline; 4-amino-N-(3-hydroxypropyl)benzamide; 3-fluoro-4-(1H-imidazol-1-yl)aniline; 1-(4-aminophenyl)pyridin-2(1H)-one; 1-(4-aminophenyl)-1-methylurea; butyl 4-aminobenzoate; 4-(5-methyl-1,2,4-oxadiazol-3-yl)aniline; 3-(2-methylthiazol-4-yl)aniline; 4-(3-methyl-1H-pyrazol-1-yl)aniline; 3-methyl-5-(2H-1,2,3-triazol-2-yl)aniline; 4-methyl-3-(2H-1,2,3-triazol-2-yl)aniline; 2-amino-2-(3-hydroxyphenyl)acetamide; 2-amino-2-(3-fluorophenyl)acetamide; 3-fluoro-5-(2H-1,2,3-triazol-2-yl)aniline; 4-fluoro-3-(2H-1,2,3-triazol-2-yl)aniline; 4-amino-2-(2H-1,2,3-triazol-2-yl)benzonitrile; 3-fluoro-4-(2H-1,2,3-triazol-2-yl)aniline; 3-(2H-tetrazol-5-yl)aniline; 3-chloro-1H-indazol-5-amine; 4-(methylthio)-7H-pyrrolo[2,3-d]pyrimidin-2-amine; 4-(2-(methoxymethyl)pyrrolidin-1-yl)aniline; 2'-methoxy-[1,1'-biphenyl]-3-amine; 4-(1-methyl-1H-pyrazol-3-yl)aniline; 3-(1-methyl-1H-pyrazol-3-yl)aniline; 3-(1-methyl-1H-pyrazol-4-yl)aniline; 4-(5-methyl-1,3,4-thiadiazol-2-yl)aniline; 3-(5-methyl-1,2,4-oxadiazol-3-yl)aniline; 3-(4-methyl-2H-1,2,3-triazol-2-yl)aniline; 3-(4-methyl-1H-1,2,3-triazol-1-yl)aniline; 3-(5-methylisoxazol-3-yl)aniline; 3-methyl-5-(2H-tetrazol-2-yl)aniline; 3-methyl-4-(2H-1,2,3-triazol-2-yl)aniline; 3-methyl-4-(1H-pyrazol-1-yl)aniline; 3-(5-methylfuran-2-yl)aniline; 2-amino-2-(m-tolyl)acetamide; 2-amino-2-(p-tolyl)acetamide; 3-amino-1H-indazole-6-carbaldehyde; 3-ethoxy-4-morpholinoaniline; 3-amino-1H-indazole-5-carbaldehyde; 1-(4-aminophenyl)piperidin-3-ol; 3-methoxy-4-((tetrahydro-2H-pyran-4-yl)oxy)aniline; 2-(4-amino-2-methoxyphenoxy)-N-methylacetamide; 2-amino-1H-benzo[d]imidazole-6-carbaldehyde; 2-(4-aminophenoxy)-N-(2-hydroxyethyl)acetamide; 5-amino-2-morpholinobenzonitrile; 1-(4-aminophenyl)piperidin-4-ol; (1-(4-aminophenyl)pyrrolidin-3-yl)methanol; 4-(4-fluoropiperidin-1-yl)aniline; 3-(methoxymethyl)-4-morpholinoaniline; 3-methoxy-4-((tetrahydrofuran-2-yl)methoxy)aniline; 4-(3-(dimethylamino)propoxy)-3-methoxyaniline; 1-(4-amino-2-methoxyphenyl)azetidin-3-ol; 4-amino-N-(2-hydroxyethyl)-2-methoxybenzamide; 1-(4-amino-2-methoxyphenyl)-2-methylpropan-2-ol; 3-(4-aminophenoxy)-2,2-dimethylpropan-1-ol; 4-(2-methylmorpholino)aniline; 6-(2-methylmorpholino)pyridin-3-amine; 3-methyl-4-(piperidin-4-yl)aniline; 4-(2-morpholinoethoxy)aniline; 3-(2-morpholinoethoxy)aniline; 3-methyl-4-morpholinoaniline; (1-(4-aminophenethyl)pyrrolidin-2-yl)methanol; 4-(2-methylpyridin-4-yl)aniline; 6-(1-methylpiperidin-4-yl)pyridin-3-amine; 2-(2-methylmorpholino)pyrimidin-5-amine; 3-methyl-4-(tetrahydro-2H-pyran-4-yl)aniline; 4-amino-N-cyclopropylbenzamide; 4-(1-methylpiperidin-3-yl)aniline; 4-(1-ethylpyrrolidin-3-yl)aniline; 5-methyl-6-morpholinopyridin-3-amine; 4-methyl-3-(trifluoromethyl)aniline; 5-aminobenzofuran-2-carboxylic acid; 2-((dimethylamino)methyl)benzofuran-5-amine; ethyl 2-((3-aminophenyl)imino)acetate; 3-fluoro-5-(trifluoromethyl)aniline; 4-amino-2-(trifluoromethyl)phenol; 5-amino-2,3-dihydrobenzofuran-2-carboxylic acid; N-(4-aminophenyl)methanesulfonamide; 7-amino-4-methyl-2H-benzo[b][1,4]oxazin-3(4H)-one; 6-amino-4-methyl-2H-benzo[b][1,4]oxazin-3(4H)-one; 3-methyl-5-(trifluoromethyl)aniline; 6-amino-1-methyl-3,4-dihydroquinolin-2(1H)-one; methyl (4-aminophenyl)(methyl)carbamate; N-(4-aminophenyl)-2-hydroxy-N-methylacetamide; 6-aminoquinolin-2(1H)-one; 6-amino-1-methylquinolin-2(1H)-one; 4-(ethylsulfonyl)aniline; N-(4-aminophenyl)-N-methylpropionamide; 4-(3,5-dimethyl-1H-pyrazol-1-yl)aniline; 2-amino-2-(3-chlorophenyl)acetamide; 5-fluoro-4-(piperidin-1-yl)pyrimidin-2-amine; 4-(2-(piperidin-1-yl)ethoxy)aniline; 4-chloro-5-(2H-1,2,3-triazol-2-yl)aniline; 4-chloro-3-(2H-1,2,3-triazol-2-yl)aniline; (1-(4-aminophenyl)-1H-1,2,3-triazol-4-yl)methanol; 3-(5-fluoropyrimidin-2-yl)aniline; 4'-fluoro-[1,1'-biphenyl]-3-amine; 3'-fluoro-[1,1'-biphenyl]-3-amine; 4-bromo-3-(2H-1,2,3-triazol-2-yl)aniline; dibenzo[b,d]furan-3-amine; 3-bromo-5-(2H-1,2,3-triazol-2-yl)aniline; 3-methoxy-5-(2H-1,2,3-triazol-2-yl)aniline; 3-methoxy-5-(1H-tetrazol-1-yl)aniline; 2-amino-2-(4-methoxyphenyl)acetamide; 1-(4-aminophenyl)-3-methylazetidin-3-ol; (4-(4-aminophenyl)morpholin-2-yl)methanol; 1-(4-amino-2-methoxyphenyl)pyrrolidin-3-ol; 2-(5-amino-2-morpholinophenoxy)ethan-1-ol; (1-(4-aminophenyl)piperidin-4-yl)methanol; 4-(4-aminophenoxy)cyclohexanol; 4-(4-aminophenyl)piperazin-2-one; 4-(3,3-difluoroazetidin-1-yl)aniline; 2-(1-(4-aminophenyl)pyrrolidin-3-yl)ethan-1-ol; 4-amino-N-(oxetan-3-yl)benzamide; 1-(4-aminophenyl)-2,2,2-trifluoroethan-1-ol; 1-(4-amino-2-methoxyphenoxy)-2-methylpropan-2-ol; 3-methoxy-4-((tetrahydro-2H-pyran-4-yl)methoxy)aniline; 4-amino-N-(2-hydroxyethyl)-N-methylbenzamide; 2-(4-aminophenoxy)-N,N-dimethylacetamide; 4-(3-fluoro-3-methylazetidin-1-yl)aniline; 3-methyl-4-(2-methylmorpholino)aniline; 4-(1-ethylpiperidin-4-yl)aniline; 3-fluoro-4-(2-methylmorpholino)aniline; 3-methyl-4-(1-methylpiperidin-4-yl)aniline; 4-(2,3-dihydroimidazo[2,1-b]thiazol-6-yl)aniline; 3-fluoro-4-(1-methylpiperidin-4-yl)aniline; 5-methyl-6-(2-methylmorpholino)pyridin-3-amine; 3-fluoro-4-(piperazin-1-ylmethyl)aniline; 4'-methoxy-[1,1'-biphenyl]-4-amine; 1-(6-amino-3,4-dihydroisoquinolin-2(1H)-yl)ethan-1-one; 4-amino-N,N-diethylbenzamide; 5-(4-ethylpiperazin-1-yl)pyridin-2-amine; 2-(isopropylsulfonyl)aniline; 3-methyl-4-(1,2,3,6-tetrahydropyridin-4-yl)aniline; 2-methyl-5-(2-morpholinoethoxy)aniline; methyl 5-aminobenzofuran-2-carboxylate; 5-amino-N-methyl-2,3-dihydrobenzofuran-2-carboxamide; methyl 5-amino-2,3-dihydrobenzofuran-2-carboxylate; 3-methoxy-5-(trifluoromethyl)aniline; 5-amino-N-methylbenzofuran-2-carboxamide; 2-((3-aminophenyl)imino)-N-(2-hydroxyethyl)acetamide; 4-chloro-3-(trifluoromethyl)aniline; 3-nitroaniline; methyl 4-amino-2,3-dihydrobenzofuran-7-carboxylate; 6-amino-N-methyl-1H-indole-1-carboxamide; ethyl 2-amino-7-oxabicyclo[4.2.0]octa-1(6),2,4-triene-8-carboxylate; 3-aminophenyl isopropylcarbamate; 3-chloro-4-morpholinoaniline; 2-(6-amino-1H-indazol-1-yl)acetamide; 1-(4-aminophenyl)azetidine-2-carboxamide; 6-amino-2-naphthamide; 3-amino-5-(2H-1,2,3-triazol-2-yl)benzonitrile; 3-amino-5-(1H-1,2,3-triazol-1-yl)benzonitrile; 4-amino-N-cyclobutylbenzamide; 3-(4-methoxypyrimidin-2-yl)aniline; 4-(6-methoxypyridin-3-yl)aniline; 3-(6-methoxypyridin-2-yl)aniline; 3-(6-methoxypyridin-3-yl)aniline; 3'-methoxy-[1,1'-biphenyl]-3-amine; 4'-methoxy-[1,1'-biphenyl]-3-amine; N-(4-aminophenyl)-3-hydroxy-N-methylpropanamide; 9-methyl-9H-carbazol-3-amine; 2-(1-(4-aminophenyl)piperidin-4-yl)ethan-1-ol; 1-(4-amino-2-methoxyphenyl)piperidin-3-ol; 1-(4-aminophenyl)-3-methylpyrrolidin-3-ol; 2-(4-(4-aminophenyl)piperazin-1-yl)ethan-1-ol; 4-(3,3-difluoropyrrolidin-1-yl)aniline; 4-(2-oxa-6-azaspiro[3.3]heptan-6-yl)aniline; 3-(2-methoxyethoxy)-4-morpholinoaniline; 3-(4-amino-2-methoxyphenoxy)-2,2-dimethylpropan-1-ol; 1-(4-amino-2-methoxyphenyl)piperidin-4-ol; (1-(4-amino-2-methoxyphenyl)pyrrolidin-3-yl)methanol; 4-(3-methoxy-3-methylazetidin-1-yl)aniline; 1-(4-amino-2-ethoxyphenoxy)-2-methylpropan-2-ol; 1-(4-amino-2-ethoxyphenyl)pyrrolidin-3-ol; 4-amino-N-ethyl-N-(2-hydroxyethyl)benzamide; 4-((4-ethylpiperazin-1-yl)methyl)aniline; 1-(4-aminophenyl)-3-ethylazetidin-3-ol; 3-methyl-4-(2-(pyrrolidin-1-yl)ethoxy)aniline; 4-methyl-3-(2-(pyrrolidin-1-yl)ethoxy)aniline; 1-(4-aminophenethyl)piperidin-4-ol; 2-(4-(4-aminophenyl)piperidin-1-yl)ethan-1- ol; 3-methyl-4-((1-methylpiperidin-4-yl)oxy)aniline; 2-methoxy-5-methyl-4-(piperidin-4-yl)aniline; 4-(1-(2-methoxyethyl)-1H-pyrazol-4-yl)aniline; 3-fluoro-4-(2-(pyrrolidin-1-yl)ethoxy)aniline; 4-amino-N-cyclopentylbenzamide; 4-(1-(2-methoxyethyl)pyrrolidin-3-yl)aniline; 2-methoxy-4-(4-methylpiperazin-1-yl)aniline; 2-(4-(4-amino-1H-pyrazol-1-yl)piperidin-1-yl)acetonitrile; (4-aminophenyl)(piperazin-1-yl)methanone; 1-(1-(2-methoxyethyl)piperidin-4-yl)-1H-pyrazol-4-amine; 4-(2-(4-methylpiperazin-1-yl)ethyl)aniline; 4-(1,2-dimethylpiperidin-4-yl)-3-fluoroaniline; methyl 2-(5-amino-1H-indazol-1-yl)acetate; methyl 2-(6-amino-1H-indazol-1-yl)acetate; 2-(5-amino-1H-indazol-1-yl)-N-methylacetamide; 3-chloro-4-(trifluoromethoxy)aniline; 4-(4,5-dichloro-1H-imidazol-1-yl)aniline; 2-(6-amino-1H-indazol-1-yl)-N-methylacetamide; (3-aminophenyl)(phenyl)methanone; methyl 3-amino-5-formamidobenzoate; 5-methoxy-2-methyl-[1,1'-biphenyl]-4-amine; 2-((3-aminophenyl)imino)-N,N-dimethylacetamide; 2-((3-aminophenyl)imino)-N-(2-(methylamino)ethyl)acetamide; ethyl 5-aminobenzofuran-2-carboxylate; 1-(4-aminophenyl)pyrrolidine-2-carboxamide; (1-(2-amino-5-fluoropyrimidin-4-yl)piperidin-4-yl)methanol; 4-amino-N-(2-hydroxyethyl)benzenesulfonamide; 4-(2-amino-5-fluoropyrimidin-4-yl)piperazin-2-one; 3-(1H-benzo[d][1,2,3]triazol-1-yl)aniline; 3-(1H-indazol-1-yl)aniline; 3-(2H-benzo[d][1,2,3]triazol-2-yl)aniline; 3-(1H-benzo[d]imidazol-1-yl)aniline; 3-(2H-indazol-2-yl)aniline; 3-(imidazo[1,2-a]pyridin-2-yl)aniline; 3-(4-aminophenyl)pyridin-2(1H)-one; 3-(benzo[d][1,3]dioxol-4-yl)aniline; 3-(benzo[d][1,3]dioxol-5-yl)aniline; 3-(2,3-dihydrobenzofuran-5-yl)aniline; 3-(imidazo[1,2-a]pyridin-6-yl)aniline; 4-(imidazo[1,2-a]pyridin-6-yl)aniline; 6-amino-N-methyl-2-naphthamide; 3-fluoro-4-(4-methyl-1H-pyrazol-1-yl)aniline; 1-(4-aminophenyl)-4-methylpiperidin-4-ol; 1-(4-amino-2-methoxyphenyl)-3-methylazetidin-3-ol; (4-(4-amino-2-methoxyphenyl)morpholin-2-yl)methanol; 2-(4-(4-aminophenyl)piperazin-1-yl)acetaldehyde; 4-(4-(3-fluoropropyl)piperazin-1-yl)aniline; 4-(4,4-difluoropiperidin-1-yl)aniline; 4-(3,3-difluoropiperidin-1-yl)aniline; 4-(8-oxa-3-azabicyclo[3.2.1]octan-3-yl)aniline; 4-amino-N-(tetrahydro-2H-pyran-4-yl)benzamide; (4-aminophenyl)(3-hydroxyazetidin-1-yl)methanone; 3-(4-amino-2-ethoxyphenoxy)-2,2-dimethylpropan-1-ol; 4-(4-ethylpiperazin-1-yl)-3-methoxyaniline; 4-(2,6-dimethylmorpholino)aniline; 1-(4-aminophenyl)-3-methylpiperidin-3-ol; 2-(4-aminophenyl)-N,2-dimethylpropanamide; 4-(1-(2-methoxyethyl)piperidin-4-yl)aniline; 4-(1-(3-fluoropropyl)piperidin-4-yl)aniline; 4-(2-(4-ethylpiperazin-1-yl)ethyl)aniline; 4-amino-N-phenylbenzamide; 3-((dimethylamino)methyl)-1H-indazol-6-amine; 1-(4-aminophenyl)-N,N-dimethylpyrrolidin-3-amine; 4-(4-ethoxypiperidin-1-yl)-3-fluoroaniline; 6-(2,6-dimethylmorpholino)pyridin-3-amine; 6-(1-(2-methoxyethyl)piperidin-4-yl)pyridin-3-amine; 4-methyl-3-(2-morpholinoethoxy)aniline; 6-amino-2,2-dimethyl-2H-benzo[b][1,4]oxazin-3(4H)-one; 3-(5-amino-1H-indazol-1-yl)-N-methylpropanamide; 3-(6-amino-1H-indazol-1-yl)-N-methylpropanamide; 5-amino-N-(2-hydroxyethyl)benzofuran-2-carboxamide; 3-(5-amino-2H-indazol-2-yl)-N-methylpropanamide; N-(3-amino-5-(trifluoromethyl)phenyl)formamide; 4-(benzyloxy)-3-chloroaniline; 6-amino-2,2-difluoro-2H-benzo[b][1,4]oxazin-3(4H)-one; 5-amino-N-(2-hydroxyethyl)-2,3-dihydrobenzofuran-2-carboxamide; 5-amino-1H-indole-2-carboxylic acid; methyl 5-amino-3-oxo-2,3-dihydrobenzofuran-2-carboxylate; methyl 2-amino-8-methyl-7-oxabicyclo[4.2.0]octa-1,3,5-triene-5-carboxylate; 2-methoxy-5-nitroaniline; N-(3-aminophenyl)pivalamide; N-(4-aminophenyl)-N-methylcyclopropanecarboxamide; N-(4-amino-2-chlorophenyl)-N-methylacetamide; 3-((4-aminophenyl)sulfonyl)propanenitrile; 2-morpholinoquinolin-6-amine; 4-amino-N-(2-methoxyethyl)benzenesulfonamide; 4-amino-N-cyclopropyl-N-methylbenzamide; tert-butyl 4-aminopiperidine-1-carboxylate; 1-(4-aminophenyl)piperidine-2-carboxamide; 3,5-difluoro-4-morpholinoaniline; 4-(4-aminophenyl)thiomorpholine-2,3-dione; 3-(2H-benzo[b][1,4]oxazin-4(3H)-yl)aniline; 3-(quinolin-3-yl)aniline; 3-(quinolin-4-yl)aniline; 3',4'-difluoro-[1,1'-biphenyl]-3-amine; 3-(quinolin-5-yl)aniline; 3-(quinolin-8-yl)aniline; 3-(2,3-dihydrobenzo[b][1,4]dioxin-6-yl)aniline; 4-(2,3-dihydrobenzo[b][1,4]dioxin-6-yl)aniline; 3-(quinolin-6-yl)aniline; 4-(methylsulfinyl)-7H-pyrrolo[2,3-d]pyrimidin-2-amine; 4-(4-(2-methoxyethyl)piperazin-1-yl)aniline; 2',4'-dimethoxy-[1,1'-biphenyl]-3-amine; 2',3'-dimethoxy-[1,1'-biphenyl]-3-amine; 3',4'-dimethoxy-[1,1'-biphenyl]-3-amine; 1-(4-aminophenyl)-N-methylpyrrolidine-2-carboxamide; tert-butyl 3-aminopiperidine-1-carboxylate; 2-(4-(4-amino-2-methoxyphenyl)piperazin-1-yl)ethan-1-ol; 1-(4-amino-2-ethoxyphenyl)-3-methylazetidin-3-ol; 4-(2-oxa-7-azaspiro[3.5]nonan-7-yl)aniline; 4-(7-oxa-2-azaspiro[3.5]nonan-2-yl)aniline; 1-(4-amino-2-methoxyphenyl)-3-methylpyrrolidin-3-ol; 1-(4-aminophenyl)-N,N-dimethylpiperidin-4-amine; 2-(4-aminophenyl)-1,1,1-trifluoropropan-2-ol; 1-(4-amino-2-fluorophenyl)-3-methylazetidin-3-ol; 4-(1-cyclopropylpiperidin-4-yl)aniline; 4-(1-(2-methoxyethyl)piperidin-4-yl)-3-methylaniline; 3-(4-(4-aminophenyl)piperidin-1-yl)propanenitrile; 4-amino-N-(3-methoxypropyl)benzenesulfonamide; 2-fluoro-5-methyl-4-(1-methylpiperidin-4-yl)aniline; 4-(1-isopropylpiperidin-4-yl)aniline; 2-(3-aminophenoxy)-1-morpholinoethan-1-one; 2-(4-(4-amino-2-methylphenyl)piperidin-1-yl)acetonitrile; 4-(1-(3-fluoropropyl)piperidin-4-yl)-3-methylaniline; ethyl 3-(5-amino-1H-indazol-1-yl)propanoate; ethyl 3-(6-amino-1H-indazol-1-yl)propanoate; 5-amino-N,N-dimethyl-2,3-dihydrobenzofuran-2-carboxamide; ethyl 2-(4-aminophenyl)-2-methylpropanoate; ethyl 3-(5-amino-2H-indazol-2-yl)propanoate; 4-fluoro-3-nitroaniline; 2-fluoro-5-nitroaniline; methyl 5-amino-1H-indole-2-carboxylate; tert-butyl (4-aminophenyl)carbamate; tert-butyl (3-aminophenyl)carbamate; 4-methyl-3-nitroaniline; 2-methyl-5-nitroaniline; 1-(4-aminophenyl)-N-methylpiperidine-2-carboxamide; tert-butyl 4-(aminomethyl)piperidine-1-carboxylate; isopropyl (4-aminophenyl)(methyl)carbamate; 2-(morpholinomethyl)quinolin-6-amine; 4-(pyrrolidin-1-yl)-7H-pyrrolo[2,3-d]pyrimidin-2-amine; benzyl 4-aminocyclohexanecarboxylate; 4-amino-N-cyclobutyl-N-methylbenzamide; 1-(4-aminophenyl)-1H-1,2,3-triazole-4-carboxamide; 2-(4-aminophenoxy)-1-morpholinoethan-1-one; 4-amino-N-cyclopropylbenzenesulfonamide; 2'-(pyrrolidin-3-yl)-[1,1'-biphenyl]-3-amine; 1-(methylsulfonyl)-1H-indazol-6-amine; N-(4-aminophenyl)-2-(dimethylamino)-N-methylacetamide; 5-(4-aminophenyl)-N,N-dimethylpyridin-2-amine; 4-(2-methyl-1-morpholinopropan-2-yl)aniline; 1-(4-amino-2-methoxyphenyl)-4-methylpiperidin-4-01; 5-amino-2-morpholinobenzamide; (4-aminophenyl)(4-hydroxypiperidin-1-yl)methanone; 3-methoxy-4-(4-(2-methoxyethyl)piperazin-1-yl)aniline; 1-(4-amino-2-methoxyphenyl)-3-methylpiperidin-3-ol; 3-(4-aminophenyl)-1,4-dimethylpiperazin-2-one; 1-(4-(4-aminophenyl)piperidin-1-yl)ethan-1-one; 4-(2-(4-(2-methoxyethyl)piperazin-1-yl)ethyl)aniline; 4-amino-N-(2-morpholinoethyl)benzamide; 2-(methylsulfonyl)-1,2,3,4-tetrahydroisoquinolin-6-amine; 1-(4-aminophenethyl)-N,N- dimethylpyrrolidin-3-amine; 3-methyl-4-(3-(4-methylpiperazin-1-yl)propoxy)aniline; 3-(4-(4-amino-2-methylphenyl)piperidin-1-yl)propanenitrile; 3-chloro-4-(2,6-dimethylmorpholino)aniline; ethyl 5-amino-1H-indole-2-carboxylate; 2-((3-aminophenyl)imino)-1-morpholinoethan-1-one; 2-((3-aminophenyl)imino)-N-(2,3-dihydroxypropyl)acetamide; 2-((3-aminophenyl)imino)-1-(piperazin-1-yl)ethan-1-one; 4-chloro-3-nitroaniline; 4-(pyrrolidin-1-ylsulfonyl)aniline; 2,2,3,3-tetrafluoro-2,3-dihydrobenzo[b][1,4]dioxin-6-amine; methyl 5-amino-2-(trifluoromethoxy)benzoate; ethyl 7-amino-1H-indole-2-carboxylate; 5-amino-N-isopropyl-2,3-dihydrobenzofuran-2-carboxamide; 1-(4-(5-aminopyridin-2-yl)piperazin-1-yl)ethan-1-one; benzyl 3-(aminomethyl)piperidine-1-carboxylate; 6-amino-N,N-dimethyl-2-naphthamide; 4-(4-aminophenyl)piperazine-1-carboxamide; 1-(4-aminophenyl)piperidine-3-carboxamide; 4-(piperidin-1-yl)-7H-pyrrolo[2,3-d]pyrimidin-2-amine; 4-amino-N-cyclobutylbenzenesulfonamide; 1-(4-aminophenyl)piperidine-4-carboxylic acid; 1-(4-aminophenyl)-4-hydroxypyrrolidine-2-carboxamide; 1-(4-aminophenyl)piperidine-4-carboxamide; 2'-(piperidin-4-yl)-[1,1'-biphenyl]-3-amine; 2'-(piperidin-3-yl)-[1μl'-biphenyl]-3-amine; 2-phenyl-1H-indol-4-amine; 2',5'-dimethoxy-[1,1'-biphenyl]-3-amine; 1-(4-aminophenyl)-N-methylpyrrolidine-3-carboxamide; tert-butyl 2-(4-aminophenoxy)acetate; (4-aminophenyl)(2-(hydroxymethyl)morpholino)methanone; 4-amino-N-methyl-N-(tetrahydro-2H-pyran-4-yl)benzamide; 1-(4-amino-2-ethoxyphenyl)-4-methylpiperidin-4-ol; (4-aminophenyl)(3-hydroxy-3-methylazetidin-1-yl)methanone; 3-(4-(4-aminophenyl)piperidin-1-yl)propane-1,2-diol; 1-(4-aminophenethyl)-N,N-dimethylpiperidin-4-amine; 4-(2,2-dimethylmorpholino)-3-methylaniline; 4-amino-N-(1-methylpiperidin-4-yl)benzamide; 4-(2-(tetrahydro-2H-pyran-4-yl)thiazol-4-yl)aniline; 4-(2-(piperidin-3-yl)thiazol-4-yl)aniline; 4-(2-(pyridin-3-yl)thiazol-4-yl)aniline; 4-(1-(piperidin-4-yl)-1H-pyrazol-4-yl)aniline; 4-(1-cyclopentylpiperidin-4-yl)aniline; 3-(1,2,3,6-tetrahydropyridin-4-yl)-1H-indazol-6-amine; 4-(1-ethylpiperidin-4-yl)-2-methoxy-5-methylaniline; methyl 4-(4-aminophenyl)piperazine-1-carboxylate; tert-butyl 2-((3-aminophenyl)imino)acetate; (5-aminobenzofuran-2-yl)(pyrrolidin-1-yl)methanone; methyl 3-amino-5-(trifluoromethyl)benzoate; 2-((3-aminophenyl)imino)-N-(3-(dimethylamino)propyl)acetamide; ethyl 6-amino-4H-benzo[b]imidazo[1,5-d][1,4]oxazine-3-carboxylate; 1-(2-amino-5-fluoropyrimidin-4-yl)piperidine-3-carboxamide; 1-(4-(4-aminophenyl)piperazin-1-yl)propan-1-one; 2-amino-4-(m-tolyl)pyrimidine-5-carboxamide; 2-amino-4-(2-(2-hydroxyethyl)piperidin-1-yl)pyrimidine-5-carboxamide; 4-(morpholinosulfonyl)aniline; 4-((thiazol-4-ylmethyl)sulfonyl)aniline; 4-((tetrahydro-2H-pyran-4-yl)sulfonyl)aniline; 3-(2H-1,2,3-triazol-2-yl)-5-(trifluoromethyl)aniline; 1-(4-aminophenyl)-N-methylpiperidine-3-carboxamide; 1-(4-aminophenyl)-N-methylpiperidine-4-carboxamide; 6-amino-2,2,4-trimethyl-2H-benzo[b][1,4]oxazin-3(4H)-one; 1-(4-(4-aminophenyl)-3-methylpiperazin-1-yl)ethan-1-one; 2-(4-aminophenylsulfonamido)acetamide; 4-(phenylsulfonyl)aniline; 3-(2H-1,2,3-triazol-2-yl)-4-(trifluoromethyl)aniline; 3-morpholino-4-(1H-pyrazol-1-yl)aniline; 3-(1H-1,2,3-triazol-1-yl)-4-(trifluoromethyl)aniline; 4-(3-(trifluoromethyl)-1H-pyrazol-1-yl)aniline; 2-(6-amino-2-oxo-3,4-dihydroquinolin-1(2H)-yl)acetic acid; 1-(4-aminophenyl)-4-hydroxy-N-methylpyrrolidine-2-carboxamide; 1-(4-aminophenyl)-N,N-dimethylpyrrolidine-2-carboxamide; 4-(4-((dimethylamino)methyl)piperidin-1-yl)-5-fluoropyrimidin-2-amine; 7-amino-2,2,4-trimethyl-2H-benzo[b][1,4]oxazin-3(4H)-one; 3-(4-methyl-3,4-dihydro-2H-benzo[b][1,4]oxazin-7-yl)aniline; N-(1-(4-aminophenyl)piperidin-4-yl)acetamide; 1-(4-(4-aminophenyl)-1,4-diazepan-1-yl)ethan-1-one; 1-(4-(4-aminophenyl)-5,6-dihydropyridin-1(2H)-yl)ethan-1-one; 1-(4-(4-aminophenyl)-1,2,3,6-tetrahydropyridin-2-yl)ethan-1-one; 2-(1-(4-aminophenyl)piperidin-4-yl)propan-2-ol; 4-(piperidin-4-yl)-3-(trifluoromethyl)aniline; 4-(1-cyclopropylpiperidin-4-yl)-3-methylaniline; 4-(piperazin-1-yl)-3-(trifluoromethyl)aniline; 1-(4-aminophenethyl)piperidine-3-carboxylic acid; 1-(4-aminophenethyl)piperidine-4-carboxylic acid; 4-morpholino-3-(trifluoromethyl)aniline; 4-amino-N-(4-chlorophenyl)benzamide; 4-(4-(4-aminophenyl)piperidin-1-yl)butan-2-one; 4-(4-aminophenyl)-N-ethylpiperidine-1-carboxamide; 4-(1-isopropylpiperidin-4-yl)-3-methylaniline; 2-(4-(4-amino-2-methylphenyl)piperidin-1-yl)acetamide; (5-aminobenzofuran-2-yl)(morpholino)methanone; 5-amino-N-(2,3-dihydroxypropyl)-2,3-dihydrobenzofuran-2-carboxamide; 5-amino-N-(2,3-dihydroxypropyl)benzofuran-2-carboxamide; 5-amino-N-(1,3-dihydroxypropan-2-yl)benzofuran-2-carboxamide; 2-amino-4-(3-methoxyphenyl)pyrimidine-5-carboxamide; 3-amino-N-methoxy-N-phenylbenzamide; 1-(4-aminophenyl)-N,N-dimethylpiperidine-2-carboxamide; 2-amino-4-(3-ethylphenyl)pyrimidine-5-carboxamide; 1-(1-(2-amino-5-fluoropyrimidin-4-yl)piperidin-4-yl)urea; 2-(1-(2-amino-5-fluoropyrimidin-4-yl)piperidin-4-yl)acetamide; 2-amino-4-(3-(hydroxymethyl)piperidin-1-yl)pyrimidine-5-carboxamide; 4-(4-(pyridin-2-yl)piperazin-1-yl)aniline; 3-(4-phenylpiperazin-1-yl)aniline; 3'-morpholino-[1,1'-biphenyl]-3-amine; 4'-morpholino-[1,1'-biphenyl]-3-amine; 3'-morpholino-[1,1'-biphenyl]-4-amine; 4'-morpholino-[1,1'-biphenyl]-4-amine; 2'-(methylsulfonyl)-[1,1'-biphenyl]-3-amine; 1-(4-(4-aminophenyl)piperazin-1-yl)-2-methoxyethan-1-one; 2',3',4'-trimethoxy-[1,1'-biphenyl]-3-amine; 4-acetyl-1-(4-aminophenyl)piperazin-2-one; (2-aminocyclohexyl)(tert-butyl)carbamate; 4-(4-(1-methylcyclopropyl)piperazin-1-yl)aniline; 2-(4-aminophenoxy)-1-(3-hydroxy-3-methylazetidin-1-yl)ethan-1-one; (4-aminophenyl)(4-hydroxy-4-methylpiperidin-1-yl)methanone; 4-(2-(4-(pyrrolidin-1-yl)piperidin-1-yl)ethyl)aniline; 1-(4-(4-amino-2-methylphenyl)piperidin-1-yl)ethan-1-one; 4-(1-(methylsulfonyl)pyrrolidin-3-yl)aniline; 4-(1-(2-morpholinoethyl)-1H-pyrazol-4-yl)aniline; 4-(1-methylpiperidin-4-yl)-3-(trifluoromethyl)aniline; 1-(4-(4-aminophenyl)piperidin-1-yl)-2-(ethylamino)ethan-1-one; 4-(1-(2,2,2-trifluoroethyl)piperidin-4-yl)aniline; 4-(4-aminophenyl)piperidine-1-carboxylate; 1-(4-(4-amino-2-methylphenyl)piperidin-1-yl)-3-methoxypropan-2-ol; 2-(4-(4-amino-2-methylphenyl)piperidin-1-yl)-N-methylacetamide; 4-(4-benzylpiperazin-1-yl)aniline; 2-((3-aminophenyl)imino)-1-(4-methylpiperazin-1-yl)ethan-1-one; 2-((3-aminophenyl)imino)-N-(2-morpholinoethyl)acetamide; (5-aminobenzofuran-2-yl)(1,4-diazepan-1-yl)methanone; (6-aminonaphthalen-2-yl)(morpholino)methanone; 1-(4-(4-amino-3-methylphenyl)piperazin-1-yl)ethan-1-one; 1-((1-(2-amino-5-fluoropyrimidin-4-yl)piperidin-4-yl)methyl)urea; 4-(2-amino-5-fluoropyrimidin-4-yl)piperazine-1-carboxamide; 1-(4-(4-amino-2-fluorophenyl)piperazin-1-yl)ethan-1-one; 1-(4-(4-aminophenyl)-2-methylpiperazin-1-yl)ethan-1-one; 4-(1-(methylsulfonyl)piperidin-4-yl)aniline; 4-(2-(4-morpholinopiperidin-1-yl)ethyl)aniline; 3-methyl-4-(1-(piperidin-4-yl)-1H-pyrazol-4-yl)aniline; 4-(1-(methylsulfonyl)piperidin-3-yl)aniline; 1-(4-(4-amino-2-methylphenyl)piperidin-1-yl)-2-(ethylamino)ethan-1-one;

1-(3-(4-aminophenyl)pyrrolidin-1-yl)-2-(dimethylamino)ethan-1-one; ethyl 3-(4-(4-aminophenyl)piperidin-1-yl)propanoate; tert-butyl 6-amino-3,4-dihydroisoquinoline-2(1H)-carboxylate; 4-(benzyloxy)-3-(trifluoromethyl)aniline; 5-amino-N-(1-hydroxy-2-methylpropan-2-yl)benzofuran-2-carboxamide; 1-((4-aminophenyl)sulfonyl)piperidin-4-ol; 4-(4-(methylsulfonyl)piperazin-1-yl)aniline; 1-(4-aminophenyl)-N,N-dimethylpiperidine-4-carboxamide; 2-amino-4-(4-(2-hydroxyethyl)-1,4-diazepan-1-yl)pyrimidine-5-carboxamide; 4-(4-aminophenyl)-N,N-dimethylpiperazine-1-carboxamide; 1-(4-(4-amino-2-chlorophenyl)piperazin-1-yl)ethan-1-one; 3-(2-amino-5-nitrophenyl)propanamide; 3-(4-(2-amino-5-fluoropyrimidin-4-yl)piperazin-1-yl)-3-oxopropanenitrile; 3-fluoro-4-(3-(trifluoromethyl)-1H-pyrazol-1-yl)aniline; (4-(4-aminophenyl)piperazin-1-yl)(cyclopropyl)methanone; 1-(3'-amino-[1,1'-biphenyl]-4-yl)piperidin-2-one; 1-(3'-amino-[1,1'-biphenyl]-3-yl)pyridin-2(1H)-one; 1-(3'-amino-[1,1'-biphenyl]-4-yl)pyridin-2(1H)-one; 4-(methylsulfonyl)-3-morpholinoaniline; 3'-(methylsulfonyl)-[1,1'-biphenyl]-4-amine; 4'-(methylsulfonyl)-[1,1'-biphenyl]-4-amine; 3'-(methylsulfonyl)-[1,1'-biphenyl]-3-amine; 4'-(methylsulfonyl)-[1,1'-biphenyl]-3-amine; methyl 4-(4-aminophenyl)-3-methylpiperazine-1-carboxylate; N-(4-aminophenyl)-2-(benzyloxy)-N-methylacetamide; 2-(4-amino-N-methylphenylsulfonamido)acetic acid; 1-(4-aminophenyl)-4-hydroxy-N,N-dimethylpyrrolidine-2-carboxamide; 1-(4-aminophenyl)-N,N-dimethylpiperidine-3-carboxamide; N-(1-(4-aminophenyl)piperidin-4-yl)-N-methylacetamide; 1-(4-(4-aminophenyl)piperidin-1-yl)-2-(dimethylamino)ethan-1-one; 4-(1-(4,4,4-trifluorobutyl)piperidin-4-yl)aniline; 3-methyl-4-(6-(piperazin-1-yl)pyridin-3-yl)aniline; 1-(1-(2-(methylsulfonyl)ethyl)piperidin-4-yl)-1H-pyrazol-4-amine; 1-(4-(5-aminopyridin-2-yl)piperidin-1-yl)-2-(dimethylamino)ethan-1-one; 4-(1-(ethylsulfonyl)piperidin-4-yl)aniline; 2-((3-aminophenyl)imino)-N-(2-(benzylamino)ethyl)acetamide; 1-(4-(4-aminophenyl)-3-methylpiperazin-1-yl)-2-methoxyethan-1-one; N-(1-(2-amino-5-fluoropyrimidin-4-yl)piperidin-4-yl)-2-cyanoacetamide; 4-((4-(methylsulfonyl)piperazin-1-yl)methyl)aniline; 4-(4-(methylsulfonyl)-1,4-diazepan-1-yl)aniline; 4-(1-(methylsulfonyl)-1,2,3,6-tetrahydropyridin-4-yl)aniline; 4-(2-(methylsulfonyl)-1,2,3,6-tetrahydropyridin-4-yl)aniline; 2-amino-4-(methyl(1-methylpiperidin-4-yl)amino)pyrimidine-5-carboxamide; 4-(4-(ethylsulfonyl)piperazin-1-yl)aniline; 1-(4-(4-aminobenzoyl)piperazin-1-yl)ethan-1-one; 4-(2-methyl-4-(methylsulfonyl)piperazin-1-yl)aniline; 2,6-diisopropyl-4-phenoxyaniline; 2-methyl-4-(4-(methylsulfonyl)piperazin-1-yl)aniline; 3-methyl-4-(1-(2-morpholinoethyl)-1H-pyrazol-4-yl)aniline; 4-(1-(2-(methylsulfonyl)ethyl)piperidin-4-yl)aniline; 1-(4-(4-amino-2-methylphenyl)piperidin-1-yl)-2-(dimethylamino)ethan-1-one; 5-amino-2-(morpholine-4-carbonyl)benzofuran-3(2H)-one; tert-butyl (6-amino-4H-chromen-4-yl)carbamate; 2-amino-4-(3,5-dimethylphenyl)pyrimidine-5-carboxamide; (1-(4-aminophenyl)piperidin-4-yl)(pyrrolidin-1-yl)methanone; 4-acetyl-1-(4-aminophenyl)piperazine-2-carboxamide; 3-(4-(4-aminophenyl)piperidin-1-yl)-1,1,1-trifluoropropan-2-ol; tert-butyl 3-(4-aminophenyl)pyrrolidine-1-carboxylate; ethyl 1-(3-aminobenzoyl)piperidine-4-carboxylate; (1-(4-aminophenyl)piperidin-4-yl)(morpholino)methanone; (1-(4-aminophenyl)piperidin-4-yl)(piperidin-1-yl)methanone; 4-acetyl-1-(4-aminophenyl)-N-methylpiperazine-2-carboxamide; tert-butyl 4-(4-aminophenyl)piperidine-1-carboxylate; butyl 2-(4-amino-N-methylphenylsulfonamido)acetate; 4-(4-(cyclopropylsulfonyl)piperazin-1-yl)aniline; N-(1-(4-aminophenyl)piperidin-4-yl)-N-methylmethanesulfonamide; 4-(4-(ethylsulfonyl)-2-methylpiperazin-1-yl)aniline; 3-methyl-4-(1-(2-(methylsulfonyl)ethyl)piperidin-4-yl)aniline; (4-aminophenyl)(4-(methylsulfonyl)piperazin-1-yl)methanone; 4-(4-(cyclopropylsulfonyl)-2-methylpiperazin-1-yl)aniline; 1-(4-(4-aminophenyl)piperidin-1-yl)-2-(methylsulfonyl)ethan-1-one; methyl 4-((6-amino-2H-indazol-2-yl)methyl)-3-methoxybenzoate; methyl 4-((6-amino-1H-indazol-1-yl)methyl)-3-methoxybenzoate; 4-((6-amino-1H-indazol-1-yl)methyl)-3-methoxy-N-methylbenzamide; 2-isopropyl-5-methylcyclohexyl 5-amino-2,3-dihydrobenzofuran-2-carboxylate; ethyl 4-amino-3-(2-amino-5-nitrobenzyl)-4-oxobutanoate; 3,4-bis(3-(trifluoromethyl)-1H-pyrazol-1-yl)aniline.

Preferably, the following compounds are excluded from the scope of the present application:

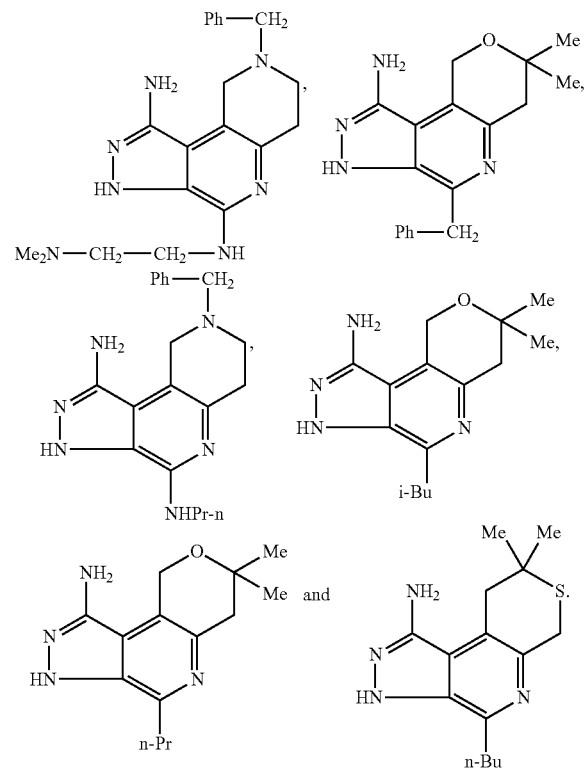

Especially preferred compounds of formula (I) are: N-(m-tolyl)-2H-pyrazolo[3,4-c]quinolin-4-amine; N-(3-(trifluoromethyl)phenyl)-2H-pyrazolo[3,4-c]quinolin-4-amine; N-(3,4,5-trimethoxyphenyl)-2H-pyrazolo[3,4-c]quinolin-4-amine; N-(1H-indazol-5-yl)-2H-pyrazolo[3,4-c]quinolin-4-amine; N-phenyl-2H-pyrazolo[3,4-c]quinolin-4-amine; N-(1H-indazol-6-yl)-2H-pyrazolo[3,4-c]quinolin-4-amine; N-(3-chlorophenyl)-2H-pyrazolo[3,4-c]quinolin-4-amine; N-(7-methyl-1H-indazol-5-yl)-2H-pyrazolo[3,4-c]quinolin-4-amine; N-(2-methoxyethyl)-2H-pyrazolo[3,4-c]quinolin-4-amine; 8-methoxy-N-(7-methyl-1H-indazol-5-yl)-2H-pyrazolo[3,4-c]quinolin-4-amine; N-(thiophen-2-ylmethyl)-2H-pyrazolo[3,4-c]quinolin-4-amine; N-(6-methyl-1H-indazol-5-yl)-2H-pyrazolo[3,4-c]quinolin-4-amine; 8-methoxy-N-phenyl-2H-pyrazolo[3,4-c]quinolin-4-amine; 8-methoxy-N-(2-methoxyethyl)-2H-pyrazolo[3,4-c]quinolin-4-amine; N-(2H-indazol-6-yl)-8-methoxy-2H-pyrazolo[3,4-c]quinolin-4-amine; methyl 4-((2H-pyrazolo[3,4-c]quinolin-4-yl)amino)benzoate; N-(1H-benzo[d]imidazol-5-yl)-2H-pyrazolo[3,4-c]quinolin-4-amine; N-(2H-indazol-7-yl)-2H-pyrazolo[3,4-c]quinolin-4-amine; 8-methoxy-N-((1-methyl-1H-pyrrol-2-yl)methyl)-2H-pyrazolo[3,4-c]quinolin-4-amine; N-(2H-indazol-7-yl)-8-methoxy-2H-pyrazolo[3,4-c]quinolin-4-amine; N-(benzo[d][1,3]dioxol-5-yl)-2H-pyrazolo[3,4-c]quinolin-4-amine; N-(pyridin-3-yl)-3H-pyrazolo[3,4-c]quinolin-4-amine; N-(1-methyl-1H-indazol-6-yl)-2H-pyrazolo[3,4-c]quinolin-4-amine; N-(6-methoxypyridin-3-yl)-2H-pyrazolo[3,4-c]quinolin-4-amine; N-(4-(4-methylpiperazin-1-yl)phenyl)-2H-pyrazolo[3,4-c]quinolin-4-amine; N-(4-(4-methyl-1,4-diazepan-1-yl)phenyl)-2H-pyrazolo[3,4-c]quinolin-4-amine; N-(pyridin-2-yl)-3H-pyrazolo[3,4-c]quinolin-4-amine; N-(5-bromopyridin-2-yl)-3H-pyrazolo[3,4-c]quinolin-4-amine; N-(isoquinolin-3-yl)-3H-pyrazolo[3,4-c]quinolin-4-amine; N-(4-methylpyridin-2-yl)-3H-pyrazolo[3,4-c]quinolin-4-amine; N-(4,6-dimethylpyridin-2-yl)-3H-pyrazolo[3,4-c]quinolin-4-amine; 8-bromo-N-(1H-indazol-6-yl)-2H-pyrazolo[3,4-c]quinolin-4-amine; N-(1H-benzo[d]imidazol-5-yl)-8-bromo-2H-pyrazolo[3,4-c]quinolin-4-amine; 8-bromo-N-(1-methyl-1H-indazol-6-yl)-2H-pyrazolo[3,4-c]quinolin-4-amine; 8-bromo-N-(1H-indazol-7-yl)-2H-pyrazolo[3,4-c]quinolin-4-amine; 8-methoxy-N-(m-tolyl)-2H-pyrazolo[3,4-c]quinolin-4-amine; N-(1H-indazol-5-yl)-8-methoxy-2H-pyrazolo[3,4-c]quinolin-4-amine; N-(1H-benzo[d]imidazol-5-yl)-8-methoxy-2H-pyrazolo[3,4-c]quinolin-4-amine; 8-methoxy-N-(1-methyl-1H-indazol-6-yl)-2H-pyrazolo[3,4-c]quinolin-4-amine; 8-bromo-N-(7-methyl-1H-indazol-5-yl)-2H-pyrazolo[3,4-c]quinolin-4-amine; 8-methoxy-N-(4-(4-methylpiperazin-1-yl)phenyl)-2H-pyrazolo[3,4-c]quinolin-4-amine; 8-bromo-N-(4-(4-methylpiperazin-1-yl)phenyl)-2H-pyrazolo[3,4-c]quinolin-4-amine; N1-(8-methoxy-2H-pyrazolo[3,4-c]quinolin-4-yl)benzene-1,3-diamine; 8-bromo-N-(1H-indazol-5-yl)-2H-pyrazolo[3,4-c]quinolin-4-amine; 6-((3H-pyrazolo[3,4-c]quinolin-4-yl)amino)-2H-benzo[b][1,4]oxazin-3(4H)-one; 6-((8-methoxy-3H-pyrazolo[3,4-c]quinolin-4-yl)amino)-2H-benzo[b][1,4]oxazin-3(4H)-one; N-(1H-benzo[d][1,2,3]triazol-5-yl)-8-methoxy-2H-pyrazolo[3,4-c]quinolin-4-amine; 3-((8-methoxy-2H-pyrazolo[3,4-c]quinolin-4-yl)amino)benzimidamide; 8-methoxy-N-(4-(piperidin-1-yl)phenyl)-2H-pyrazolo[3,4-c]quinolin-4-amine; N1-(8-methoxy-2H-pyrazolo[3,4-c]quinolin-4-yl)-N4,N4-dimethylbenzene-1,4-diamine; 3-((8-methoxy-2H-pyrazolo[3,4-c]quinolin-4-yl)amino)benzamide; N-(3,4-dimethoxyphenyl)-8-methoxy-2H-pyrazolo[3,4-c]quinolin-4-amine; 8-methoxy-N-(4-morpholinophenyl)-2H-pyrazolo[3,4-c]quinolin-4-amine; 8-methoxy-N-(2-methyl-1H-benzo[d]imidazol-6-yl)-2H-pyrazolo[3,4-c]quinolin-4-amine; N-(1H-indazol-5-yl)-8H-pyrazolo[3,4-c][1,5]naphthyridin-6-amine; 4-((8-methoxy-2H-pyrazolo[3,4-c]quinolin-4-yl)amino)benzoic acid; 4-((8-methoxy-2H-pyrazolo[3,4-c]quinolin-4-yl)amino)benzamide; 4-((8-methoxy-2H-pyrazolo[3,4-c]quinolin-4-yl)amino)benzonitrile; 8-methoxy-N-(3-methoxyphenyl)-2H-pyrazolo[3,4-c]quinolin-4-amine; 8-methoxy-N-(4-methoxyphenyl)-2H-pyrazolo[3,4-c]quinolin-4-amine; 3-((8-methoxy-2H-pyrazolo[3,4-c]quinolin-4-yl)amino)benzonitrile; N-(8-methoxy-2H-pyrazolo[3,4-c]quinolin-4-yl)benzo[c][1,2,5]thiadiazol-5-amine; 3-((8-methoxy-2H-pyrazolo[3,4-c]quinolin-4-yl)amino)pyridin-2(1H)-one; N-(2-ethoxyphenyl)-8-methoxy-2H-pyrazolo[3,4-c]quinolin-4-amine; 8-methoxy-N-(1H-pyrazol-3-yl)-2H-pyrazolo[3,4-c]quinolin-4-amine; 8-methoxy-N-(3,4,5-trimethoxyphenyl)-2H-pyrazolo[3,4-c]quinolin-4-amine; 5-((8-methoxy-2H-pyrazolo[3,4-c]quinolin-4-yl)amino)-1H-pyrazole-4-carboxamide; 8-methoxy-N-(2-phenoxyphenyl)-2H-pyrazolo[3,4-c]quinolin-4-amine; 8-methoxy-N-(3-phenoxyphenyl)-2H-pyrazolo[3,4-c]quinolin-4-amine; 5-((8-methoxy-2H-pyrazolo[3,4-c]quinolin-4-yl)amino)-1H-benzo[d]imidazol-2(3H)-one; N-(1H-indol-5-yl)-8-methoxy-3H-pyrazolo[3,4-c]quinolin-4-amine; N-(4-(aminomethyl)phenyl)-8-methoxy-3H-pyrazolo[3,4-c]quinolin-4-amine; N-(1H-indazol-6-yl)-8-methoxy-2H-pyrazolo[3,4-c]quinolin-4-amine; N-(1H-indol-6-yl)-8-methoxy-3H-pyrazolo[3,4-c]quinolin-4-amine; N1-(8-methoxy-2H-pyrazolo[3,4-c]quinolin-4-yl)-N3,N3-dimethylbenzene-1,3-diamine; 8-methoxy-N-(3-phenyl-1H-pyrazol-5-yl)-2H-pyrazolo[3,4-c]quinolin-4-amine; N1,N1-diethyl-N4-(8-methoxy-2H-pyrazolo[3,4-c]quinolin-4-yl)benzene-1,4-diamine; 8-methoxy-N-(4-(pyrrolidin-1-yl)phenyl)-2H-pyrazolo[3,4-c]quinolin-4-amine; N3-(8-methoxy-3H-pyrazolo[3,4-c]quinolin-4-yl)-4H-1,2,4-triazole-3,5-diamine; 8-methoxy-N-(3-morpholinophenyl)-3H-pyrazolo[3,4-c]quinolin-4-amine; N-(1H-indol-5-yl)-2H-pyrazolo[3,4-c]quinolin-4-amine; 8-bromo-N-(4-(piperidin-1-yl)phenyl)-2H-pyrazolo[3,4-c]quinolin-4-amine; N1-(8-bromo-2H-pyrazolo[3,4-c]quinolin-4-yl)-N4,N4-dimethylbenzene-1,4-diamine; N-(3-cyclobutyl-1H-pyrazol-5-yl)-8-methoxy-2H-pyrazolo[3,4-c]quinolin-4-amine; N-(4-(4,5-dihydro-1H-imidazol-2-yl)phenyl)-8-methoxy-2H-pyrazolo[3,4-c]quinolin-4-amine; 4-(4-((8-methoxy-2H-pyrazolo[3,4-c]quinolin-4-yl)amino)phenyl)morpholin-3-one; N-(8-methoxy-2H-pyrazolo[3,4-c]quinolin-4-yl)-2,2-dimethyl-3,4-dihydro-2H-benzo[b][1,4]thiazin-6-amine; N-(4-morpholinophenyl)-8H-pyrazolo[3,4-c][1,5]naphthyridin-6-amine; N-(1H-indazol-5-yl)-2-methoxy-8H-pyrazolo[3,4-c][1,5]naphthyridin-6-amine; N-(1H-indazol-6-yl)-2H-pyrazolo[3,4-c][1,7]naphthyridin-4-amine; 7,8-diethoxy-N-(1H-indazol-6-yl)-2H-pyrazolo[3,4-c]quinolin-4-amine; 7-((8-methoxy-2H-pyrazolo[3,4-c]quinolin-4-yl)amino)-3,4-dihydroquinolin-2(1H)-one; 6-((8-methoxy-3H-pyrazolo[3,4-c]quinolin-4-yl)amino)-2H-benzo[b][1,4]thiazin-3(4H)-one; N-(5-(tert-butyl)-1H-pyrazol-3-yl)-8-methoxy-3H-pyrazolo[3,4-c]quinolin-4-amine; 8-methoxy-N-(3-methyl-1H-pyrazol-5-yl)-3H-pyrazolo[3,4-c]quinolin-4-amine; N-(5-cyclopropyl-1H-pyrazol-3-yl)-8-methoxy-3H-pyrazolo[3,4-c]quinolin-4-amine; N-(4-(1H-tetrazol-5-yl)phenyl)-8-methoxy-3H-pyrazolo[3,4-c]quinolin-4-amine; 8-bromo-N-(1H-indol-5-yl)-2H-pyrazolo[3,4-c]quinolin-4-amine; N-(benzo[d][1,3]dioxol-5-yl)-8-methoxy-2H-pyrazolo[3,4-c]quinolin-4-amine; N-(2,3-dihydrobenzo[b][1,4]dioxin-6-yl)-8-methoxy-2H-pyrazolo[3,4-c]quinolin-4-amine; 8-methoxy-N-(4-(1-methylpiperidin-4-yl)phenyl)-2H-pyrazolo[3,4-c]quinolin-4-amine; 8-methoxy-N-(6-morpholinopyridin-3-yl)-3H-pyrazolo[3,4-c]quinolin-4-amine; 8-methoxy-N-(4-(2-methoxyethoxy)phenyl)-3H-pyrazolo[3,4-c]quinolin-4-amine; N-(4-ethoxy-3-methoxyphenyl)-8-methoxy-3H-pyrazolo[3,4-c]quinolin-4-amine; 1-(4-((8-methoxy-3H-pyrazolo[3,4-c]quinolin-4-yl)amino)phenyl)pyrrolidin-2-one; 8-methoxy-N-(4-thiomorpholinophenyl)-3H-pyrazolo[3,4-c]quinolin-4-amine; 5-((8-methoxy-3H-pyrazolo[3,4-c]quinolin-4-yl)amino)benzo[d]oxazol-2(3H)-one; N-(8-methoxy-3H-pyrazolo[3,4-c]quinolin-4-yl)-3,4-dihydro-2H-benzo[b][1,4]oxazin-6-amine; 7-((8-methoxy-3H-pyrazolo[3,4-c]quinolin-4-yl)amino)quinazolin-4-ol; 4-(4-((8-methoxy-3H-pyrazolo[3,4-c]quinolin-4-yl)amino)phenyl)thiomorpholine 1,1-dioxide; 2-(4-((8-methoxy-3H-pyrazolo[3,4-c]quinolin-4-yl)amino)phenyl)acetamide; 3-((8-methoxy-3H-pyrazolo[3,4-c]quinolin-4-yl)amino)phenol; N-(3,4-diethoxyphenyl)-8-methoxy-3H-pyrazolo[3,4-c]quinolin-4-amine; 8-bromo-N-(4-morpholinophenyl)-2H-pyrazolo[3,4-c]quinolin-4-amine; 6-((8-bromo-2H- pyrazolo[3,4-c]quinolin-4-yl)amino)-2H-benzo[b][1,4]oxazin-3(4H)-one; 6-((8-methoxy-2H-pyrazolo[3,4-c]quinolin-4-yl)amino)-1H-benzo[d][1,3]oxazine-2,4-dione; 2-methoxy-5-((8-methoxy-2H-pyrazolo[3,4-c]quinolin-4-yl)amino)phenol; 8-bromo-N-(1H-pyrazol-3-yl)-2H-pyrazolo[3,4-c]quinolin-4-amine; 8-methoxy-N-(3-methoxyphenyl)-N-methyl-3H-pyrazolo[3,4-c]quinolin-4-amine; N-(3-((8-methoxy-3H-pyrazolo[3,4-c]quinolin-4-yl)amino)phenyl)acetamide; 8-methoxy-N-(1H-pyrazol-4-yl)-3H-pyrazolo[3,4-c]quinolin-4-amine; N-(3,4-dimethoxyphenyl)-7,8-dimethoxy-2H-pyrazolo[3,4-c]quinolin-4-amine; N-(3,4-dimethoxyphenyl)-8H-pyrazolo[3,4-c][1,5]naphthyridin-6-amine; N-(4-fluoro-3-methoxyphenyl)-8-methoxy-2H-pyrazolo[3,4-c]quinolin-4-amine; N-(3-fluoro-4-methoxyphenyl)-8-methoxy-2H-pyrazolo[3,4-c]quinolin-4-amine; 8-methoxy-N-(1-methyl-1H-benzo[d]imidazol-5-yl)-2H-pyrazolo[3,4-c]quinolin-4-amine; 1-(3-((8-methoxy-2H-pyrazolo[3,4-c]quinolin-4-yl)amino)phenyl)ethan-1-one; N-(4-((8-methoxy-2H-pyrazolo[3,4-c]quinolin-4-yl)amino)phenyl)acetamide; 8-methoxy-N-(pyridin-2-yl)-2H-pyrazolo[3,4-c]quinolin-4-amine; 8-methoxy-N-(1H-pyrrolo[2,3-b]pyridin-6-yl)-2H-pyrazolo[3,4-c]quinolin-4-amine; 3-((8-methoxy-2H-pyrazolo[3,4-c]quinolin-4-yl)amino)benzenesulfonamide; 4-((8-methoxy-2H-pyrazolo[3,4-c]quinolin-4-yl)amino)benzenesulfonamide; 7,8-dimethoxy-N-(4-morpholinophenyl)-2H-pyrazolo[3,4-c]quinolin-4-amine; 7,8-dimethoxy-N-(4-(4-methylpiperazin-1-yl)phenyl)-2H-pyrazolo[3,4-c]quinolin-4-amine; N1-(7,8-dimethoxy-2H-pyrazolo[3,4-c]quinolin-4-yl)-N4,N4-dimethylbenzene-1,4-diamine; N-(1H-indazol-6-yl)-7,8-dimethoxy-2H-pyrazolo[3,4-c]quinolin-4-amine; N2-(8-methoxy-2H-pyrazolo[3,4-c]quinolin-4-yl)pyridine-2,6-diamine; 8-methoxy-N-(1,2,3-trimethyl-1H-indol-5-yl)-2H-pyrazolo[3,4-c]quinolin-4-amine; N2-(8-methoxy-2H-pyrazolo[3,4-c]quinolin-4-yl)pyrimidine-2,4-diamine; 8-methoxy-N-(5-(methylthio)-4H-1,2,4-triazol-3-yl)-2H-pyrazolo[3,4-c]quinolin-4-amine; N-(5-cyclopropyl-4H-1,2,4-triazol-3-yl)-8-methoxy-2H-pyrazolo[3,4-c]quinolin-4-amine; N-(2-methoxy-5-((8-methoxy-2H-pyrazolo[3,4-c]quinolin-4-yl)amino)phenyl)acetamide; N-(1H-benzo[d]imidazol-2-yl)-8-methoxy-2H-pyrazolo[3,4-c]quinolin-4-amine; N-(1H-imidazol-2-yl)-8-methoxy-2H-pyrazolo[3,4-c]quinolin-4-amine; 1-(4-((8-methoxy-2H-pyrazolo[3,4-c]quinolin-4-yl)amino)phenyl)ethan-1-one; N-(4H-benzo[d][1,3]dioxin-6-yl)-8-methoxy-2H-pyrazolo[3,4-c]quinolin-4-amine; N-(1,3-dihydroisobenzofuran-5-yl)-8-methoxy-2H-pyrazolo[3,4-c]quinolin-4-amine; 8-methoxy-N-(1-methyl-1H-benzo[d]imidazol-6-yl)-2H-pyrazolo[3,4-c]quinolin-4-amine; N-(8-methoxy-2H-pyrazolo[3,4-c]quinolin-4-yl)-4,5-dimethylthiazol-2-amine; N-(5-cyclopropyl-1H-pyrazol-3-yl)-7,8-dimethoxy-2H-pyrazolo[3,4-c]quinolin-4-amine; N-(7,8-dimethoxy-2H-pyrazolo[3,4-c]quinolin-4-yl)-3,4-dihydro-2H-benzo[b][1,4]oxazin-6-amine; 5-((7,8-dimethoxy-2H-pyrazolo[3,4-c]quinolin-4-yl)amino)-2-methoxyphenol; 8-methoxy-N-(2-methyl-4-(4-methylpiperazin-1-yl)phenyl)-2H-pyrazolo[3,4-c]quinolin-4-amine; 8-methoxy-N-(4-methylpyridin-2-yl)-2H-pyrazolo[3,4-c]quinolin-4-amine; 8-methoxy-N-(6-methylpyridin-2-yl)-2H-pyrazolo[3,4-c]quinolin-4-amine; N-(4,6-dimethylpyridin-2-yl)-8-methoxy-2H-pyrazolo[3,4-c]quinolin-4-amine; N-(8-methoxy-2H-pyrazolo[3,4-c]quinolin-4-yl)-4-methylthiazol-2-amine; N-(8-methoxy-2H-pyrazolo[3,4-c]quinolin-4-yl)-4,5,6,7-tetrahydrobenzo[d]thiazol-2-amine; 8-methoxy-N-(4-phenoxyphenyl)-2H-pyrazolo[3,4-c]quinolin-4-amine; 8-methoxy-N-(2-methyl-1,2,3,4-tetrahydrobenzo[4,5]imidazo[1,2-a]pyrazin-8-yl)-2H-pyrazolo[3,4-c]quinolin-4-amine; 8-methoxy-N-(4-(pyridin-4-ylmethyl)phenyl)-2H-pyrazolo[3,4-c]quinolin-4-amine; 4-((8-methoxy-2H-pyrazolo[3,4-c]quinolin-4-yl)amino)benzene-1,2-diol; 8-methoxy-N-(4-((1-methylpiperidin-4-yl)oxy)phenyl)-2H-pyrazolo[3,4-c]quinolin-4-amine; 1-(4-(4-((8-methoxy-2H-pyrazolo[3,4-c]quinolin-4-yl)amino)phenyl)piperazin-1-yl)ethan-1-one; 8-methoxy-N-(6-(4-methylpiperazin-1-yl)pyridin-3-yl)-2H-pyrazolo[3,4-c]quinolin-4-amine; 6-methoxy-N-(4-(4-methylpiperazin-1-yl)phenyl)-2H-pyrazolo[3,4-c]quinolin-4-amine; N-(3,4-dimethoxyphenyl)-6-methoxy-2H-pyrazolo[3,4-c]quinolin-4-amine; N-(6-methoxy-2H-pyrazolo[3,4-c]quinolin-4-yl)-3,4-dihydro-2H-benzo[b][1,4]oxazin-6-amine; N-(5-cyclopropyl-1H-pyrazol-3-yl)-6-methoxy-2H-pyrazolo[3,4-c]quinolin-4-amine; 6-methoxy-N-(4-morpholinophenyl)-2H-pyrazolo[3,4-c]quinolin-4-amine; N-(1H-indazol-6-yl)-6-methoxy-2H-pyrazolo[3,4-c]quinolin-4-amine; N-(1H-indazol-6-yl)-7-methoxy-2H-pyrazolo[3,4-c]quinolin-4-amine; N-(7-methoxy-2H-pyrazolo[3,4-c]quinolin-4-yl)-3,4-dihydro-2H-benzo[b][1,4]oxazin-6-amine; N-(3,4-dimethoxyphenyl)-7-methoxy-2H-pyrazolo[3,4-c]quinolin-4-amine; 7-methoxy-N-(4-(4-methylpiperazin-1-yl)phenyl)-2H-pyrazolo[3,4-c]quinolin-4-amine; 7-methoxy-N-(4-morpholinophenyl)-2H-pyrazolo[3,4-c]quinolin-4-amine; N4-(8-methoxy-2H-pyrazolo[3,4-c]quinolin-4-yl)-N1,N1,2-trimethylbenzene-1,4-diamine; N-(4-(4-cyclopropylpiperazin-1-yl)phenyl)-8-methoxy-2H-pyrazolo[3,4-c]quinolin-4-amine; 8-methoxy-2H-pyrazolo[3,4-c]quinolin-4-amine; N-(3-fluoro-4-morpholinophenyl)-8-methoxy-2H-pyrazolo[3,4-c]quinolin-4-amine; 7-((8-methoxy-2H-pyrazolo[3,4-c]quinolin-4-yl)amino)quinoxalin-2(1H)-one; 8-methoxy-N-(3-methyl-4-(4-methylpiperazin-1-yl)phenyl)-2H-pyrazolo[3,4-c]quinolin-4-amine; 8-methoxy-N-(4-(piperazin-1-yl)phenyl)-2H-pyrazolo[3,4-c]quinolin-4-amine; N-(4-((dimethylamino)methyl)phenyl)-8-methoxy-2H-pyrazolo[3,4-c]quinolin-4-amine; N-(2-fluoro-4-morpholinophenyl)-8-methoxy-2H-pyrazolo[3,4-c]quinolin-4-amine; N-(4-(4-ethylpiperazin-1-yl)phenyl)-8-methoxy-2H-pyrazolo[3,4-c]quinolin-4-amine; 8-((8-methoxy-2H-pyrazolo[3,4-c]quinolin-4-yl)amino)-4,5-dihydro-1H-benzo[b]azepin-2(3H)-one; 5-((8-methoxy-2H-pyrazolo[3,4-c]quinolin-4-yl)amino)-1,3-dimethyl-1H-benzo[d]imidazol-2(3H)-one; N-(4-benzylphenyl)-8-methoxy-2H-pyrazolo[3,4-c]quinolin-4-amine; 8-methoxy-N-(2-methyl-4-morpholinophenyl)-2H-pyrazolo[3,4-c]quinolin-4-amine; N1-(8-methoxy-2H-pyrazolo[3,4-c]quinolin-4-yl)-N4-methyl-N4-(1-methylpiperidin-4-yl)benzene-1,4-diamine; 8-methoxy-N-(4-(2-morpholinoethyl)phenyl)-2H-pyrazolo[3,4-c]quinolin-4-amine; N-(3-chloro-4-(4-methylpiperazin-1-yl)phenyl)-8-methoxy-2H-pyrazolo[3,4-c]quinolin-4-amine; 8-methoxy-N-(1,2,3,4-tetrahydroquinolin-7-yl)-2H-pyrazolo[3,4-c]quinolin-4-amine; 4-((1H-indazol-6-yl)amino)-2H-pyrazolo[3,4-c]quinoline-8-carbonitrile; N-(9-methoxy-2H-pyrazolo[3,4-c]quinolin-4-yl)-3,4-dihydro-2H-benzo[b][1,4]oxazin-6-amine; N-(5-cyclopropyl-1H-pyrazol-3-yl)-9-methoxy-2H-pyrazolo[3,4-c]quinolin-4-amine; N-(3,4-dimethoxyphenyl)-9-methoxy-2H-pyrazolo[3,4-c]quinolin-4-amine; 9-methoxy-N-(4-(4-methylpiperazin-1-yl)phenyl)-2H-pyrazolo[3,4-c]quinolin-4-amine; 9-methoxy-N-(4-morpholinophenyl)-2H-pyrazolo[3,4-c]quinolin-4-amine; N-(1H-indazol-6-yl)-9-methoxy-2H-pyrazolo[3,4-c]quinolin-4-amine; N1-(8-methoxy-2H-pyrazolo[3,4-c]quinolin-4-yl)cyclohexane-1,2-diamine; 8-methoxy-N-(pyridin-4-yl)-2H-pyrazolo[3,4-c]quinolin-4-amine; 8-methoxy-N-(6-methoxypyridin-3-yl)-2H-pyrazolo[3,4-c]quinolin-4-amine; N-(3,4-dimethoxyphenyl)-1-methyl-2H-pyrazolo[3,4-c]quinolin-4-amine; 1-methyl-N-(4-(4-methylpiperazin-1-yl)phenyl)-2H-pyrazolo[3,4-c]quinolin-4-amine; N-(1H-indazol-6-yl)-1-methyl-2H-pyrazolo[3,4-c]quinolin-4-amine; N-(3,4-dimethoxyphenyl)-1-(trifluoromethyl)-2H-pyrazolo[3,4-c]quinolin-4-amine; N-(4-(4-methylpiperazin-1-yl)phenyl)-1-(trifluoromethyl)-2H-pyrazolo[3,4-c]quinolin-4-amine; N-(1H-indazol-6-yl)-1-(trifluoromethyl)-2H-pyrazolo[3,4-c]quinolin-4-amine; N-(3,4-dimethoxyphenyl)-1-nitro-2H-pyrazolo[3,4-c]quinolin-4-amine; N-(4-(4-methylpiperazin-1-yl)phenyl)-1-nitro-2H-pyrazolo[3,4-c]quinolin-4-amine; 2-(4-((8-methoxy-2H-pyrazolo[3,4-c]quinolin-4-yl)amino)phenyl)-N-(4-methoxyphenethyl)acetamide; 4-((3,4-dimethoxyphenyl)amino)-2H-pyrazolo[3,4-c]quinoline-8-carbonitrile; 4-((4-morpholinophenyl)amino)-2H-pyrazolo[3,4-c]quinoline-8-carbonitrile; N-(3,4-dimethoxyphenyl)-1-methyl-7H-isothiazolo[5,4-b]pyrazolo[4,3-d]pyridin-5-amine; N-(1H-indazol-6-yl)-1-methyl-7H-isothiazolo[5,4-b]pyrazolo[4,3-d]pyridin-5-amine; 1-methyl-N-(4-(4-methylpiperazin-1-yl)phenyl)-7H-isothiazolo[5,4-b]pyrazolo[4,3-d]pyridin-5-amine; 8-methoxy-N-(3-(piperazin-1-yl)phenyl)-2H-pyrazolo[3,4-c]quinolin-4-amine; N-(2-(diethylamino)ethyl)-4-((8-methoxy-2H-pyrazolo[3,4-c]quinolin-4-yl)amino)benzamide; 8-methoxy-N-(2-(4-methylpiperazin-1-yl)pyrimidin-5-yl)-2H-pyrazolo[3,4-c]quinolin-4-amine; 7-((8-methoxy-3H-pyrazolo[3,4-c]quinolin-4-yl)amino)-2H-benzo[b][1,4]oxazin-3(4H)-one; N-(8-methoxy-3H-pyrazolo[3,4-c]quinolin-4-yl)-3,4-dihydro-2H-benzo[b][1,4]oxazin-7-amine; 4-((3,4-dimethoxyphenyl)amino)-1-methyl-2H-pyrazolo[3,4-c]quinoline-7-carbonitrile; 4-((1H-indazol-6-yl)amino)-1-methyl-2H-pyrazolo[3,4-c]quinoline-7-carbonitrile; 8-methoxy-N-(3-(4-methylpiperazin-1-yl)phenyl)-2H-pyrazolo[3,4-c]quinolin-4-amine; 8-methoxy-N-(3-(2-(piperazin-1-yl)ethoxy)phenyl)-2H-pyrazolo[3,4-c]quinolin-4-amine; 8-methoxy-N-(6-methyl-5,6,7,8-tetrahydro-1,6-naphthyridin-3-yl)-2H-pyrazolo[3,4-c]quinolin-4-amine; (4-((8-methoxy-2H-pyrazolo[3,4-c]quinolin-4-yl)amino)phenyl)(pyrrolidin-1-yl)methanone; (4-((8-methoxy-2H-pyrazolo[3,4-c]quinolin-4-yl)amino)phenyl)(morpholino)methanone; N-(4-((dimethylamino)methyl)phenyl)-6-methoxy-2H-pyrazolo[3,4-c]quinolin-4-amine; 8-methoxy-N-(4-(pyrrolidin-1-ylmethyl)phenyl)-2H-pyrazolo[3,4-c]quinolin-4-amine; (4-((8-methoxy-2H-pyrazolo[3,4-c]quinolin-4-yl)amino)phenyl)(4-methylpiperazin-1-yl)methanone; N2-(2-(dimethylamino)ethyl)-N5-(8-methoxy-2H-pyrazolo[3,4-c]quinolin-4-yl)pyrimidine-2,5-diamine; 8-methoxy-N-(4-(morpholinomethyl)phenyl)-2H-pyrazolo[3,4-c]quinolin-4-amine; 8-methoxy-N-(4-((4-methylpiperazin-1-yl)methyl)phenyl)-2H-pyrazolo[3,4-c]quinolin-4-amine; N-(4-(4-ethylpiperazin-1-yl)phenyl)-6-methoxy-2H-pyrazolo[3,4-c]quinolin-4-amine; N-(4-(4-ethylpiperazin-1-yl)-3-fluorophenyl)-8-methoxy-2H-pyrazolo[3,4-c]quinolin-4-amine; N-(4-(2-(4-benzylpiperidin-1-yl)ethyl)phenyl)-8-methoxy-2H-pyrazolo[3,4-c]quinolin-4-amine; N-(4-((4-benzylpiperidin-1-yl)methyl)phenyl)-8-methoxy-2H-pyrazolo[3,4-c]quinolin-4-amine; 8-((6-methoxy-2H-pyrazolo[3,4-c]quinolin-4-yl)amino)-4,5-dihydro-1H-benzo[b]azepin-2(3H)-one; N-(1H-benzo[d]imidazol-5-yl)-6-methoxy-2H-pyrazolo[3,4-c]quinolin-4-amine; N-(4-(4-cyclopropylpiperazin-1-yl)phenyl)-9-methoxy-2H-pyrazolo[3,4-c]quinolin-4-amine; 8-methoxy-N-(p-tolyl)-2H-pyrazolo[3,4-c]quinolin-4-amine; N-(6-(2-(dimethylamino)ethoxy)pyridin-3-yl)-8-methoxy-2H-pyrazolo[3,4-c]quinolin-4-amine; N-(3-fluoro-4-morpholinophenyl)-6-methoxy-2H-pyrazolo[3,4-c]quinolin-4-amine; 6-methoxy-N-(4-thiomorpholinophenyl)-2H-pyrazolo[3,4-c]quinolin-4-amine; 6-methoxy-N-(2-methyl-1H-benzo[d]imidazol-5-yl)-2H-pyrazolo[3,4-c]quinolin-4-amine; N-(benzo[d][1,3]dioxol-5-yl)-6-methoxy-2H-pyrazolo[3,4-c]quinolin-4-amine; 6-((6-methoxy-2H-pyrazolo[3,4-c]quinolin-4-yl)amino)-2H-benzo[b][1,4]oxazin-3(4H)-one; N-(3,4-dimethoxyphenyl)-6,8-dimethoxy-2H-pyrazolo[3,4-c]quinolin-4-amine; N-(4-(4-cyclopropylpiperazin-1-yl)phenyl)-6,8-dimethoxy-2H-pyrazolo[3,4-c]quinolin-4-amine; N2-(3-(dimethylamino)propyl)-N5-(8-methoxy-2H-pyrazolo[3,4-c]quinolin-4-yl)pyridine-2,5-diamine; N2-(2-(dimethylamino)ethyl)-N5-(8-methoxy-2H-pyrazolo[3,4-c]quinolin-4-yl)pyridine-2,5-diamine; 8-methoxy-N-(6-((1-methylpiperidin-4-yl)oxy)pyridin-3-yl)-2H-pyrazolo[3,4-c]quinolin-4-amine; N-(1H-indazol-5-yl)-7-methoxy-2H-pyrazolo[3,4-c]quinolin-4-amine; 8-((7-methoxy-2H-pyrazolo[3,4-c]quinolin-4-yl)amino)-4,5-dihydro-1H-benzo[b]azepin-2(3H)-one; dihydrobenzo[b][1,4]dioxin-6-yl)-6-methoxy-2H-pyrazolo[3,4-c]quinolin-4-amine; N-(4-((dimethylamino)methyl)phenyl)-7-methoxy-2H-pyrazolo[3,4-c]quinolin-4-amine; N-(4-(4-ethylpiperazin-1-yl)phenyl)-7-methoxy-2H-pyrazolo[3,4-c]quinolin-4-amine; 6-methoxy-N-phenyl-2H-pyrazolo[3,4-c]quinolin-4-amine; N-(4-(4-cyclopropylpiperazin-1-yl)phenyl)-7-methoxy-2H-pyrazolo[3,4-c]quinolin-4-amine; N-(1H-benzo[d]imidazol-5-yl)-7-methoxy-2H-pyrazolo[3,4-c]quinolin-4-amine; 7-methoxy-N-(2-methyl-1H-benzo[d]imidazol-5-yl)-2H-pyrazolo[3,4-c]quinolin-4-amine; N-(2,3-dihydrobenzo[b][1,4]dioxin-6-yl)-7-methoxy-2H-pyrazolo[3,4-c]quinolin-4-amine; 6-((7-methoxy-2H-pyrazolo[3,4-c]quinolin-4-yl)amino)-2H-benzo[b][1,4]oxazin-3(4H)-one; N-(benzo[d][1,3]dioxol-5-yl)-7-methoxy-2H-pyrazolo[3,4-c]quinolin-4-amine; N-(1H-indazol-5-yl)-6-methoxy-2H-pyrazolo[3,4-c]quinolin-4-amine; N-(4-(4-cyclopentylpiperazin-1-yl)phenyl)-8-methoxy-2H-pyrazolo[3,4-c]quinolin-4-amine; N-(4-(4-isobutylpiperazin-1-yl)phenyl)-8-methoxy-2H-pyrazolo[3,4-c]quinolin-4-amine; N-(4-(4-isopropylpiperazin-1-yl)phenyl)-8-methoxy-2H-pyrazolo[3,4-c]quinolin-4-amine; N-(4-(4-(cyclopropylmethyl)piperazin-1-yl)phenyl)-8-methoxy-2H-pyrazolo[3,4-c]quinolin-4-amine; N-(4-(4-(tert-butyl)piperazin-1-yl)phenyl)-8-methoxy-2H-pyrazolo[3,4-c]quinolin-4-amine; 6-methoxy-N-(p-tolyl)-2H-pyrazolo[3,4-c]quinolin-4-amine; methyl 4-((3,4-dimethoxyphenyl)amino)-2H-pyrazolo[4,3-d]thieno[3,4-b]pyridine-6-carboxylate; methyl 4-(4-(4-cyclopropylpiperazin-1-yl)phenyl)amino)-2H-pyrazolo[4,3-d]thieno[3,4-b]pyridine-6-carboxylate; 2-(4-(4-((8-methoxy-2H-pyrazolo[3,4-c]quinolin-4-yl)amino)phenyl)piperazin-1-yl)acetic acid; 6-methoxy-N-(4-((4-methylpiperazin-1-yl)methyl)phenyl)-2H-pyrazolo[3,4-c]quinolin-4-amine; 2-(2-methoxy-4-((8-methoxy-2H-pyrazolo[3,4-c]quinolin-4-yl)amino)phenoxy)acetic acid; (4-((8-methoxy-2H-pyrazolo[3,4-c]quinolin-4-yl)amino)phenyl)methanol; N-(4-(4-(2-(dimethylamino)ethyl)piperazin-1-yl)phenyl)-8-methoxy-2H-pyrazolo[3,4-c]quinolin-4-amine; 6,8-dimethoxy-N-(4-((4-methylpiperazin-1-yl)methyl)phenyl)-2H-pyrazolo[3,4-c]quinolin-4-amine; (4-((6,8-dimethoxy-2H-pyrazolo[3,4-c]quinolin-4-yl)amino)phenyl)(4-methylpiperazin-1-yl)methanone; N-(4-((dimethylamino)methyl)phenyl)-6,8-dimethoxy-2H-pyrazolo[3,4-c]quinolin-4-amine; 2-(4-((8-methoxy-2H-pyrazolo[3,4-c]quinolin-4-yl)amino)phenyl)acetic acid; 6-((8-methoxy-2H-pyrazolo[3,4-c]quinolin-4-yl)amino)-2-naphthoic acid; 3-((8-methoxy-2H-pyrazolo[3,4-c]quinolin-4-yl)amino)benzoic acid; 4'-((8-methoxy-2H-pyrazolo[3,4-c]quinolin-4-yl)amino)-[1,1'-biphenyl]-4-carboxylic acid; 1-(4-((8-methoxy-2H-pyrazolo[3,4-c]quinolin-4-yl)amino)phenyl)-3-(m-tolyl)urea; 2-(4-((8-methoxy-2H-pyrazolo[3, 4-c]quinolin-4-yl)amino)phenoxy)acetic acid; 6-((8-methoxy-2H-pyrazolo[3,4-c]quinolin-4-yl)amino)-2H-benzo[b][1,4]oxazin-3(4H)-one; 4-(4-((8-methoxy-2H-pyrazolo[3,4-c]quinolin-4-yl)amino)phenyl)thiomorpholine 1,1-dioxide; 8-methoxy-N-(4-thiomorpholinophenyl)-2H-pyrazolo[3,4-c]quinolin-4-amine; 8-methoxy-N-(2-methylisoindolin-5-yl)-2H-pyrazolo[3,4-c]quinolin-4-amine; (3-methoxy-4-((8-methoxy-2H-pyrazolo[3,4-c]quinolin-4-yl)amino)phenyl)(4-(4-methylpiperazin-1-yl)piperidin-1-yl)methanone; 3-((8-hydroxy-2H-pyrazolo[3,4-c]quinolin-4-yl)amino)benzoic acid; 1-(4-(((6,8-dimethoxy-2H-pyrazolo[3,4-c]quinolin-4-yl)amino)phenyl)-3-(m-tolyl)urea; 1-(4-(((7-methoxy-2H-pyrazolo[3,4-c]quinolin-4-yl)amino)phenyl)-3-(m-tolyl)urea; 1-(4-((7,8-dimethoxy-2H-pyrazolo[3,4-c]quinolin-4-yl)amino)phenyl)-3-(m-tolyl)urea; N-(2-(dimethylamino)ethyl)-4-((8-methoxy-2H-pyrazolo[3,4-c]quinolin-4-yl)amino)-N-methylbenzamide; (4-((8-methoxy-2H-pyrazolo[3,4-c]quinolin-4-yl)amino)phenyl)(2-(methoxymethyl)pyrrolidin-1-yl)methanone; azetidin-1-yl(4-((8-methoxy-2H-pyrazolo[3,4-c]quinolin-4-yl)amino)phenyl)methanone; 4-((8-methoxy-2H-pyrazolo[3,4-c]quinolin-4-yl)amino)-N,N-dimethylbenzamide; (4-((8-methoxy-2H-pyrazolo[3,4-c]quinolin-4-yl)amino)phenyl)(4-methyl-1,4-diazepan-1-yl)methanone; 1-(4-((8-methoxy-2H-pyrazolo[3,4-c]quinolin-4-yl)amino)benzoyl)piperidin-4-one; (4-((8-methoxy-2H-pyrazolo[3,4-c]quinolin-4-yl)amino)phenyl)(1,4-dioxa-8-azaspiro[4.5]decan-8-yl)methanone; (3-(dimethylamino)pyrrolidin-1-yl)(4-((8-methoxy-2H-pyrazolo[3,4-c]quinolin-4-yl)amino)phenyl)methanone; 8-methoxy-N-(1-methyl-1,2,3,4-tetrahydroquinolin-6-yl)-2H-pyrazolo[3,4-c]quinolin-4-amine; 8-methoxy-N-(3-(pentafluorosulfanyl)phenyl)-2H-pyrazolo[3,4-c]quinolin-4-amine; N-(4-fluorophenyl)-8-methoxy-2H-pyrazolo[3,4-c]quinolin-4-amine; N-(3,4-difluorophenyl)-8-methoxy-2H-pyrazolo[3,4-c]quinolin-4-amine; 2,2,2-trifluoro-N-(4-((8-methoxy-2H-pyrazolo[3,4-c]quinolin-4-yl)amino)phenyl)acetamide; 3-((6-((8-methoxy-2H-pyrazolo[3,4-c]quinolin-4-yl)amino)-2H-benzo[b][1,4]oxazin-3-yl)amino)propan-1-ol; N6-(8-methoxy-2H-pyrazolo[3,4-c]quinolin-4-yl)-N3-phenethyl-2H-benzo[b][1,4]oxazine-3,6-diamine; N-(3,5-difluorophenyl)-8-methoxy-2H-pyrazolo[3,4-c]quinolin-4-amine; N-(3-fluoro-4-methylphenyl)-8-methoxy-2H-pyrazolo[3,4-c]quinolin-4-amine; 8-methoxy-N-(3,4,5-trifluorophenyl)-2H-pyrazolo[3,4-c]quinolin-4-amine; 8-methoxy-N-(4-nitrophenyl)-2H-pyrazolo[3,4-c]quinolin-4-amine; 8-methoxy-N-(3-methoxy-4-morpholinophenyl)-2H-pyrazolo[3,4-c]quinolin-4-amine; 8-methoxy-N-(3-(methylsulfonyl)phenyl)-2H-pyrazolo[3,4-c]quinolin-4-amine; 1,1,1,3,3,3-hexafluoro-2-(4-((8-methoxy-2H-pyrazolo[3,4-c]quinolin-4-yl)amino)phenyl)propan-2-ol; (4-((8-fluoro-3H-pyrazolo[3,4-c]quinolin-4-yl)amino)phenyl)(pyrrolidin-1-yl)methanone; 1-(4-(4-((8-fluoro-3H-pyrazolo[3,4-c]quinolin-4-yl)amino)phenyl)piperazin-1-yl)ethan-1-one; 6-((8-fluoro-3H-pyrazolo[3,4-c]quinolin-4-yl)amino)-2H-benzo[b][1,4]oxazin-3(4H)-one; 8-fluoro-N-(4-morpholinophenyl)-3H-pyrazolo[3,4-c]quinolin-4-amine; 8-fluoro-N-(4-(4-methylpiperazin-1-yl)phenyl)-3H-pyrazolo[3,4-c]quinolin-4-amine; N-(3,4-dimethoxyphenyl)-8-fluoro-3H-pyrazolo[3,4-c]quinolin-4-amine; N-(4-(difluoromethoxy)-3-methoxyphenyl)-8-methoxy-2H-pyrazolo[3,4-c]quinolin-4-amine; N-(3-fluoro-4-(trifluoromethyl)phenyl)-8-methoxy-2H-pyrazolo[3,4-c]quinolin-4-amine; N-(3-fluoro-4-(trifluoromethoxy)phenyl)-8-methoxy-2H-pyrazolo[3,4-c]quinolin-4-amine; N-(2,3-dimethoxyphenyl)-8-methoxy-2H-pyrazolo[3,4-c]quinolin-4-amine; N-(2,4-dimethoxyphenyl)-8-methoxy-2H-pyrazolo[3,4-c]quinolin-4-amine; 8-iodo-N-(4-(4-methylpiperazin-1-yl)phenyl)-3H-pyrazolo[3,4-c]quinolin-4-amine; 6-((7-fluoro-3H-pyrazolo[3,4-c]quinolin-4-yl)amino)-2H-benzo[b][1,4]oxazin-3(4H)-one; 7-fluoro-N-(4-morpholinophenyl)-3H-pyrazolo[3,4-c]quinolin-4-amine; N-(3,4-dimethoxyphenyl)-7-fluoro-3H-pyrazolo[3,4-c]quinolin-4-amine; 7-fluoro-N-(4-(4-methylpiperazin-1-yl)phenyl)-3H-pyrazolo[3,4-c]quinolin-4-amine; 9-methoxy-N-(3-(methylsulfonyl)phenyl)-3H-pyrazolo[3,4-c]quinolin-4-amine; 7-((9-methoxy-3H-pyrazolo[3,4-c]quinolin-4-yl)amino)-3,4-dihydroquinolin-2(1H)-one; 1-(4-(4-((9-methoxy-3H-pyrazolo[3,4-c]quinolin-4-yl)amino)phenyl)piperazin-1-yl)ethan-1-one; N-(3,5-dimethoxyphenyl)-8-methoxy-2H-pyrazolo[3,4-c]quinolin-4-amine; (4-((7-fluoro-3H-pyrazolo[3,4-c]quinolin-4-yl)amino)phenyl)(pyrrolidin-1-yl)methanone; 4-((8-methoxy-2H-pyrazolo[3,4-c]quinolin-4-yl)amino)-N,N-dimethylbenzenesulfonamide; N-cyclopropyl-3-((8-methoxy-2H-pyrazolo[3,4-c]quinolin-4-yl)amino)benzenesulfonamide; N-(4-(2H-1,2,3-triazol-2-yl)phenyl)-8-methoxy-2H-pyrazolo[3,4-c]quinolin-4-amine; 8-methoxy-N-(3-(methylsulfinyl)phenyl)-2H-pyrazolo[3,4-c]quinolin-4-amine; N-(3-(2H-1,2,3-triazol-2-yl)phenyl)-8-methoxy-2H-pyrazolo[3,4-c]quinolin-4-amine; 3-((8-methoxy-2H-pyrazolo[3,4-c]quinolin-4-yl)amino)-N-methylbenzenesulfonamide; 8-methoxy-N-(3-(morpholinosulfonyl)phenyl)-2H-pyrazolo[3,4-c]quinolin-4-amine; 8-methoxy-N-(3-((trifluoromethyl)sulfonyl)phenyl)-2H-pyrazolo[3,4-c]quinolin-4-amine; 2-(3-((8-methoxy-2H-pyrazolo[3,4-c]quinolin-4-yl)amino)phenyl)sulfonyl)ethan-1-01; 9-methoxy-N-(2-methylisoindolin-5-yl)-3H-pyrazolo[3,4-c]quinolin-4-amine; N-(4-((dimethylamino)methyl)phenyl)-9-methoxy-3H-pyrazolo[3,4-c]quinolin-4-amine; N-(3,4-dimethoxyphenyl)-8-iodo-3H-pyrazolo[3,4-c]quinolin-4-amine; 8-iodo-N-(4-morpholinophenyl)-3H-pyrazolo[3,4-c]quinolin-4-amine; (4-((8-iodo-3H-pyrazolo[3,4-c]quinolin-4-yl)amino)phenyl)(pyrrolidin-1-yl)methanone; 1-(4-(4-((8-iodo-3H-pyrazolo[3,4-c]quinolin-4-yl)amino)phenyl)piperazin-1-yl)ethan-1-one; 4-fluoro-N-(4-((8-methoxy-2H-pyrazolo[3,4-c]quinolin-4-yl)amino)phenyl)benzamide; 8-methoxy-N-(4-morpholino-3-nitrophenyl)-2H-pyrazolo[3,4-c]quinolin-4-amine; N-(2,4-difluorophenyl)-8-methoxy-2H-pyrazolo[3,4-c]quinolin-4-amine; N-(3,4-dimethoxyphenyl)-9-fluoro-3H-pyrazolo[3,4-c]quinolin-4-amine; 9-fluoro-N-(3-(methylsulfonyl)phenyl)-3H-pyrazolo[3,4-c]quinolin-4-amine; 9-fluoro-N-(4-(4-(4-methylpiperazin-1-yl)piperidin-1-yl)phenyl)-3H-pyrazolo[3,4-c]quinolin-4-amine; 9-fluoro-N-(3-fluoro-4-morpholinophenyl)-3H-pyrazolo[3,4-c]quinolin-4-amine.

The present invention further provides pharmaceutical compositions comprising one or more compounds of formula (I), (Ia), (Ib), (Ic) and/or (Id) as defined herein or a pharmaceutically acceptable ester, prodrug, hydrate, solvate or salt thereof, optionally in combination with a pharmaceutically acceptable carrier.

The pharmaceutical composition optionally comprises one or more of the following compounds or is administered in combination with one or more of these compounds:

Chlorhexidine; polynoxylin; domiphen; oxyquinoline; neomycin; miconazole; natamycin; various; hexetidine; tetracycline; mepartricin; metronidazole; clotrimazole; chlortetracycline; doxycycline; minocycline; triamcinolone; dexamethasone; hydrocortisone; epinephrine; benzydamine; adrenalone; amlexanox; becaplermin; algeldrate; aloglutamol; magaldrate; almagate; hydrotalcite; almasilate; cimetidine; ranitidine; famotidine; nizatidine; niperotidine; roxatidine; lafutidine; misoprostol; enprostil; omeprazole; pantoprazole; lansoprazole; rabeprazole; esomeprazole; carbenoxolone; sucralfate; pirenzepine; proglumide; gefarnate; sulglicotide; acetoxolone; zolimidine; troxipide; oxyphencyclimine; camylofin; mebeverine; trimebutine; rociverine; dicycloverine; dihexyverine; difemerine; piperidolate; benzilone; glycopyrronium; oxyphenonium; penthienate; propantheline; methantheline; tridihexethyl; isopropamide; hexocyclium; poldine; mepenzolate; bevonium; pipenzolate; diphemanil; fenpiverinium; dimethylaminopropionylphenothiazine; nicofetamide; tiropramide; papaverine; drotaverine; moxaverine; alosetron; tegaserod; cilansetron; prucalopride; fenpiprane; diisopromine; chlorbenzoxamine; pinaverium; fenoverine; idanpramine; proxazole; alverine; trepibutone; isometheptene; caroverine; phloroglucinol; silicones; trimethyldiphenylpropylamine; atropine; hyoscyamine; butylscopolamine; methylatropine; methylscopolamine; fentonium; metoclopramide; cisapride; domperidone; bromopride; alizapride; clebopride; ondansetron; granisetron; tropisetron; dolasetron; palonosetron; scopolamine; chlorobutanol; metopimazine; dronabinol; nabilone; aprepitant; casopitant; piprozolin; hymecromone; cyclobutyrol; silymarin; citiolone; epomediol; oxyphenisatine; bisacodyl; dantron; phenolphthalein; cascara; bisoxatin; ethulose; sterculia; linseed; methylcellulose; lactulose; lactitol; pentaerithrityl; macrogol; mannitol; sorbitol; glycerol; oil; alvimopan; lubiprostone; nystatin; streptomycin; paromomycin; kanamycin; vancomycin; colistin; rifaximin; phthalylsulfathiazole; sulfaguanidine; succinylsulfathiazole; broxyquinoline; acetarsol; nifuroxazide; nifurzide; pectin; kaolin; crospovidone; attapulgite; diosmectite; diphenoxylate; opium; loperamide; difenoxin; prednisolone; prednisone; betamethasone; tixocortol; budesonide; beclometasone; sulfasalazine; mesalazine; olsalazine; balsalazide; ceratonia; racecadotril; phentermine; fenfluramine; amfepramone; dexfenfluramine; mazindol; etilamfetamine; cathine; clobenzorex; mefenorex; sibutramine; orlistat; rimonabant; diastase; pepsin; tilactase; phenformin; metformin; buformin; glibenclamide; chlorpropamide; tolbutamide; glibornuride; tolazamide; carbutamide; glipizide; gliquidone; gliclazide; metahexamide; glisoxepide; glimepiride; acetohexamide; glymidine; acarbose; miglitol; voglibose; troglitazone; rosiglitazone; pioglitazone; sitagliptin; vildagliptin; saxagliptin; alogliptin; repaglinide; nateglinide; exenatide; pramlintide; benfluorex; liraglutide; mitiglinide; tolrestat; betacarotene; ergocalciferol; dihydrotachysterol; alfacalcidol; calcitriol; colecalciferol; calcifediol; sulbutiamine; benfotiamine; nicotinamide; biotin; inositol; tocofersolan; dexpanthenol; pantethine; androstanolone; stanozolol; metandienone; metenolone; oxymetholone; quinbolone; prasterone; oxandrolone; norethandrolone; nandrolone; ethylestrenol; levocarnitine; ademetionine; glutamine; mercaptamine; betaine; alglucerase; imiglucerase; laronidase; sacrosidase; galsulfase; idursulfase; nitisinone; miglustat; sapropterin; dicoumarol; phenindione; warfarin; phenprocoumon; acenocoumarol; clorindione; diphenadione; tioclomarol; heparin; dalteparin; enoxaparin; nadroparin; parnaparin; reviparin; danaparoid; tinzaparin; sulodexide; bemiparin; ditazole; cloricromen; picotamide; clopidogrel; ticlopidine; dipyridamole; epoprostenol; indobufen; iloprost; abciximab; aloxiprin; eptifibatide; tirofiban; triflusal; beraprost; treprostinil; prasugrel; streptokinase; alteplase; anistreplase; urokinase; fibrinolysin; brinase; reteplase; saruplase; ancrod; tenecteplase; desirudin; lepirudin; argatroban; melagatran; ximelagatran; bivalirudin; defibrotide; fondaparinux; rivaroxaban; camostat; phytomenadione; menadione; thrombin; collagen; etamsylate; carbazochrome; batroxobin; romiplostim; eltrombopag; dextriferron; cyanocobalamin; hydroxocobalamin; cobamamide; mecobalamin; erythropoietin; albumin; dextran; hydroxyethylstarch; erythrocytes; thrombocytes; carbohydrates; electrolytes; trometamol; carbamide; cetylpyridinium; nitrofural; sulfamethizole; taurolidine; noxytiolin; glucose; glycine; lysine; hyaluronidase; chymotrypsin; trypsin; desoxyribonuclease; bromelains; hematin; acetyldigitoxin; acetyldigoxin; digitoxin; digoxin; deslanoside; metildigoxin; gitoformate; proscillaridin; g-strophanthin; cymarin; peruvoside; quinidine; procainamide; disopyramide; sparteine; ajmaline; prajmaline; lorajmine; lidocaine; mexiletine; tocamide; aprindine; propafenone; flecamide; lorcamide; encamide; amiodarone; bunaftine; dofetilide; ibutilide; tedisamil; moracizine; cibenzoline; etilefrine; isoprenaline; norepinephrine; dopamine; norfenefrine; phenylephrine; dobutamine; oxedrine; metaraminol; methoxamine; mephentermine; dimetofrine; prenalterol; dopexamine; gepefrine; ibopamine; midodrine; octopamine; fenoldopam; cafedrine; arbutamine; theodrenaline; aminone; milrinone; enoximone; bucladesine; angiotensinamide; xamoterol; levosimendan; propatylnitrate; troInitrate; tenitramine; flosequinan; prenylamine; oxyfedrine; benziodarone; carbocromen; hexobendine; etafenone; heptaminol; imolamine; dilazep; trapidil; molsidomine; efloxate; cinepazet; cloridarol; nicorandil; linsidomine; nesiritide; alprostadil; camphora; indometacin; creatinolfosfate; fosfocreatine; ubidecarenone; adenosine; tiracizine; acadesine; trimetazidine; ibuprofen; ivabradine; ranolazine; icatibant; regadenoson; rescinnamine; reserpine; deserpidine; methoserpidine; bietaserpine; clonidine; guanfacine; tolonidine; moxonidine; rilmenidine; trimetaphan; mecamylamine; prazosin; indoramin; trimazosin; doxazosin; urapidil; betanidine; guanethidine; guanoxan; debrisoquine; guanoclor; guanazodine; guanoxabenz; diazoxide; dihydralazine; hydralazine; endralazine; cadralazine; minoxidil; nitroprusside; pinacidil; veratrum; metirosine; pargyline; ketanserin; bosentan; ambrisentan; sitaxentan; bendroflumethiazide; hydroflumethiazide; hydrochlorothiazide; chlorothiazide; polythiazide; trichlormethiazide; cyclopenthiazide; methyclothiazide; cyclothiazide; mebutizide; quinethazone; clopamide; chlortalidone; mefruside; clofenamide; metolazone; meticrane; xipamide; indapamide; clorexolone; fenquizone; mersalyl; theobromine; cicletanine; furosemide; bumetanide; piretanide; torasemide; muzolimine; etozolin; spironolactone; canrenone; eplerenone; amiloride; triamterene; tolvaptan; conivaptan; isoxsuprine; buphenine; bamethan; phentolamine; tolazoline; ciclonicate; pentifylline; pentoxifylline; nicergoline; dihydroergocristine; kallidinogenase; cyclandelate; phenoxybenzamine; vincamine; moxisylyte; bencyclane; vinburnine; suloctidil; buflomedil; naftidrofuryl; butalamine; visnadine; cetiedil; cinepazide; ifenprodil; azapetine; fasudil; fluorometholone; fluocortolone; fluocinonide; tetracaine; benzocaine; cinchocaine; procaine; oxetacaine; pramocaine; tribenoside; organoheparinoid; polidocanol; phenol; rutoside; monoxerutin; diosmin; troxerutin; hidrosmin; alprenolol; oxprenolol; pindolol; propranolol; timolol; sotalol; nadolol; mepindolol; carteolol; tertatolol; bopindolol; bupranolol; penbutolol; cloranolol; practolol; metoprolol; atenolol; acebutolol; betaxolol; bevantolol; bisoprolol; celiprolol; esmolol; epanolol; s-atenolol; nebivolol; talinolol; labetalol; carvedilol; amlodipine; felodipine; isradipine; nicardipine; nifedipine; nimodipine; nisoldipine; nitrendipine; lacidipine; nilvadipine; manidipine; barnidipine; lercanidipine; cilnidipine; benidipine; mibefradil; verapamil; gallopamil; diltiazem; fendiline; bepridil; lidoflazine; perhexyline; captopril; enalapril;

lisinopril; perindopril; ramipril; quinapril; benazepril; cilazapril; fosinopril; trandolapril; spirapril; delapril; moexipril; temocapril; zofenopril; imidapril; losartan; eprosartan; valsartan; irbesartan; tasosartan; candesartan; telmisartan; remikiren; aliskiren; simvastatin; lovastatin; pravastatin; fluvastatin; atorvastatin; cerivastatin; rosuvastatin; pitavastatin; clofibrate; bezafibrate; gemfibrozil; fenofibrate; simfibrate; ronifibrate; ciprofibrate; etofibrate; clofibride; colestyramine; colestipol; colextran; colesevelam; niceritrol; nicofuranose; acipimox; dextrothyroxine; probucol; tiadenol; meglutol; policosanol; ezetimibe; hachimycin; pecilocin; pyrrolnitrin; griseofulvin; econazole; chlormidazole; isoconazole; tiabendazole; tioconazole; ketoconazole; sulconazole; bifonazole; oxiconazole; fenticonazole; omoconazole; sertaconazole; fluconazole; flutrimazole; bromochlorosalicylanilide; methylrosaniline; tribromometacresol; chlorphenesin; ticlatone; sulbentine; haloprogin; ciclopirox; terbinafine; amorolfine; dimazole; tolnaftate; tolciclate; flucytosine; naftifine; butenafine; octinoxate; dextranomer; crilanomer; enoxolone; collagenase; thonzylamine; mepyramine; thenalidine; tripelennamine; chloropyramine; promethazine; tolpropamine; dimetindene; clemastine; bamipine; isothipendyl; diphenhydramine; chlorphenoxamine; oxybuprocaine; quinisocaine; dithranol; trioxysalen; methoxsalen; calcipotriol; tacalcitol; tazarotene; bergapten; etretinate; acitretin; demeclocycline; oxytetracycline; chloramphenicol; bacitracin; gentamicin; tyrothricin; mupirocin; virginiamycin; amikacin; retapamulin; sulfathiazole; mafenide; sulfanilamide; sulfamerazine; idoxuridine; tromantadine; aciclovir; podophyllotoxin; inosine; penciclovir; lysozyme; ibacitabine; edoxudine; imiquimod; docosanol; methylprednisolone; clobetasone; flumetasone; fluocortin; fluperolone; fluprednidene; desonide; alclometasone; clocortolone; fluclorolone; desoximetasone; diflucortolone; fludroxycortide; diflorasone; amcinonide; halometasone; mometasone; fluticasone; prednicarbate; difluprednate; ulobetasol; clobetasol; halcinonide; aminoacridine; euflavine; dibrompropamidine; propamidine; hexamidine; polihexanide; hexachlorophene; policresulen; triclosan; chloroxylenol; biphenylol; iodine/octylphenoxypolyglycolether; povidone-iodine; iodine; diiodohydroxypropane; dequalinium; chlorquinaldol; clioquinol; benzalkonium; cetrimonium; cetrimide; mercurochrome; thiomersal; silver; eosin; propanol; isopropanol; ethanol; framycetin; benzododecinium; iodoform; bithionol; sulfur; tioxolone; mesulfen; tretinoin; retinol; adapalene; isotretinoin; motretinide; clindamycin; erythromycin; meclocycline; resorcinol; dapsone; ichtasol; xenysalate; others; tacrolimus; pimecrolimus; mequinol; tiratricol; oxaceprol; finasteride; hydroquinone; monobenzone; eflornithine; diclofenac; alitretinoin; candicidin; carfecillin; pentamycin; diiodohydroxyquinoline; Sulfonamides: sulfatolamide; ornidazole; azanidazole; propenidazole; butoconazole; terconazole; clodantoin; nifuratel; furazolidone; protiofate; methylergometrine; ergometrine; dinoprost; dinoprostone; gemeprost; carboprost; sulprostone; ritodrine; fenoterol; bromocriptine; lisuride; cabergoline; quinagolide; metergoline; terguride; naproxen; flunoxaprofen; atosiban; norethisterone; lynestrenol; levonorgestrel; quingestanol; megestrol; medroxyprogesterone; norgestrienone; etonogestrel; desogestrel; fluoxymesterone; methyltestosterone; testosterone; mesterolone; ethinylestradiol; estradiol; estriol; chlorotrianisene; estrone; promestriene; dienestrol; diethylstilbestrol; methallenestril; moxestrol; tibolone; gestonorone; hydroxyprogesterone; progesterone; dydrogesterone; medrogestone; nomegestrol; demegestone; chlormadinone; promegestone; allylestrenol; ethisterone; etynodiol; methylestrenolone; urofollitropin; cyclofenil; clomifene; epimestrol; cyproterone; danazol; gestrinone; mifepristone; raloxifene; bazedoxifene; emepronium; flavoxate; meladrazine; oxybutynin; terodiline; propiverine; tolterodine; solifenacin; trospium; darifenacin; fesoterodine; sildenafil; yohimbine; apomorphine; tadalafil; vardenafil; phenazopyridine; succinimide; dapoxetine; alfuzosin; tamsulosin; terazosin; silodosin; dutasteride; corticotropin; tetracosactide; thyrotropin; somatropin; somatrem; mecasermin; sermorelin; pegvisomant; vasopressin; desmopressin; lypressin; terlipressin; ornipressin; argipressin; demoxytocin; oxytocin; carbetocin; gonadorelin; nafarelin; histrelin; somatostatin; octreotide; lanreotide; vapreotide; ganirelix; cetrorelix; aldosterone; fludrocortisone; desoxycortone; paramethasone; cortisone; prednylidene; rimexolone; deflazacort; cloprednol; meprednisone; cortivazol; trilostane; methylthiouracil; propylthiouracil; benzylthiouracil; carbimazole; thiamazole; diiodotyrosine; dibromotyrosine; glucagon; teriparatide; elcatonin; cinacalcet; paricalcitol; doxercalciferol; lymecycline; metacycline; rolitetracycline; penimepicycline; clomocycline; tigecycline; thiamphenicol; ampicillin; pivampicillin; carbenicillin; amoxicillin; carindacillin; bacampicillin; epicillin; pivmecillinam; azlocillin; mezlocillin; mecillinam; piperacillin; ticarcillin; metampicillin; talampicillin; sulbenicillin; temocillin; hetacillin; benzylpenicillin; phenoxymethylpenicillin; propicillin; azidocillin; pheneticillin; penamecillin; clometocillin; dicloxacillin; cloxacillin; meticillin; oxacillin; flucloxacillin; sulbactam; tazobactam; sultamicillin; cefalexin; cefaloridine; cefalotin; cefazolin; cefadroxil; cefazedone; cefatrizine; cefapirin; cefradine; cefacetrile; cefroxadine; ceftezole; cefoxitin; cefuroxime; cefamandole; cefaclor; cefotetan; cefonicid; cefotiam; loracarbef; cefmetazole; cefprozil; ceforanide; cefotaxime; ceftazidime; cefsulodin; ceftriaxone; cefmenoxime; latamoxef; ceftizoxime; cefixime; cefodizime; cefetamet; cefpiramide; cefoperazone; cefpodoxime; ceftibuten; cefdinir; cefditoren; cefcapene; cefepime; cefpirome; cefozopran; meropenem; ertapenem; doripenem; biapenem; trimethoprim; brodimoprim; iclaprim; sulfaisodimidine; sulfadimidine; sulfapyridine; sulfafurazole; sulfathiourea; sulfamethoxazole; sulfadiazine; sulfamoxole; sulfadimethoxine; sulfalene; sulfametomidine; sulfametoxydiazine; sulfamethoxypyridazine; sulfaperin; sulfaphenazole; sulfamazone; spiramycin; midecamycin; oleandomycin; roxithromycin; josamycin; troleandomycin; clarithromycin; azithromycin; miocamycin; rokitamycin; dirithromycin; flurithromycin; telithromycin; lincomycin; pristinamycin; quinupristin/dalfopristin; streptoduocin; tobramycin; netilmicin; sisomicin; dibekacin; ribostamycin; isepamicin; arbekacin; ofloxacin; ciprofloxacin; pefloxacin; enoxacin; temafloxacin; norfloxacin; lomefloxacin; fleroxacin; sparfloxacin; rufloxacin; grepafloxacin; levofloxacin; trovafloxacin; moxifloxacin; gemifloxacin; gatifloxacin; prulifloxacin; pazufloxacin; garenoxacin; rosoxacin; cinoxacin; flumequine; teicoplanin; telavancin; dalbavancin; oritavancin; tinidazole; nitrofurantoin; nifurtoinol; fosfomycin; xibornol; clofoctol; spectinomycin; methenamine; nitroxoline; linezolid; daptomycin; itraconazole; voriconazole; posaconazole; caspofungin; micafungin; anidulafungin; cycloserine; rifampicin; rifamycin; rifabutin; rifapentine; capreomycin; isoniazid; protionamide; tiocarlide; ethionamide; pyrazinamide; ethambutol; terizidone; morinamide; clofazimine; metisazone; vidarabine; ribavirin; ganciclovir; famciclovir; valaciclovir; cidofovir; valganciclovir; brivudine; rimantadine; foscarnet; fosfonet; saquinavir; indinavir; ritonavir; nelfinavir; amprenavir; lopinavir; fosamprenavir; atazanavir; tipranavir; darunavir; zidovudine; didanosine; zalcitabine; stavudine; lamivudine; abacavir; emtricitabine; entecavir; telbivudine; clevudine; nevirapine; delavirdine; efavirenz; etravirine; zanamivir; oseltamivir; moroxydine; pleconaril; enfuvirtide; raltegravir; maraviroc; maribavir; palivizumab; nebacumab; diphtheria-poliomyelitis-tetanus; diphtheria-pertussis-poliomyelitis-tetanus; diphtheria-rubella-tetanus; cyclophosphamide; chlorambucil; melphalan; chlormethine; ifosfamide; trofosfamide; prednimustine; bendamustine; busulfan; treosulfan; mannosulfan; thiotepa; triaziquone; carboquone; carmustine; lomustine; semustine; streptozocin; fotemustine; nimustine; ranimustine; etoglucid; mitobronitol; pipobroman; temozolomide; dacarbazine; methotrexate; raltitrexed; pemetrexed; pralatrexate; mercaptopurine; tioguanine; cladribine; fludarabine; clofarabine; nelarabine; cytarabine; fluorouracil; tegafur; carmofur; gemcitabine; capecitabine; azacitidine; decitabine; vinblastine; vincristine; vindesine; vinorelbine; vinflunine; etoposide; teniposide; demecolcine; paclitaxel; docetaxel; trabectedin; dactinomycin; doxorubicin; daunorubicin; epirubicin; aclarubicin; zorubicin; idarubicin; mitoxantrone; pirarubicin; valrubicin; bleomycin; plicamycin; mitomycin; ixabepilone; cisplatin; carboplatin; oxaliplatin; satraplatin; procarbazine; edrecolomab; rituximab; trastuzumab; alemtuzumab; gemtuzumab; cetuximab; bevacizumab; panitumumab; catumaxomab; ofatumumab; temoporfin; efaproxiral; imatinib; gefitinib; erlotinib; sunitinib; sorafenib; dasatinib; lapatinib; nilotinib; temsirolimus; everolimus; pazopanib; amsacrine; asparaginase; altretamine; hydroxycarbamide; lonidamine; pentostatin; miltefosine; masoprocol; estramustine; mitoguazone; topotecan; tiazofurine; irinotecan; mitotane; pegaspargase; bexarotene; bortezomib; celecoxib; anagrelide; oblimersen; vorinostat; romidepsin; fosfestrol; buserelin; leuprorelin; goserelin; triptorelin; tamoxifen; toremifene; fulvestrant; flutamide; nilutamide; bicalutamide; aminoglutethimide; formestane; anastrozole; letrozole; vorozole; exemestane; abarelix; degarelix; filgrastim; molgramostim; sargramostim; lenograstim; ancestim; pegfilgrastim; aldesleukin; oprelvekin; lentinan; roquinimex; pegademase; pidotimod; thymopentin; immunocyanin; tasonermin; mifamurtide; plerixafor; muromonab-CD3; sirolimus; leflunomide; alefacept; gusperimus; efalizumab; abetimus; natalizumab; abatacept; eculizumab; etanercept; infliximab; afelimomab; adalimumab; golimumab; daclizumab; basiliximab; anakinra; rilonacept; ustekinumab; mepolizumab; tocilizumab; canakinumab; ciclosporin; azathioprine; thalidomide; lenalidomide; phenylbutazone; mofebutazone; oxyphenbutazone; clofezone; kebuzone; sulindac; tolmetin; zomepirac; alclofenac; bumadizone; etodolac; lonazolac; fentiazac; acemetacin; difenpiramide; oxametacin; proglumetacin; ketorolac; aceclofenac; bufexamac; piroxicam; tenoxicam; droxicam; lornoxicam; meloxicam; ketoprofen; fenoprofen; fenbufen; benoxaprofen; suprofen; pirprofen; flurbiprofen; indoprofen; oxaprozin; ibuproxam; dexibuprofen; alminoprofen; dexketoprofen; rofecoxib; valdecoxib; parecoxib; etoricoxib; lumiracoxib; nabumetone; azapropazone; glucosamine; proquazone; orgotein; nimesulide; feprazone; diacerein; morniflumate; tenidap; oxycinchophen; auranofin; aurothioglucose; aurotioprol; penicillamine; bucillamine; etofenamate; felbinac; bendazac; suxibuzone; nifenazone; capsaicin; zucapsaicin; alcuronium; tubocurarine; dimethyltubocurarine; suxamethonium; pancuronium; gallamine; vecuronium; atracurium; hexafluoronium; cisatracurium; phenprobamate; carisoprodol; methocarbamol; styramate; febarbamate; chlormezanone; chlorzoxazone; baclofen; tizanidine; pridinol; tolperisone; thiocolchicoside; mephenesin; tetrazepam; cyclobenzaprine; eperisone; fenyramidol; dantrolene; allopurinol; tisopurine; febuxostat; probenecid; sulfinpyrazone; benzbromarone; isobromindione; colchicine; cinchophen; pegloticase; ipriflavone; denosumab; hydroquinine; chymopapain; halothane; chloroform; enflurane; trichloroethylene; isoflurane; desflurane; sevoflurane; methohexital; hexobarbital; thiopental; narcobarbital; fentanyl; alfentanil; sufentanil; phenoperidine; anileridine; remifentanil; droperidol; ketamine; propanidid; alfaxalone; etomidate; propofol; esketamine; xenon; metabutethamine; chloroprocaine; bupivacaine; mepivacaine; prilocalne; butanilicaine; etidocaine; articaine; ropivacaine; levobupivacaine; cocaine; dyclonine; morphine; hydromorphone; nicomorphine; oxycodone; dihydrocodeine; diamorphine; papavereturn; ketobemidone; pethidine; dextromoramide; piritramide; dextropropoxyphene; bezitramide; pentazocine; phenazocine; buprenorphine; butorphanol; nalbuphine; tilidine; tramadol; dezocine; meptazinol; tapentadol; salicylamide; salsalate; ethenzamide; dipyrocetyl; benorilate; diflunisal; guacetisal; phenazone; aminophenazone; propyphenazone; paracetamol; phenacetin; bucetin; propacetamol; rimazolium; glafenine; floctafenine; viminol; nefopam; flupirtine; ziconotide; methoxyflurane; nabiximols; dihydroergotamine; ergotamine; methysergide; flumedroxone; sumatriptan; naratriptan; zolmitriptan; rizatriptan; almotriptan; eletriptan; frovatriptan; pizotifen; iprazochrome; dimetotiazine; oxetorone; methylphenobarbital; phenobarbital; primidone; barbexaclone; metharbital; ethotoin; phenyloin; mephenyloin; fosphenyloin; paramethadione; trimethadione; ethadione; ethosuximide; phensuximide; mesuximide; clonazepam; carbamazepine; oxcarbazepine; rufinamide; eslicarbazepine; valpromide; vigabatrin; progabide; tiagabine; sultiame; phenacemide; lamotrigine; felbamate; topiramate; gabapentin; pheneturide; levetiracetam; zonisamide; pregabalin; stiripentol; lacosamide; carisbamate; beclamide; trihexyphenidyl; biperiden; metixene; procyclidine; profenamine; dexetimide; phenglutarimide; mazaticol; bornaprine; tropatepine; etanautine; benzatropine; etybenzatropine; levodopa; melevodopa; amantadine; pergolide; ropinirole; pramipexole; piribedil; rotigotine; selegiline; rasagiline; tolcapone; entacapone; budipine; chlorpromazine; levomepromazine; promazine; acepromazine; triflupromazine; cyamemazine; chlorproethazine; dixyrazine; fluphenazine; perphenazine; prochlorperazine; thiopropazate; trifluoperazine; acetophenazine; thioproperazine; butaperazine; perazine; periciazine; thioridazine; mesoridazine; pipotiazine; haloperidol; trifluperidol; melperone; moperone; pipamperone; bromperidol; benperidol; fluanisone; oxypertine; molindone; sertindole; ziprasidone; flupentixol; clopenthixol; chlorprothixene; tiotixene; zuclopenthixol; fluspirilene; pimozide; penfluridol; loxapine; clozapine; olanzapine; quetiapine; asenapine; clotiapine; #sulpiride; sultopride; tiapride; remoxipride; amisulpride; veralipride; levosulpiride; lithium; prothipendyl; risperidone; mosapramine; zotepine; aripiprazole; paliperidone; diazepam; chlordiazepoxide; medazepam; oxazepam; lorazepam; adinazolam; bromazepam; clobazam; ketazolam; prazepam; alprazolam; halazepam; pinazepam; camazepam; nordazepam; fludiazepam; etizolam; clotiazepam; cloxazolam; tofisopam; hydroxyzine; captodiame; meprobamate; emylcamate; mebutamate; benzoctamine; buspirone; mephenoxalone; gedocarnil; etifoxine; pentobarbital; amobarbital; butobarbital; barbital; aprobarbital; secobarbital; talbutal; vinylbital; vinbarbital; cyclobarbital; heptabarbital; reposal; etallobarbital; allobarbital; proxibarbal; chloralodol; dichloralphenazone; paraldehyde; flurazepam; nitrazepam; flunitrazepam; estazolam; triazolam; lormetazepam; temazepam; midazolam; brotizolam; quazepam; loprazolam; doxefazepam; cinolazepam; glutethimide; methyprylon; pyrithyldione; zopiclone; zolpidem; zaleplon; eszopiclone; melatonin; ramelteon; methaqualone; clomethiazole; bromisoval; carbromal; propiomazine; triclofos; ethchlorvynol; valerian; hexapropymate; bromides; apronal; valnoctamide; methylpentynol; niaprazine; dexmedetomidine; desipramine; imipramine; clomipramine; opipramol; trimipramine; lofepramine; dibenzepin; amitriptyline; nortriptyline; protriptyline; doxepin; iprindole; melitracen; butriptyline; dosulepin; amoxapine; dimetacrine; aminepine; maprotiline; quinupramine; zimeldine; fluoxetine; citalopram; paroxetine; sertraline; alaproclate; fluvoxamine; etoperidone; escitalopram; isocarboxazid; nialamide; phenelzine; tranylcypromine; iproniazide; iproclozide; moclobemide; toloxatone; oxitriptan; tryptophan; mianserin; nomifensine; trazodone; nefazodone; minaprine; bifemelane; viloxazine; oxaflozane; mirtazapine; bupropion; medifoxamine; tianeptine; pivagabine; venlafaxine; milnacipran; reboxetine; gepirone; duloxetine; agomelatine; desvenlafaxine; amfetamine; dexamfetamine; metamfetamine; methylphenidate; pemoline; fencamfamin; modafinil; fenozolone; atomoxetine; fenetylline; dexmethylphenidate; caffeine; propentofylline; meclofenoxate; pyritinol; piracetam; deanol; fipexide; citicoline; oxiracetam; pirisudanol; linopirdine; nizofenone; aniracetam; acetylcarnitine; idebenone; prolintane; pipradrol; pramiracetam; adrafinil; vinpocetine; tacrine; donepezil; rivastigmine; galantamine; memantine; neostigmine; pyridostigmine; distigmine; ambenonium; carbachol; bethanechol; pilocarpine; cevimeline; nicotine; varenicline; disulfuram; acamprosate; naltrexone; methadone; levacetylmethadol; lofexidine; betahistine; cinnarizine; flunarizine; acetylleucine; tirilazad; riluzole; xaliproden; amifampridine; tetrabenazine; tilbroquinol; nimorazole; secnidazole; diloxanide; clefamide; etofamide; teclozan; arsthinol; difetarsone; glycobiarsol; chiniofon; emetine; phanquinone; mepacrine; atovaquone; trimetrexate; tenonitrozole; dihydroemetine; fumagillin; nitazoxanide; chloroquine; hydroxychloroquine; primaquine; amodiaquine; proguanil; quinine; mefloquine; pyrimethamine; artemisinin; artemether; artesunate; artemotil; artenimol; halofantrine; benznidazole; nifurtimox; melarsoprol; praziquantel; oxamniquine; metrifonate; niridazole; stibophen; triclabendazole; mebendazole; albendazole; ciclobendazole; flubendazole; fenbendazole; piperazine; diethylcarbamazine; pyrantel; oxantel; levamisole; ivermectin; pyrvinium; bephenium; niclosamide; desaspidin; dichlorophen; dixanthogen; thiram; clofenotane; lindane; pyrethrum; bioallethrin; phenothrin; permethrin; malathion; quassia; cyfluthrin; cypermethrin; decamethrin; tetramethrin; diethyltoluamide; dimethylphthalate; dibutylphthalate; dibutylsuccinate; dimethylcarbate; etohexadiol; cyclopentamine; ephedrine; oxymetazoline; tetryzoline; xylometazoline; naphazoline; tramazoline; metizoline; tuaminoheptane; fenoxazoline; tymazoline; levocabastine; azelastine; antazoline; nedocromil; olopatadine; flunisolide; ritiometan; phenylpropanolamine; pseudoephedrine; ambazone; benzethonium; myristyl-benzalkonium; hexylresorcinol; fusafungine; gramicidin; orciprenaline; salbutamol; terbutaline; rimiterol; hexoprenaline; isoetarine; pirbuterol; tretoquinol; carbuterol; tulobuterol; salmeterol; formoterol; clenbuterol; reproterol; procaterol; bitolterol; indacaterol; ciclesonide; fenspiride; methoxyphenamine; bambuterol; diprophylline; proxyphylline; theophylline; aminophylline; etamiphylline; bamifylline; bufylline; doxofylline; zafirlukast; pranlukast; montelukast; ibudilast; eprozinol; omalizumab; seratrodast; roflumilast; tyloxapol; guaifenesin; ipecacuanha; senega; creosote; guaiacolsulfonate; levoverbenone; acetylcysteine; bromhexine; carbocisteine; eprazinone; mesna; ambroxol; sobrerol; domiodol; letosteine; stepronin; tiopronin; neltenexine; erdosteine; ethylmorphine; hydrocodone; codeine; normethadone; noscapine; pholcodine; dextromethorphan; thebacon; dimemorfan; acetyldihydrocodeine; benzonatate; benproperine; clobutinol; isoaminile; pentoxyverine; oxolamine; oxeladin; clofedanol; pipazetate; butamirate; fedrilate; zipeprol; dibunate; droxypropine; prenoxdiazine; dropropizine; cloperastine; meprotixol; piperidione; tipepidine; morclofone; nepinalone; levodropropizine; dimethoxanate; bromazine; diphenylpyraline; carbinoxamine; doxylamine; brompheniramine; dexchlorpheniramine; chlorphenamine; pheniramine; dexbrompheniramine; talastine; histapyrrodine; methapyrilene; alimemazine; thiethylperazine; methdilazine; hydroxyethylpromethazine; thiazinam; mequitazine; oxomemazine; buclizine; cyclizine; chlorcyclizine; meclozine; oxatomide; cetirizine; levocetirizine; cyproheptadine; phenindamine; triprolidine; pyrrobutamine; azatadine; astemizole; terfenadine; loratadine; mebhydrolin; deptropine; ketotifen; acrivastine; tritoqualine; ebastine; pimethixene; epinastine; mizolastine; fexofenadine; desloratadine; rupatadine; doxapram; nikethamide; pentetrazol; etamivan; bemegride; prethcamide; almitrine; dimefline; mepixanox; dihydrostreptomycin; micronomicin; azidamfenicol; sulfadicramide; sulfacetamide; sulfafenazol; trifluridine; interferon; fomivirsen; bibrocathol; picloxydine; medrysone; formocortal; loteprednol; pranoprofen; nepafenac; bromfenac; dipivefrine; apraclonidine; brimonidine; ecothiopate; demecarium; physostigmine; fluostigmine; aceclidine; acetylcholine; paraoxon; acetazolamide; diclofenamide; dorzolamide; brinzolamide; methazolamide; levobunolol; metipranolol; befunolol; latanoprost; unoprostone; bimatoprost; travoprost; tafluprost; dapiprazole; cyclopentolate; homatropine; tropicamide; lodoxamide; emedastine; proxymetacaine; fluorescein; hypromellose; verteporfin; anecortave; pegaptanib; ranibizumab; guaiazulen; alum; iodoheparinate; nalorphine; edetates; pralidoxime; thiosulfate; dimercaprol; obidoxime; protamine; naloxone; flumazenil; methionine; cholinesterase; glutathione; fomepizole; sugammadex; deferoxamine; deferiprone; deferasirox; sevelamer; dexrazoxane; amifostine; rasburicase; palifermin; glucarpidase; oxygen; helium; nitrogen; nalfurafine; sincalide; ceruletide; metyrapone; corticorelin; somatorelin; galactose; sulfobromophthalein; tuberculin; betazole; pentagastrin; phenolsulfonphthalein; alsactide; protirelin; secretin; bentiromide; iodamide; methiodal; diodone; metrizamide; iohexyl; iopamidol; iopromide; iotrolan; ioversol; iopentol; iodixanol; iomeprol; iobitridol; ioxilan; adipiodone; iopydol; propyliodone; iofendylate; gadodiamide; gadoteridol; mangafodipir; gadoversetamide; gadobutrol; gadofosveset; ferumoxsil; ferristene; perflubron; perflenapent.

It is a further object of the present invention to provide a compound of formula (I), (Ia), (Ib), (Ic) and/or (Id) as defined herein or a pharmaceutical composition as defined herein for the preparation of a medicament for the treatment of one or more diseases mentioned herein.

Preferably the compounds of the present invention may be used for the treatment and/or prevention of the following conditions:

respiratory tract/obstructive airways diseases and disorders including:

rhinorrhea, tracheal constriction, airway contraction, acute-, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofulous rhinitis, perennial allergic rhinitis, seasonal rhinitis (including rhinitis nervosa (hay fever) and vasomotor rhinitis), pollinosis, asthma (such as bronchial, atopic, allergic, intrinsic, extrinsic, exercise-induced, cold air-induced, occupational, bacterial infection-induced, and dust asthma particularly chronic or inveterate asthma (e.g. late asthma and airways hyper-responsiveness)), bronchitis (including chronic, acute, arachidic, catarrhal, croupus, phthinoid and eosinophilic bronchitis), cardiobronchitis, pneumoconiosis, chronic inflammatory disease of the lung which result in interstitial fibrosis, such as interstitial lung disease (ILD) (e.g., idiopathic pulmonary fibrosis, or ILD associated with rheumatoid arthritis, or other autoimmune conditions), acute lung injury (ALI), adult respiratory distress syndrome (ARDS), chronic obstructive pulmonary, airways or lung disease (CORD, COAD, COLD or COPD, such as irreversible COPD), chronic sinusitis, conjunctivitis (e.g. allergic conjunctivitis), cystic fibrosis, extrinsic allergic alveolitis (like farmer's lung and related diseases), fibroid lung, hypersensitivity lung diseases, hypersensitivity pneumonitis, idiopathic interstitial pneumonia, nasal congestion, nasal polyposis, otitis media, and cough (chronic cough associated with inflammation or iatrogenic induced), pleurisy, pulmonary congestion, emphysema, bronchiectasis, sarcoidosis, lung fibrosis, including cryptogenic fibrosing alveolitis, fibrosis complicating anti-neoplastic therapy and chronic infection, including tuberculosis and aspergillosis and other fungal infections, vasculitic and thrombotic disorders of the lung vasculature, and pulmonary hypertension, acute viral infection including the common cold, and infection due to respiratory syncytial virus, influenza, coronavirus (including SARS) and adenovirus, allergic bronchopulmonary mycosis, emphysema, diffuse panbronchiolitis, systemic anaphylaxis or hypersensitivity responses, drug allergies (e.g., to penicillin, cephalosporins), insect sting allergies, and food related allergies which may have effects remote from the gut (such as migraine, rhinitis and eczema), anaphylactic shock, vascular spasms;

bone and joint related diseases and disorders including:

osteoporosis, arthritis (including rheumatic, infectious, autoimmune, chronic, malignant), seronegative spondyloarthropathies (such as ankylosing spondylitis, rheumatoid spondylitis, psoriatic arthritis, enthesopathy, Bechet's disease, Marie-Strumpell arthritis, arthritis of inflammatory bowel disease, and Reiter's disease), systemic sclerosis, osteoarthritis, osteoarthrosis, both primary and secondary to e.g. congenital hip dysplasia, cervical and lumbar spondylitis, and low back and neck pain, Still's disease, reactive arthritis and undifferentiated spondarthropathy, septic arthritis and other infection-related arthropathies and bone disorders such as tuberculosis, including Pott's disease and Poncet's syndrome, acute and chronic crystal-induced synovitis including urate gout, calcium pyrophosphate deposition disease, and calcium apatite related tendon, bursar and synovial inflammation, primary and secondary Sjogren's syndrome, systemic sclerosis and limited scleroderma, mixed connective tissue disease, and undifferentiated connective tissue disease, inflammatory myopathies including, polymalgia rheumatica, juvenile arthritis including idiopathic inflammatory arthritides of whatever joint distribution and associated syndromes, other joint disease (such as intervertebral disc degeneration or temporomandibular joint degeneration), rheumatic fever and its systemic complications, vasculitides including giant cell arteritis, Takayasu's arteritis, polyarteritis nodosa, microscopic polyarteritis, and vasculitides to associated with viral infection, hypersensitivity reactions, cryoglobulins, paraproteins, low back pain, Familial Mediterranean fever, Muckle-Wells syndrome, and Familial Hibenian Fever, Kikuchi disease, drug-induced arthalgias, tendonititides, polychondritis, and myopathies, osteoporosis, osteomalacia like osteoporosis, osteopenia, osteogenesis imperfects, osteopetrosis, osteofibrosis, osteonecrosis, Paget's disease of bone, hypophosphatemia, Felty's syndrome, Still's disease, slack of artificial joint implant, sprain or strain of muscle or joint, tendinitis, fasciitis, periarthritis humeroscapularis, cervico-omo-brachial syndrome, tenosynovitis;

Skin and eye related diseases and disorders including:

glaucoma, ocular hypertension, cataract, retinal detachment, psoriasis (including psoriasis vulgaris, pustular psoriasis, arthritic psoriasis, erythroderma psoriaticum), palmoplantar pustulosis, xerodoma, eczematous diseases (like atopic dermatitis, ultraviolet radiation dermatitis, contact dermatitis, and seborrheic dermatitis), phytodermatitis, photodermatitis, cutaneous eosinophilias, chronic skin ulcers, cutaneous lupus erythematosus, contact hypersensitivity/allergic contact dermatitis (including sensitivity to poison ivy, sumac, or oak), and eosinophilic folliculitis (Ofuji's disease), pruritus, drug eruptions, urticaria (acute or chronic, allergic or non-allergic), acne, erythema, dermatitis herpetiformis, scleroderma, vitiligo, lichen planus, lichen sclerosus et atrophica, pyodenna gangrenosum, skin sarcoid, pemphigus, ocular pemphigus, pemphigoid, epidennolysis bullosa, angioedema, vasculitides, toxic erythemas, cutaneous eosinophilias, alopecia greata, male-pattern baldness, Sweet's syndrome, Stevens-Johnson syndrome, Weber-Christian syndrome, erythema multiforme, cellulitis, botl, infective and non infective, panniculitis, cutaneous Lymphomas, non-melanoma skin cancer and other dysplastic lesions, blepharitis, iritis, anterior and posterior uveitis, choroiditis, autoimmune, degenerative or inflammatory disorders affecting the retina, ophthalmitis including sympathetic ophthalmitis, sarcoidosis, xerosis infections including viral, fungal, and bacterial, allergic conjunctivitis, increased fibrosis, keloids, keloplasty, post-surgical scars, epidermolysis bullosa, dry eye, ocular inflammation, allergic conjunctivitis, vernal conjunctivitis, vernal keratoconjunctivitis, and giant papillary conjunctivitis, ocular angiogenesis, cornea damage and scar, all forms of macular degeneration, macular edema, macular dystrophy, abnormal wound healing, scleritis, episcleritis, pachydermia, peripheral ulcerative keratitis, fungal keratitis, herpetic keratitis, invasive aspergillosis; conical cornea, dystorphia epithelialis corneae, severe intraocular inflammation;

gastrointestinal tract and abdominal related diseases and disorders including:

celiac/coeliac disease (e.g. celiac sprue), cholecystitis, enteritis (including infectious, ischemic, radiation, drug-induced, and eosinophilic gastroenteritis), eosinophilic esophagitis, eosinophilic gastrointestinal inflammation, allergen induced diarrhea, enteropathy associated with seronegative arthropathies, gastritis, autoimmune atrophic gastritis, ischemic bowel disease, inflammatory bowel disease (Crohn's disease and ulcerative colitis), colitis, Mooren's ulcer, irritable bowel syndrome, necrotizing enterocolitis, gut ischemia, glossitis, gingivitis, periodontitis, oesophagitis, including reflux, proctitis, fibrosis and cirrhosis of the liver, pancreatitis, both acute and chronic, pancreatic fibrosis, pancreatic sclerosis, pancreatolithiasis, hepatic cirrhosis, hepatitis (congestive, autoimmune, acute, fulminant, chronic, drug-induced, alcoholic, lupoid, steatohepatitis and chronic viral), fatty liver, primary biliary cirrhosis, hepatic porphyria, and gastrointestinal related allergic disorders, spastic colon, diverticulitis, gastroenteric bleeding, Behcet's disease; partial liver resection, acute liver necrosis (e.g. necrosis caused by toxins, viral hepatitis, shock or anoxia), hemolytic uremic syndrome;

hematological disorders including:

anemias, coagulation, myeloproliferative disorders, hemorrhagic disorders, leukopenia, eosinophilic disorders, leukemias (e.g. myelogenous, lymphomas, plasma cell dyscrasias, disorders of the spleen, Banti's disease, hemophilia, purpura (including idiopathic thrombocytopenic purpura), Wiskott-Aldrich syndrome;

metabolic disorders including:

obesity, amyloidosis, disturbances of the amino and acid metabolism like branched chain disease, hyperaminoacidemia, hyperaminoaciduria, disturbances of the metabolism of urea, hyperammonemia, mucopolysaccharidoses e.g. Maroteaux-Lamy syndrome, storage disease like glycogen storage diseases and lipid storage diseases, glycogenosis I diseases like Cori's disease, malabsorption diseases like intestinal carbohydrate malabsorption, oligosaccharidase deficiency like maltase-, lactase-, sucrase-insufficiency, disorders of the metabolism of fructose, disorders of the metabolism of galactose, galactosaemia, disturbances of carbohydrate utilization like diabetes, hypoglycemia, disturbances of pyruvate metabolism, hypolipidemia, hypolipoproteinemia, hyperlipidemia, hyperlipoproteinemia, carnitine or carnitine acyltransferase deficiency, disturbances of the porphyrin metabolism, porphyrins, disturbances of the purine metabolism, lysosomal diseases, metabolic diseases of nerves and nervous systems like gangliosidoses, sphingolipidoses, sulfatidoses, leucodystrophies, Lesch-Nyhan syndrome;

cerebellar dysfunction, disturbances of brain metabolism like:

dementia, Alzheimer's disease, Huntington's chores, Parkinson's disease, Pick's disease, toxic encepha-lopathy, demyelinating neuropathies like inflammatory neuropathy, Guillain-Barre syndrome; Meniere's disease and radiculopathy, primary and secondary metabolic disorders associated with hormonal defects like any disorder stemming from either an hyperfunction or hypofunction of some hormone-secreting endocrine gland and any combination thereof. Sipple's syndrome, pituitary gland dysfunction and its effects on other endocrine glands, such as the thyroid, adrenals, ovaries, and testes, acromegaly, hyper- and hypothyroidism, euthyroid goiter, euthyroid sick syndrome, thyroiditis, and thyroid cancer, over or underproduction of the adrenal steroid hormones, adrenogenital syndrome, Cushing's syndrome, Addison's disease of the adrenal cortex, Addison's pernicious anemia, primary and secondary aldosteronism, diabetes insipidus, diabetes mellitus, carcinoid syndrome, disturbances caused by the dysfunction of the parathyroid glands, pancreatic islet cell dysfunction, diabetes, disturbances of the endocrine system of the female like estrogen deficiency, resistant ovary syndrome; muscle weakness, myotonia. Duchenne's and other muscular dystrophies, dystrophia myotonica of Steinert, mitochondrial myopathies like I disturbances of the catabolic metabolism in the muscle, carbohydrate and lipid storage myopathies, glycogenoses, myoglobinuria, malignant hyperthermia, polymyalgia rheumatics, dermatomyositis, multiple myositis, primary myocardial disease, cardiomyopathy; disorders of the ectoderm, neurofibromatosis, scleroderma and polyar teritis, Louis-Bar syndrome, von Hippel-Lindau disease, Sturge-Weber syndrome, tuberous sclerosis, amyloidosis, porphyria; sexual dysfunction of the male and female; confused states and seizures due to inappropriate secretion of antidiuretic hormone from the pituitary gland, Liddle's syndrome, Bartter's syndrome, Fanconi's I syndrome, and renal electrolyte wasting;

transplant rejection related conditions including:

acute and chronic allograft rejection following solid organ transplant, for example, transplantation of kidney, heart, liver, lung, and cornea, chronic graft versus host disease, skin graft rejection, and bone marrow transplant rejection, immunosuppresion;

genitourinary related conditions including:

nephritis (interstitial, acute interstitial (allergic), and glomerulonephritis), nephrotic syndrome, cystitis including acute and chronic (interstitial) cystitis and Hunner's ulcer, acute and chronic urethritis, prostatitis, epididymitis, oophoritis, salpingitis, vulvo vaginitis, vulvovaginal candidiasis, Peyronie's disease, and erectile dysfunction, renal disease, renal fibrosis, nephropyelitis, secondary contracted kidney, steroid dependent and steroid-resistant nephrosis, Goodpasture's syndrome;

CNS related diseases and disorders including:

neurodegenerative diseases, Alzheimer's disease and other cementing disorders including CJD and nvCJD, amyloidosis, and other demyelinating syndromes, cerebral atherosclerosis and vasculitis, temporal arteritis, myasthenia gravis, acute and chronic so pain (acute, intermittent or persistent, whether of central or peripheral origin) including post-operative, visceral pain, headache, migraine, neuralgia (including trigeminal), atypical facial pain, joint and bone pain, pain arising from cancer and tumor invasion, neuropathic pain syndromes including diabetic, post-herpetic, and HIV-associated neuropathies, neurosarcoidosis, to brain injuries, cerebrovascular diseases and their consequences, Parkinson's disease, corticobasal degeneration, motor neuron disease, dementia, including ALS (Amyotrophic lateral sclerosis), multiple sclerosis, traumatic brain injury, stroke, post-stroke, post-traumatic brain injury, and small-vessel cerebrovascular disease, dementias, vascular dementia, dementia with Lewy bodies, frontotemporal dementia and Parkinsonism linked 1 to chromosome 17, frontotemporal dementias, including Pick's disease, progressive supranuclear palsy, corticobasal degeneration, Huntington's disease, thalamic degeneration, HIV dementia, schizophrenia with dementia, and Korsakoff's psychosis, within the meaning of the definition are also considered to be CNS disorders central and peripheral nervous system complications of malignant, infectious or autoimmune processes, algesia, cerebral infarction, attack, cerebral ischemia, head injury, spinal cord injury, myelopathic muscular atrophy, Shy-Drager syndrome, Reye's syndrome, progressive multifocal leukoencephalopathy, normal pressure hydrocephalus, sclerosing panencephalitis, frontal lobe type dementia, acute anterior poliomyelitis (poliomyelitis), poliomyelitis neurosis, viral encephalitis, allergic encephalomyelitis, epileptic encephalopathies, Creutzfeldt-Jakob disease, Kuru disease, bovine spongiform encephalopathy (mad cow disease), scrapie, epilepsy, cerebral amyloid angiopathy, depression, mania, manic-depressive psychosis, hereditary cerebellar ataxia, peripheral neuropathy, Nasu-Hakola syndrome, Machado-Joseph disease;

inflammatory or immunological diseases or disorders including:

general inflammation (of the ocular, nasal, pulmonary, and gastrointestinal passages), mastocytosis/mast cell disorders (cutaneous, systemic, mast cell activation syndrome, and pediatric mast cell diseases), mastitis (mammary gland), vaginitis, vasculitis (e.g., necrotizing, cutaneous, and hypersensitivity vasculitis), Wegener granulamatosis, myyositis (including polyinyositis, dermatomyositis), basophil related diseases including basophilic leukemia and basophilic leukocytosis, and eosinophil related diseases such as Churg-Strauss syndrome, eosinophilic granuloma, lupus erythematosus (such as, systemic lupus erythematosus, subacute cutaneous lupus erythematosus, and discoid lupus erythematosus), chronic thyroiditis, Hashimoto's thyroiditis, Grave's disease, type I diabetes, complications arising from diabetes mellitus, other immune disorders, eosinophilia fasciitis, hyper IgE syndrome, Addison's disease, antiphospholipid syndrome, immunodeficiency disease, acquired immune deficiency syndrome (AIDS), leprosy, Sezary syndrome, paraneoplastic syndromes, and other autoimmune disorders, fervescence, myositis, nervous diseases selected from multiple myositis, bursitis, Evans syndrome, leukotriene B4-mediated diseases, idiopathic hypoparathyroidism, nephrotic syndrome lupus, immunosuppression;

cardiovascular diseases and disorders including:

congestive heart failure, myocardial infarction, ischemic diseases of the heart, all kinds of atrial and ventricular arrhythmias, hypertension, cerebral trauma, occlusive vascular disease, stroke, cerebrovascular disorder, atherosclerosis, restenosis, affecting the coronary and peripheral is circulation, pericarditis, myocarditis, inflammatory and auto-immune cardiomyopathies including myocardial sarcoid, endocarditis, valvulitis, and aortitis including infective (e.g. syphilitic), hypertensive vascular diseases, peripheral vascular diseases, and atherosclerosis, vasculitides, disorders of the proximal and peripheral veins including phlebitis and thrombosis, including deep vein thrombosis and complications of varicose veins, aortic aneurism, periarteritis nodosa, cardiac fibrosis, post-myocardial infarction, idiopathic cardiomyopathy; angioplasty;

oncological diseases and disorders including:

common cancers (prostate, breast, lung, ovarian, pancreatic, bowel and colon, abdomen, stomach (and any other digestive system cancers), liver, pancreas, peritoneum, endocrine glands (adrenal, parathyroid, pituitary, testicles, ovary, thymus, thyroid), eye, head, neck, nervous system (central and peripheral), lymphatic system, blood, pelvic, skin, bone, soft tissue, spleen, thoracic, urogenital, and brain tumors), breast cancer, genitourinary cancer, lung cancer, gastrointestinal cancer, epidermoid cancer, melanoma, ovarian cancer, pancreas cancer, neuroblastoma, malignancies affecting the bone marrow (including the leukaemias) and lymphoproliferative systems, such as Hodgkin's and non-Hodgkin's lymphoma, B-cell lymphoma, follicular lymphoma, metastatic disease and tumour recurrences, and paraneoplastic syndromes, as well as hypergammaglobulinemia, lymphoproliferative diseases, disorders, and/or conditions, paraproteinemias, purpura (including idiopathic thrombocytopenic purpura), Waldenstron's Macroglobulinemia, Gaucher's Disease, histiocytosis, retinoblastoma and any other hyperproliferative disease, sarcomata, cachexia, tumor growth, tumor invasion, metastasis, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia, keratoleukoma and other diseases and disorders including:

pain, migraine, sleep disorders, fever, sepsis, idiopathic thrombocytopenia pupura, post-operative adhesions, flushing, ischemic/reperfusion injury in the heart, brain, peripheral limbs, bacterial infection, viral infection, fungal infection, thrombosis, endotoxin shock, septic shock, thermal regulation including fever, Raynaud's disease, gangrene, diseases requiring anti-coagulation therapy, congestive heart failure, mucus secretion disorders, pulmonary hypotension, prostanoid-induced smooth muscle contract associated with dysmenorrhea and premature labor, premature delivery, reperfusion injury, burn, thermal injury, hemorrhage or traumatic shock, menstrual pain, menstrual cramp, dysmenorrhea, periodontosis, rickettsial infectious disease, protozoal disease, reproduction disease, toothache, pain after tooth extraction, Herpes zoster, Herpes simplex, retroperitoneal fibrosis, various radiation injuries and the like.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage may be adjusted to the individual requirements in each particular case including the specific compound being administered, the route of administration, the condition being treated, as well as the patient being treated.

Examples of pharmacologically acceptable salts of sufficiently basic compounds of formula (I), (Ia), (Ib), (Ic) and (Id) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of formula (I), (Ia), (Ib), (Ic) and (Id) may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of formula (I), (Ia), (Ib), (Ic) and (Id). Compounds of formula (I), (Ia), (Ib), (Ic) and (Id) may be solvated, especially hydrated. The hydratization/hydration may occur during the process of production or as a consequence of the hygroscopic nature of the initially water free compounds of formula (I), (Ia), (Ib), (Ic) and (Id). The solvates and/or hydrates may e.g. be present in solid or liquid form.

It should be appreciated that certain compounds of formula (I), (Ia), (Ib), (Ic) and (Id) may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention. Since the compounds of formula (I), (Ia), (Ib), (Ic) and (Id)

may contain asymmetric C-atoms, they may be present either as achiral compounds, mixtures of diastereomers, mixtures of enantiomers or as optically pure compounds. The present invention comprises both all pure enantiomers and all pure diastereomers, and also the mixtures thereof in any mixing ratio.

According to a further embodiment of the present invention, one or more hydrogen atoms of the compounds of the present invention may be replaced by deuterium. Deuterium modification improves the metabolic properties of a drug with little or no change in its intrinsic pharmacology. Deuterium substitution at specific molecular positions improves metabolic stability, reduces formation of toxic metabolites and/or increases the formation of desired active metabolites. Accordingly, the present invention also encompasses the partially and fully deuterated compounds of formula (I), (Ia), (Ib) and (Ic). The term hydrogen also encompasses deuterium.

The therapeutic use of compounds according to formula (I), (Ia), (Ib), (Ic) and (Id), their pharmacologically acceptable salts, solvates and hydrates, respectively, as well as formulations and pharmaceutical compositions also lie within the scope of the present invention.

The pharmaceutical compositions according to the present invention comprise at least one compound of formula (I), (Ia), (Ib), (Ic) and (Id) as an active ingredient and, optionally, carrier substances and/or adjuvants.

The present invention also relates to pro-drugs which are composed of a compound of formula (I), (Ia), (Ib), (Ic) and/or (Id) and at least one pharmacologically acceptable protective group which will be cleaved off under physiological conditions, such as an alkoxy-, arylalkyloxy-, acyl-, acyloxymethyl group (e.g. pivaloyloxymethyl), an 2-alkyl-, 2-aryl- or 2-arylalkyl-oxycarbonyl-2-alkylidene ethyl group or an acyloxy group as defined herein, e.g. ethoxy, benzyloxy, acetyl or acetyloxy or, especially for a compound of formula (I), (Ia), (Ib), (Ic) and/or (Id), carrying a hydroxy group (—OH): a sulfate, a phosphate (-OPO₃ or —OCH₂OPO₃) or an ester of an amino acid. Especially preferred are pro-drugs of the hydroxy group of a compound of formula (I), (Ia), (Ib), (Ic) and/or (Id).

As used herein, the term pharmaceutically acceptable ester especially refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Preferably, the present invention also relates to a prodrug, a biohydrolyzable ester, a biohydrolyzable amide, a polymorph, tautomer, stereoisomer, metabolite, N-oxide, biohydrolyzable carbamate, biohydrolyzable ether, physiologically functional derivative, atropisomer, or in vivo-hydrolysable precursor, diastereomer or mixture of diastereomers, chemically protected form, affinity reagent, complex, chelate and a stereoisomer of the compounds of formula (I), (Ia), (Ib), (Ic) and/or (Id).

As mentioned above, therapeutically useful agents that contain compounds of formula (I), (Ia), (Ib), (Ic) and/or (Id), their solvates, salts or formulations are also comprised in the scope of the present invention. In general, compounds of formula (I), (Ia), (Ib), (Ic) and/or (Id) will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 10 mg to about 10,000 mg, preferably from about 20 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

The present invention refers furthermore to compounds of formulas (II), (IIIa) and/or (IIIb) wherein $R^2$ and Cy are defined as above and PG is a protecting group.

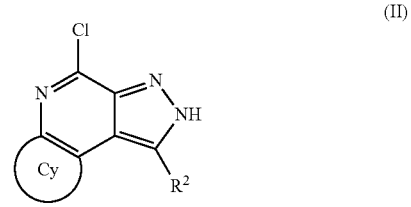

(II)

-continued

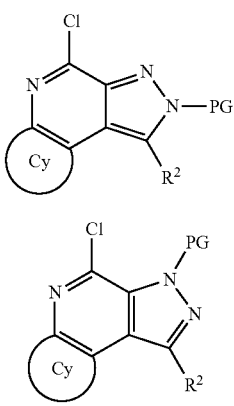

Protecting groups are known to a person skilled in the art and e.g. described in P. J. Kocienski, Protecting Groups, Georg Thieme Verlag, Stuttgart, 1994 and in T. W. Greene, P. G. M. Wuts, Protective Groups in Organic Synthesis, John Wiley & Sons, New York, 1999.

Preferably, PG is a 4-methoxy benzyl group or a Carboxybenzyl (Cbz or Z) group; especially preferably, PG is a 4-methoxy benzyl group.

Preferred compounds of formula (II) are: 4-chloro-2H-pyrazolo[3,4-c]quinoline; 4-chloro-8-methoxy-2H-pyrazolo[3,4-c]quinoline; 8-bromo-4-chloro-2H-pyrazolo[3,4-c]quinoline; 6-chloro-8H-pyrazolo[3,4-c][1,5]naphthyridine; 6-chloro-2-methoxy-8H-pyrazolo[3,4-c][1,5]naphthyridine; 4-chloro-2H-pyrazolo[3,4-c][1,7]naphthyridine; 4-chloro-7,8-diethoxy-2H-pyrazolo[3,4-c]quinoline; 4-chloro-7,8-dimethoxy-2H-pyrazolo[3,4-c]quinoline; 4-chloro-6-methoxy-2H-pyrazolo[3,4-c]quinoline; 4-chloro-7-methoxy-2H-pyrazolo[3,4-c]quinoline; 4-chloro-2H-pyrazolo[3,4-c]quinoline-8-carbonitrile; 4-chloro-9-methoxy-2H-pyrazolo[3,4-c]quinoline; 4-chloro-1-methyl-2H-pyrazolo[3,4-c]quinoline; 4-chloro-1-(trifluoromethyl)-2H-pyrazolo[3,4-c]quinoline; 4-chloro-1-nitro-2H-pyrazolo[3,4-c]quinoline; 5-chloro-1-methyl-7H-isothiazolo[5,4-b]pyrazolo[4,3-d]pyridine; 4-chloro-1-methyl-2H-pyrazolo[3,4-c]quinoline-7-carbonitrile; 4-chloro-6,8-dimethoxy-2H-pyrazolo[3,4-c]quinoline; methyl 4-chloro-2H-pyrazolo[4,3-d]thieno[3,4-b]pyridine-6-carboxylate; 4-chloro-2H-pyrazolo[3,4-c]quinolin-8-ol; 4-chloro-8-fluoro-2H-pyrazolo[3,4-c]quinoline; 4-chloro-8-iodo-2H-pyrazolo[3,4-c]quinoline; 4-chloro-7-fluoro-2H-pyrazolo[3,4-c]quinoline; 4-chloro-9-fluoro-2H-pyrazolo[3,4-c]quinoline.

Preferred compounds of formula (IIIa) and (IIIb) are: 4-chloro-2-(4-methoxybenzyl)-2H-pyrazolo[3,4-c]quinoline; 4-chloro-8-methoxy-2-(4-methoxybenzyl)-2H-pyrazolo[3,4-c]quinoline; 8-bromo-4-chloro-2-(4-methoxybenzyl)-2H-pyrazolo[3,4-c]quinoline; 6-chloro-8-(4-methoxybenzyl)-8H-pyrazolo[3,4-c][1,5]naphthyridine; 6-chloro-2-methoxy-8-(4-methoxybenzyl)-8H-pyrazolo[3,4-c][1,5]naphthyridine; 4-chloro-2-(4-methoxybenzyl)-2H-pyrazolo[3,4-c][1,7]naphthyridine; 4-chloro-7,8-diethoxy-2-(4-methoxybenzyl)-2H-pyrazolo[3,4-c]quinoline; 4-chloro-7,8-dimethoxy-2-(4-methoxybenzyl)-2H-pyrazolo[3,4-c]quinoline; 4-chloro-6-methoxy-2-(4-methoxybenzyl)-2H-pyrazolo[3,4-c]quinoline; 4-chloro-7-methoxy-2-(4-methoxybenzyl)-2H-pyrazolo[3,4-c]quinoline; 4-chloro-2-(4-methoxybenzyl)-2H-pyrazolo[3,4-c]quinoline-8-carbonitrile; 4-chloro-9-methoxy-2-(4-methoxybenzyl)-2H-pyrazolo[3,4-c]quinoline; 4-chloro-2-(4-methoxybenzyl)-1-methyl-2H-pyrazolo[3,4-c]quinoline; 4-chloro-2-(4-methoxybenzyl)-1-(trifluoromethyl)-2H-pyrazolo[3,4-c]quinoline; 4-chloro-2-(4-methoxybenzyl)-1-nitro-2H-pyrazolo[3,4-c]quinoline; 5-chloro-7-(4-methoxybenzyl)-1-methyl-7H-isothiazolo[5,4-b]pyrazolo[4,3-d]pyridine; 4-chloro-2-(4-methoxybenzyl)-1-methyl-2H-pyrazolo[3,4-c]quinoline-7-carbonitrile; 4-chloro-6,8-dimethoxy-2-(4-methoxybenzyl)-2H-pyrazolo[3,4-c]quinoline; methyl 4-chloro-2-(4-methoxybenzyl)-2H-pyrazolo[4,3-d]thieno[3,4-b]pyridine-6-carboxylate; 4-chloro-2-(4-methoxybenzyl)-2H-pyrazolo[3,4-c]quinolin-8-ol; 4-chloro-8-fluoro-2-(4-methoxybenzyl)-2H-pyrazolo[3,4-c]quinoline; 4-chloro-8-iodo-2-(4-methoxybenzyl)-2H-pyrazolo[3,4-c]quinoline; 4-chloro-7-fluoro-2-(4-methoxybenzyl)-2H-pyrazolo[3,4-c]quinoline; 4-chloro-9-fluoro-2-(4-methoxybenzyl)-2H-pyrazolo[3,4-c]quinoline.

General Synthesis

The following routes may be used to provide chloride intermediates. These chloride intermediates may then be used in an amination reaction with various amines and a subsequent deprotection to provide the final products:

Route A

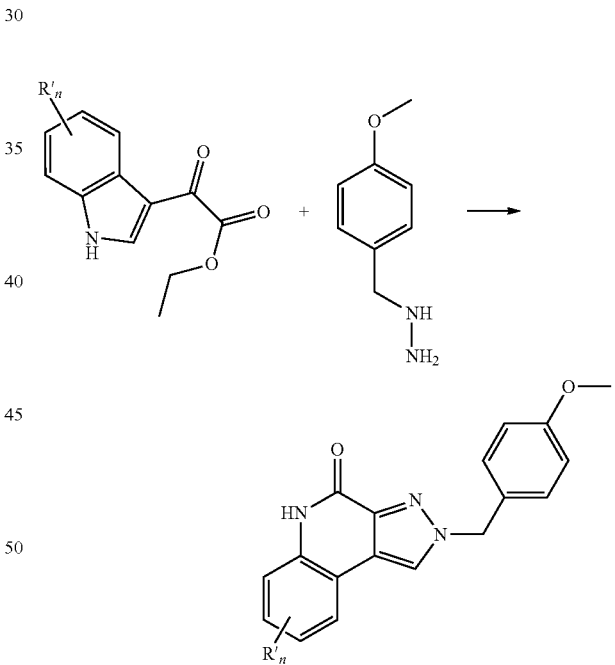

(1H-Indol-3-yl)-oxo-acetic acid ethyl ester (or alternatively methyl ester) is reacted with (4-methoxybenzyl)-hydrazine hydrochloride. This results in the formation of 2-(4-Methoxy-benzyl)-2,5-dihydro-pyrazolo[3,4-c]quinolin-4-one.

In the same way using hydrazine hydrate or hydrazine hydrochloride the corresponding none protected tricycles could be synthesized.

The residues R' correspond e.g. to residues $R^6$, $R^7$, $R^8$ and/or $R^9$ of formula (Ia) and n may be 0, 1, 2, 3 or 4.

Route B—Via Suzuki Coupling

Route B1

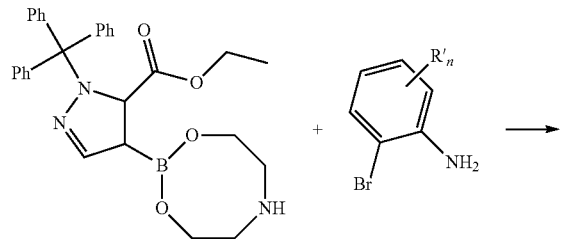

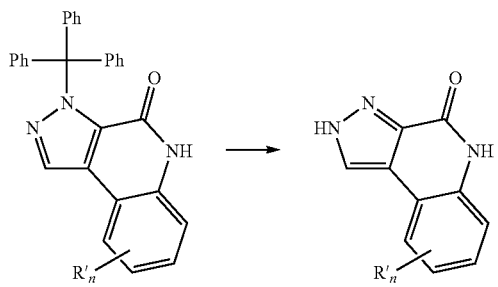

4-[1,3,6,2]Dioxazaborocan-2-yl-2-trityl-2H-pyrazole-3-carboxylic acid ethyl ester is coupled under Suzuki conditions with 2-bromo-phenylamine to provide the 2,5-dihydro-pyrazolo[3,4-c]quinolin-4-one.

Route B2

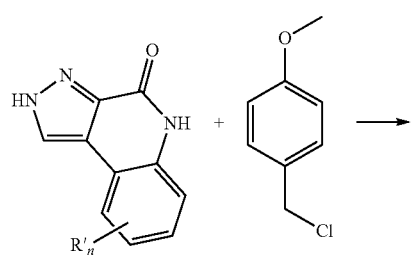

The weak trityl protection group is removed under acidic condition and substituted in Step B3.

Route B3

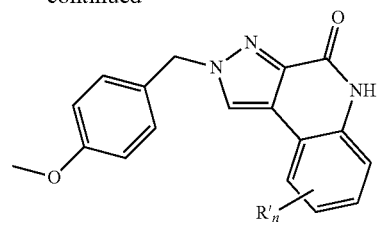

2,5-dihydro-pyrazolo[3,4-c]quinolin-4-one is reacted with para-methoxy benzylchloride. This results in the formation of 2-(4-Methoxy-benzyl)-2,5-dihydro-pyrazolo[3,4-c]quinolin-4-one

Route C—Via Suzuki Coupling

Route C1

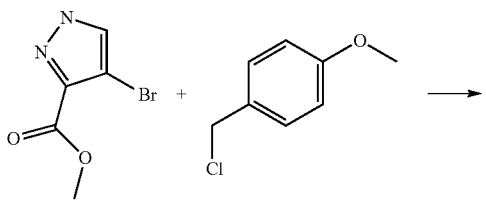

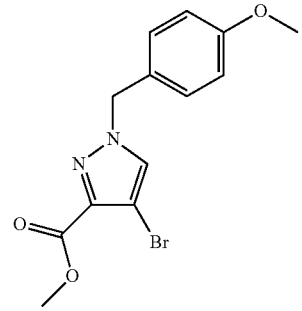

Protection of the pyrazole building block using para-methoxy-benzylchloride.

Route C2

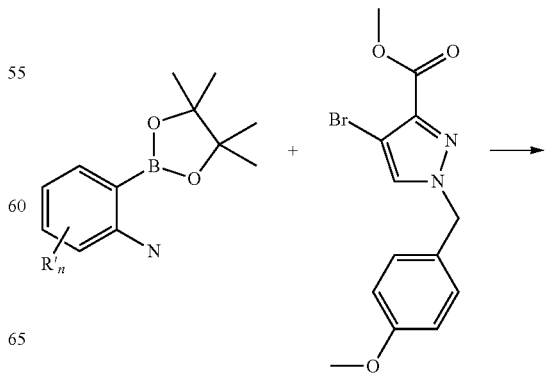

-continued

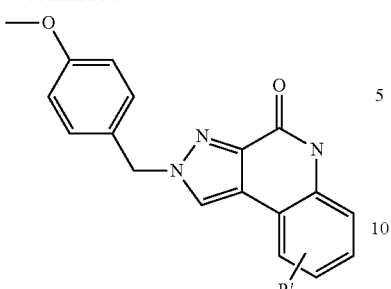

The protected pyrazole is coupled under Suzuki conditions with 2-amino-phenylboronate to provide 2-(4-Methoxy-benzyl)-2,5-dihydro-pyrazolo[3,4-c]quinolin-4-one.

Chlorination:

The provided amides, using e.g. the above routes, may be used in a chlorination step:

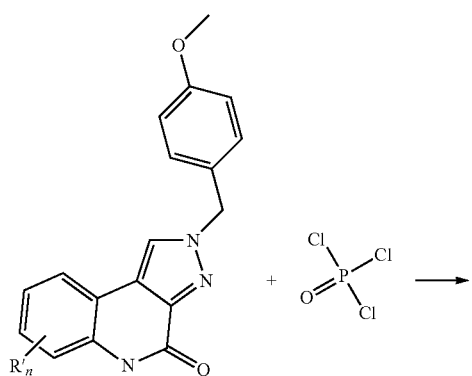

2-(4-Methoxy-benzyl)-2,5-dihydro-pyrazolo[3,4-c]quinolin-4-one is suspended in POCl3. The reaction mixture is heated resulting in the formation of 4-Chloro-2-(4-methoxy-benzyl)-2H-pyrazolo[3,4-c]quinoline.

Amination:

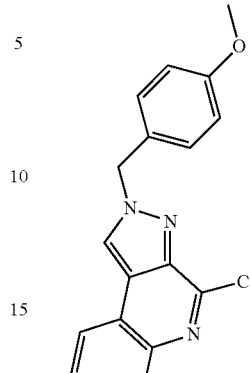

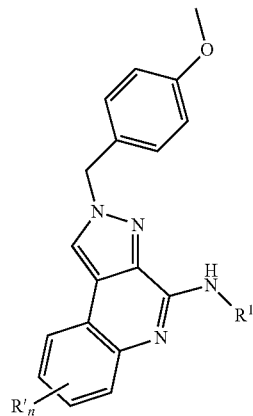

4-Chloro-2-(4-methoxy-benzyl)-2H-pyrazolo[3,4-c]quinoline is reacted with the corresponding amine to result in the formation of the protected final product.

Deprotection:

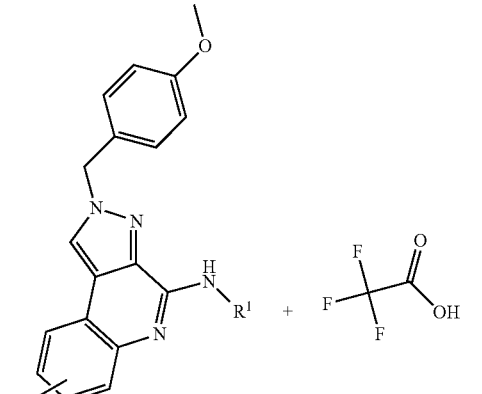

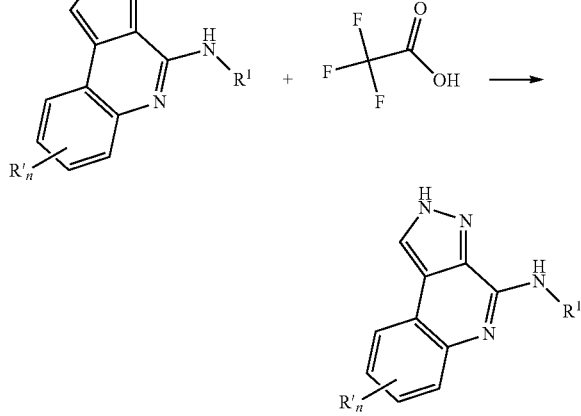

In a final step the para-methoxy-benzyl protection group is removed with TFA to provide final product for biological characterisation.

EXAMPLES

Materials and Methods

Biological Assays—Protein Kinase Assays
SYK Assay

In the assay OMNIA® KINASE ASSAY by Invitrogen Corporation (Carlsbad) the effect of invention of a compound on the phosphorylation is determined by measurement of fluorescence intensity of a chelation-enhanced fluorophore called SOX. Upon phosphorylation of the peptide by the kinase of interest, Mg2+ is chelated to form a bridge between the SOX moiety and the phosphate group that is transferred to the specific tyrosine on the peptide. The fluorescence intensity is directly proportional to the amount of peptide phosphorylation.

To the wells of an 384 well small volume plate (Greiner, Frickenhausen) are added (i) the compound under test in 5% DMSO/distilled water (2 µl), (ii) 16 µl of the master mix containing ATP, DTT, Kinase Reaction Buffer, Omina Peptide Substrate Tyr 7 resulting in a final concentration of 1 mM ATP, 0.2 mM DTT and 10 µM Peptide Substrate.

The Master Mix and the assay plate was incubated to reaction temperature before the measurement (30° C.). The reaction was started with addition of (iii) 2 µl 4 µg/ml SYK kinase (Invitrogen, Carlsbad). During measurement fluorescence intensitiy readings were collected using a TECAN M1000 at a wavelength of λex 360/λem 485 nm every 30 s for 30 minutes. The reaction velocity was plotted versus the inhibitor concentration to determine the IC50 using XLFit 5.0 (IDBS, Guildford) to fit to a sigmoidal dose response curve, and the apparent Ki values were calculated from the IC50 using the Cheng-Prusoff equation (Cheng, Y.; Prusoff, W. H. Biochem. Pharmacol. 22, 3099-3108, 1973).

The ATP dependency was determined according to Lai C-J-, Wu J C A Simple Kinetic Method for Rapid Mechanistic Analysis of Reversible Enzyme Inhibitors. Assays and Drug Dev. Technologies. 2003; 1(4):527-535. To demonstrate a competition effect of the test compounds towards ATP the corresponding test compound was used at the 50% inhibitory concentration. Assay conditions as described previously were maintained. ATP concentrations used was 1000, 333, 100, 33.3, 10, 3.3, 1 µM.

LRRK2—LRRK2 G2019S—Assay

In the assay LanthaScreen™ Eu Kinase Binding Assay by Invitrogen Corporation (Carlsbad) the effect of invention of a compound on the phosphorylation is determined by measurement of fluorescence intensity emission ratio based on the binding and displacement of a proprietary, Alexa Fluor® 647-labeled, ATP-competitive kinase inhibitor scaffold (kinase tracer) to the kinase of interest. Binding of the tracer to the kinase is detected using a europium-labeled anti-tag antibody, which binds to the kinase of interest. Simultaneous binding of both the tracer and antibody to the kinase results in a high degree of FRET (fluorescence resonance energy transfer) from the europium (Eu) donor fluorophore to the Alexa Fluor® 647 acceptor fluorophore on the kinase tracer. Binding of an inhibitor to the kinase competes for binding with the tracer, resulting in a loss of FRET. The fluorescence intensity ratio is directly proportional to the amount of peptide phosphorylation.

To the wells of an 384 well small volume plate (Greiner, Frickenhausen) are added (i) the compound under test in 5% DMSO/distilled water (5 µl), (ii) 5 µl of the kinase antibody mixture resulting in a final concentration 5 nM LRRK2 or their mutants, 2 nM EU-Anti-GST antibody in 1× kinase buffer A. The reaction was started with addition of (iii) 5 µl resulting in a final concentration of 10 nM tracer 236. The assay plate was incubated at RT for 1 h and fluorescence intensitiy readings were collected using a TECAN M1000 at two wavelengthes of λex 340/λem 615 nm and λex 340/λem 665 nm with a delay time of 100 µs and an integration time of 200 µs after 60 minutes. The emission ratio was calculated by division of the acceptor/tracer emission (665 nM) by the antibody/donor emission (615 nM). The inhibitor concentration was plotted versus the emission ratio to determine the IC50 using XLFit 5.0 (IDBS, Guildford) to fit to a sigmoidal dose response curve with a variable slope.

MYLK Assay

In the assay LanthaScreen™ Eu Kinase Binding Assay by Invitrogen Corporation (Carlsbad) the effect of invention of a compound on the phosphorylation is determined by measurement of fluorescence intensity emission ratio based on the binding and displacement of a proprietary, Alexa Fluor® 647-labeled, ATP-competitive kinase inhibitor scaffold (kinase tracer) to the kinase of interest as described above.

To the wells of an 384 well small volume plate (Greiner, Frickenhausen) are added (i) the compound under test in 5% DMSO/distilled water (5 µl), (ii) 5 µl of the kinase antibody mixture resulting in a final concentration 5 nM MYLK, 2 nM EU-Anti-GST antibody in 1× kinase buffer A. The reaction was started with addition of (iii) 5 µl resulting in a final concentration of 30 nM tracer 236. The assay plate was incubated at RT for 1 h and fluorescence intensitiy readings were collected using a TECAN M1000 at two wavelengthes of λex 340/λem 615 nm and λex 340/λem 665 nm with a delay time of 100 µs and an integration time of 200 µs after 60 minutes. The emission ratio was calculated by division of the acceptor/tracer emission (665 nM) by the antibody/donor emission (615 nM). The inhibitor concentration was plotted versus the emission ratio to determine the IC50 using XLFit 5.0 (IDBS, Guildford) to fit to a sigmoidal dose response curve with a variable slope.

Biological Assays—Cellular Assay
LAD2 Assay

The inhibition of Syk may also be determined by examining IgE mediated release of histamine in vitro using human conjunctival tissue mast cells or in LAD2 mast cells (Leuk Res. 2003 Aug. 27(8):677-82). Human conjunctival tissue mast cells (HCTMCs) are obtained using the methodology outlined in U.S. Pat. No. 5,360,720, for example.

Briefly, HCTMCs are enzymatically released from human conjunctival tissues and then partially enriched by density centrifugation over a PERCOLL® cushion. A monodispersed cell suspension is obtained from the resulting pellet, and these cells are used for a histamine release assay. Cells are exposed to drug or control prior to stimulation with anti-human IgE, which triggers mast cell degranulation and histamine release to the supernatant. Histamine is then measured in the supernatant by EIA (Beckman Coulter), RIA (Beckman Coulter) or other method known to one of skill in the art. A decrease in histamine release drug treated cells indicates that the compound has potential for further investigation.

The LAD2 mast cell line is used in much the same way with the exception that the cells are passively sensitized with human IgE myeloma prior to stimulation with anti-human IgE to cross-link receptor bound IgE and trigger degranulation.

General Procedures for Synthesis of Compounds Chromatogtaphy

The compound verification via analytical HPLC-MS was done after purification using the following instrumentation, column and method:

Analytical Method for Compound Purity
Instrumentation:
  Agilent MSD 1100
Analytical Methods:
Solvents:
  A: acetonitrile
  B: H2O
  C: 2% HCOOH in acetonitrile
  D: 0.1% NEt3 in acetonitrile
The following analytical methods were used:

Method A
  Column SunFire C18 from Waters 2.1×50 mm 2.5 µm particle size, thermostated @ 40°
Gradient:

| Time [min] | % B | % C | % D | Flow [mL/min] |
|---|---|---|---|---|
| 0 | 90 | 5 | 0 | 0.6 |
| 2.5 | 10 | 5 | 0 | 0.6 |
| 4 | 10 | 5 | 0 | 0.6 |
| 4.5 | 90 | 5 | 0 | 0.6 |
| 6 | 90 | 5 | 0 | 0.6 |

Stop time @ 7 min
MS: ESI positive, Mass scan from 100 to 800
gradient fragmentation: 50 to 125V
UV: detection @ 220 and 254 nm Method B
  Column ODS-AQ from YMC 4.0×50 mm 2.5 µm particle size, thermostated @ RT
Gradient:

| Time [min] | % B | % C | % D | Flow [mL/min] |
|---|---|---|---|---|
| 0 | 90 | 5 | 0 | 1.3 |
| 2.5 | 10 | 5 | 0 | 1.3 |
| 4 | 10 | 5 | 0 | 1.3 |
| 4.5 | 90 | 5 | 0 | 1.3 |
| 6 | 90 | 5 | 0 | 1.3 |

Stop time @ 7 min
MS: ESI positive, Mass scan from 100 to 800
gradient fragmentation: 50 to 125V
UV: detection @ 220 and 254 nm Method C
  Column ODS-AQ from YMC 2.1×50 mm 3 µm particle size, thermostated @ 40° C.
Gradient:

| Time [min] | % B | % C | % D | Flow [mL/min] |
|---|---|---|---|---|
| 0 | 90 | 5 | 0 | 0.6 |
| 2.5 | 10 | 5 | 0 | 0.6 |
| 4 | 10 | 5 | 0 | 0.6 |
| 4.5 | 90 | 5 | 0 | 0.6 |
| 6 | 90 | 5 | 0 | 0.6 |

Stop time @ 7 min
MS: ESI positive, Mass scan from 100 to 800
gradient fragmentation: 50 to 125V
UV: detection @ 220 and 254 nm Method D
  Column ODS-AQ from YMC 2.1×50 mm 3 µm particle size, incl. GuardCol 2.1×10 mm, 3 µm particle size thermostated @ 40° C.
Gradient:

| Time [min] | % B | % C | % D | Flow [mL/min] |
|---|---|---|---|---|
| 0 | 90 | 5 | 0 | 0.6 |
| 10.0 | 10 | 5 | 0 | 0.6 |
| 13.0 | 10 | 5 | 0 | 0.6 |
| 14.0 | 90 | 5 | 0 | 0.6 |

Stop time @ 15 min
MS: ESI positive, Mass scan from 100 to 800
gradient fragmentation: 50 to 125V
UV: detection @ 220 and 254 nm Method E
  Column ODS-AQ from YMC 2.1×50 mm 3 µm particle size, thermostated @ 40° C.
Gradient:

| Time [min] | % B | % C | % D | Flow [mL/min] |
|---|---|---|---|---|
| 0 | 90 | 5 | 0 | 0.6 |
| 5.0 | 10 | 5 | 0 | 0.6 |
| 7.0 | 10 | 5 | 0 | 0.6 |
| 8.0 | 90 | 5 | 0 | 0.6 |

Stop time @ 10 min
MS: ESI positive, Mass scan from 100 to 800
gradient fragmentation: 50 to 125V
UV: detection @ 220 and 254 nm Method F
  Column SunFire C18 from Waters 2.1×50 mm 2.5 µm particle size, thermostated @ 40°
Gradient:

| Time [min] | % B | % C | % D | Flow [mL/min] |
|---|---|---|---|---|
| 0 | 90 | 5 | 0 | 1.2 |
| 7.0 | 10 | 5 | 0 | 1.2 |
| 8.5 | 10 | 5 | 0 | 1.2 |
| 9.0 | 90 | 5 | 0 | 1.2 |
| 11.0 | 90 | 5 | 0 | 1.2 |

Stop time @ 12 min
MS: ESI positive, Mass scan from 100 to 800
gradient fragmentation: 50 to 125V
UV: detection @ 220 and 254 nm Method G
  Column YMC C80S 4.0×50 mm 4 µm particle size, thermostated @ 40°
Gradient:

| Time [min] | % B | % C | % D | Flow [mL/min] |
|---|---|---|---|---|
| 0 | 90 | 5 | 0 | 1.5 |
| 2.5 | 10 | 5 | 0 | 1.5 |
| 4.0 | 10 | 5 | 0 | 1.5 |
| 4.5 | 90 | 5 | 0 | 1.5 |
| 6.0 | 90 | 5 | 0 | 1.5 |

Stop time @ 6 min
MS: ESI positive, Mass scan from 100 to 800
gradient fragmentation: 50 to 125V
UV: detection @ 220 and 254 nm Method H Column Waters XBridge C18 2.1×50 mm 2.5 μm particle size,
thermostated @ 40°
Gradient:

| Time [min] | % B | % C | % D | Flow [mL/min] |
|---|---|---|---|---|
| 0 | 90 | 5 | 0 | 0.55 |
| 2.5 | 10 | 5 | 0 | 0.55 |
| 4.0 | 10 | 5 | 0 | 0.55 |
| 4.5 | 90 | 5 | 0 | 0.55 |
| 6.0 | 90 | 5 | 0 | 0.55 |

Stop time @ 6 min
MS: ESI positive, Mass scan from 100 to 800
gradient fragmentation: 50 to 125V
UV: detection @ 220 and 254 nm Method I Column Waters XBridge C18 2.1×50 mm 2.5 μm particle size,
thermostated @ 40°
Gradient:

| Time [min] | % B | % C | % D | Flow [mL/min] |
|---|---|---|---|---|
| 0 | 90 | 0 | 5 | 0.55 |
| 2.5 | 10 | 0 | 5 | 0.55 |
| 4.0 | 10 | 0 | 5 | 0.55 |
| 4.5 | 90 | 0 | 5 | 0.55 |
| 6.0 | 90 | 0 | 5 | 0.55 |

Stop time @ 6 min
MS: ESI positive, Mass scan from 100 to 800
gradient fragmentation: 50 to 125V
UV: detection @ 220 and 254 nm Method J Column Waters SunFire C18 2.1×50 mm, 2.5 μm particle size thermostated@40° C.
Gradient:

| Time[min] | % B | % C | % D | Flow[mL/min] |
|---|---|---|---|---|
| 0 | 90 | 5 | 0 | 0.6 |
| 10 | 10 | 5 | 0 | 0.6 |
| 13 | 10 | 5 | 0 | 0.6 |
| 14 | 90 | 5 | 0 | 0.6 |

Stoptime@15 min
MS: ESI positive, Mass scan from 100 to 800
gradient fragmentation: 50 to 125V
UV: detection @ 220 and 254 nm Method K Column YMC ODS-AQ 2.1×50 mm, 3 μm particle size incl. GuardCol 2.1×10 mm, 3 μm particle size thermostated@40° C.
Gradient:

| Time[min] | % B | % C | % D | Flow[mL/min] |
|---|---|---|---|---|
| 0 | 99 | 5 | 0 | 0.6 |
| 2.5 | 10 | 5 | 0 | 0.6 |
| 4 | 10 | 5 | 0 | 0.6 |
| 4.5 | 99 | 5 | 0 | 0.6 |
| 6 | 99 | 5 | 0 | 0.6 |

Stoptime@7 min
MS: ESI positive, Mass scan from 100 to 800
gradient fragmentation: 50 to 125V
UV: detection @ 220 and 254 nm Method L Column YMC TriArt C18 2.0×50 mm, 1.9 μm, #TA12SP90502WT thermostated@40° C.
Gradient:

| Time[min] | % B | % C | % D | Flow[mL/min] |
|---|---|---|---|---|
| 0 | 90 | 5 | 0 | 0.45 |
| 0.5 | 90 | 5 | 0 | 0.45 |
| 4.5 | 10 | 5 | 0 | 0.45 |
| 5.5 | 10 | 5 | 0 | 0.45 |
| 5.6 | 90 | 5 | 0 | 0.45 |

Stoptime@10 min
MS: ESI positive, Mass scan from 100 to 800
gradient fragmentation: 50 to 125V
UV: detection @ 220 and 254 nm Purification and Characterisation:

The resulting crude reaction products were purified in an automatic process using a semi-preparative HPLC-MS with mass-triggered sampling of the desired peak:

Purification Via Semi-Preparative HPLC-MS

Instrumentation:
2× Varian PrepStar SD-1
1× Dionex P580 Pump 1 Channel (MakeUP I)
1× Dionex AXP-MS (MakeUP II)
1× Dionex MSQ
1× Dionex UVD 340V—Prep Flow Cell
Gilson 215 Liquid Handler Column:
SunFire Prep C18 OBD 5 μm 19×50 mm Typical Method:
Column Flow: 30 ml/min
Solvent A: methanol, 0.3% acetic acid
Solvent B: water, 0.3% acetic acid Typical Time Table for Gradient:

| Time (min) | Solv. A | Solv. B |
|---|---|---|
| 0.0 | 30.00 | 70.00 |
| 10.0 | 100.00 | 0.00 |
| 14.0 | 100.00 | 0.00 |
| 14.4 | 30.00 | 70.00 |
| 16.4 | 30.00 | 70.00 |

Detection:
UV 254 nm, Mass Spectrometer Detector (API-ES, positive)

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different workup or purification techniques. Where reactions are carried out using microwave irradiation, the microwave used is an Initiator 60 supplied by Biotage. The actual power supplied varies during the course of the reaction in order to maintain a constant temperature.

ABBREVIATIONS

DCM=Dichloromethane
DMF=N,N-Dimethylformamide
THF=Tetrahydrofuran
MeOH=Methanol
TFA=Trifluoroacetic acid
TEA=Triethylamine
Lithium bis(trimethylsilyl)amide
rm=Reaction mixture
rt=Room temperature
AcOH=Acetic acid
MeCN=Acetonitrile
EtOH=Ethanol
EtOAc=Ethyl Acetate
LCMS=Mass spectrometry directed high pressure liquid chromatography
UV=Ultraviolet
DMSO=Dimethylsulphoxide

INTERMEDIATES

Route A

Intermediate #1

4-chloro-2-(4-methoxybenzyl)-2H-pyrazolo[3,4-c]quinoline (1H-Indol-3-yl)-oxo-acetic acid ethyl ester (10 mmol) was suspended in EtOH (25 mL) and HOAc (3 mL). The 4-methoxy-benzyl hydrazine hydrochloride (11.5 mmol) was added. The mixture was refluxed for 24 h, then stirred for 16 h at rt. The reaction was monitored by LCMS. The mixture was concentrated, resuspended in EtOH (10 mL). The solid product was collected by filtration, washed with EtOH and Et2O. The filtrated was concentrated and portioned between EtOAc and water. The organic layer was dried (Na2SO4), filtrated and concentrated. The material was pure enough for further reactions. 2-(4-Methoxy-benzyl)-2,5-dihydro-pyrazolo[3,4-c]quinolin-4-one (4.4 mmol) was suspended in POCl$_3$. The mixture was heated to 100° C. After 0.5 h LCMS showed reaction completion. The mixture was cooled to rt, and stirred overnight. The mixture was concentrated to dryness, cooled to 0° C., and quenched with ice/water. The mixture was extracted with DCM. The organic layer was washed with NaHCO3 sat. aq. and water, dried (Na2SO4) filtered and concentrated.

The product was used without further purification.

Intermediate #2

8-bromo-4-chloro-2-(4-methoxybenzyl)-2H-pyrazolo[3,4-c]quinoline 5-bromo-(1H-Indol-3-yl)-oxo-acetic acid ethyl ester (10 mmol) was suspended in EtOH (25 mL) and HOAc (3 mL). The methoxybenzyl hydrazine hydrochloride (11.5 mmol) was added. The mixture was refluxed for 24 h, then stirred for 16 h at rt. The reaction was monitored by LCMS. The mixture was concentrated, resuspended in EtOH (10 mL). The solid product was collected by filtration, washed with EtOH and Et2O. The filtrated was concentrated and portioned between EtOAc and water. The organic layer was dried (Na2SO4), filtrated and concentrated. The material was pure enough for further reactions. 8-Bromo-2-(4-Methoxy-benzyl)-2,5-dihydro-pyrazolo[3,4-c]quinolin-4-one (4.4 mmol) was suspended in POCl$_3$. The mixture was heated to 100° C. After 0.5 h LCMS showed reaction completion. The mixture was cooled to rt, and stirred overnight. The mixture was concentrated to dryness, cooled to 0° C., and quenched with ice/water. The mixture was extracted with DCM. The organic layer was washed with NaHCO3 sat. aq. and water, dried (Na2SO4) filtered and concentrated.

The product was used without further purification.

Intermediate #3

4-chloro-8-methoxy-2-(4-methoxybenzyl)-2H-pyrazolo[3,4-c]quinoline 5-methoxy-(1H-Indol-3-yl)-oxo-acetic acid ethyl ester (10 mmol) was suspended in EtOH (25 mL) and HOAc (3 mL). The methoxybenzyl hydrazine hydrochloride (11.5 mmol) was added. The mixture was refluxed for 24 h, then stirred for 16 h at rt. The reaction was monitored by LCMS. The mixture was concentrated, resuspended in EtOH (10 mL). The solid product was collected by filtration, washed with EtOH and Et2O. The filtrated was concentrated and portioned between EtOAc and water. The organic layer was dried (Na2SO4), filtrated and concentrated. The material was pure enough for further reactions. 8-Methoxy-2-(4-Methoxy-benzyl)-2,5-dihydro-pyrazolo[3,4-c]quinolin-4-one (4.4 mmol) was suspended in POCl$_3$. The mixture was heated to 100° C. After 0.5 h LCMS showed reaction completion. The mixture was cooled to rt, and stirred overnight. The mixture was concentrated to dryness, cooled to 0° C., and quenched with ice/water. The mixture was extracted with DCM. The organic layer was washed with NaHCO3 sat. aq. and water, dried (Na2SO4) filtered and concentrated.

The product was used without further purification.

The following intermediates were synthesised using the corresponding method described in the synthesis of Intermediate #1-#3

Intermediate #4

4-chloro-6-methoxy-2-(4-methoxybenzyl)-2H-pyrazolo[3,4-c]quinoline

Intermediate #5

4-chloro-7-methoxy-2-(4-methoxybenzyl)-2H-pyrazolo[3,4-c]quinoline

Intermediate #6

4-chloro-9-methoxy-2-(4-methoxybenzyl)-2H-pyrazolo[3,4-c]quinoline

Intermediate #7

4-chloro-6,8-dimethoxy-2-(4-methoxybenzyl)-2H-pyrazolo[3,4-c]quinoline

Intermediate #8

4-chloro-2-(4-methoxybenzyl)-2H-pyrazolo[3,4-c]quinolin-8-ol

Intermediate #9

4-chloro-8-fluoro-2-(4-methoxybenzyl)-2H-pyrazolo[3,4-c]quinoline

Intermediate #10

4-chloro-8-iodo-2-(4-methoxybenzyl)-2H-pyrazolo[3,4-c]quinoline

Intermediate #11

4-chloro-7-fluoro-2-(4-methoxybenzyl)-2H-pyrazolo[3,4-c]quinoline

Intermediate #12

4-chloro-9-fluoro-2-(4-methoxybenzyl)-2H-pyrazolo[3,4-c]quinoline

Route B

Intermediate #13

6-chloro-8-(4-methoxybenzyl)-8H-pyrazolo[3,4-c][1,5]naphthyridine

In a microwave vessel, 2-Bromo-3-amino-pyridine (3.14 mmol), 4-[1,3,6,2]Dioxazaborocan-2-yl-2-trityl-2H-pyrazole-3-carboxylic acid ethyl ester (1.1 eq), Pd(dppf)2Cl2xCH$_2$CL$_2$ [1,1'-Bis(diphenylphosphino)-ferrocene]dichloropalladium(II), complex with dichloromethane (0.314 mmol) were mixed together in 2M aqueous sodium carbonate (1.5 ml) and anhydrous DMF (10 ml). The mixture was heated in a microwave reactor for 30 min at 120° C.

DCM was added and filtered over diatomaceous earth. Water was added to the filtrate and the material extracted with DCM. The organic extracts were washed with brine, dried over Na2SO4 and the solvents removed in Vacuo. The resulting solid used without further purification in the next step.

The residue of the reaction was dissolved in 4M HCl in 1,4-dioxane (4 ml). The reaction mixture was steered at room temperature over night. The resulting precipitate was filtered.

A solution of the filtrate (7 mmol, 1 eq. in DMF (10 ml)) was added to a suspension of 60% NaH in Oil (3 eq.) in anhydrous DMF (25 ml) at 0° C. After the complete addition the cooling bath was removed and the mixture stirred at rt for 0.5 h and a solution of 4-methoxybenzyl chloride (PMB-Cl) (1.5 ml, 11 mmol, 1.5 eq.) was added. After stirring at rt for 1 h the reaction mixture was poured onto water (30 ml) and extracted with DCM.

The organic phase was washed with water, brine, dried and concentrated in vacuo.

The residue, crude product, was used without further purification in next step (chlorination).

The following intermediates were synthesised using the corresponding synthesis method of Intermediate #8

Intermediate #14

6-chloro-2-methoxy-8-(4-methoxybenzyl)-8H-pyrazolo[3,4-c][1,5]naphthyridine

Intermediate #15

4-chloro-2-(4-methoxybenzyl)-2H-pyrazolo[3,4-c][1,7]naphthyridine

Intermediate #16

4-chloro-7,8-diethoxy-2-(4-methoxybenzyl)-2H-pyrazolo[3,4-c]quinoline

Intermediate #17

4-chloro-7,8-dimethoxy-2-(4-methoxybenzyl)-2H-pyrazolo[3,4-c]quinoline

Route C

Intermediate #18

4-chloro-2-(4-methoxybenzyl)-2H-pyrazolo[3,4-c]quinoline-8-carbonitrile

In a microwave vessel, 2-Amino-5-cyano-phenylboronic acid (3.14 mmol), 4-Bromo-1H-pyrazole-3-carboxylic acid methyl ester (1.1 eq), Pd(dppf)2Cl2xCH$_2$CL$_2$ [1,1'-Bis(diphenylphosphino)-ferrocene]dichloropalladium(II), complex with dichloromethane (0.314 mmol) were mixed together in 2M aqueous sodium carbonate (1.5 ml) and anhydrous DMF (10 ml).

The mixture was heated in a microwave reactor for 30 min at 120° C.

DCM was added and filtered over diatomaceous earth. Water was added to the filtrate and the material extracted with DCM. The organic extracts were washed with brine, dried over Na2SO4 and the solvents removed in Vacuo. The resulting solid used without further purification in the next step.

A solution of the solid (7 mmol, 1 eq. in DMF (10 ml)) was added to a suspension of 60% NaH in Oil (3 eq.) in anhydrous DMF (25 ml) at 0° C. After the complete addition the cooling bath was removed and the mixture stirred at rt for 0.5 h and a solution of 4-methoxybenzyl chloride (PMB- Cl) (1.5 ml, 11 mmol, 1.5 eq.) was added. After stirring at rt for 1 h the reaction mixture was poured onto water (30 ml) and extracted with DCM.

The organic phase was washed with water, brine, dried and concentrated in vacuo.

The residue, crude product, was used without further purification in next step (chlorination).

Intermediate #19

4-chloro-2-(4-methoxybenzyl)-1-methyl-2H-pyrazolo[3,4-c]quinoline

Intermediate #20

4-chloro-2-(4-methoxybenzyl)-1-(trifluoromethyl)-2H-pyrazolo[3,4-c]quinoline

Intermediate #21

4-chloro-2-(4-methoxybenzyl)-1-nitro-2H-pyrazolo[3,4-c]quinoline

Intermediate #22

5-chloro-7-(4-methoxybenzyl)-1-methyl-7H-isothiazolo[5,4-b]pyrazolo[4,3-d]pyridine Intermediate #23

4-chloro-2-(4-methoxybenzyl)-1-methyl-2H-pyrazolo[3,4-c]quinoline-7-carbonitrile Intermediate #24 methyl-4-chloro-2-(4-methoxybenzyl)-2H-pyrazolo[4,3-d]thieno[3,4-b]pyridine-6-carboxylate Products Example #1

Preparation of (2H-Pyrazolo[3,4-c]quinolin-4-yl)-m-tolyl-amine 4-chloro-2-(4-methoxybenzyl)-2H-pyrazolo[3,4-c]quinoline (0.16 mmol) and m-toluidine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 274.1415 g/mol
HPLC-MS: analytical method A
rt: 2.56 min—found mass: 275 (m/z+H)

Example #2

Preparation of (2H-Pyrazolo[3,4-c]quinolin-4-yl)-(3-trifluoromethyl-phenyl)-amine 4-chloro-2-(4-methoxybenzyl)-2H-pyrazolo[3,4-c]quinoline (0.16 mmol) and 3-(trifluoromethyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 328.1052 g/mol
HPLC-MS: analytical method A
rt: 3.48 min—found mass: 329.4 (m/z+H)

Example #3

Preparation of (2H-Pyrazolo[3,4-c]quinolin-4-yl)-(3,4,5-trimethoxy-phenyl)-amine 4-chloro-2-(4-methoxybenzyl)-2H-pyrazolo[3,4-c]quinoline (0.16 mmol) and 3,4,5-trimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 350.1637 g/mol
HPLC-MS: analytical method A
rt: 2.55 min—found mass: 351.4 (m/z+H)

Example #4

Preparation of (1H-Indazol-5-yl)-(2H-pyrazolo[3,4-c]quinolin-4-yl)-amine 4-chloro-2-(4-methoxybenzyl)-2H-pyrazolo[3,4-c]quinoline (0.16 mmol) and 1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 300.1265 g/mol
HPLC-MS: analytical method E
rt: 3.34 min—found mass: 301.4 (m/z+H)

Example #5

Preparation of Phenyl-(2H-pyrazolo[3,4-c]quinolin-4-yl)-amine 4-chloro-2-(4-methoxybenzyl)-2H-pyrazolo[3,4-c]quinoline (0.16 mmol) and aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 260.1219 g/mol
HPLC-MS: analytical method A
rt: 2.43 min—found mass: 261.4 (m/z+H)

Example #6

Preparation of (1H-Indazol-6-yl)-(2H-pyrazolo[3,4-c]quinolin-4-yl)-amine 4-chloro-2-(4-methoxybenzyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 300.1265 g/mol
HPLC-MS: analytical method G
rt: 1.45 min—found mass: 301.4 (m/z+H)

Example #7

Preparation of (3-Chloro-phenyl)-(2H-pyrazolo[3,4-c]quinolin-4-yl)-amine 4-chloro-2-(4-methoxybenzyl)-2H-pyrazolo[3,4-c]quinoline (0.16 mmol) and 3-chloroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 294.0803 g/mol
HPLC-MS: analytical method A
rt: 3.15 min—found mass: 295.8 (m/z+H)

Example #8

Preparation of (7-Methyl-1H-indazol-5-yl)-(2H-pyrazolo[3,4-c]quinolin-4-yl)-amine 4-chloro-2-(4-methoxybenzyl)-2H-pyrazolo[3,4-c]quinoline (0.16 mmol) and 7-methyl-1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 314.146 g/mol
HPLC-MS: analytical method A
rt: 1.93 min—found mass: 315.4 (m/z+H)

Example #9

Preparation of (2-Methoxy-ethyl)-(2H-pyrazolo[3,4-c]quinolin-4-yl)-amine 4-chloro-2-(4-methoxybenzyl)-2H-pyrazolo[3,4-c]quinoline (0.16 mmol) and 2-methoxyethan-1-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 242.1379 g/mol
HPLC-MS: analytical method G
rt: 0.99 min—found mass: 243.3 (m/z+H)

Example #10

Preparation of (8-Methoxy-2H-pyrazolo[3,4-c]quinolin-4-yl)-(7-methyl-1H-indazol-5-yl)-amine 4-chloro-8-methoxy-2-(4-methoxybenzyl)-2H-pyrazolo[3,4-c]quinoline (0.16 mmol) and 7-methyl-1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 344.1599 g/mol
HPLC-MS: analytical method F
rt: 3.88 min—found mass: 345.4 (m/z+H)

Example #11

Preparation of N-(thiophen-2-ylmethyl)-2H-pyrazolo[3,4-c]quinolin-4-amine 4-chloro-2-(4-methoxybenzyl)-2H-pyrazolo[3,4-c]quinoline (0.16 mmol) and thiophen-2-ylmethanamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
    exact mass: 280.0939 g/mol
    HPLC-MS: analytical method G
    rt: 1.50 min—found mass: 281.4 (m/z+H)

Example #12

Preparation of (6-Methyl-1H-indazol-5-yl)-(2H-pyrazolo[3,4-c]quinolin-4-yl)-amine 4-chloro-2-(4-methoxybenzyl)-2H-pyrazolo[3,4-c]quinoline (0.16 mmol) and 6-methyl-1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
    exact mass: 314.146 g/mol
    HPLC-MS: analytical method G
    rt: 1.30 min—found mass: 315.4 (m/z+H)

Example #13

Preparation of (8-Methoxy-2H-pyrazolo[3,4-c]quinolin-4-yl)-phenyl-amine 4-chloro-8-methoxy-2-(4-methoxybenzyl)-2H-pyrazolo[3,4-c]quinoline (0.16 mmol) and aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
    exact mass: 290.1359 g/mol
    HPLC-MS: analytical method B
    rt: 1.824 min—found mass: 291.1 (m/z+H)

Example #14

Preparation of (2-Methoxy-ethyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 2-methoxyethan-1-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
    exact mass: 272.1518 g/mol
    HPLC-MS: analytical method A
    rt: 1.80 min—found mass: 273.4 (m/z+H)

Example #15

Preparation of (2H-Indazol-6-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 2H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
    exact mass: 330.1404 g/mol
    HPLC-MS: analytical method G
    rt: 1.51 min—found mass: 331.4 (m/z+H)

Example #16

Preparation of 4-(2H-Pyrazolo[3,4-c]quinolin-4-ylamino)-benzoic acid methyl ester 4-chloro-2-(4-methoxybenzyl)-2H-pyrazolo[3,4-c]quinoline (0.16 mmol) and 4-Amino-benzoic acid methyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
    exact mass: 318.1298 g/mol
    HPLC-MS: analytical method A
    rt: 3.18 min—found mass: 319.4 (m/z+H)

Example #17

Preparation of (1H-Benzoimidazol-5-yl)-(2H-pyrazolo[3,4-c]quinolin-4-yl)-amine 4-chloro-2-(4-methoxybenzyl)-2H-pyrazolo[3,4-c]quinoline (0.16 mmol) and 1H-benzo[d]imidazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
    exact mass: 300.1265 g/mol
    HPLC-MS: analytical method A
    rt: 0.46 min—found mass: 301 (m/z+H)

Example #18

Preparation of N-(thiophen-2-ylmethyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and thiophen-2-ylmethanamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 310.1079 g/mol
HPLC-MS: analytical method A
rt: 2.05 min—found mass: 311.4 (m/z+H)

Example #19

Preparation of (2H-Indazol-7-yl)-(2H-pyrazolo[3,4-c]quinolin-4-yl)-amine 4-chloro-2-(4-methoxybenzyl)-2H-pyrazolo[3,4-c]quinoline (0.16 mmol) and 2H-indazol-7-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 300.1265 g/mol
HPLC-MS: analytical method F
rt: 3.89 min—found mass: 301.4 (m/z+H)

Example #20

Preparation of (8-Methoxy-2H-pyrazolo[3,4-c]quinolin-4-yl)-(1-methyl-1H-pyrrol-2-ylmethyl)-amine 4-chloro-8-methoxy-2-(4-methoxybenzyl)-2H-pyrazolo[3,4-c]quinoline (0.16 mmol) and (1-methyl-1H-pyrrol-2-yl)methanamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 307.1684 g/mol
HPLC-MS: analytical method A
rt: 3.62 min—found mass: 308.4 (m/z+H)

Example #21

Preparation of (2H-Indazol-7-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 2H-indazol-7-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 330.1404 g/mol
HPLC-MS: analytical method A
rt: 2.10 min—found mass: 331.4 (m/z+H)

Example #22

Preparation of Benzo[1,3]dioxol-5-yl-(2H-pyrazolo[3,4-c]quinolin-4-yl)-amine 4-chloro-2-(4-methoxybenzyl)-2H-pyrazolo[3,4-c]quinoline (0.16 mmol) and benzo[d][1,3]dioxol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative
HPLC-MS and freeze dried from water/t-BuOH 4/1.
exact mass: 304.1103 g/mol
HPLC-MS: analytical method E
rt: 3.66 min—found mass: 305.1 (m/z+H)

Example #23

Preparation of (3H-Pyrazolo[3,4-c]quinolin-4-yl)-pyridin-3-yl-amine 4-chloro-2-(4-methoxybenzyl)-2H-pyrazolo[3,4-c]quinoline (0.16 mmol) and pyridin-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 261.115 g/mol
HPLC-MS: analytical method E
rt: 3.44 min—found mass: 262.3 (m/z+H)

Example #24

Preparation of (1-Methyl-1H-indazol-6-yl)-(2H-pyrazolo[3,4-c]quinolin-4-yl)-amine 4-chloro-2-(4-methoxybenzyl)-2H-pyrazolo[3,4-c]quinoline (0.16 mmol) and 1-methyl-1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 314.146 g/mol
HPLC-MS: analytical method E
rt: 3.63 min—found mass: 315.3 (m/z+H)

Example #25

Preparation of (6-Methoxy-pyridin-3-yl)-(2H-pyrazolo[3,4-c]quinolin-4-yl)-amine 4-chloro-2-(4-methoxybenzyl)-2H-pyrazolo[3,4-c]quinoline (0.16 mmol) and 6-methoxypyridin-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 291.1289 g/mol
HPLC-MS: analytical method E
rt: 3.46 min—found mass: 292.3 (m/z+H)

Example #26

Preparation of [4-(4-Methyl-piperazin-1-yl)-phenyl]-(2H-pyrazolo[3,4-c]quinolin-4-yl)-amine 4-chloro-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 358.2245 g/mol
HPLC-MS: analytical method E
rt: 3 min—found mass: 359.2 (m/z+H)

Example #27

Preparation of [4-(4-Methyl-[1,4]diazepan-1-yl)-phenyl]-(2H-pyrazolo[3,4-c]quinolin-4-yl)-amine 4-chloro-2-(4-methoxybenzyl)-2H-pyrazolo[3,4-c]quinoline (0.16 mmol) and 4-(4-methyl-1,4-diazepan-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 372.2441 g/mol
HPLC-MS: analytical method E
rt: 2.76 min—found mass: 373.2 (m/z+H)

Example #28

Preparation of (3H-Pyrazolo[3,4-c]quinolin-4-yl)-pyridin-2-yl-amine

Pyridin-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 261.115 g/mol
HPLC-MS: analytical method B
rt: 1.78 min—found mass: 262.1 (m/z+H)

Example #29

Preparation of (5-Bromo-pyridin-2-yl)-(3H-pyrazolo[3,4-c]quinolin-4-yl)-amine 5-bromopyridin-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 339.0228 g/mol
HPLC-MS: analytical method A
rt: 2.22 min—found mass: 340.0 (m/z+H)

Example #30

Preparation of Isoquinolin-3-yl-(3H-pyrazolo[3,4-c]quinolin-4-yl)-amine isoquinolin-3-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 311.133 g/mol
  HPLC-MS: analytical method A
  rt: 2.29 min—found mass: 312.1 (m/z+H)

Example #31

Preparation of (4-Methyl-pyridin-2-yl)-(3H-pyrazolo[3,4-c]quinolin-4-yl)-amine 4-methylpyridin-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 275.1345 g/mol
  HPLC-MS: analytical method B
  rt: 1.86 min—found mass: 276.1 (m/z+H)

Preparation of (4,6-Dimethyl-pyridin-2-yl)-(3H-pyrazolo[3,4-c]quinolin-4-yl)-amine 4,6-dimethylpyridin-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 289.154 g/mol
  HPLC-MS: analytical method B
  rt: 1.89 min—found mass: 290.2 (m/z+H)

Example #33

Preparation of (8-Bromo-2H-pyrazolo[3,4-c]quinolin-4-yl)-(1H-indazol-6-yl)-amine 8-bromo-4-chloro-2-(4-methoxybenzyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 378.0344 g/mol
  HPLC-MS: analytical method A
  rt: 2.39 min—found mass: 379.0 (m/z+H)

Example #34

Preparation of (1H-Benzoimidazol-5-yl)-(8-bromo-2H-pyrazolo[3,4-c]quinolin-4-yl)-amine 8-bromo-4-chloro-2-(4-methoxybenzyl)-2H-pyrazolo[3,4-c]quinoline (0.16 mmol) and 1H-benzo[d]imidazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 378.0344 g/mol
  HPLC-MS: analytical method B
  rt: 1.68 min—found mass: 379.0 (m/z+H)

Example #35

Preparation of (8-Bromo-2H-pyrazolo[3,4-c]quinolin-4-yl)-(1-methyl-1H-indazol-6-yl)-amine 8-bromo-4-chloro-2-(4-methoxybenzyl)-2H-pyrazolo[3,4-c]quinoline (0.16 mmol) and 1-methyl-1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 392.0539 g/mol
  HPLC-MS: analytical method A
  rt: 2.72 min—found mass: 393.0 (m/z+H)

Example #36

Preparation of (8-Bromo-2H-pyrazolo[3,4-c]quinolin-4-yl)-(1H-indazol-7-yl)-amine 8-bromo-4-chloro-2-(4-methoxybenzyl)-2H-pyrazolo[3,4-c]quinoline (0.16 mmol) and 1H-indazol-7-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 378.0344 g/mol
  HPLC-MS: analytical method A
  rt: 2.62 min—found mass: 379.0 (m/z+H)

Example #37

Preparation of (8-Methoxy-2H-pyrazolo[3,4-c]quinolin-4-yl)-m-tolyl-amine 4-chloro-8-methoxy-2-(4-methoxybenzyl)-2H-pyrazolo[3,4-c]quinoline (0.16 mmol) and m-toluidine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 304.1554 g/mol
HPLC-MS: analytical method A
rt: 2.10 min—found mass: 305.2 (m/z+H)

Example #38

Preparation of (1H-Indazol-5-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 330.1404 g/mol
HPLC-MS: analytical method B
rt: 1.70 min—found mass: 331.1 (m/z+H)

Example #39

Preparation of (1H-Benzoimidazol-5-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 1H-benzo[d]imidazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 330.1404 g/mol
HPLC-MS: analytical method B
rt: 1.39 min—found mass: 331.1 (m/z+H)

Example #40

Preparation of (8-Methoxy-2H-pyrazolo[3,4-c]quinolin-4-yl)-(1-methyl-1H-indazol-6-yl)-amine 4-chloro-8-methoxy-2-(4-methoxybenzyl)-2H-pyrazolo[3,4-c]quinoline (0.16 mmol) and 1-methyl-1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 344.1599 g/mol
HPLC-MS: analytical method B
rt: 1.82 min—found mass: 345.1 (m/z+H)

Example #41

Preparation of (8-Bromo-2H-pyrazolo[3,4-c]quinolin-4-yl)-(7-methyl-1H-indazol-5-yl)-amine 8-bromo-4-chloro-2-(4-methoxybenzyl)-2H-pyrazolo[3,4-c]quinoline (0.16 mmol) and 7-methyl-1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 392.0539 g/mol
HPLC-MS: analytical method A
rt: 2.29 min—found mass: 393.0 (m/z+H)

Example #42

Preparation of (8-Methoxy-2H-pyrazolo[3,4-c]quinolin-4-yl)-[4-(4-methyl-piperazin-1-yl)-phenyl]-amine 4-chloro-8-methoxy-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 388.2385 g/mol
HPLC-MS: analytical method B
rt: 1.43 min—found mass: 389.2 (m/z+H)

Example #43

Preparation of (8-Bromo-2H-pyrazolo[3,4-c]quinolin-4-yl)-[4-(4-methyl-piperazin-1-yl)-phenyl]-amine 8-bromo-4-chloro-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 436.1324 g/mol
HPLC-MS: analytical method B
rt: 1.57 min—found mass: 437.1 (m/z+H)

Example #44

Preparation of N-(8-Methoxy-2H-pyrazolo[3,4-c]quinolin-4-yl)-benzene-1,3-diamine 4-chloro-8-methoxy-2-(4-methoxybenzyl)-2H-pyrazolo[3,4-c]quinoline (0.16 mmol) and benzene-1,3-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 305.1484 g/mol
HPLC-MS: analytical method B
rt: 1.67 min—found mass: 306.1 (m/z+H)

Example #45

Preparation of (8-Bromo-2H-pyrazolo[3,4-c]quinolin-4-yl)-(1H-indazol-5-yl)-amine 8-bromo-4-chloro-2-(4-methoxybenzyl)-2H-pyrazolo[3,4-c]quinoline (0.16 mmol) and 1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 378.0344 g/mol
HPLC-MS: analytical method B
rt: 1.85 min—found mass: 379.0 (m/z+H)

Example #46

Preparation of 6-(3H-Pyrazolo[3,4-c]quinolin-4-ylamino)-4H-benzo[1,4]oxazin-3-one 4-chloro-2-(4-methoxybenzyl)-2H-pyrazolo[3,4-c]quinoline (0.16 mmol) and 6-amino-2H-benzo[b][1,4]oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 331.1223 g/mol
HPLC-MS: analytical method I
rt: 2.36 min—found mass: 332.1 (m/z+H)

Example #47

Preparation of 6-(8-Methoxy-3H-pyrazolo[3,4-c]quinolin-4-ylamino)-4H-benzo[1,4]oxazin-3-one 4-chloro-8-methoxy-2-(4-methoxybenzyl)-2H-pyrazolo[3,4-c]quinoline (0.16 mmol) and 6-amino-2H-benzo[b][1,4]oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 361.1363 g/mol
HPLC-MS: analytical method I
rt: 2.42 min—found mass: 362.1 (m/z+H)

Example #48

Preparation of (1H-Benzotriazol-5-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 1H-benzo[d][1,2,3]triazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 331.1334 g/mol
HPLC-MS: analytical method B
rt: 1.66 min—found mass: 332.1 (m/z+H)

Example #49

Preparation of 3-(8-Methoxy-2H-pyrazolo[3,4-c]quinolin-4-ylamino)-benzamidine 4-chloro-8-methoxy-2-(4-methoxybenzyl)-2H-pyrazolo[3,4-c]quinoline (0.16 mmol) and 3-aminobenzimidamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 332.1604 g/mol
HPLC-MS: analytical method B
rt: 1.44 min—found mass: 333.1 (m/z+H)

Example #50

Preparation of (8-Methoxy-2H-pyrazolo[3,4-c]quinolin-4-yl)-(4-piperidin-1-yl-phenyl)-amine 4-chloro-8-methoxy-2-(4-methoxybenzyl)-2H-pyrazolo[3,4-c]quinoline (0.16 mmol) and 4-(piperidin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 373.226 g/mol
HPLC-MS: analytical method B
rt: 1.83 min—found mass: 374.2 (m/z+H)

Example #51

Preparation of N-(8-Methoxy-2H-pyrazolo[3,4-c]quinolin-4-yl)-N',N'-dimethyl-benzene-1,4-diamine 4-chloro-8-methoxy-2-(4-methoxybenzyl)-2H-pyrazolo[3,4-c]quinoline (0.16 mmol) and N1,N1-dimethylbenzene-1,4-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 333.1874 g/mol
HPLC-MS: analytical method I
rt: 2.50 min—found mass: 334.2 (m/z+H)

Example #52

Preparation of 3-(8-Methoxy-2H-pyrazolo[3,4-c]quinolin-4-ylamino)-benzamide 4-chloro-8-methoxy-2-(4-methoxybenzyl)-2H-pyrazolo[3,4-c]quinoline (0.16 mmol) and 3-aminobenzamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 333.1423 g/mol
HPLC-MS: analytical method B
rt: 1.65 min—found mass: 334.1 (m/z+H)

Example #53

Preparation of (3,4-Dimethoxy-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 350.1638 g/mol
HPLC-MS: analytical method B
rt: 1.84 min—found mass: 351.1 (m/z+H)

Example #54

Preparation of (8-Methoxy-2H-pyrazolo[3,4-c]quinolin-4-yl)-(4-morpholin-4-yl-phenyl)-amine 4-chloro-8-methoxy-2-(4-methoxybenzyl)-2H-pyrazolo[3,4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 375.2008 g/mol
HPLC-MS: analytical method B
rt: 1.87 min—found mass: 367.2 (m/z+H)

Example #55

Preparation of (8-Methoxy-2H-pyrazolo[3,4-c]quinolin-4-yl)-(2-methyl-3H-benzoimidazol-5-yl)-amine 4-chloro-8-methoxy-2-(4-methoxybenzyl)-2H-pyrazolo[3,4-c]quinoline (0.16 mmol) and 2-methyl-1H-benzoimidazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 344.1599 g/mol
HPLC-MS: analytical method B
rt: 1.39 min—found mass: 345.2 (m/z+H)

Example #56

Preparation of (1H-Indazol-5-yl)-(2H-2,3,5,9-tetraaza-cyclopenta[a]naphthalen-4-yl)-amine 6-chloro-8-(4-methoxybenzyl)-8H-pyrazolo[3,4-c][1,5]naphthyridine (0.16 mmol) and 1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 301.1195 g/mol
HPLC-MS: analytical method B
rt: 1.48 min—found mass: 302.1 (m/z+H)

Example #57

Preparation of 4-(8-Methoxy-2H-pyrazolo[3,4-c]quinolin-4-ylamino)-benzoic-acid 4-chloro-8-methoxy-2-(4-methoxybenzyl)-2H-pyrazolo[3,4-c]quinoline (0.16 mmol) and 4-aminobenzoic (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 334.1242 g/mol
HPLC-MS: analytical method B
rt: 1.87 min—found mass: 335.1 (m/z+H)

Example #58

Preparation of 4-(8-Methoxy-2H-pyrazolo[3,4-c]quinolin-4-ylamino)-benzamide 4-chloro-8-methoxy-2-(4-methoxybenzyl)-2H-pyrazolo[3,4-c]quinoline (0.16 mmol) and 4-aminobenzamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 333.1423 g/mol
HPLC-MS: analytical method B
rt: 1.66 min—found mass: 334.1 (m/z+H)

Example #59

Preparation of 4-(8-Methoxy-2H-pyrazolo[3,4-c]quinolin-4-ylamino)-benzonitrile 4-chloro-8-methoxy-2-(4-methoxybenzyl)-2H-pyrazolo[3,4-c]quinoline (0.16 mmol) and 4-aminobenzonitrile (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 315.1279 g/mol
HPLC-MS: analytical method B
rt: 2.51 min—found mass: 317.1 (m/z+H)

Example #60

Preparation of (3-Methoxy-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 3-methoxyaniline (2 eq., 0.3 mmol) were suspended in MeOH (dry, 3 mL) in a microwave vial (2-5 ml), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 320.1498 g/mol
HPLC-MS: analytical method B
rt: 1.90 min—found mass: 321.1 (m/z+H)

Example #61

Preparation of (4-Methoxy-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-methoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 320.1498 g/mol
HPLC-MS: analytical method B
rt: 1.86 min—found mass: 321.1 (m/z+H)

Example #62

Preparation of 3-(8-Methoxy-2H-pyrazolo[3,4-c]quinolin-4-ylamino)-benzonitrile 4-chloro-8-methoxy-2-(4-methoxybenzyl)-2H-pyrazolo[3,4-c]quinoline (0.16 mmol) and 3-aminobenzonitrile (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 315.1279 g/mol
HPLC-MS: analytical method B
rt: 2.19 min—found mass: 316.1 (m/z+H)

Example #63

Preparation of Benzo[c][1,2,5]thiadiazol-5-yl-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and benzo[c][1,2,5]thiadiazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5-min at 140° C. The reaction mixture was concentrated and purified by semi-preparative HPLC-MS and freeze dried from water/t-BuOH 4/1.

exact mass: 348.0925 g/mol
HPLC-MS: analytical method B
rt: 2.47 min—found mass: 349.1 (m/z+H)

Example #64

Preparation of 3-(8-Methoxy-2H-pyrazolo[3,4-c]quinolin-4-ylamino)-1H-pyridin-2-one 4-chloro-8-methoxy-2-(4-methoxybenzyl)-2H-pyrazolo[3,4-c]quinoline (0.16 mmol) and 3-aminopyridin-2(1H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 307.1233 g/mol
HPLC-MS: analytical method B
rt: 1.69 min—found mass: 308.1 (m/z+H)

Example #65

Preparation of (2-Ethoxy-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 2-ethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 334.1693 g/mol
HPLC-MS: analytical method B
rt: 1.96 min—found mass: 335.1 (m/z+H)

Example #66

Preparation of (8-Methoxy-2H-pyrazolo[3,4-c]quinolin-4-yl)-(1H-pyrazol-3-yl)-amine 4-chloro-8-methoxy-2-(4-methoxybenzyl)-2H-pyrazolo[3,4-c]quinoline (0.16 mmol) and 1H-pyrazol-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 280.1224 g/mol
HPLC-MS: analytical method B
rt: 1.73 min—found mass: 281.1 (m/z+H)

Example #67

Preparation of (8-Methoxy-2H-pyrazolo[3,4-c]quinolin-4-yl)-(3,4,5-trimethoxy-phenyl)-amine 4-chloro-8-methoxy-2-(4-methoxybenzyl)-2H-pyrazolo[3,4-c]quinoline (0.16 mmol) and 3,4,5-trimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 380.1777 g/mol
HPLC-MS: analytical method B
rt: 1.89 min—found mass: 381.1 (m/z+H)

Example #68

Preparation of 5-(8-Methoxy-2H-pyrazolo[3,4-c]quinolin-4-ylamino)-1H-pyrazole-4-carboxamide 4-chloro-8-methoxy-2-(4-methoxybenzyl)-2H-pyrazolo[3,4-c]quinoline (0.16 mmol) and 5-amino-1H-pyrazole-4-carboxamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 323.1288 g/mol
HPLC-MS: analytical method B
rt: 1.70 min—found mass: 324.1 (m/z+H)

Example #69

Preparation of (8-Methoxy-2H-pyrazolo[3,4-c]quinolin-4-yl)-(2-phenoxy-phenyl)-amine 4-chloro-8-methoxy-2-(4-methoxybenzyl)-2H-pyrazolo[3,4-c]quinoline (0.16 mmol) and 2-phenoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 382.1674 g/mol
HPLC-MS: analytical method B
rt: 2.17 min—found mass: 383.1 (m/z+H)

Example #70

Preparation of (8-Methoxy-2H-pyrazolo[3,4-c]quinolin-4-yl)-(3-phenoxy-phenyl)-amine 4-chloro-8-methoxy-2-(4-methoxybenzyl)-2H-pyrazolo[3,4-c]quinoline (0.16 mmol) and 3-phenoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 382.1674 g/mol
HPLC-MS: analytical method B
rt: 2.36 min—found mass: 383.1 (m/z+H)

Example #71

Preparation of 5-(8-Methoxy-2H-pyrazolo[3,4-c]quinolin-4-ylamino)-1,3-dihydro-benzoimidazol-2-one 4-chloro-8-methoxy-2-(4-methoxybenzyl)-2H-pyrazolo[3,4-c]quinoline (0.16 mmol) and 5-amino-1H-benzo[d]imidazol-2(3H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 346.1348 g/mol
HPLC-MS: analytical method B
rt: 1.59 min—found mass: 347.1 (m/z+H)

Example #72

Preparation of (1H-Indol-5-yl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 1H-indol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 329.1474 g/mol
HPLC-MS: analytical method B
rt: 1.93 min—found mass: 330.1 (m/z+H)

Example #73

Preparation of (4-Aminomethyl-phenyl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and (4-Amino-benzyl)-carbamic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for min at 140° C. The reaction mixture was concentrated and purified by semi-preparative HPLC-MS and freeze dried from water/t-BuOH 4/1.
exact mass: 319.1679 g/mol
HPLC-MS: analytical method B
rt: 1.32 min—found mass: 320.2 (m/z+H)

Example #74

Preparation of (1H-Indazol-6-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 330.1404 g/mol
HPLC-MS: analytical method B
rt: 1.78 min—found mass: 331.1 (m/z+H)

Example #75

Preparation of (1H-Indol-6-yl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 1H-indol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 329.1474 g/mol
HPLC-MS: analytical method B
rt: 1.84 min—found mass: 330.1 (m/z+H)

Example #76

Preparation of N-(8-Methoxy-2H-pyrazolo[3,4-c]quinolin-4-yl)-N',N'-dimethyl-benzene-1,3-diamine 4-chloro-8-methoxy-2-(4-methoxybenzyl)-2H-pyrazolo[3,4-c]quinoline (0.16 mmol) and N1,N1-dimethylbenzene-1,3-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 333.1874 g/mol
HPLC-MS: analytical method B
rt: 1.95 min—found mass: 334.2 (m/z+H)

Example #77

Preparation of (8-Methoxy-2H-pyrazolo[3,4-c]quinolin-4-yl)-(5-phenyl-2H-pyrazol-3-yl)-amine 4-chloro-8-methoxy-2-(4-methoxybenzyl)-2H-pyrazolo[3,4-c]quinoline (0.16 mmol) and 3-phenyl-1H-pyrazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 356.1594 g/mol
HPLC-MS: analytical method B
rt: 2.06 min—found mass: 357.1 (m/z+H)

Example #78

Preparation of N,N-Diethyl-N'-(8-methoxy-2H-pyrazolo[3,4-c]quinolin-4-yl)-benzene-1,4-diamine 4-chloro-8-methoxy-2-(4-methoxybenzyl)-2H-pyrazolo[3,4-c]quinoline (0.16 mmol) and N1,N1-diethylbenzene-1,4-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 361.2265 g/mol
HPLC-MS: analytical method B
rt: 1.77 min—found mass: 334.2 (m/z+H)

Example #79

Preparation of (8-Methoxy-2H-pyrazolo[3,4-c]quinolin-4-yl)-(4-pyrrolidin-1-yl-phenyl)-amine 4-chloro-8-methoxy-2-(4-methoxybenzyl)-2H-pyrazolo[3,4-c]quinoline (0.16 mmol) and 4-(pyrrolidin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 359.2065 g/mol
HPLC-MS: analytical method B
rt: 2.15 min—found mass: 360.2 (m/z+H)

Example #80

Preparation of N-(8-Methoxy-3H-pyrazolo[3,4-c]quinolin-4-yl)-4H-[1,2,4]triazole-3,5-diamine 4H-1,2,4-triazole-3,5-diamine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 296.1279 g/mol
HPLC-MS: analytical method B
rt: 2.13 min—found mass: 297.1 (m/z+H)

Example #81

Preparation of (8-Methoxy-3H-pyrazolo[3,4-c]quinolin-4-yl)-(3-morpholin-4-yl-phenyl)-amine 4-chloro-8-methoxy-2-(4-methoxybenzyl)-2H-pyrazolo[3,4-c]quinoline (0.16 mmol) and 3-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 375.2008 g/mol
HPLC-MS: analytical method B
rt: 1.87 min—found mass: 376.2 (m/z+H)

Example #82

Preparation of (1H-Indol-5-yl)-(2H-pyrazolo[3,4-c]quinolin-4-yl)-amine 4-chloro-2-(4-methoxybenzyl)-2H-pyrazolo[3,4-c]quinoline (0.16 mmol) and 1H-indol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 299.1335 g/mol
HPLC-MS: analytical method B
rt: 1.86 min—found mass: 300.1 (m/z+H)

Example #83

Preparation of (8-Bromo-2H-pyrazolo[3,4-c]quinolin-4-yl)-(4-piperidin-1-yl-phenyl)-amine 8-bromo-4-chloro-2-(4-methoxybenzyl)-2H-pyrazolo[3,4-c]quinoline (0.16 mmol) and 4-(piperidin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 421.1198 g/mol
HPLC-MS: analytical method B
rt: 2.09 min—found mass: 422.1 (m/z+H)

Example #84

Preparation of N-(8-Bromo-2H-pyrazolo[3,4-c]quinolin-4-yl)-N',N'-dimethyl-benzene-1,4-diamine 8-bromo-4-chloro-2-(4-methoxybenzyl)-2H-pyrazolo[3,4-c]quinoline (0.16 mmol) and N1,N1-dimethylbenzene-1,4-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 381.0814 g/mol
HPLC-MS: analytical method B
rt: 2.06 min—found mass: 382.1 (m/z+H)

Example #85

Preparation of (5-Cyclobutyl-2H-pyrazol-3-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 3-cyclobutyl-1H-pyrazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 334.1805 g/mol
HPLC-MS: analytical method B
rt: 2.02 min—found mass: 335.2 (m/z+H)

Example #86

Preparation of [4-(4,5-Dihydro-1H-imidazol-2-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4,5-dihydro-1H-imidazol-2-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for min at 140° C. The reaction mixture was concentrated and purified by semi-preparative HPLC-MS and freeze dried from water/t-BuOH 4/1.

exact mass: 358.1794 g/mol
HPLC-MS: analytical method B
rt: 1.69 min—found mass: 359.2 (m/z+H)

Example #87

Preparation of 4-[4-(8-Methoxy-2H-pyrazolo[3,4-c]quinolin-4-ylamino)-phenyl]-morpholin-3-one 4-chloro-8-methoxy-2-(4-methoxybenzyl)-2H-pyrazolo[3,4-c]quinoline (0.16 mmol) and 4-(4-aminophenyl)morpholin-3-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 389.1752 g/mol
HPLC-MS: analytical method B
rt: 1.72 min—found mass: 390.2 (m/z+H)

Example #88

Preparation of (2,2-Dimethyl-3,4-dihydro-2H-benzo[1,4]thiazin-6-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 2,2-dimethyl-3,4-dihydro-2H-benzo[b][1,4]thiazin-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 391.178 g/mol
HPLC-MS: analytical method B
rt: 2.19 min—found mass: 392.1 (m/z+H)

Example #89

Preparation of (4-Morpholin-4-yl-phenyl)-(2H-2,3,5,9-tetraaza-cyclopenta[a]naphthalen-4-yl)-amine 6-chloro-8-(4-methoxybenzyl)-8H-pyrazolo[3,4-c][1,5]naphthyridine (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 346.18 g/mol
HPLC-MS: analytical method A
rt: 1.87 min—found mass: 347.2 (m/z+H)

Example #90

Preparation of (1H-Indazol-5-yl)-(8-methoxy-2H-2,3,5,9-tetraaza-cyclopenta[a]naphthalen-4-yl)-amine 6-chloro-2-methoxy-8-(4-methoxybenzyl)-8H-pyrazolo[3,4-c][1,5]naphthyridine (0.16 mmol) and 1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 331.1334 g/mol
HPLC-MS: analytical method A
rt: 1.97 min—found mass: 332.1 (m/z+H)

Example #91

Preparation of (1H-Indazol-6-yl)-(2H-2,3,5,7-tetraaza-cyclopenta[a]naphthalen-4-yl)-amine 4-chloro-2-(4-methoxybenzyl)-2H-pyrazolo[3,4-c][1,7]naphthyridine (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 301.1195 g/mol
HPLC-MS: analytical method A
rt: 1.51 min—found mass: 302.0 (m/z+H)

Example #92

Preparation of (7,8-Diethoxy-2H-pyrazolo[3,4-c]quinolin-4-yl)-(1H-indazol-6-yl)-amine 4-chloro-7,8-diethoxy-2-(4-methoxybenzyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 388.1933 g/mol
HPLC-MS: analytical method A
rt: 2.20 min—found mass: 389.2 (m/z+H)

Example #93

Preparation of 7-(8-Methoxy-2H-pyrazolo[3,4-c]quinolin-4-ylamino)-3,4-dihydro-1H-quinolin-2-one 4-chloro-8-methoxy-2-(4-methoxybenzyl)-2H-pyrazolo[3,4-c]quinoline (0.16 mmol) and 7-amino-3,4-dihydroquinolin-2(1H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 359.1614 g/mol
HPLC-MS: analytical method B
rt: 1.75 min—found mass: 360.2 (m/z+H)

Example #94

Preparation of 6-(8-Methoxy-3H-pyrazolo[3,4-c]quinolin-4-ylamino)-4H-benzo[1,4]thiazin-3-one 4-chloro-8-methoxy-2-(4-methoxybenzyl)-2H-pyrazolo[3,4-c]quinoline (0.16 mmol) and 6-amino-2H-benzo[b][1,4]thiazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 377.1134 g/mol
HPLC-MS: analytical method B
rt: 1.88 min—found mass: 378.1 (m/z+H)

Example #95

Preparation of (5-tert-Butyl-1H-pyrazol-3-yl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 5-(tert-butyl)-1H-pyrazol-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 336.2004 g/mol
HPLC-MS: analytical method B
rt: 2.05 min—found mass: 337.2 (m/z+H)

Example #96

Preparation of (8-Methoxy-3H-pyrazolo[3,4-c]quinolin-4-yl)-(5-methyl-2H-pyrazol-3-yl)-amine 4-chloro-8-methoxy-2-(4-methoxybenzyl)-2H-pyrazolo[3,4-c]quinoline (0.16 mmol) and 3-methyl-1H-pyrazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 294.1419 g/mol
HPLC-MS: analytical method B
rt: 1.82 min—found mass: 295.1 (m/z+H)

Example #97

Preparation of (5-Cyclopropyl-1H-pyrazol-3-yl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 5-cyclopropyl-1H-pyrazol-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 320.1609 g/mol
HPLC-MS: analytical method B
rt: 1.95 min—found mass: 321.1 (m/z+H)

Example #98

Preparation of (8-Methoxy-3H-pyrazolo[3,4-c]quinolin-4-yl)-[4-(1H-tetrazol-5-yl)-phenyl]-amine 4-chloro-8-methoxy-2-(4-methoxybenzyl)-2H-pyrazolo[3,4-c]quinoline (0.16 mmol) and 4-(1H-tetrazol-5-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 358.1454 g/mol
HPLC-MS: analytical method B
rt: 1.89 min—found mass: 359.1 (m/z+H)

Example #99

Preparation of (8-Bromo-2H-pyrazolo[3,4-c]quinolin-4-yl)-(1H-indol-5-yl)-amine 8-bromo-4-chloro-2-(4-methoxybenzyl)-2H-pyrazolo[3,4-c]quinoline (0.16 mmol) and 1H-indol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 377.0414 g/mol
HPLC-MS: analytical method B
rt: 2.06 min—found mass: 378.1 (m/z+H)

Example #100

Preparation of Benzo[1,3]dioxol-5-yl-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and benzo[d][1,3]dioxol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 334.1242 g/mol
HPLC-MS: analytical method B
rt: 1.87 min—found mass: 335.1 (m/z+H)

Example #101

Preparation of (2,3-Dihydro-benzo[1,4]dioxin-6-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 2,3-dihydrobenzo[b][1,4]dioxin-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 348.1438 g/mol
HPLC-MS: analytical method B
rt: 1.89 min—found mass: 349.1 (m/z+H)

Example #102

Preparation of (8-Methoxy-2H-pyrazolo[3,4-c]quinolin-4-yl)-[4-(1-methyl-piperidin-4-yl)-phenyl]-amine 4-chloro-8-methoxy-2-(4-methoxybenzyl)-2H-pyrazolo[3,4-c]quinoline (0.16 mmol) and 4-(1-methylpiperidin-4-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 387.2455 g/mol
HPLC-MS: analytical method B
rt: 1.98 min—found mass: 388.2 (m/z+H)

Example #103

Preparation of (8-Methoxy-3H-pyrazolo[3,4-c]quinolin-4-yl)-(6-morpholin-4-yl-pyridin-3-yl)-amine 4-chloro-8-methoxy-2-(4-methoxybenzyl)-2H-pyrazolo[3,4-c]quinoline (0.16 mmol) and 6-morpholinopyridin-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 376.1938 g/mol
HPLC-MS: analytical method B
rt: 1.75 min—found mass: 377.2 (m/z+H)

Example #104

Preparation of [4-(2-Methoxy-ethoxy)-phenyl]-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(2-methoxyethoxy)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 364.1833 g/mol
HPLC-MS: analytical method B
rt: 1.90 min—found mass: 365.2 (m/z+H)

Example #105

Preparation of (4-Ethoxy-3-methoxy-phenyl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-ethoxy-3-methoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 364.1832 g/mol
HPLC-MS: analytical method B
rt: 1.99 min—found mass: 365.2 (m/z+H)

Example #106

Preparation of 1-[(4-(8-Methoxy-3H-pyrazolo[3,4-c]quinolin-4-ylamino)-phenyl]-pyrrolidin-2-one 4-chloro-8-methoxy-2-(4-methoxybenzyl)-2H-pyrazolo[3,4-c]quinoline (0.16 mmol) and 1-(4-aminophenyl)pyrrolidin-2-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 373.1808 g/mol
HPLC-MS: analytical method B
rt: 1.81 min—found mass: 374.2 (m/z+H)

Example #107

Preparation of (8-Methoxy-3H-pyrazolo[3,4-c]quinolin-4-yl)-(4-thiomorpholin-4-yl-phenyl)-amine 4-chloro-8-methoxy-2-(4-methoxybenzyl)-2H-pyrazolo[3,4-c]quinoline (0.16 mmol) and 4-thiomorpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 391.1779 g/mol
HPLC-MS: analytical method B
rt: 2.10 min—found mass: 392.2 (m/z+H)

Example #108

Preparation of 5-(8-Methoxy-3H-pyrazolo[3,4-c]quinolin-4-ylamino)-3H-benzooxazol-2-one 4-chloro-8-methoxy-2-(4-methoxybenzyl)-2H-pyrazolo[3,4-c]quinoline (0.16 mmol) and 5-aminobenzo[d]oxazol-2(3H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 347.1168 g/mol
HPLC-MS: analytical method B
rt: 1.74 min—found mass: 348.1 (m/z+H)

Example #109

Preparation of (3,4-Dihydro-2H-benzo[1,4]oxazin-6-yl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 6-Amino-2,3-dihydro-benzo[1,4]oxazine-4-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 347.1619 g/mol
HPLC-MS: analytical method B
rt: 1.87 min—found mass: 348.2 (m/z+H)

Example #110

Preparation of 7-(8-Methoxy-3H-pyrazolo[3,4-c]quinolin-4-ylamino)-quinazolin-4-ol 4-chloro-8-methoxy-2-(4-methoxybenzyl)-2H-pyrazolo[3,4-c]quinoline (0.16 mmol) and 7-aminoquinazolin-4-ol (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 358.1343 g/mol
HPLC-MS: analytical method B
rt: 1.88 min—found mass: 359.2 (m/z+H)

Example #111

Preparation of [4-(1,1-Dioxo-1lambda-6-thiomorpholin-4-yl)-phenyl]-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-aminophenyl)thiomorpholine
1,1 dioxide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 423.1667 g/mol
HPLC-MS: analytical method B
rt: 1.78 min—found mass: 424.1 (m/z+H)

Example #112

Preparation of 2-[4-(8-Methoxy-3H-pyrazolo[3,4-c]quinolin-4-ylamino)-phenyl]-acetamide 4-chloro-8-methoxy-2-(4-methoxybenzyl)-2H-pyrazolo[3,4-c]quinoline (0.16 mmol) and 2-(4-aminophenyl)acetamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 347.1619 g/mol
HPLC-MS: analytical method B
rt: 1.64 min—found mass: 348.2 (m/z+H)

Example #113

Preparation of 3-(8-Methoxy-3H-pyrazolo[3,4-c]quinolin-4-ylamino)-phenol 4-chloro-8-methoxy-2-(4-methoxybenzyl)-2H-pyrazolo[3,4-c]quinoline (0.16 mmol) and 3-aminophenol (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 306.1303 g/mol
HPLC-MS: analytical method B
rt: 1.76 min—found mass: 307.1 (m/z+H)

Example #114

Preparation of (3,4-Diethoxy-phenyl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 3,4-diethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 378.2027 g/mol
HPLC-MS: analytical method B
rt: 2.04 min—found mass: 379.2 (m/z+H)

Example #115

Preparation of (8-Bromo-2H-pyrazolo[3,4-c]quinolin-4-yl)-(4-morpholin-4-yl-phenyl)-amine 8-bromo-4-chloro-2-(4-methoxybenzyl)-2H-pyrazolo[3,4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 423.0947 g/mol
HPLC-MS: analytical method B
rt: 2.05 min—found mass: 424.1 (m/z+H)

Example #116

Preparation of 6-(8-Bromo-2H-pyrazolo[3,4-c]quinolin-4-ylamino)-4H-benzo[1,4]oxazin-3-one 8-bromo-4-chloro-2-(4-methoxybenzyl)-2H-pyrazolo[3,4-c]quinoline (0.16 mmol) and 6-amino-2H-benzo[b][1,4]oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 409.0302 g/mol
HPLC-MS: analytical method B
rt: 1.98 min—found mass: 410.0 (m/z+H)

Example #117

Preparation of 6-(8-Methoxy-2H-pyrazolo[3,4-c]
quinolin-4-ylamino)-1H-benzo[d][1,3]oxazine-2,4-
dione 4-chloro-8-methoxy-2-(4-methoxybenzyl)-2H-pyrazolo
[3,4-c]quinoline (0.16 mmol) and 6-amino-1H-benzo[d][1,
3]oxazine-2,4-dione (2 eq., 0.3 mmol) were suspended in
MeOH (dry, 3 mL) in a microwave vial (2-5 mL), HCl in
dioxane (4M, 3 drops) was added. The reaction mixture was
irradiated in a microwave reactor for 5 min at 140° C. The
reaction mixture was evaporated and used without further
purification. The residue was dissolved in TFA (3 mL). The
reaction mixture was irradiated in a microwave reactor for 5
min at 140° C. The reaction mixture was concentrated and
purified by semi-preparative HPLC-MS and freeze dried
from water/t-BuOH 4/1.
exact mass: 375.1107 g/mol
HPLC-MS: analytical method B
rt: 1.77 min—found mass: 376.1 (m/z+H)

Example #118

Preparation of 2-Methoxy-5-(8-methoxy-2H-pyra-
zolo[3,4-c]quinolin-4-ylamino)-phenol 4-chloro-8-methoxy-2-(4-methoxybenzyl)-2H-pyrazolo
[3,4-c]quinoline (0.16 mmol) and 5-amino-2-methoxyphe-
nol (2 eq., 0.3 mmol) were suspended in MeOH (dry, 3 mL)
in a microwave vial (2-5 mL), HCl in dioxane (4M, 3 drops)
was added. The reaction mixture was irradiated in a micro-
wave reactor for 5 min at 140° C. The reaction mixture was
evaporated and used without further purification. The resi-
due was dissolved in TFA (3 mL). The reaction mixture was
irradiated in a microwave reactor for 5 min at 140° C. The
reaction mixture was concentrated and purified by semi-
preparative HPLC-MS and freeze dried from water/t-BuOH
4/1.
exact mass: 336.1442 g/mol
HPLC-MS: analytical method B
rt: 1.74 min—found mass: 337.1 (m/z+H)

Example #119

Preparation of (8-Bromo-2H-pyrazolo[3,4-c]quino-
lin-4-yl)-(1H-pyrazol-3-yl)-amine 8-bromo-4-chloro-2-(4-methoxybenzyl)-2H-pyrazolo[3,
4-c]quinoline (0.16 mmol) and 1H-pyrazol-3-amine (2 eq.,
0.3 mmol) were suspended in MeOH (dry, 3 mL) in a
microwave vial (2-5 mL), HCl in dioxane (4M, 3 drops) was
added. The reaction mixture was irradiated in a microwave
reactor for 5 min at 140° C. The reaction mixture was
evaporated and used without further purification. The resi-
due was dissolved in TFA (3 mL). The reaction mixture was
irradiated in a microwave reactor for 5 min at 140° C. The
reaction mixture was concentrated and purified by semi-
preparative HPLC-MS and freeze dried from water/t-BuOH
4/1.
exact mass: 328.0163 g/mol
HPLC-MS: analytical method B
rt: 1.84 min—found mass: 329.0 (m/z+H)

Example #120

Preparation of N-[3-(8-Methoxy-3H-pyrazolo[3,4-c]
quinolin-4-ylamino)-phenyl]-acetamide 4-chloro-8-methoxy-2-(4-methoxybenzyl)-2H-pyrazolo
[3,4-c]quinoline (0.16 mmol) and N-(3-aminophenyl)acet-
amide (2 eq., 0.3 mmol) were suspended in MeOH (dry, 3
mL) in a microwave vial (2-5 mL), HCl in dioxane (4M, 3
drops) was added. The reaction mixture was irradiated in a
microwave reactor for 5 min at 140° C. The reaction mixture
was evaporated and used without further purification. The
residue was dissolved in TFA (3 mL). The reaction mixture
was irradiated in a microwave reactor for 5 min at 140° C.
The reaction mixture was concentrated and purified by
semi-preparative HPLC-MS and freeze dried from water/t-
BuOH 4/1.
exact mass: 347.1618 g/mol
HPLC-MS: analytical method B
rt: 1.73 min—found mass: 348.1 (m/z+H)

Example #121

Preparation of (8-Methoxy-3H-pyrazolo[3,4-c]qui-
nolin-4-yl)-(1H-pyrazol-4-yl)-amine 4-chloro-8-methoxy-2-(4-methoxybenzyl)-2H-pyrazolo
[3,4-c]quinoline (0.16 mmol) and 1H-pyrazol-4-amine (2
eq., 0.3 mmol) were suspended in MeOH (dry, 3 mL) in a
microwave vial (2-5 mL), HCl in dioxane (4M, 3 drops) was
added. The reaction mixture was irradiated in a microwave
reactor for 5 min at 140° C. The reaction mixture was
evaporated and used without further purification. The resi-
due was dissolved in TFA (3 mL). The reaction mixture was
irradiated in a microwave reactor for 5 min at 140° C. The
reaction mixture was concentrated and purified by semi-
preparative HPLC-MS and freeze dried from water/t-BuOH
4/1.
exact mass: 280.1224 g/mol
HPLC-MS: analytical method B
rt: 1.54 min—found mass: 281.1 (m/z+H)

Example #122

Preparation of (3,4-Dimethoxy-phenyl)-(7,8-dime-
thoxy-2H-pyrazolo[3,4-c]quinolin-4-yl)-amine 4-chloro-7,8-dimethoxy-2-(4-methoxybenzyl)-2H-pyra-
zolo[3,4-c]quinoline (0.16 mmol) and 3,4-dimethoxyaniline
(2 eq., 0.3 mmol) were suspended in MeOH (dry, 3 mL) in
a microwave vial (2-5 mL), HCl in dioxane (4M, 3 drops)
was added. The reaction mixture was irradiated in a micro-
wave reactor for 5 min at 140° C. The reaction mixture was
evaporated and used without further purification. The resi-
due was dissolved in TFA (3 mL). The reaction mixture was
irradiated in a microwave reactor for 5 min at 140° C. The
reaction mixture was concentrated and purified by semi-
preparative HPLC-MS and freeze dried from water/t-BuOH
4/1.
exact mass: 380.1776 g/mol
HPLC-MS: analytical method I
rt: 2.19 min—found mass: 381.2 (m/z+H)

Example #123

Preparation of (3,4-Dimethoxy-phenyl)-(2H-2,3,5,9-
tetraaza-cyclopenta[a]naphthalen-4-yl)-amine 6-chloro-8-(4-methoxybenzyl)-8H-pyrazolo[3,4-c][1,5]
naphthyridine (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 321.1428 g/mol
HPLC-MS: analytical method A
rt: 1.92 min—found mass: 322.1 (m/z+H)

Example #124

Preparation of (4-Fluoro-3-methoxy-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-fluoro-3-methoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 338.1377 g/mol
HPLC-MS: analytical method B
rt: 1.97 min—found mass: 339.1 (m/z+H)

Example #125

Preparation of (3-Fluoro-4-methoxy-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 3-fluoro-4-methoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 338.1377 g/mol
HPLC-MS: analytical method B
rt: 1.98 min—found mass: 339.1 (m/z+H)

Example #126

Preparation of (8-Methoxy-2H-pyrazolo[3,4-c]quinolin-4-yl)-(1-methyl-1H-benzoimidazol-5-yl)-amine 4-chloro-8-methoxy-2-(4-methoxybenzyl)-2H-pyrazolo[3,4-c]quinoline (0.16 mmol) and 1-methyl-1H-benzoimidazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 344.1599 g/mol
HPLC-MS: analytical method B
rt: 1.51 min—found mass: 345.2 (m/z+H)

Example #127

Preparation of 1-[3-(8-Methoxy-2H-pyrazolo[3,4-c]quinolin-4-ylamino)-phenyl]-ethanone 4-chloro-8-methoxy-2-(4-methoxybenzyl)-2H-pyrazolo[3,4-c]quinoline (0.16 mmol) and 1-(3-aminophenyl)ethan-1-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 332.1493 g/mol
HPLC-MS: analytical method B
rt: 1.92 min—found mass: 333.1 (m/z+H)

Example #128

Preparation of N-[4-(8-Methoxy-2H-pyrazolo[3,4-c]quinolin-4-ylamino)-phenyl]-acetamide 4-chloro-8-methoxy-2-(4-methoxybenzyl)-2H-pyrazolo[3,4-c]quinoline (0.16 mmol) and N-(4-aminophenyl)acetamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 347.1618 g/mol
HPLC-MS: analytical method B
rt: 1.73 min—found mass: 348.2 (m/z+H)

Example #129

Preparation of (8-Methoxy-2H-pyrazolo[3,4-c]quinolin-4-yl)-pyridin-2-yl-amine

Pyridin-2-yl-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 291.1289 g/mol
  HPLC-MS: analytical method B
  rt: 1.937 min—found mass: 292.1 (m/z+H)

Example #130

Preparation of (8-Methoxy-2H-pyrazolo[3,4-c]quinolin-4-yl)-(1H-pyrrolo[2,3-b]pyridin-6-yl)-amine 1H-pyrrolo[2,3-b]pyridin-6-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 330.1404 g/mol
  HPLC-MS: analytical method B
  rt: 2.352 min—found mass: 331.1 (m/z+H)

Example #131

Preparation of 3-(8-Methoxy-2H-pyrazolo[3,4-c]quinolin-4-ylamino)-benzenesulfonamide 4-chloro-8-methoxy-2-(4-methoxybenzyl)-2H-pyrazolo[3,4-c]quinoline (0.16 mmol) and 3-aminobenzenesulfonamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 369.1087 g/mol
  HPLC-MS: analytical method B
  rt: 1.791 min—found mass: 370.1 (m/z+H)

Example #132

Preparation of 4-(8-Methoxy-2H-pyrazolo[3,4-c]quinolin-4-ylamino)-benzenesulfonamide 4-chloro-8-methoxy-2-(4-methoxybenzyl)-2H-pyrazolo[3,4-c]quinoline (0.16 mmol) and 4-aminobenzenesulfonamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 369.1087 g/mol
  HPLC-MS: analytical method B
  rt: 1.881 min—found mass: 370.1 (m/z+H)

Example #133

Preparation of (7,8-Dimethoxy-2H-pyrazolo[3,4-c]quinolin-4-yl)-(4-morpholin-4-yl-phenyl)-amine 4-chloro-7,8-dimethoxy-2-(4-methoxybenzyl)-2H-pyrazolo[3,4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 405.2148 g/mol
  HPLC-MS: analytical method B
  rt: 1.83 min—found mass: 406 (m/z+H)

Example #134

Preparation of (7,8-Dimethoxy-2H-pyrazolo[3,4-c]quinolin-4-yl)-[4-(4-methyl-piperazin-1-yl)-phenyl]-amine 4-chloro-7,8-dimethoxy-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 418.2524 g/mol
  HPLC-MS: analytical method B
  rt: 1.43 min—found mass: 419 (m/z+H)

Example #135

Preparation of N-(7,8-Dimethoxy-2H-pyrazolo[3,4-c]quinolin-4-yl)-N',N'-dimethyl-benzene-1,4-diamine 4-chloro-7,8-dimethoxy-2-(4-methoxybenzyl)-2H-pyrazolo[3,4-c]quinoline (0.16 mmol) and N1,N1-dimethylbenzene-1,4-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 363.2013 g/mol
HPLC-MS: analytical method B
rt: 1.87 min—found mass: 364 (m/z+H)

Example #136

Preparation of (7,8-Dimethoxy-2H-pyrazolo[3,4-c] quinolin-4-yl)-(1H-indazol-6-yl)-amine 4-chloro-7,8-dimethoxy-2-(4-methoxybenzyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 360.1543 g/mol
HPLC-MS: analytical method B
rt: 1.98 min—found mass: 361 (m/z+H)

Example #137

Preparation of N-(8-Methoxy-2H-pyrazolo[3,4-c] quinolin-4-yl)-pyridine-2,6-diamine Pyridine-2,6-diamine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 306.1414 g/mol
HPLC-MS: analytical method B
rt: 1.905 min—found mass: 307.1 (m/z+H)

Example #138

Preparation of (8-Methoxy-2H-pyrazolo[3,4-c]quinolin-4-yl)-(1,2,3-trimethyl-1H-indol-5-yl)-amine 4-chloro-8-methoxy-2-(4-methoxybenzyl)-2H-pyrazolo[3,4-c]quinoline (0.16 mmol) and 1,2,3-trimethyl-1H-indol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 371.206 g/mol
HPLC-MS: analytical method B
rt: 2.207 min—found mass: 372.2 (m/z+H)

Example #139

Preparation of N2-(8-methoxy-2H-pyrazolo[3,4-c] quinolin-4-yl)pyrimidine-2,4-diamine 4-chloro-8-methoxy-2-(4-methoxybenzyl)-2H-pyrazolo[3,4-c]quinoline (0.16 mmol) and pyrimidine-2,4-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 307.1344 g/mol
HPLC-MS: analytical method B
rt: 1.695 min—found mass: 308.1 (m/z+H)

Example #140

Preparation of (8-Methoxy-2H-pyrazolo[3,4-c]quinolin-4-yl)-(5-methylsulfanyl-4H-[1,2,4]triazol-3-yl)-amine 5-(methylthio)-4H-1,2,4-triazol-3-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 327.1064 g/mol
HPLC-MS: analytical method B
rt: 2.73 min—found mass: 328.1 (m/z+H)

Example #141

Preparation of (5-Cyclopropyl-4H-[1,2,4]triazol-3-yl)-(8-methoxy-2H-pyrazolo[3,4-c]quinolin-4-yl)-amine 5-cyclopropyl-4H-1,2,4-triazol-3-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 321.154 g/mol
 HPLC-MS: analytical method B
 rt: 1.895 min—found mass: 322.1 (m/z+H)

Example #142

Preparation of N-[2-Methoxy-5-(8-methoxy-2H-pyrazolo[3,4-c]quinolin-4-ylamino)-phenyl]-acetamide 4-chloro-8-methoxy-2-(4-methoxybenzyl)-2H-pyrazolo[3,4-c]quinoline (0.16 mmol) and N-(5-amino-2-methoxy-phenyl)acetamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 377.1758 g/mol
 HPLC-MS: analytical method B
 rt: 1.793 min—found mass: 378.2 (m/z+H)

Example #143

Preparation of (1H-Benzoimidazol-2-yl)-(8-methoxy-2H-pyrazolo[3,4-c]quinolin-4-yl)-amine 1H-benzoimidazol-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 330.1404 g/mol
 HPLC-MS: analytical method B
 rt: 1.936 min—found mass: 330.2 (m/z+H)

Example #144

Preparation of (1H-Imidazol-2-yl)-(8-methoxy-2H-pyrazolo[3,4-c]quinolin-4-yl)-amine 1H-imidazol-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 280.1224 g/mol
 HPLC-MS: analytical method B
 rt: 1.924 min—found mass: 331.1 (m/z+H)

Example #145

Preparation of 1-[4-(8-Methoxy-2H-pyrazolo[3,4-c]quinolin-4-ylamino)-phenyl]-ethanone 4-chloro-8-methoxy-2-(4-methoxybenzyl)-2H-pyrazolo[3,4-c]quinoline (0.16 mmol) and 1-(4-aminophenyl)ethan-1-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 332.1493 g/mol
 HPLC-MS: analytical method B
 rt: 2.196 min—found mass: 333.1 (m/z+H)

Example #146

Preparation of (4H-Benzo[1,3]dioxin-6-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4H-benzo[d][1,3]dioxin-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 348.1438 g/mol
 HPLC-MS: analytical method B
 rt: 1.844 min—found mass: 349.1 (m/z+H)

Example #147

Preparation of (1,3-Dihydro-isobenzofuran-5-yl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 1,3-dihydroisobenzofuran-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 332.1493 g/mol
HPLC-MS: analytical method B
rt: 1.806 min—found mass: 333.1 (m/z+H)

Example #148

Preparation of (8-Methoxy-2H-pyrazolo[3,4-c]quinolin-4-yl)-(3-methyl-3H-benzoimidazol-5-yl)-amine 4-chloro-8-methoxy-2-(4-methoxybenzyl)-2H-pyrazolo[3,4-c]quinoline (0.16 mmol) and 1-methyl-1H-benzoimidazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 344.1599 g/mol
HPLC-MS: analytical method B
rt: 1.518 min—found mass: 345.1 (m/z+H)

Example #149

Preparation of (4,5-Dimethyl-thiazol-2-yl)-(8-methoxy-2H-pyrazolo[3,4-c]quinolin-4-yl)-amine 4,5-dimethylthiazol-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 325.1205 g/mol
HPLC-MS: analytical method B
rt: 2.397 min—found mass: 326.1 (m/z+H)

Example #150

Preparation of (5-Cyclopropyl-1H-pyrazol-3-yl)-(7,8-dimethoxy-2H-pyrazolo[3,4-c]quinolin-4-yl)-amine 4-chloro-7,8-dimethoxy-2-(4-methoxybenzyl)-2H-pyrazolo[3,4-c]quinoline (0.16 mmol) and 5-cyclopropyl-1H-pyrazol-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 350.1748 g/mol
HPLC-MS: analytical method A
rt: 2.05 min—found mass: 351 (m/z+H)

Example #151

Preparation of (3,4-Dihydro-2H-benzo[1,4]oxazin-6-yl)-(7,8-dimethoxy-2H-pyrazolo[3,4-c]quinolin-4-yl)-amine 4-chloro-7,8-dimethoxy-2-(4-methoxybenzyl)-2H-pyrazolo[3,4-c]quinoline (0.16 mmol) and 6-Amino-2,3-dihydro-benzo[1,4]oxazine-4-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 377.1758 g/mol
HPLC-MS: analytical method A
rt: 2.06 min—found mass: 378 (m/z+H)

Example #152

Preparation of 5-(7,8-Dimethoxy-2H-pyrazolo[3,4-c]quinolin-4-ylamino)-2-methoxy-phenol 4-chloro-7,8-dimethoxy-2-(4-methoxybenzyl)-2H-pyrazolo[3,4-c]quinoline (0.16 mmol) and 5-amino-2-methoxyphenol (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 366.1581 g/mol
HPLC-MS: analytical method A
rt: 1.96 min—found mass: 367 (m/z+H)

Example #153

Preparation of (8-Methoxy-2H-pyrazolo[3,4-c]quinolin-4-yl)-[2-methyl-4-(4-methyl-piperazin-1-yl)-phenyl]-amine 4-chloro-8-methoxy-2-(4-methoxybenzyl)-2H-pyrazolo[3,4-c]quinoline (0.16 mmol) and 2-methyl-4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 402.258 g/mol
HPLC-MS: analytical method C
rt: 1.457 min—found mass: 403.2 (m/z+H)

Example #154

Preparation of (8-Methoxy-2H-pyrazolo[3,4-c]quinolin-4-yl)-(4-methyl-pyridin-2-yl)-amine 4-methylpyridin-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 305.1484 g/mol
HPLC-MS: analytical method C
rt: 1.902 min—found mass: 306.1 (m/z+H)

Example #155

Preparation of (8-Methoxy-2H-pyrazolo[3,4-c]quinolin-4-yl)-(6-methyl-pyridin-2-yl)-amine 6-methylpyridin-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 305.1484 g/mol
HPLC-MS: analytical method C
rt: 1.964 min—found mass: 306.2 (m/z+H)

Example #156

Preparation of (4,6-Dimethyl-pyridin-2-yl)-(8-methoxy-2H-pyrazolo[3,4-c]quinolin-4-yl)-amine 4,6-dimethylpyridin-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 319.1679 g/mol
HPLC-MS: analytical method C
rt: 1.996 min—found mass: 320.2 (m/z+H)

Example #157

Preparation of (8-Methoxy-2H-pyrazolo[3,4-c]quinolin-4-yl)-(4-methyl-thiazol-2-yl)-amine 4-methylthiazol-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 311.1009 g/mol
HPLC-MS: analytical method C
rt: 2.382 min—found mass: 312.1 (m/z+H)

Example #158

Preparation of (8-Methoxy-2H-pyrazolo[3,4-c]quinolin-4-yl)-(4,5,6,7-tetrahydro-benzothiazol-2-yl)-amine 4,5,6,7-tetrahydrobenzo[d]thiazol-2-amine (0.4 mmol 2 eq.) was dissolved in THF (dry, 3 mL) in a microwave vial (2-5 mL) LiHMDS 2M in THF (0.6 mmol 4 eq.) was added. The mixture was stirred for 20 min at r.t. and then added to a solution of 4-chloro-8-methoxy-2-(4-methoxybenzyl)-2H-pyrazolo[3,4-c]quinoline (0.16 mmol, 1 eq.) in pyridine (2 mL). The reaction mixture was irradiated in a microwave reactor for 20 min at 200° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 351.1395 g/mol
HPLC-MS: analytical method C
rt: 2.642 min—found mass: 352.1 (m/z+H)

Example #159

Preparation of (8-Methoxy-2H-pyrazolo[3,4-c]quinolin-4-yl)-(4-phenoxy-phenyl)-amine 4-chloro-8-methoxy-2-(4-methoxybenzyl)-2H-pyrazolo[3,4-c]quinoline (0.16 mmol) and 4-phenoxyaniline (2 eq., 0.3 mmol) were suspended in MeOH (dry, 3 mL) in a microwave vial (2-5 ml), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 382.1674 g/mol
HPLC-MS: analytical method C
rt: 2.223 min—found mass: 383.2 (m/z+H)

Example #160

Preparation of (8-Methoxy-2H-pyrazolo[3,4-c]quinolin-4-yl)-(2-methyl-1,2,3,4-tetrahydro-benzo[4,5]imidazo[1,2-a]pyrazin-8-yl)-amine 4-chloro-8-methoxy-2-(4-methoxybenzyl)-2H-pyrazolo[3,4-c]quinoline (0.16 mmol) and 2-methyl-1,2,3,4-tetrahydrobenzo[4,5]imidazo[1,2-a]pyrazin-8-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 399.211 g/mol
  HPLC-MS: analytical method C
  rt: 1.385 min—found mass: 400.2 (m/z+H)

Example #161

Preparation of (8-Methoxy-2H-pyrazolo[3,4-c]quinolin-4-yl)-(4-pyridin-4-ylmethyl-phenyl)-amine 4-chloro-8-methoxy-2-(4-methoxybenzyl)-2H-pyrazolo[3,4-c]quinoline (0.16 mmol) and 4-(pyridin-4-ylmethyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL) The reaction mixture was irradiated in a microwave reactor for 5 min at 140° C. The reaction mixture was concentrated and purified by semi-preparative HPLC-MS and freeze dried from water/t-BuOH 4/1.
  exact mass: 381.1855 g/mol
  HPLC-MS: analytical method C
  rt: 1.496 min—found mass: 382.2 (m/z+H)

Example #162

Preparation of 4-(8-Methoxy-2H-pyrazolo[3,4-c]quinolin-4-ylamino)-benzene-1,2-diol 4-chloro-8-methoxy-2-(4-methoxybenzyl)-2H-pyrazolo[3,4-c]quinoline (0.16 mmol) and 4-aminobenzene-1,2-diol (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 322.1247 g/mol
  HPLC-MS: analytical method C
  rt: 1.628 min—found mass: 323.1 (m/z+H)

Example #163

Preparation of (8-Methoxy-2H-pyrazolo[3,4-c]quinolin-4-yl)-[4-(1-methyl-piperidin-4-yloxy)-phenyl]-amine 4-chloro-8-methoxy-2-(4-methoxybenzyl)-2H-pyrazolo[3,4-c]quinoline (0.16 mmol) and 4-((1-methylpiperidin-4-yl)oxy)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 403.2399 g/mol
  HPLC-MS: analytical method C
  rt: 1.460 min—found mass: 404.2 (m/z+H)

Example #164

Preparation of 1-{4-[4-(8-Methoxy-2H-pyrazolo[3,4-c]quinolin-4-ylamino)-phenyl]-piperazin-1-yl}-ethanone 4-chloro-8-methoxy-2-(4-methoxybenzyl)-2H-pyrazolo[3,4-c]quinoline (0.16 mmol) and 1-(4-(4-aminophenyl)piperazin-1-yl)ethan-1-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 416.2324 g/mol
  HPLC-MS: analytical method C
  rt: 1.707 min—found mass: 417.2 (m/z+H)

Example #165

Preparation of (8-Methoxy-2H-pyrazolo[3,4-c]quinolin-4-yl)-[6-(4-methyl-piperazin-1-yl)-pyridin-3-yl]-amine 4-chloro-8-methoxy-2-(4-methoxybenzyl)-2H-pyrazolo[3,4-c]quinoline (0.16 mmol) and 6-(4-methylpiperazin-1-yl)pyridin-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 389.2315 g/mol
  HPLC-MS: analytical method C
  rt: 1.356 min—found mass: 390.2 (m/z+H)

Example #166

Preparation of (6-Methoxy-2H-pyrazolo[3,4-c]quinolin-4-yl)-[4-(4-methyl-piperazin-1-yl)-phenyl]-amine 4-chloro-6-methoxy-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 388.2384 g/mol
 HPLC-MS: analytical method C
 rt: 1.43 min—found mass: 389 (m/z+H)

Example #167

Preparation of (3,4-Dimethoxy-phenyl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 350.1637 g/mol
 HPLC-MS: analytical method C
 rt: 1.84 min—found mass: 351 (m/z+H)

Example #168

Preparation of (3,4-Dihydro-2H-benzo[1,4]oxazin-6-yl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 6-Amino-2,3-dihydro-benzo[1,4]oxazine-4-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 347.1618 g/mol
 HPLC-MS: analytical method A
 rt: 2.08 min—found mass: 348 (m/z+H)

Example #169

Preparation of (5-Cyclopropyl-1H-pyrazol-3-yl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 5-cyclopropyl-1H-pyrazol-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 320.1609 g/mol
 HPLC-MS: analytical method C
 rt: 1.9 min—found mass: 321 (m/z+H)

Example #170

Preparation of (6-Methoxy-2H-pyrazolo[3,4-c]quinolin-4-yl)-(4-morpholin-4-yl-phenyl)-amine 4-chloro-6-methoxy-2-(4-methoxybenzyl)-2H-pyrazolo[3,4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 375.2007 g/mol
 HPLC-MS: analytical method C
 rt: 1.87 min—found mass: 376 (m/z+H)

Example #171

Preparation of (1H-Indazol-6-yl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 330.1404 g/mol
 HPLC-MS: analytical method C
 rt: 1.74 min—found mass: 331 (m/z+H)

Example #172

Preparation of (1H-Indazol-6-yl)-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 330.1404 g/mol
  HPLC-MS: analytical method H
  rt: 2.32 min—found mass: 331 (m/z+H)

Example #173

Preparation of (3,4-Dihydro-2H-benzo[1,4]oxazin-6-yl)-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 6-Amino-2,3-dihydro-benzo[1,4]oxazine-4-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 347.1618 g/mol
  HPLC-MS: analytical method C
  rt: 1.83 min—found mass: 348 (m/z+H)

Example #174

Preparation of (5-Cyclopropyl-1H-pyrazol-3-yl)-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 5-cyclopropyl-1H-pyrazol-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 320.1609 g/mol
  HPLC-MS: analytical method C
  rt: 1.88 min—found mass: 321 (m/z+H)

Example #175

Preparation of (3,4-Dimethoxy-phenyl)-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 350.1637 g/mol
  HPLC-MS: analytical method C
  rt: 1.82 min—found mass: 351 (m/z+H)

Example #176

Preparation of (7-Methoxy-2H-pyrazolo[3,4-c]quinolin-4-yl)-[4-(4-methyl-piperazin-1-yl)-phenyl]-amine 4-chloro-7-methoxy-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 388.2384 g/mol
  HPLC-MS: analytical method A
  rt: 0.83 min—found mass: 389 (m/z+H)

Example #177

Preparation of (7-Methoxy-2H-pyrazolo[3,4-c]quinolin-4-yl)-(4-morpholin-4-yl-phenyl)-amine 4-chloro-7-methoxy-2-(4-methoxybenzyl)-2H-pyrazolo[3,4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 375.2007 g/mol
  HPLC-MS: analytical method A
  rt: 1.99 min—found mass: 376 (m/z+H)

Example #178

Preparation of N4-(8-Methoxy-2H-pyrazolo[3,4-c]quinolin-4-yl)-2,N1,N1-trimethyl-benzene-1,4-diamine 4-chloro-8-methoxy-2-(4-methoxybenzyl)-2H-pyrazolo[3,4-c]quinoline (0.16 mmol) and N1,N1,2-trimethylbenzene-1,4-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 347.2069 g/mol
  HPLC-MS: analytical method A
  rt: 2.095 min—found mass: 348.2 (m/z+H)

Example #179

Preparation of [4-(4-Cyclopropyl-piperazin-1-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-cyclopropylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 414.2575 g/mol
  HPLC-MS: analytical method A
  rt: 1.386 min—found mass: 415.2 (m/z+H)

Example #181

Preparation of (3-Fluoro-4-morpholin-4-yl-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 3-fluoro-4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 393.1888 g/mol
  HPLC-MS: analytical method C
  rt: 1.942 min—found mass: 394.2 (m/z+H)

Example #182

Preparation of 7-(8-Methoxy-2H-pyrazolo[3,4-c]quinolin-4-ylamino)-3,4-dihydro-1H-quinoxalin-2-one 4-chloro-8-methoxy-2-(4-methoxybenzyl)-2H-pyrazolo[3,4-c]quinoline (0.16 mmol) and 7-amino-3,4-dihydroquinoxalin-2(1H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 360.1544 g/mol
  HPLC-MS: analytical method C
  rt: 1.61 min—found mass: 361.1 (m/z+H)

Example #183

Preparation of (8-Methoxy-2H-pyrazolo[3,4-c]quinolin-4-yl)-[3-methyl-4-(4-methyl-piperazin-1-yl)-phenyl]-amine 4-chloro-8-methoxy-2-(4-methoxybenzyl)-2H-pyrazolo[3,4-c]quinoline (0.16 mmol) and 3-methyl-4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 402.258 g/mol.
  HPLC-MS: analytical method C
  rt: 1.526 min—found mass: 403.2 (m/z+H)

Example #184

Preparation of (8-Methoxy-2H-pyrazolo[3,4-c]quinolin-4-yl)-(4-piperazin-1-yl-phenyl)-amine 4-chloro-8-methoxy-2-(4-methoxybenzyl)-2H-pyrazolo[3,4-c]quinoline (0.16 mmol) and 4-(4-Amino-phenyl)-piperazine-1-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 374.219 g/mol
  HPLC-MS: analytical method C
  rt: 1.370 min—found mass: 375.2 (m/z+H)

Example #185

Preparation of (4-Dimethylaminomethyl-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-((dimethylamino)methyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 347.2069 g/mol
  HPLC-MS: analytical method C
  rt: 1.388 min—found mass: 348.2 (m/z+H)

Example #186

Preparation of (2-Fluoro-4-morpholin-4-yl-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 2-fluoro-4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 393.1888 g/mol
  HPLC-MS: analytical method C
  rt: 1.902 min—found mass: 394.2 (m/z+H)

Example #187

Preparation of [4-(4-Ethyl-piperazin-1-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-ethylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 402.258 g/mol
  HPLC-MS: analytical method C
  rt: 1.415 min—found mass: 403.2 (m/z+H)

Example #188

Preparation of 8-(8-Methoxy-2H-pyrazolo[3,4-c]quinolin-4-ylamino)-1,3,4,5-tetrahydro-benzo[b]azepin-2-one 4-chloro-8-methoxy-2-(4-methoxybenzyl)-2H-pyrazolo[3,4-c]quinoline (0.16 mmol) and 8-amino-4,5-dihydro-1H-benzo[b]azepin-2(3H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 373.1809 g/mol
  HPLC-MS: analytical method C
  rt: 1.753 min—found mass: 374.2 (m/z+H)

Example #189

Preparation of 5-(8-Methoxy-2H-pyrazolo[3,4-c]quinolin-4-ylamino)-1,3-dimethyl-1,3-dihydro-benzoimidazol-2-one 4-chloro-8-methoxy-2-(4-methoxybenzyl)-2H-pyrazolo[3,4-c]quinoline (0.16 mmol) and 5-amino-1,3-dimethyl-1H-benzo[d]imidazol-2(3H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 374.1739 g/mol
  HPLC-MS: analytical method C
  rt: 1.704 min—found mass: 375.2 (m/z+H)

Example #190

Preparation of (4-Benzyl-phenyl)-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-benzylaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 380.1925 g/mol
  HPLC-MS: analytical method C
  rt: 2.288 min—found mass: 381.2 (m/z+H)

Example #191

Preparation of (8-Methoxy-2H-pyrazolo[3,4-c]quinolin-4-yl)-(2-methyl-4-morpholin-4-yl-phenyl)-amine 4-chloro-8-methoxy-2-(4-methoxybenzyl)-2H-pyrazolo[3,4-c]quinoline (0.16 mmol) and 2-methyl-4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 389.2203 g/mol
HPLC-MS: analytical method C
rt: 1.884 min—found mass: 390.2 (m/z+H)

Example #192

Preparation of N-(8-Methoxy-2H-pyrazolo[3,4-c]quinolin-4-yl)-N'-methyl-N'-(1-methyl-piperidin-4-yl)-benzene-1,4-diamine 4-chloro-8-methoxy-2-(4-methoxybenzyl)-2H-pyrazolo[3,4-c]quinoline (0.16 mmol) and N1-methyl-N1-(1-methylpiperidin-4-yl)benzene-1,4-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 416.2775 g/mol
HPLC-MS: analytical method C
rt: 1.508 min—found mass: 417.2 (m/z+H)

Example #193

Preparation of (8-Methoxy-2H-pyrazolo[3,4-c]quinolin-4-yl)-[4-(2-morpholin-4-yl-ethyl)-phenyl]-amine 4-chloro-8-methoxy-2-(4-methoxybenzyl)-2H-pyrazolo[3,4-c]quinoline (0.16 mmol) and 4-(2-morpholinoethyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 403.2399 g/mol
HPLC-MS: analytical method C
rt: 1.416 min—found mass: 404.2 (m/z+H)

Example #194

Preparation of 7-(8-Methoxy-2H-pyrazolo[3,4-c]quinolin-4-ylamino)-1H-quinoxalin-2-one 4-chloro-8-methoxy-2-(4-methoxybenzyl)-2H-pyrazolo[3,4-c]quinoline (0.16 mmol) and 7-aminoquinoxalin-2(1H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 358.1343 g/mol
HPLC-MS: analytical method A
rt: 2.268 min—found mass: 359.1 (m/z+H)

Example #195

Preparation of [3-Chloro-4-(4-methyl-piperazin-1-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 3-chloro-4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 422.1968 g/mol
HPLC-MS: analytical method A
rt: 1.768 min—found mass: 423.2 (m/z+H)

Example #196

Preparation of (8-Methoxy-2H-pyrazolo[3,4-c]quinolin-4-yl)-(1,2,3,4-tetrahydro-quinolin-7-yl)-amine 4-chloro-8-methoxy-2-(4-methoxybenzyl)-2H-pyrazolo[3,4-c]quinoline (0.16 mmol) and 7-Amino-3,4-dihydro-2H-quinoline-1-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 345.187 g/mol
HPLC-MS: analytical method C
rt: 2.156 min—found mass: 346.2 (m/z+H)

Example #197

Preparation of 4-(1H-Indazol-6-ylamino)-2H-pyrazolo[3,4-c]quinoline-8-carbonitrile 4-chloro-2-(4-methoxybenzyl)-2H-pyrazolo[3,4-c]quinoline-8-carbonitrile (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 325.1185 g/mol
HPLC-MS: analytical method C
rt: 2.07 min—found mass: 326 (m/z+H)

Example #198

Preparation of (3,4-Dihydro-2H-benzo[1,4]oxazin-6-yl)-(9-methoxy-2H-pyrazolo[3,4-c]quinolin-4-yl)-amine 4-chloro-9-methoxy-2-(4-methoxybenzyl)-2H-pyrazolo[3,4-c]quinoline (0.16 mmol) and 6-Amino-2,3-dihydro-benzo[1,4]oxazine-4-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 347.1619 g/mol
HPLC-MS: analytical method C
rt: 1.83 min—found mass: 348 (m/z+H)

Example #199

Preparation of (5-Cyclopropyl-1H-pyrazol-3-yl)-(9-methoxy-2H-pyrazolo[3,4-c]quinolin-4-yl)-amine 4-chloro-9-methoxy-2-(4-methoxybenzyl)-2H-pyrazolo[3,4-c]quinoline (0.16 mmol) and 5-cyclopropyl-1H-pyrazol-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 320.1609 g/mol
HPLC-MS: analytical method C
rt: 1.89 min—found mass: 321 (m/z+H)

Example #200

Preparation of (3,4-Dimethoxy-phenyl)-(9-methoxy-2H-pyrazolo[3,4-c]quinolin-4-yl)-amine 4-chloro-9-methoxy-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 350.1637 g/mol
HPLC-MS: analytical method C
rt: 1.83 min—found mass: 351 (m/z+H)

Example #201

Preparation of (9-Methoxy-2H-pyrazolo[3,4-c]quinolin-4-yl)-[4-(4-methyl-piperazin-1-yl)-phenyl]-amine 4-chloro-9-methoxy-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 388.2384 g/mol
HPLC-MS: analytical method C
rt: 1.44 min—found mass: 389 (m/z+H)

Example #202

Preparation of (9-Methoxy-2H-pyrazolo[3,4-c]quinolin-4-yl)-(4-morpholin-4-yl-phenyl)-amine 4-chloro-9-methoxy-2-(4-methoxybenzyl)-2H-pyrazolo[3,4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 375.2008 g/mol
HPLC-MS: analytical method C
rt: 1.84 min—found mass: 376 (m/z+H)

Example #203

Preparation of (1H-Indazol-6-yl)-(9-methoxy-2H-pyrazolo[3,4-c]quinolin-4-yl)-amine 4-chloro-9-methoxy-2-(4-methoxybenzyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 330.1404 g/mol
HPLC-MS: analytical method C
rt: 1.75 min—found mass: 331 (m/z+H)

Example #204

Preparation of (1S,2R)—N-(8-Methoxy-2H-pyrazolo[3,4-c]quinolin-4-yl)-cyclohexane-1,2-diamine 4-chloro-8-methoxy-2-(4-methoxybenzyl)-2H-pyrazolo[3,4-c]quinoline (0.16 mmol) and ((1R,2S)-2-Amino-cyclohexyl)-carbamic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 311.2085 g/mol
HPLC-MS: analytical method C
rt: 1.373 min—found mass: 312.2 (m/z+H)

Example #205

Preparation of (8-Methoxy-2H-pyrazolo[3,4-c]quinolin-4-yl)-pyridin-4-yl-amine 4-chloro-8-methoxy-2-(4-methoxybenzyl)-2H-pyrazolo[3,4-c]quinoline (0.16 mmol) and pyridin-4-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 291.1289 g/mol
HPLC-MS: analytical method C
rt: 1.790 min—found mass: 292.2 (m/z+H)

Example #206

Preparation of (8-Methoxy-2H-pyrazolo[3,4-c]quinolin-4-yl)-(6-methoxy-pyridin-3-yl)-amine 4-chloro-8-methoxy-2-(4-methoxybenzyl)-2H-pyrazolo[3,4-c]quinoline (0.16 mmol) and 6-methoxypyridin-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 321.1428 g/mol
HPLC-MS: analytical method C
rt: 1.790 min—found mass: 322.1 (m/z+H)

Example #207

Preparation of (3,4-Dimethoxy-phenyl)-(1-methyl-2H-pyrazolo[3,4-c]quinolin-4-yl)-amine 4-chloro-2-(4-methoxybenzyl)-1-methyl-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 334.1693 g/mol
HPLC-MS: analytical method C
rt: 1.84 min—found mass: 335 (m/z+H)

Example #208

Preparation of [4-(4-Methyl-piperazin-1-yl)-phenyl]-(1-methyl-2H-pyrazolo[3,4-c]quinolin-4-yl)-amine 4-chloro-2-(4-methoxybenzyl)-1-methyl-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 372.244 g/mol
HPLC-MS: analytical method C
rt: 1.43 min—found mass: 373 (m/z+H)

Example #209

Preparation of (1H-Indazol-6-yl)-(1-methyl-2H-pyrazolo[3,4-c]quinolin-4-yl)-amine 4-chloro-2-(4-methoxybenzyl)-1-methyl-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 314.146 g/mol
HPLC-MS: analytical method C
rt: 1.78 min—found mass: 315 (m/z+H)

Example #210

Preparation of (3,4-Dimethoxy-phenyl)-(1-trifluoromethyl-2H-pyrazolo[3,4-c]quinolin-4-yl)-amine 4-chloro-2-(4-methoxybenzyl)-1-(trifluoromethyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 388.133 g/mol
HPLC-MS: analytical method C
rt: 2.84 min—found mass: 389 (m/z+H)

Example #211

Preparation of [4-(4-Methyl-piperazin-1-yl)-phenyl]-(1-trifluoromethyl-2H-pyrazolo[3,4-c]quinolin-4-yl)-amine 4-chloro-2-(4-methoxybenzyl)-1-(trifluoromethyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 426.2077 g/mol
HPLC-MS: analytical method C
rt: 2.01 min—found mass: 427 (m/z+H)

Example #212

Preparation of (1H-Indazol-6-yl)-(1-trifluoromethyl-2H-pyrazolo[3,4-c]quinolin-4-yl)-amine 4-chloro-2-(4-methoxybenzyl)-1-(trifluoromethyl)-2H-pyrazolo[3,4-c]quinoline (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 368.1098 g/mol
HPLC-MS: analytical method C
rt: 2.81 min—found mass: 369 (m/z+H)

Example #213

Preparation of (3,4-Dimethoxy-phenyl)-(1-nitro-2H-pyrazolo[3,4-c]quinolin-4-yl)-amine 4-chloro-2-(4-methoxybenzyl)-1-nitro-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 365.131 g/mol
HPLC-MS: analytical method C
rt: 2.53 min—found mass: 366 (m/z+H)

Example #214

Preparation of [4-(4-Methyl-piperazin-1-yl)-phenyl]-(1-nitro-2H-pyrazolo[3,4-c]quinolin-4-yl)-amine 4-chloro-2-(4-methoxybenzyl)-1-nitro-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 403.2058 g/mol
HPLC-MS: analytical method C
rt: 1.84 min—found mass: 404 (m/z+H)

Example #215

Preparation of N-[2-(4-Methoxy-phenyl)-ethyl]-2-[(4-(8-methoxy-2H-pyrazolo[3,4-c]quinolin-4-ylamino)-phenyl]-acetamide 4-chloro-8-methoxy-2-(4-methoxybenzyl)-2H-pyrazolo[3,4-c]quinoline (0.16 mmol) and 2-(4-aminophenyl)-N-(4-methoxyphenethyl)acetamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 481.2519 g/mol
HPLC-MS: analytical method C
rt: 2.065 min—found mass: 482.3 (m/z+H)

Example #216

Preparation of 4-(3,4-Dimethoxy-phenylamino)-2H-pyrazolo[3,4-c]quinoline-8-carbonitrile 4-chloro-2-(4-methoxybenzyl)-2H-pyrazolo[3,4-c]quinoline-8-carbonitrile (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 345.1418 g/mol
HPLC-MS: analytical method A
rt: 2.35 min—found mass: 346 (m/z+H)

Example #217

Preparation of 4-(4-Morpholin-4-yl-phenylamino)-2H-pyrazolo[3,4-c]quinoline-8-carbonitrile 4-chloro-2-(4-methoxybenzyl)-2H-pyrazolo[3,4-c]quinoline-8-carbonitrile (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 370.179 g/mol
HPLC-MS: analytical method A
rt: 2.31 min—found mass: 371 (m/z+H)

Example #218

Preparation of (3,4-Dimethoxy-phenyl)-(1-methyl-7H-3-thia-2,4,6,7-tetraaza-as-indacen-5-yl)-amine 5-chloro-7-(4-methoxybenzyl)-1-methyl-7H-isothiazolo[5,4-b]pyrazolo[4,3-d]pyridine (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 341.1148 g/mol
HPLC-MS: analytical method C
rt: 2.42 min—found mass: 342 (m/z+H)

Example #219

Preparation of (1H-Indazol-6-yl)-(1-methyl-7H-3-thia-2,4,6,7-tetraaza-as-indacen-5-yl)-amine 5-chloro-7-(4-methoxybenzyl)-1-methyl-7H-isothiazolo[5,4-b]pyrazolo[4,3-d]pyridine (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 321.0915 g/mol
HPLC-MS: analytical method A
rt: 2.62 min—found mass: 322 (m/z+H)

Example #220

Preparation of [4-(4-Methyl-piperazin-1-yl)-phenyl]-(1-methyl-7H-3-thia-2,4,6,7-tetraaza-as-indacen-5-yl)-amine 5-chloro-7-(4-methoxybenzyl)-1-methyl-7H-isothiazolo[5,4-b]pyrazolo[4,3-d]pyridine (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 379.1896 g/mol
HPLC-MS: analytical method A
rt: 1.87 min—found mass: 380 (m/z+H)

Example #221

Preparation of (8-Methoxy-2H-pyrazolo[3,4-c]quinolin-4-yl)-(3-piperazin-1-yl-phenyl)-amine 4-chloro-8-methoxy-2-(4-methoxybenzyl)-2H-pyrazolo[3,4-c]quinoline (0.16 mmol) and 4-(3-Amino-phenyl)-piperazine-1-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 374.219 g/mol
HPLC-MS: analytical method C
rt: 1.497 min—found mass: 375.2 (m/z+H)

Example #222

Preparation of N-(2-Diethylamino-ethyl)-4-(8-methoxy-2H-pyrazolo[3,4-c]quinolin-4-ylamino)-benzamide 4-chloro-8-methoxy-2-(4-methoxybenzyl)-2H-pyrazolo[3,4-c]quinoline (0.16 mmol) and 4-amino-N-(2-(diethylamino)ethyl)benzamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 432.2719 g/mol
HPLC-MS: analytical method C
rt: 1.604 min—found mass: 433.2 (m/z+H)

Example #223

Preparation of (8-Methoxy-2H-pyrazolo[3,4-c]quinolin-4-yl)-[2-(4-methyl-piperazin-1-yl)-pyrimidin-5-yl]-amine 4-chloro-8-methoxy-2-(4-methoxybenzyl)-2H-pyrazolo[3,4-c]quinoline (0.16 mmol) and 2-(4-methylpiperazin-1-yl)pyrimidin-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 390.2245 g/mol
HPLC-MS: analytical method C
rt: 1.431 min—found mass: 391.2 (m/z+H)

Example #224

Preparation of 7-(8-Methoxy-3H-pyrazolo[3,4-c]quinolin-4-ylamino)-4H-benzo[1,4]oxazin-3-one 4-chloro-8-methoxy-2-(4-methoxybenzyl)-2H-pyrazolo[3,4-c]quinoline (0.16 mmol) and 7-amino-2H-benzo[b][1,4]oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 361.1363 g/mol
HPLC-MS: analytical method C
rt: 1.722 min—found mass: 362.1 (m/z+H)

Example #225

Preparation of (3,4-Dihydro-2H-benzo[1,4]oxazin-7-yl)-(8-methoxy-3H-pyrazolo[3,4-c]quinolin-4-yl)-amine 4-chloro-8-methoxy-2-(4-methoxybenzyl)-2H-pyrazolo[3,4-c]quinoline (0.16 mmol) and 6-Amino-2,3-dihydro-benzo[1,4]oxazine-4-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 347.1619 g/mol
HPLC-MS: analytical method C
rt: 1.839 min—found mass: 348.1 (m/z+H)

Example #226

Preparation of 4-(3,4-Dimethoxy-phenylamino)-1-methyl-2H-pyrazolo[3,4-c]quinoline-7-carbonitrile 4-chloro-2-(4-methoxybenzyl)-1-methyl-2H-pyrazolo[3,4-c]quinoline-7-carbonitrile (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 359.1613 g/mol
HPLC-MS: analytical method C
rt: 2.03 min—found mass: 360 (m/z+H)

Example #227

Preparation of 4-(1H-Indazol-6-ylamino)-1-methyl-2H-pyrazolo[3,4-c]quinoline-7-carbonitrile 4-chloro-2-(4-methoxybenzyl)-1-methyl-2H-pyrazolo[3,4-c]quinoline-7-carbonitrile (0.16 mmol) and 1H-indazol-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 339.138 g/mol
HPLC-MS: analytical method C
rt: 2.13 min—found mass: 340 (m/z+H)

Example #228

Preparation of (8-Methoxy-2H-pyrazolo[3,4-c]quinolin-4-yl)-[3-(4-methyl-piperazin-1-yl)-phenyl]-amine 4-chloro-8-methoxy-2-(4-methoxybenzyl)-2H-pyrazolo[3,4-c]quinoline (0.16 mmol) and 3-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 388.2385 g/mol
HPLC-MS: analytical method C
rt: 1.513 min—found mass: 389.1 (m/z+H)

Example #229

Preparation of (8-Methoxy-2H-pyrazolo[3,4-c]quinolin-4-yl)-[3-(2-piperazin-1-yl-ethoxy)-phenyl]-amine 4-chloro-8-methoxy-2-(4-methoxybenzyl)-2H-pyrazolo[3,4-c]quinoline (0.16 mmol) and 4-[2-(3-Amino-phenoxy)-ethyl]-piperazine-1-carboxylic acid tert-butyl ester (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 418.2524 g/mol
HPLC-MS: analytical method C
rt: 1.446 min—found mass: 419.2 (m/z+H)

Example #230

Preparation of (8-Methoxy-2H-pyrazolo[3,4-c]quinolin-4-yl)-(6-methyl-5,6,7,8-tetrahydro-[1,6]naphthyridin-3-yl)-amine 4-chloro-8-methoxy-2-(4-methoxybenzyl)-2H-pyrazolo[3,4-c]quinoline (0.16 mmol) and 6-methyl-5,6,7,8-tetrahydro-1,6-naphthyridin-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 360.1995 g/mol
HPLC-MS: analytical method C
rt: 1.441 min—found mass: 361.1 (m/z+H)

Example #231

Preparation of [4-(8-Methoxy-2H-pyrazolo[3,4-c]quinolin-4-ylamino)-phenyl]-pyrrolidin-1-yl-methanone 4-chloro-8-methoxy-2-(4-methoxybenzyl)-2H-pyrazolo[3,4-c]quinoline (0.16 mmol) and (4-aminophenyl)(pyrrolidin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 387.2003 g/mol
HPLC-MS: analytical method C
rt: 1.911 min—found mass: 388.1 (m/z+H)

Example #232

Preparation of [4-(8-Methoxy-2H-pyrazolo[3,4-c]quinolin-4-ylamino)-phenyl]-morpholin-4-yl-methanone 4-chloro-8-methoxy-2-(4-methoxybenzyl)-2H-pyrazolo[3,4-c]quinoline (0.16 mmol) and (4-aminophenyl)(morpholino)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 403.1947 g/mol
HPLC-MS: analytical method C
rt: 1.806 min—found mass: 404.1 (m/z+H)

Example #233

Preparation of (4-Dimethylaminomethyl-phenyl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 4-((dimethylamino)methyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 347.2069 g/mol
HPLC-MS: analytical method C
rt: 1.44 min—found mass: 348 (m/z+H)

Example #234

Preparation of (8-Methoxy-2H-pyrazolo[3,4-c]quinolin-4-yl)-(4-pyrrolidin-1-ylmethyl-phenyl)-amine 4-chloro-8-methoxy-2-(4-methoxybenzyl)-2H-pyrazolo[3,4-c]quinoline (0.16 mmol) and (4-Amino-phenyl)-pyrrolidin-1-yl-methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and dissolved in THF (dry) LiAlH4 powder was added (excess, 2 by 2 eq) until completion of reaction is observed (by LCMS). The reaction was queched with water (1 mL per gram LiAlH4), then NaOH (ca. 15% aq., 1 mL per g LiAlH4), water (3 mL per gram LiALH4). The mixture was filtered, washed with THF, MeOH, MeCN (ca. 10 ML each). The reaction mixture was concentrated and purified by semi-preparative HPLC-MS and freeze dried from water/t-BuOH 4/1.
exact mass: 373.226 g/mol
HPLC-MS: analytical method C
rt: 1.480 min—found mass: 374.2 (m/z+H)

Example #235

Preparation of (4-((8-methoxy-2H-pyrazolo[3,4-c]quinolin-4-yl)amino)phenyl)(4-methylpiperazin-1-yl)methanone 4-chloro-8-methoxy-2-(4-methoxybenzyl)-2H-pyrazolo[3,4-c]quinoline (0.16 mmol) and (4-aminophenyl)(4-methylpiperazin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 416.2324 g/mol
HPLC-MS: analytical method C
rt: 1.429 min—found mass: 417.2 (m/z+H)

Example #236

Preparation of N2-(2-(dimethylamino)ethyl)-N5-(8-methoxy-2H-pyrazolo[3,4-c]quinolin-4-yl)pyrimidine-2,5-diamine 4-chloro-8-methoxy-2-(4-methoxybenzyl)-2H-pyrazolo[3,4-c]quinoline (0.16 mmol) and N2-(2-(dimethylamino)ethyl)pyrimidine-2,5-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 378.225 g/mol
HPLC-MS: analytical method C
rt: 1.425 min—found mass: 390.2 (m/z+H)

Example #237

Preparation of (8-Methoxy-2H-pyrazolo[3,4-c]quinolin-4-yl)-(4-morpholin-4-ylmethyl-phenyl)-amine 4-chloro-8-methoxy-2-(4-methoxybenzyl)-2H-pyrazolo[3,4-c]quinoline (0.16 mmol) and (4-Amino-phenyl)-morpholin-4-yl-methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and dissolved in THF (dry) LiAlH4 powder was added (excess, 2 by 2 eq) until completion of reaction is observed (by LCMS). The reaction was queched with water (1 mL per gram LiAlH4), then NaOH (ca. 15% aq., 1 mL per g LiAlH4), water (3 mL per gram LiALH4). The mixture was filtered, washed with THF, MeOH, MeCN (ca. 10 mL each). The reaction mixture was concentrated and purified by semi-preparative HPLC-MS and freeze dried from water/t-BuOH 4/1.
exact mass: 389.2204 g/mol
HPLC-MS: analytical method C
rt: 1.425 min—found mass: 390.2 (m/z+H)

Example #238

Preparation of (8-Methoxy-2H-pyrazolo[3,4-c]quinolin-4-yl)-[4-(4-methyl-piperazin-1-ylmethyl)-phenyl]-amine 4-chloro-8-methoxy-2-(4-methoxybenzyl)-2H-pyrazolo[3,4-c]quinoline (0.16 mmol) and (4-Amino-phenyl)-(4-methyl-piperazin-1-yl)-methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and dissolved in THF (dry) LiAlH4 powder was added (excess, 2 by 2 eq) until completion of reaction is observed (by LCMS). The reaction was queched with water (1 mL per gram LiAlH4), then NaOH (ca. 15% aq., 1 mL per g LiAlH4), water (3 mL per gram LiALH4). The mixture was filtered, washed with THF, MeOH, MeCN (ca. 10 mL each). The reaction mixture was concentrated and purified by semi-preparative HPLC-MS and freeze dried from water/t-BuOH 4/1.
exact mass: 402.258 g/mol
HPLC-MS: analytical method C
rt: 1.456 min—found mass: 403.2 (m/z+H)

155

Example #239

Preparation of [4-(4-Ethyl-piperazin-1-yl)-phenyl]-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 4-(4-ethylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 402.2581 g/mol
HPLC-MS: analytical method C
rt: 1.49 min—found mass: 403 (m/z+H)

Example #240

Preparation of [4-(4-ethyl-piperazin-1-yl)-3-fluoro-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-ethylpiperazin-1-yl)-3-fluoroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 420.2459 g/mol
HPLC-MS: analytical method C
rt: 1.531 min—found mass: 421.2 (m/z+H)

Example #241

Preparation of 8-((6-methoxy-2H-pyrazolo[3,4-c]quinolin-4-yl)amino)-4,5-dihydro-1H-benzo[b]azepin-2(3H)-one 4-chloro-6-methoxy-2-(4-methoxybenzyl)-2H-pyrazolo[3,4-c]quinoline (0.16 mmol) and 8-amino-4,5-dihydro-1H-benzo[b]azepin-2(3H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

156 exact mass: 373.1808 g/mol
HPLC-MS: analytical method C
rt: 1.78 min—found mass: 374 (m/z+H)

Example #242

Preparation of (1H-benzoimidazol-5-yl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 1H-benzoimidazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 330.1404 g/mol
HPLC-MS: analytical method C
rt: 1.48 min—found mass: 331 (m/z+H)

Example #243

Preparation of [4-(4-cyclopropyl-piperazin-1-yl)-phenyl]-(9-methoxy-2H-pyrazolo[3,4-c]quinolin-4-yl)-amine 4-chloro-9-methoxy-2-(4-methoxybenzyl)-2H-pyrazolo[3,4-c]quinoline (0.16 mmol) and 4-(4-cyclopropylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 414.2574 g/mol
HPLC-MS: analytical method C
rt: 1.536 min—found mass: 415.2 (m/z+H)

Example #244

Preparation of (8-Methoxy-2H-pyrazolo[3,4-c]quinolin-4-yl)-p-tolyl-amine 4-chloro-8-methoxy-2-(4-methoxybenzyl)-2H-pyrazolo[3,4-c]quinoline (0.16 mmol) and p-toluidine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 304.1554 g/mol
HPLC-MS: analytical method C
rt: 1.942 min—found mass: 305.1 (m/z+H)

Example #245

Preparation of [6-(2-Dimethylamino-ethoxy)-pyridin-3-yl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 6-(2-(dimethylamino)ethoxy)pyridin-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 378.2139 g/mol
HPLC-MS: analytical method C
rt: 1.406 min—found mass: 379.2 (m/z+H)

Example #246

Preparation of (3-Fluoro-4-morpholin-4-yl-phenyl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 3-fluoro-4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 393.1887 g/mol
HPLC-MS: analytical method C
rt: 1.97 min—found mass: 394 (m/z+H)

Example #247

Preparation of (6-Methoxy-2H-pyrazolo[3,4-c]quinolin-4-yl)-(4-thiomorpholin-4-yl-phenyl)-amine 4-chloro-6-methoxy-2-(4-methoxybenzyl)-2H-pyrazolo[3,4-c]quinoline (0.16 mmol) and 4-thiomorpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 391.1779 g/mol
HPLC-MS: analytical method C
rt: 2.09 min—found mass: 392 (m/z+H)

Example #248

Preparation of (6-Methoxy-2H-pyrazolo[3,4-c]quinolin-4-yl)-(2-methyl-1H-benzoimidazol-5-yl)-amine 4-chloro-6-methoxy-2-(4-methoxybenzyl)-2H-pyrazolo[3,4-c]quinoline (0.16 mmol) and 2-methyl-1H-benzoimidazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 344.1599 g/mol
HPLC-MS: analytical method C
rt: 143 min—found mass: 345 (m/z+H)

Example #249

Preparation of Benzo[1,3]dioxol-5-yl-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and benzo[d][1,3]dioxol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 334.1242 g/mol
HPLC-MS: analytical method C
rt: 1.918 min—found mass: 335.1 (m/z+H)

Example #250

Preparation of 6-((6-methoxy-2H-pyrazolo[3,4-c]quinolin-4-yl)amino)-2H-benzo[b][1,4]oxazin-3(4H)-one 4-chloro-6-methoxy-2-(4-methoxybenzyl)-2H-pyrazolo[3,4-c]quinoline (0.16 mmol) and 6-amino-2H-benzo[b][1,4]oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 361.1362 g/mol
HPLC-MS: analytical method C
rt: 1.776 min—found mass: 362.1 (m/z+H)

Example #251

Preparation of (3,4-Dimethoxy-phenyl)-(6,8-dimethoxy-2H-pyrazolo[3,4-c]quinolin-4-yl)-amine 4-chloro-6,8-dimethoxy-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 380.1777 g/mol
HPLC-MS: analytical method A
rt: 2.262 min—found mass: 381.2 (m/z+H)

Example #252

Preparation of [4-(4-Cyclopropyl-piperazin-1-yl)-phenyl]-(6,8-dimethoxy-2H-pyrazolo[3,4-c]quinolin-4-yl)-amine 4-chloro-6,8-dimethoxy-2-(4-methoxybenzyl)-2H-pyrazolo[3,4-c]quinoline (0.16 mmol) and 4-(4-cyclopropylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 444.2714 g/mol
HPLC-MS: analytical method A
rt: 1.825 min—found mass: 445.3 (m/z+H)

Example #253

Preparation of N2-(3-(dimethylamino)propyl)-N5-(8-methoxy-2H-pyrazolo[3,4-c]quinolin-4-yl)pyridine-2,5-diamine 4-chloro-8-methoxy-2-(4-methoxybenzyl)-2H-pyrazolo[3,4-c]quinoline (0.16 mmol) and N2-(3-(dimethylamino)propyl)pyridine-2,5-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 391.2515 g/mol
HPLC-MS: analytical method H
rt: 0.985 min—found mass: 392.2 (m/z+H)

Example #254

Preparation of N2-(2-(dimethylamino)ethyl)-N5-(8-methoxy-2H-pyrazolo[3,4-c]quinolin-4-yl)pyridine-2,5-diamine 4-chloro-8-methoxy-2-(4-methoxybenzyl)-2H-pyrazolo[3,4-c]quinoline (0.16 mmol) and N2-(2-(dimethylamino)ethyl)pyridine-2,5-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 377.232 g/mol
HPLC-MS: analytical method H
rt: 0.681 min—found mass: 378.2 (m/z+H)

Example #255

Preparation of (8-Methoxy-2H-pyrazolo[3,4-c]quinolin-4-yl)-[6-(1-methyl-piperidin-4-yloxy)-pyridin-3-yl]-amine 4-chloro-8-methoxy-2-(4-methoxybenzyl)-2H-pyrazolo[3,4-c]quinoline (0.16 mmol) and 6-((1-methylpiperidin-4-yl)oxy)pyridin-3-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 404.2329 g/mol
HPLC-MS: analytical method H
rt: 1.032 min—found mass: 405.2 (m/z+H)

Example #256

Preparation of (1H-Indazol-5-yl)-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 330.1404 g/mol
HPLC-MS: analytical method C
rt: 2.14 min—found mass: 331 (m/z+H)

Example #257

Preparation of 8-((7-methoxy-2H-pyrazolo[3,4-c]quinolin-4-yl)amino)-4,5-dihydro-1H-benzo[b]azepin-2(3H)-one 4-chloro-7-methoxy-2-(4-methoxybenzyl)-2H-pyrazolo[3,4-c]quinoline (0.16 mmol) and 8-amino-4,5-dihydro-1H-benzo[b]azepin-2(3H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 373.1808 g/mol
HPLC-MS: analytical method H
rt: 2.42 min—found mass: 374 (m/z+H)

Example #258

Preparation of (2,3-Dihydro-benzo[1,4]dioxin-6-yl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 2,3-dihydrobenzo[b][1,4]dioxin-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 348.1437 g/mol
HPLC-MS: analytical method H
rt: 2.44 min—found mass: 349 (m/z+H)

Example #259

Preparation of (4-Dimethylaminomethyl-phenyl)-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 4-((dimethylamino)methyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 347.2069 g/mol
HPLC-MS: analytical method H
rt: 2.414 min—found mass: 374 (m/z+H)

Example #260

Preparation of [4-(4-Ethyl-piperazin-1-yl)-phenyl]-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 4-(4-ethylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 402.258 g/mol
HPLC-MS: analytical method H
rt: 192 min—found mass: 403 (m/z+H)

Example #261

Preparation of (6-Methoxy-2H-pyrazolo[3,4-c]quinolin-4-yl)-phenyl-amine 4-chloro-6-methoxy-2-(4-methoxybenzyl)-2H-pyrazolo[3,4-c]quinoline (0.16 mmol) and aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 290.1359 g/mol
HPLC-MS: analytical method A
rt: 2.216 min—found mass: 291.2 (m/z+H)

Example #262

Preparation of [4-(4-Cyclopropyl-piperazin-1-yl)-phenyl]-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 4-(4-cyclopropylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 414.2574 g/mol
HPLC-MS: analytical method H
rt: 2.02 min—found mass: 415 (m/z+H)

Example #263

Preparation of (1H-Benzoimidazol-5-yl)-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 1H-benzoimidazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 330.1404 g/mol
HPLC-MS: analytical method H
rt: 1.99 min—found mass: 331 (m/z+H)

Example #264

Preparation of (7-Methoxy-2H-pyrazolo[3,4-c]quinolin-4-yl)-(2-methyl-1H-benzoimidazol-5-yl)-amine 4-chloro-7-methoxy-2-(4-methoxybenzyl)-2H-pyrazolo[3,4-c]quinoline (0.16 mmol) and 2-methyl-1H-benzoimidazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 344.1599 g/mol
HPLC-MS: analytical method H
rt: 1.92 min—found mass: 345 (m/z+H)

Example #265

Preparation of (2,3-Dihydro-benzo[1,4]dioxin-6-yl)-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and 2,3-dihydrobenzo[b][1,4]dioxin-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 348.1437 g/mol
HPLC-MS: analytical method H
rt: 236 min—found mass: 349 (m/z+H)

Example #266

Preparation of 6-((7-methoxy-2H-pyrazolo[3,4-c]quinolin-4-yl)amino)-2H-benzo[b][1,4]oxazin-3(4H)-one 4-chloro-7-methoxy-2-(4-methoxybenzyl)-2H-pyrazolo[3,4-c]quinoline (0.16 mmol) and 6-amino-2H-benzo[b][1,4]oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 361.1362 g/mol
HPLC-MS: analytical method H
rt: 2.31 min—found mass: 362 (m/z+H)

Example #267

Preparation of Benzo[1,3]dioxol-5-yl-(7-methoxy-2H-pyrazolo[3,4-c]quinolin-4-yl)-amine 4-chloro-7-methoxy-2-(4-methoxybenzyl)-2H-pyrazolo[3,4-c]quinoline (0.16 mmol) and benzo[d][1,3]dioxol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 334.1242 g/mol
HPLC-MS: analytical method H
rt: 243 min—found mass: 335 (m/z+H)

Example #268

Preparation of (1H-Indazol-5-yl)-(6-methoxy-2H-pyrazolo[3,4-c]quinolin-4-yl)-amine 4-chloro-6-methoxy-2-(4-methoxybenzyl)-2H-pyrazolo[3,4-c]quinoline (0.16 mmol) and 1H-indazol-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 330.1404 g/mol
HPLC-MS: analytical method H
rt: 2.23 min—found mass: 331 (m/z+H)

Example #269

Preparation of [4-(4-Cyclopentyl-piperazin-1-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-cyclopentylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 442.2965 g/mol
HPLC-MS: analytical method C
rt: 1.965 min—found mass: 443.3 (m/z+H)

Example #270

Preparation of [4-(4-Isobutyl-piperazin-1-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-isobutylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 430.297 g/mol
HPLC-MS: analytical method C
rt: 1.948 min—found mass: 431.3 (m/z+H)

Example #271

Preparation of [4-(4-Isopropyl-piperazin-1-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-isopropylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 416.2775 g/mol
HPLC-MS: analytical method C
rt: 1.213 min—found mass: 417.3 (m/z+H)

Example #272

Preparation of [4-(4-Cyclopropylmethyl-piperazin-1-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-(cyclopropylmethyl)piperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 428.277 g/mol
HPLC-MS: analytical method C
rt: 1.905 min—found mass: 429.3 (m/z+H)

Example #273

Preparation of [4-(4-tert-Butyl-piperazin-1-yl)-phenyl]-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-(tert-butyl)piperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 430.297 g/mol
HPLC-MS: analytical method C
rt: 1.863 min—found mass: 431.3 (m/z+H)

Example #274

Preparation of (6-Methoxy-2H-pyrazolo[3,4-c]quinolin-4-yl)-p-tolyl-amine 4-chloro-6-methoxy-2-(4-methoxybenzyl)-2H-pyrazolo[3,4-c]quinoline (0.16 mmol) and p-toluidine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 304.1554 g/mol
HPLC-MS: analytical method A
rt: 2.239 min—found mass: 305.2 (m/z+H)

Example #275

Preparation of 4-((3,4-dimethoxyphenyl)amino)-2H-pyrazolo[4,3-d]thieno[3,4-b]pyridine-6-carboxylic acid methyl ester methyl-4-chloro-2-(4-methoxybenzyl)-2H-pyrazolo[4,3-d]thieno[3,4-b]pyridine-6-carboxylate (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 384.1101 g/mol
HPLC-MS: analytical method C
rt: 2.34 min—found mass: 385 (m/z+H)

Example #276

Preparation of 4-((4-(4-cyclopropylpiperazin-1-yl)phenyl)amino)-2H-pyrazolo[4,3-d]thieno[3,4-b]pyridine-6-carboxylic acid methyl ester methyl-4-chloro-2-(4-methoxybenzyl)-2H-pyrazolo[4,3-d]thieno[3,4-b]pyridine-6-carboxylate (0.16 mmol) and 4-(4-cyclopropylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 448.2039 g/mol
HPLC-MS: analytical method C
rt: 1.84 min—found mass: 348 (m/z+H)

Example #277

Preparation of 2-(4-(4-((8-methoxy-2H-pyrazolo[3,4-c]quinolin-4-yl)amino)phenyl)piperazin-1-yl)acetic-acid 4-chloro-8-methoxy-2-(4-methoxybenzyl)-2H-pyrazolo[3,4-c]quinoline (0.16 mmol) and 2-(4-(4-aminophenyl)piperazin-1-yl)acetic-acid (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 432.2267 g/mol
HPLC-MS: analytical method D
rt: 2.390 min—found mass: 433.3 (m/z+H)

Example #278

Preparation of (6-Methoxy-2H-pyrazolo[3,4-c]quinolin-4-yl)-[4-(4-methyl-piperazin-1-ylmethyl)-phenyl]-amine 4-chloro-6-methoxy-2-(4-methoxybenzyl)-2H-pyrazolo[3,4-c]quinoline (0.16 mmol) and (4-Amino-phenyl)-(4-methyl-piperazin-1-yl)-methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and dissolved in THF (dry) LiAlH4 powder was added (excess, 2 by 2 eq) until completion of reaction is observed (by LCMS). The reaction was queched with water (1 mL per gram LiAlH4), then NaOH (ca. 15% aq., 1 mL per g LiAlH4), water (3 mL per gram LiALH4). The mixture was filtered, washed with THF, MeOH, MeCN (ca. 10 ML each). The reaction mixture was concentrated and purified by semi-preparative HPLC-MS and freeze dried from water/t-BuOH 4/1.

exact mass: 402.2579 g/mol
HPLC-MS: analytical method C
rt: 1.840 min—found mass: 403.3 (m/z+H)

Example #279

Preparation of 2-(2-methoxy-4-((8-methoxy-2H-pyrazolo[3,4-c]quinolin-4-yl)amino)phenoxy)acetic-acid 4-chloro-8-methoxy-2-(4-methoxybenzyl)-2H-pyrazolo[3,4-c]quinoline (0.16 mmol) and 2-(4-amino-2-methoxyphenoxy)acetic-acid (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 394.1521 g/mol
HPLC-MS: analytical method D
rt: 3.179 min—found mass: 395.1 (m/z+H)

Example #280

Preparation of (4-((8-methoxy-2H-pyrazolo[3,4-c]quinolin-4-yl)amino)phenyl)methanol 4-chloro-8-methoxy-2-(4-methoxybenzyl)-2H-pyrazolo[3,4-c]quinoline (0.16 mmol) and (4-aminophenyl)methanol (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 320.1498 g/mol
  HPLC-MS: analytical method D
  rt: 3.38 min—found mass: 321.1 (m/z+H)

Example #281

Preparation of {4-[4-(2-Dimethylamino-ethyl)-piperazin-1-yl]-phenyl}-(8-methoxy-2H-pyrazolo[3,4-c]quinolin-4-yl)-amine 4-chloro-8-methoxy-2-(4-methoxybenzyl)-2H-pyrazolo[3,4-c]quinoline (0.16 mmol) and 4-(4-(2-(dimethylamino)ethyl)piperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 445.3095 g/mol
  HPLC-MS: analytical method A
  rt: 0.756 min—found mass: 446.3 (m/z+H)

Example #282

Preparation of (6,8-Dimethoxy-2H-pyrazolo[3,4-c]quinolin-4-yl)-[4-(4-methyl-piperazin-1-ylmethyl)-phenyl]-amine 4-chloro-6,8-dimethoxy-2-(4-methoxybenzyl)-2H-pyrazolo[3,4-c]quinoline (0.16 mmol) and (4-Amino-phenyl)-(4-methyl-piperazin-1-yl)-methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and dissolved in THF (dry) LiAlH4 powder was added (excess, 2 by 2 eq) until completion of reaction is observed (by LCMS). The reaction was quechled with water (1 mL per gram LiAlH4), then NaOH (ca. 15% aq., 1 mL per g LiAlH4), water (3 mL per gram LiALH4). The mixture was filtered, washed with THF, MeOH, MeCN (ca. 10 ML each). The reaction mixture was concentrated and purified by semi-preparative HPLC-MS and freeze dried from water/t-BuOH 4/1.
  exact mass: 432.2719 g/mol
  HPLC-MS: analytical method D
  rt: 2.758 min—found mass: 433.2 (m/z+H)

Example #283

Preparation of (4-((6,8-dimethoxy-2H-pyrazolo[3,4-c]quinolin-4-yl)amino)phenyl)(4-methylpiperazin-1-yl)methanone 4-chloro-6,8-dimethoxy-2-(4-methoxybenzyl)-2H-pyrazolo[3,4-c]quinoline (0.16 mmol) and (4-aminophenyl)(4-methylpiperazin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 446.2462 g/mol
  HPLC-MS: analytical method D
  rt: 2.720 min—found mass: 447.2 (m/z+H)

Example #284

Preparation of (6,8-Dimethoxy-2H-pyrazolo[3,4-c]quinolin-4-yl)-(4-dimethylaminomethyl-phenyl)-amine 4-chloro-6,8-dimethoxy-2-(4-methoxybenzyl)-2H-pyrazolo[3,4-c]quinoline (0.16 mmol) and 4-((dimethylamino)methyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 377.2209 g/mol
  HPLC-MS: analytical method D
  rt: 2.563 min—found mass: 378.2 (m/z+H)

Example #285

Preparation of 2-(4-((8-methoxy-2H-pyrazolo[3,4-c]quinolin-4-yl)amino)phenyl)acetic acid 4-chloro-8-methoxy-2-(4-methoxybenzyl)-2H-pyrazolo[3,4-c]quinoline (0.16 mmol) and 2-(4-aminophenyl)acetic acid (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 348.1437 g/mol
  HPLC-MS: analytical method D
  rt: 3.760 min—found mass: 349 (m/z+H)

Example #286

Preparation of 6-((8-methoxy-2H-pyrazolo[3,4-c]quinolin-4-yl)amino)-2-naphthoic acid 4-chloro-8-methoxy-2-(4-methoxybenzyl)-2H-pyrazolo[3,4-c]quinoline (0.16 mmol) and 6-amino-2-naphthoic acid (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 384.1422 g/mol
- HPLC-MS: analytical method D
- rt: 4.767 min—found mass: 385 (m/z+H)

Example #287

Preparation of 3-((8-methoxy-2H-pyrazolo[3,4-c]quinolin-4-yl)amino)benzoic acid 4-chloro-8-methoxy-2-(4-methoxybenzyl)-2H-pyrazolo[3,4-c]quinoline (0.16 mmol) and 3-aminobenzoic acid (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 334.1242 g/mol
- HPLC-MS: analytical method D
- rt: 3.827 min—found mass: 335 (m/z+H)

Example #288

Preparation of 4'-((8-methoxy-2H-pyrazolo[3,4-c]quinolin-4-yl)amino)-[1,1'-biphenyl]-4-carboxylic acid 4-chloro-8-methoxy-2-(4-methoxybenzyl)-2H-pyrazolo[3,4-c]quinoline (0.16 mmol) and 4'-amino-[1,1'-biphenyl]-4-carboxylic acid (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 410.1612 g/mol
- HPLC-MS: analytical method D
- rt: 5.035 min—found mass: 411 (m/z+H)

Example #289

Preparation of 1-(4-((8-methoxy-2H-pyrazolo[3,4-c]quinolin-4-yl)amino)phenyl)-3-(m-tolyl)urea 4-chloro-8-methoxy-2-(4-methoxybenzyl)-2H-pyrazolo[3,4-c]quinoline (0.16 mmol) and 1-(4-aminophenyl)-3-(m-tolyl)urea (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 438.2115 g/mol
- HPLC-MS: analytical method D
- rt: 5.37 min—found mass: 439 (m/z+H)

Example #290

Preparation of 2-(4-((8-methoxy-2H-pyrazolo[3,4-c]quinolin-4-yl)amino)phenoxy)acetic acid 4-chloro-8-methoxy-2-(4-methoxybenzyl)-2H-pyrazolo[3,4-c]quinoline (0.16 mmol) and 2-(4-aminophenoxy)acetic acid (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 364.1382 g/mol
- HPLC-MS: analytical method A
- rt: 1.956 min—found mass: 365 (m/z+H)

Example #291

Preparation of 6-((8-methoxy-2H-pyrazolo[3,4-c]quinolin-4-yl)amino)-2H-benzo[b][1,4]oxazin-3(4H)-one 4-chloro-8-methoxy-2-(4-methoxybenzyl)-2H-pyrazolo[3,4-c]quinoline (0.16 mmol) and 6-amino-2H-benzo[b][1,4]oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 361.1363 g/mol
- HPLC-MS: analytical method D
- rt: 3.699 min—found mass: 362 (m/z+H)

Example #292

Preparation of 4-(4-((8-methoxy-2H-pyrazolo[3,4-c]quinolin-4-yl)amino)phenyl)thiomorpholine 1,1-dioxide 4-chloro-8-methoxy-2-(4-methoxybenzyl)-2H-pyrazolo[3,4-c]quinoline (0.16 mmol) and 4-(4-aminophenyl)thiomorpholine 1,1-dioxide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for min at 140° C. The reaction mixture was concentrated and purified by semi-preparative HPLC-MS and freeze dried from water/t-BuOH 4/1.
 exact mass: 423.1667 g/mol
 HPLC-MS: analytical method D
 rt: 3.876 min—found mass: 424 (m/z+H)

Example #293

Preparation of 8-methoxy-N-(4-thiomorpholinophenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 4-thiomorpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 391.1779 g/mol
 HPLC-MS: analytical method D
 rt: 4.931 min—found mass: 392 (m/z+H)

Example #294

Preparation of 8-methoxy-N-(2-methylisoindolin-5-yl)-2H-pyrazolo[3,4-c]quinolin-4-amine 4-chloro-8-methoxy-2-(4-methoxybenzyl)-2H-pyrazolo[3,4-c]quinoline (0.16 mmol) and 2-methylisoindolin-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 345.1870 g/mol
 HPLC-MS: analytical method D
 rt: 0.557 min—found mass: 346 (m/z+H)

Example #295

Preparation of (3-methoxy-4-((8-methoxy-2H-pyrazolo[3,4-c]quinolin-4-yl)amino)phenyl)(4-(4-methylpiperazin-1-yl)piperidin-1-yl)methanone 4-chloro-8-methoxy-2-(4-methoxybenzyl)-2H-pyrazolo[3,4-c]quinoline (0.16 mmol) and (4-amino-3-methoxyphenyl)(4-(4-methylpiperazin-1-yl)piperidin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 529.3362 g/mol
 HPLC-MS: analytical method D
 rt: 0.59 min—found mass: 530 (m/z+H)

Example #296

Preparation of 3-((8-hydroxy-2H-pyrazolo[3,4-c]quinolin-4-yl)amino)benzoic acid 4-chloro-2-(4-methoxybenzyl)-2H-pyrazolo[3,4-c]quinolin-8-ol (0.16 mmol) and 3-aminobenzoic acid (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 320.1047 g/mol
 HPLC-MS: analytical method D
 rt: 2.77 min—found mass: 321 (m/z+H)

Example #297

Preparation of 1-(4-((6,8-dimethoxy-2H-pyrazolo[3,4-c]quinolin-4-yl)amino)phenyl)-3-(m-tolyl)urea 4-chloro-6,8-dimethoxy-2-(4-methoxybenzyl)-2H-pyrazolo[3,4-c]quinoline (0.16 mmol) and 1-(4-aminophenyl)-3-(m-tolyl)urea (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
 exact mass: 468.2254 g/mol
 HPLC-MS: analytical method D
 rt: 5.341 min—found mass: 469 (m/z+H)

Example #298

Preparation of 1-(4-((7-methoxy-2H-pyrazolo[3,4-c]quinolin-4-yl)amino)phenyl)-3-(m-tolyl)urea 4-chloro-7-methoxy-2-(4-methoxybenzyl)-2H-pyrazolo[3,4-c]quinoline (0.16 mmol) and 1-(4-aminophenyl)-3-(m-tolyl)urea (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 438.2115 g/mol
HPLC-MS: analytical method D
rt: 5.139 min—found mass: 439 (m/z+H)

Example #299

Preparation of 1-(4-((7,8-dimethoxy-2H-pyrazolo[3,4-c]quinolin-4-yl)amino)phenyl)-3-(m-tolyl)urea 4-chloro-7,8-dimethoxy-2-(4-methoxybenzyl)-2H-pyrazolo[3,4-c]quinoline (0.16 mmol) and 1-(4-aminophenyl)-3-(m-tolyl)urea (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 468.2253 g/mol
HPLC-MS: analytical method D
rt: 4.907 min—found mass: 469 (m/z+H)

Example #300

Preparation of N-(2-(dimethylamino)ethyl)-4-((8-methoxy-2H-pyrazolo[3,4-c]quinolin-4-yl)amino)-N-methylbenzamide 4-chloro-8-methoxy-2-(4-methoxybenzyl)-2H-pyrazolo[3,4-c]quinoline (0.16 mmol) and 4-amino-N-(2-(dimethylamino)ethyl)-N-methylbenzamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 418.2524 g/mol
HPLC-MS: analytical method C
rt: 1.83 min—found mass: 419 (m/z+H)

Example #301

Preparation of (4-((8-methoxy-2H-pyrazolo[3,4-c]quinolin-4-yl)amino)phenyl)(2-(methoxymethyl)pyrrolidin-1-yl)methanone 4-chloro-8-methoxy-2-(4-methoxybenzyl)-2H-pyrazolo[3,4-c]quinoline (0.16 mmol) and (4-aminophenyl) (2-(methoxymethyl)pyrrolidin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 431.2338 g/mol
HPLC-MS: analytical method A
rt: 2.41 min—found mass: 432 (m/z+H)

Example #302

Preparation of azetidin-1-yl(4-((8-methoxy-2H-pyrazolo[3,4-c]quinolin-4-yl)amino)phenyl)methanone 4-chloro-8-methoxy-2-(4-methoxybenzyl)-2H-pyrazolo[3,4-c]quinoline (0.16 mmol) and (4-aminophenyl)(azetidin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 373.1808 g/mol
HPLC-MS: analytical method A
rt: 2.30 min—found mass: 374 (m/z+H)

Example #303

Preparation of 4-((8-methoxy-2H-pyrazolo[3,4-c]quinolin-4-yl)amino)-N,N-dimethylbenzamide 4-chloro-8-methoxy-2-(4-methoxybenzyl)-2H-pyrazolo[3,4-c]quinoline (0.16 mmol) and 4-amino-N,N-dimethylbenzamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 361.1814 g/mol
HPLC-MS: analytical method A
rt: 2.12 min—found mass: 362 (m/z+H)

Example #304

Preparation of (4-((8-methoxy-2H-pyrazolo[3,4-c]quinolin-4-yl)amino)phenyl)(4-methyl-1,4-diazepan-1-yl)methanone 4-chloro-8-methoxy-2-(4-methoxybenzyl)-2H-pyrazolo[3,4-c]quinoline (0.16 mmol) and (4-aminophenyl)(4-methyl-1,4-diazepan-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 430.2519 g/mol
HPLC-MS: analytical method C
rt: 1.83 min—found mass: 431 (m/z+H)

Example #305

Preparation of 1-(4-((8-methoxy-2H-pyrazolo[3,4-c]quinolin-4-yl)amino)benzoyl)piperidin-4-one 4-chloro-8-methoxy-2-(4-methoxybenzyl)-2H-pyrazolo[3,4-c]quinoline (0.16 mmol) and 1-(4-aminobenzoyl)piperidin-4-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 415.1942 g/mol
HPLC-MS: analytical method A
rt: 2.12 min—found mass: 416 (m/z+H)

Example #306

Preparation of (4-((8-methoxy-2H-pyrazolo[3,4-c]quinolin-4-yl)amino)phenyl)(1,4-dioxa-8-azaspiro[4.5]decan-8-yl)methanone 4-chloro-8-methoxy-2-(4-methoxybenzyl)-2H-pyrazolo[3,4-c]quinoline (0.16 mmol) and (4-aminophenyl)(1,4-dioxa-8-azaspiro[4.5]decan-8-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 459.2276 g/mol
HPLC-MS: analytical method A
rt: 2.38 min—found mass: 460 (m/z+H)

Example #307

Preparation of (3-(dimethylamino)pyrrolidin-1-yl)(4-((8-methoxy-2H-pyrazolo[3,4-c]quinolin-4-yl)amino)phenyl)methanone 4-chloro-8-methoxy-2-(4-methoxybenzyl)-2H-pyrazolo[3,4-c]quinoline (0.16 mmol) and (4-aminophenyl)(3-(dimethylamino)pyrrolidin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 430.2519 g/mol
HPLC-MS: analytical method C
rt: 1.89 min—found mass: 431 (m/z+H)

Example #308

Preparation of 8-methoxy-N-(1-methyl-1,2,3,4-tetrahydroquinolin-6-yl)-2H-pyrazolo[3,4-c]quinolin-4-amine 4-chloro-8-methoxy-2-(4-methoxybenzyl)-2H-pyrazolo[3,4-c]quinoline (0.16 mmol) and 1-methyl-1,2,3,4-tetrahydroquinolin-6-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 359.2065 g/mol
HPLC-MS: analytical method D
rt: 4.77 min—found mass: 360 (m/z+H)

Example #309

Preparation of 8-methoxy-N-(3-(pentafluorosulfanyl)phenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 3-Aminophenylsulphur pentafluoride (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 416.0869 g/mol
HPLC-MS: analytical method D
rt: 7.747 min—found mass: 417 (m/z+H)

Example #310

Preparation of N-(4-fluorophenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 4-fluoroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 308.1238 g/mol
HPLC-MS: analytical method D
rt: 4 min—found mass: 309 (m/z+H)

Example #311

Preparation of N-(3,4-difluorophenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 3,4-difluoroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 326.1117 g/mol
HPLC-MS: analytical method D
rt: 5.31 min—found mass: 327 (m/z+H)

Example #312

Preparation of 2,2,2-trifluoro-N-(4-((8-methoxy-2H-pyrazolo[3,4-c]quinolin-4-yl)amino)phenyl)acetamide 4-chloro-8-methoxy-2-(4-methoxybenzyl)-2H-pyrazolo[3,4-c]quinoline (0.16 mmol) and N-(4-aminophenyl)-2,2,2-trifluoroacetamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 401.1256 g/mol
HPLC-MS: analytical method D
rt: 4.89 min—found mass: 402 (m/z+H)

Example #313

Preparation of 3-((6-((8-methoxy-2H-pyrazolo[3,4-c]quinolin-4-yl)amino)-2H-benzo[b][1,4]oxazin-3-yl)amino)propan-1-ol 4-chloro-8-methoxy-2-(4-methoxybenzyl)-2H-pyrazolo[3,4-c]quinoline (0.16 mmol) and 3-((6-amino-2H-benzo[b][1,4]oxazin-3-yl)amino)propan-1-ol (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 418.2072 g/mol
HPLC-MS: analytical method D
rt: 3.136 min—found mass: 419 (m/z+H)

Example #314

Preparation of N6-(8-methoxy-2H-pyrazolo[3,4-c]quinolin-4-yl)-N3-phenethyl-2H-benzo[b][1,4]oxazine-3,6-diamine 4-chloro-8-methoxy-2-(4-methoxybenzyl)-2H-pyrazolo[3,4-c]quinoline (0.16 mmol) and N3-phenethyl-2H-benzo[b][1,4]oxazine-3,6-diamine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 464.2305 g/mol
HPLC-MS: analytical method C
rt: 2.322 min—found mass: 465 (m/z+H)

Example #315

Preparation of N-(3,5-difluorophenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 3,5-difluoroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 326.1117 g/mol
HPLC-MS: analytical method D
rt: 6.98 min—found mass: 327 (m/z+H)

Example #316

Preparation of N-(3-fluoro-4-methylphenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 3-fluoro-4-methylaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 322.1433 g/mol
HPLC-MS: analytical method D
rt: 5.191 min—found mass: 323 (m/z+H)

Example #317

Preparation of 8-methoxy-N-(3,4,5-trifluorophenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 3,4,5-trifluoroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 344.0996 g/mol
HPLC-MS: analytical method D
rt: 7.303 min—found mass: 345 (m/z+H)

Example #318

Preparation of 8-methoxy-N-(4-nitrophenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 4-nitroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 335.1172 g/mol
HPLC-MS: analytical method D
rt: 7.227 min—found mass: 336 (m/z+H)

Example #319

Preparation of 8-methoxy-N-(3-methoxy-4-morpholinophenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 3-methoxy-4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 405.2148 g/mol
HPLC-MS: analytical method D
rt: 3.996 min—found mass: 406 (m/z+H)

Example #320

Preparation of 8-methoxy-N-(3-(methylsulfonyl)phenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 3-(methylsulfonyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 368.1158 g/mol
HPLC-MS: analytical method D
rt: 4.716 min—found mass: 370 (m/z+H)

Example #321

Preparation of 1,1,1,3,3,3-hexafluoro-2-(4-((8-methoxy-2H-pyrazolo[3,4-c]quinolin-4-yl)amino)phenyl)propan-2-ol 4-chloro-8-methoxy-2-(4-methoxybenzyl)-2H-pyrazolo[3,4-c]quinoline (0.16 mmol) and 2-(4-aminophenyl)-1,1,1,3,3,3-hexafluoropropan-2-ol (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 456.1162 g/mol
HPLC-MS: analytical method D
rt: 6.425 min—found mass: 457 (m/z+H)

Example #322

Preparation of (4-((8-fluoro-3H-pyrazolo[3,4-c]quinolin-4-yl)amino)phenyl) (pyrrolidin-1-yl)methanone 4-chloro-8-fluoro-2-(4-methoxybenzyl)-2H-pyrazolo[3,4-c]quinoline (0.16 mmol) and (4-aminophenyl)(pyrrolidin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 375.1744 g/mol
HPLC-MS: analytical method D
rt: 5.249 min—found mass: 376 (m/z+H)

Example #323

Preparation of 1-(4-(4-((8-fluoro-3H-pyrazolo[3,4-c]quinolin-4-yl)amino)phenyl)piperazin-1-yl)ethan-1-one 4-chloro-8-fluoro-2-(4-methoxybenzyl)-2H-pyrazolo[3,4-c]quinoline (0.16 mmol) and 1-(4-(4-aminophenyl)piperazin-1-yl)ethan-1-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 404.2064 g/mol
  HPLC-MS: analytical method D
  rt: 4.104 min—found mass: 405 (m/z+H)

Example #324

Preparation of 6-((8-fluoro-3H-pyrazolo[3,4-c]quinolin-4-yl)amino)-2H-benzo[b][1,4]oxazin-3(4H)-one 4-chloro-8-fluoro-2-(4-methoxybenzyl)-2H-pyrazolo[3,4-c]quinoline (0.16 mmol) and 6-amino-2H-benzo[b][1,4]oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 349.1103 g/mol
  HPLC-MS: analytical method D
  rt: 3.913 min—found mass: 350 (m/z+H)

Example #325

Preparation of 8-fluoro-N-(4-morpholinophenyl)-3H-pyrazolo[3,4-c]quinolin-4-amine 4-chloro-8-fluoro-2-(4-methoxybenzyl)-2H-pyrazolo[3,4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 363.1749 g/mol
  HPLC-MS: analytical method D
  rt: 3.964 min—found mass: 364 (m/z+H)

Example #326

Preparation of 8-fluoro-N-(4-(4-methylpiperazin-1-yl)phenyl)-3H-pyrazolo[3,4-c]quinolin-4-amine 4-chloro-8-fluoro-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 376.2125 g/mol
  HPLC-MS: analytical method K
  rt: 2.316 min—found mass: 377 (m/z+H)

Example #327

Preparation of N-(3,4-dimethoxyphenyl)-8-fluoro-3H-pyrazolo[3,4-c]quinolin-4-amine 4-chloro-8-fluoro-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 338.1377 g/mol
  HPLC-MS: analytical method D
  rt: 4.006 min—found mass: 339 (m/z+H)

Example #328

Preparation of N-(4-(difluoromethoxy)-3-methoxyphenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 4-(difluoromethoxy)-3-methoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
  exact mass: 386.1396 g/mol
  HPLC-MS: analytical method D
  rt: 5.34 min—found mass: 387 (m/z+H)

Example #329

Preparation of N-(3-fluoro-4-(trifluoromethyl)phenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 3-fluoro-4-(trifluoromethyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 376.1070 g/mol
- HPLC-MS: analytical method D
- rt: 8.413 min—found mass: 377 (m/z+H)

Example #330

Preparation of N-(3-fluoro-4-(trifluoromethoxy) phenyl)-8-methoxy-2H-pyrazolo[3,4-c]quinolin-4-amine 4-chloro-8-methoxy-2-(4-methoxybenzyl)-2H-pyrazolo [3,4-c]quinoline (0.16 mmol) and 3-fluoro-4-(trifluoromethoxy)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 392.1015 g/mol
- HPLC-MS: analytical method D
- rt: 7.887 min—found mass: 393 (m/z+H)

Example #331

Preparation of N-(2,3-dimethoxyphenyl)-8-methoxy-2H-pyrazolo[3,4-c]quinolin-4-amine 4-chloro-8-methoxy-2-(4-methoxybenzyl)-2H-pyrazolo [3,4-c]quinoline (0.16 mmol) and 2,3-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 350.1638 g/mol
- HPLC-MS: analytical method D
- rt: 4.507 min—found mass: 352 (m/z+H)

Example #332

Preparation of N-(2,4-dimethoxyphenyl)-8-methoxy-2H-pyrazolo[3,4-c]quinolin-4-amine 4-chloro-8-methoxy-2-(4-methoxybenzyl)-2H-pyrazolo [3,4-c]quinoline (0.16 mmol) and 2,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 350.1637 g/mol
- HPLC-MS: analytical method D
- rt: 4.22 min—found mass: 352 (m/z+H)

Example #333

Preparation of 8-iodo-N-(4-(4-methylpiperazin-1-yl) phenyl)-3H-pyrazolo[3,4-c]quinolin-4-amine 4-chloro-8-iodo-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for min at 140° C. The reaction mixture was concentrated and purified by semi-preparative HPLC-MS and freeze dried from water/t-BuOH 4/1.
- exact mass: 484.1185 g/mol
- HPLC-MS: analytical method L
- rt: 3.25 min—found mass: 485 (m/z+H)

Example #334

Preparation of 6-((7-fluoro-3H-pyrazolo[3,4-c]quinolin-4-yl)amino)-2H-benzo[b][1,4]oxazin-3(4H)-one 4-chloro-7-fluoro-2-(4-methoxybenzyl)-2H-pyrazolo[3, 4-c]quinoline (0.16 mmol) and 6-amino-2H-benzo[b][1,4] oxazin-3(4H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
- exact mass: 349.1102 g/mol
- HPLC-MS: analytical method L
- rt: 3.856 min—found mass: 350 (m/z+H)

Example #335

Preparation of 7-fluoro-N-(4-morpholinophenyl)-3H-pyrazolo[3,4-c]quinolin-4-amine 4-chloro-7-fluoro-2-(4-methoxybenzyl)-2H-pyrazolo[3, 4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 363.1748 g/mol
HPLC-MS: analytical method L
rt: 3.846 min—found mass: 364 (m/z+H)

Example #336

Preparation of N-(3,4-dimethoxyphenyl)-7-fluoro-3H-pyrazolo[3,4-c]quinolin-4-amine 4-chloro-7-fluoro-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 338.1377 g/mol
HPLC-MS: analytical method D
rt: 4.269 min—found mass: 339 (m/z+H)

Example #337

Preparation of 7-fluoro-N-(4-(4-methylpiperazin-1-yl)phenyl)-3H-pyrazolo[3,4-c]quinolin-4-amine 4-chloro-7-fluoro-2-(4-methoxybenzyl)-2H-pyrazolo[3,4-c]quinoline (0.16 mmol) and 4-(4-methylpiperazin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 376.2125 g/mol
HPLC-MS: analytical method K
rt: 2.39 min—found mass: 377 (m/z+H)

Example #338

Preparation of 9-methoxy-N-(3-(methylsulfonyl)phenyl)-3H-pyrazolo[3,4-c]quinolin-4-amine 4-chloro-9-methoxy-2-(4-methoxybenzyl)-2H-pyrazolo[3,4-c]quinoline (0.16 mmol) and 3-(methylsulfonyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 368.1157 g/mol
HPLC-MS: analytical method D
rt: 5.01 min—found mass: 369 (m/z+H)

Example #339

Preparation of 7-((9-methoxy-3H-pyrazolo[3,4-c]quinolin-4-yl)amino)-3,4-dihydroquinolin-2(1H)-one 4-chloro-9-methoxy-2-(4-methoxybenzyl)-2H-pyrazolo[3,4-c]quinoline (0.16 mmol) and 7-amino-3,4-dihydroquinolin-2(1H)-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 359.1613 g/mol
HPLC-MS: analytical method D
rt: 4.03 min—found mass: 360 (m/z+H)

Example #340

Preparation of 1-(4-(4-((9-methoxy-3H-pyrazolo[3,4-c]quinolin-4-yl)amino)phenyl)piperazin-1-yl)ethan-1-one 4-chloro-9-methoxy-2-(4-methoxybenzyl)-2H-pyrazolo[3,4-c]quinoline (0.16 mmol) and 1-(4-(4-aminophenyl)piperazin-1-yl)ethan-1-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 416.2323 g/mol
HPLC-MS: analytical method D
rt: 4.14 min—found mass: 417 (m/z+H)

Example #341

Preparation of N-(3,5-dimethoxyphenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 3,5-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 350.1638 g/mol
HPLC-MS: analytical method L
rt: 4.111 min—found mass: 351 (m/z+H)

Example #342

Preparation of (4-((7-fluoro-3H-pyrazolo[3,4-c]quinolin-4-yl)amino)phenyl)(pyrrolidin-1-yl)methanone 4-chloro-7-fluoro-2-(4-methoxybenzyl)-2H-pyrazolo[3,4-c]quinoline (0.16 mmol) and (4-aminophenyl)(pyrrolidin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 375.1743 g/mol

HPLC-MS: analytical method D rt: 5.78 min—found mass: 376 (m/z+H)

Example #343

Preparation of 4-((8-methoxy-2H-pyrazolo[3,4-c]quinolin-4-yl)amino)-N,N-dimethylbenzenesulfonamide 4-chloro-8-methoxy-2-(4-methoxybenzyl)-2H-pyrazolo[3,4-c]quinoline (0.16 mmol) and 4-amino-N,N-dimethylbenzenesulfonamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 397.1478 g/mol

HPLC-MS: analytical method D rt: 6.424 min—found mass: 398 (m/z+H)

Example #344

Preparation of N-cyclopropyl-3-((8-methoxy-2H-pyrazolo[3,4-c]quinolin-4-yl)amino)benzenesulfonamide 4-chloro-8-methoxy-2-(4-methoxybenzyl)-2H-pyrazolo[3,4-c]quinoline (0.16 mmol) and 3-amino-N-cyclopropylbenzenesulfonamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 409.1473 g/mol

HPLC-MS: analytical method L rt: 4.619 min—found mass: 410 (m/z+H)

Example #345

Preparation of N-(4-(2H-1,2,3-triazol-2-yl)phenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 4-(2H-1,2,3-triazol-2-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 357.1524 g/mol

HPLC-MS: analytical method D rt: 5.381 min—found mass: 358 (m/z+H)

Example #346

Preparation of 8-methoxy-N-(3-(methylsulfinyl)phenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 3-(methylsulfinyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 352.1213 g/mol

HPLC-MS: analytical method L rt: 3.752 min—found mass: 353 (m/z+H)

Example #347

Preparation of N-(3-(2H-1,2,3-triazol-2-yl)phenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 3-(2H-1,2,3-triazol-2-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 357.1524 g/mol
HPLC-MS: analytical method L
rt: 4.707 min—found mass: 358 (m/z+H)

Example #348

Preparation of 3-((8-methoxy-2H-pyrazolo[3,4-c]quinolin-4-yl)amino)-N-methylbenzenesulfonamide 4-chloro-8-methoxy-2-(4-methoxybenzyl)-2H-pyrazolo[3,4-c]quinoline (0.16 mmol) and 3-amino-N-methylbenzenesulfonamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 383.1283 g/mol
HPLC-MS: analytical method L
rt: 4.283 min—found mass: 384 (m/z+H)

Example #349

Preparation of 8-methoxy-N-(3-(morpholinosulfonyl)phenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 3-(morpholinosulfonyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 439.1611 g/mol
HPLC-MS: analytical method L
rt: 4.78 min—found mass: 440 (m/z+H)—

Example #350

Preparation of 8-methoxy-N-(3-((trifluoromethyl)sulfonyl)phenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 3-((trifluoromethyl)sulfonyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 422.0794 g/mol
HPLC-MS: analytical method D
rt: 7.966 min—found mass: 423 (m/z+H)

Example #351

Preparation of 2-((3-((8-methoxy-2H-pyrazolo[3,4-c]quinolin-4-yl)amino)phenyl)sulfonyl)ethan-1-ol 4-chloro-8-methoxy-2-(4-methoxybenzyl)-2H-pyrazolo[3,4-c]quinoline (0.16 mmol) and 2-((3-aminophenyl)sulfonyl)ethan-1-ol (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 398.1296 g/mol
HPLC-MS: analytical method L
rt: 3.995 min—found mass: 399 (m/z+H)

Example #352

Preparation of 9-methoxy-N-(2-methylisoindolin-5-yl)-3H-pyrazolo[3,4-c]quinolin-4-amine 4-chloro-9-methoxy-2-(4-methoxybenzyl)-2H-pyrazolo[3,4-c]quinoline (0.16 mmol) and 2-methylisoindolin-5-amine (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 345.1869 g/mol
HPLC-MS: analytical method K
rt: 2.24 min—found mass: 345 (m/z+H)

Example #353

Preparation of N-(4-((dimethylamino)methyl)phenyl)-9-methoxy-3H-pyrazolo[3,4-c]quinolin-4-amine 4-chloro-9-methoxy-2-(4-methoxybenzyl)-2H-pyrazolo[3,4-c]quinoline (0.16 mmol) and 4-((dimethylamino)methyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 347.2069 g/mol
HPLC-MS: analytical method K
rt: 2.32 min—found mass: 348 (m/z+H)

Example #354

Preparation of N-(3,4-dimethoxyphenyl)-8-iodo-3H-pyrazolo[3,4-c]quinolin-4-amine 4-chloro-8-iodo-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 446.0438 g/mol
HPLC-MS: analytical method D
rt: 5.553 min—found mass: 447 (m/z+H)

Example #355

Preparation of 8-iodo-N-(4-morpholinophenyl)-3H-pyrazolo[3,4-c]quinolin-4-amine 4-chloro-8-iodo-2-(4-methoxybenzyl)-2H-pyrazolo[3,4-c]quinoline (0.16 mmol) and 4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 471.0809 g/mol
HPLC-MS: analytical method D
rt: 5.438 min—found mass: 472 (m/z+H)

Example #356

Preparation of (4-((8-iodo-3H-pyrazolo[3,4-c]quinolin-4-yl)amino)phenyl)(pyrrolidin-1-yl)methanone 4-chloro-8-iodo-2-(4-methoxybenzyl)-2H-pyrazolo[3,4-c]quinoline (0.16 mmol) and (4-aminophenyl)(pyrrolidin-1-yl)methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 483.0804 g/mol
HPLC-MS: analytical method L
rt: 5.219 min—found mass: 484 (m/z+H)

Example #357

Preparation of 1-(4-(4-((8-iodo-3H-pyrazolo[3,4-c]quinolin-4-yl)amino)phenyl)piperazin-1-yl)ethan-1-one 4-chloro-8-iodo-2-(4-methoxybenzyl)-2H-pyrazolo[3,4-c]quinoline (0.16 mmol) and 1-(4-(4-aminophenyl)piperazin-1-yl)ethan-1-one (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 512.1124 g/mol
HPLC-MS: analytical method L
rt: 4.101 min—found mass: 513 (m/z+H)

Example #358

Preparation of 4-fluoro-N-(4-((8-methoxy-2H-pyrazolo[3,4-c]quinolin-4-yl)amino)phenyl)benzamide 4-chloro-8-methoxy-2-(4-methoxybenzyl)-2H-pyrazolo[3,4-c]quinoline (0.16 mmol) and N-(4-aminophenyl)-4-fluorobenzamide (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 427.1673 g/mol
HPLC-MS: analytical method L
rt: 1.104 min—found mass: 428 (m/z+H)

Example #359

Preparation of 8-methoxy-N-(4-morpholino-3-nitrophenyl)-2H-pyrazolo[3,4-c]quinolin-4-amine 4-chloro-8-methoxy-2-(4-methoxybenzyl)-2H-pyrazolo[3,4-c]quinoline (0.16 mmol) and 4-morpholino-3-nitroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.
exact mass: 420.1822 g/mol
HPLC-MS: analytical method D
rt: 6.145 min—found mass: 421 (m/z+H)

Example #360

Preparation of N-(2,4-difluorophenyl)-8-methoxy-2H-pyrazolo[3,4-c]quinolin-4-amine 4-chloro-8-methoxy-2-(4-methoxybenzyl)-2H-pyrazolo[3,4-c]quinoline (0.16 mmol) and 2,4-difluoroaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 326.1117 g/mol

HPLC-MS: analytical method D rt: 4.99 min—found mass: 327 (m/z+H)

Example #361

Preparation of N-(3,4-dimethoxyphenyl)-9-fluoro-3H-pyrazolo[3,4-c]quinolin-4-amine 4-chloro-9-fluoro-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 338.1377 g/mol

HPLC-MS: analytical method D rt: 2.81 min—found mass: 339 (m/z+H)

Example #362

Preparation of 9-fluoro-N-(3-(methylsulfonyl)phenyl)-3H-pyrazolo[3,4-c]quinolin-4-amine 4-chloro-9-fluoro-2-(4-methoxybenzyl)-2H-pyrazolo[3,4-c]quinoline (0.16 mmol) and 3-(methylsulfonyl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 356.0898 g/mol

HPLC-MS: analytical method D rt: 6.24 min—found mass: 357 (m/z+H)

Example #363

Preparation of 9-fluoro-N-(4-(4-(4-methylpiperazin-1-yl)piperidin-1-yl)phenyl)-3H-pyrazolo[3,4-c]quinolin-4-amine 4-chloro-9-fluoro-2-(4-methoxybenzyl)-2H-pyrazolo[3,4-c]quinoline (0.16 mmol) and 4-(4-(4-methylpiperazin-1-yl)piperidin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 459.3026 g/mol

HPLC-MS: analytical method K rt: 2.35 min—found mass: 460 (m/z+H)

Example #364

Preparation of 9-fluoro-N-(3-fluoro-4-morpholinophenyl)-3H-pyrazolo[3,4-c]quinolin-4-amine 4-chloro-9-fluoro-2-(4-methoxybenzyl)-2H-pyrazolo[3,4-c]quinoline (0.16 mmol) and 3-fluoro-4-morpholinoaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 381.1627 g/mol

HPLC-MS: analytical method K rt: 6.38 min—found mass: 382 (m/z+H)

Biological Data

SYK Activities:

Ki Lower than 10 nM:

Example #40; Example #43; Example #47; Example #56; Example #67; Example #85; Example #93; Example #97; Example #118; Example #164; Example #169; Example #177; Example #184; Example #187; Example #188; Example #197; Example #209; Example #217; Example #222; Example #226; Example #233; Example #246; Example #251; Example #257; Example #263; Example #266; Example #270; Example #271; Example #272; Example #291; Example #292; Example #293; Example #318; Example #333; Example #358; Example #359; Example #362;

Ki Between 10 nM and 100 nM:

Example #6; Example #10; Example #13; Example #15; Example #34; Example #38; Example #39; Example #41; Example #42; Example #44; Example #45; Example #46; Example #50; Example #51; Example #53; Example #54; Example #55; Example #57; Example #58; Example #60; Example #61; Example #66; Example #71; Example #73; Example #74; Example #77; Example #78; Example #84; Example #86; Example #88; Example #91; Example #92;

Example #94; Example #95; Example #96; Example #100; Example #101; Example #102; Example #103; Example #104; Example #105; Example #107; Example #109; Example #111; Example #112; Example #113; Example #115; Example #120; Example #121; Example #122; Example #123; Example #124; Example #125; Example #128; Example #132; Example #133; Example #134; Example #135; Example #136; Example #142; Example #147; Example #150; Example #151; Example #152; Example #159; Example #160; Example #161; Example #162; Example #163; Example #165; Example #166; Example #167; Example #168; Example #170; Example #171; Example #172; Example #173; Example #175; Example #176; Example #178; Example #179; Example #181; Example #182; Example #183; Example #185; Example #189; Example #192; Example #193; Example #195; Example #196; Example #199; Example #201; Example #202; Example #203; Example #206; Example #207; Example #208; Example #216; Example #219; Example #224; Example #228; Example #232; Example #234; Example #235; Example #237; Example #238; Example #239; Example #240; Example #241; Example #242; Example #243; Example #244; Example #247; Example #250; Example #254; Example #255; Example #256; Example #259; Example #260; Example #261; Example #262; Example #264; Example #265; Example #267; Example #268; Example #273; Example #274; Example #276; Example #277; Example #280; Example #281; Example #282; Example #283; Example #284; Example #286; Example #289; Example #290; Example #294; Example #300; Example #301; Example #302; Example #308; Example #310; Example #311; Example #313; Example #314; Example #317; Example #319; Example #324; Example #325; Example #326; Example #334; Example #335; Example #336; Example #337; Example #339; Example #340; Example #343; Example #344; Example #348; Example #353; Example #355; Example #357; Example #363;

Ki Between 100 nM and 1000 nM:
Example #2; Example #3; Example #4; Example #5; Example #8; Example #17; Example #22; Example #23; Example #24; Example #25; Example #26; Example #27; Example #28; Example #30; Example #35; Example #37; Example #49; Example #52; Example #59; Example #72; Example #75; Example #76; Example #79; Example #81; Example #82; Example #83; Example #87; Example #90; Example #98; Example #99; Example #106; Example #108; Example #110; Example #114; Example #117; Example #119; Example #126; Example #131; Example #138; Example #139; Example #141; Example #144; Example #146; Example #148; Example #154; Example #156; Example #157; Example #158; Example #190; Example #191; Example #194; Example #198; Example #200; Example #210; Example #211; Example #212; Example #213; Example #214; Example #218; Example #220; Example #221; Example #223; Example #225; Example #227; Example #229; Example #230; Example #231; Example #236; Example #245; Example #248; Example #249; Example #252; Example #253; Example #258; Example #269; Example #275; Example #278; Example #279; Example #285; Example #287; Example #288; Example #296; Example #297; Example #299; Example #303; Example #309; Example #312; Example #315; Example #320; Example #321; Example #323; Example #327; Example #328; Example #331; Example #332; Example #338; Example #341; Example #342; Example #345; Example #346; Example #347; Example 049; Example #350; Example #351; Example #354; Example #356; Example #361;

LRRK2 Activites:
IC50 Lower than 10 nM:
Example #77; Example #85; Example #88; Example #93; Example #286; Example #302;

IC50 Between 10 nM and 100 nM:
Example #42; Example #44; Example #47; Example #51; Example #54; Example #56; Example #74; Example #87; Example #94; Example #95; Example #96; Example #97; Example #109; Example #111; Example #118; Example #120; Example #131; Example #132; Example #147; Example #150; Example #161; Example #164; Example #165; Example #169; Example #183; Example #187; Example #188; Example #192; Example #198; Example #199; Example #202; Example #203; Example #209; Example #234; Example #235; Example #237; Example #240; Example #266; Example #269; Example #271; Example #272; Example #277; Example #281; Example #291; Example #292; Example #293; Example #295; Example #300; Example #301; Example #303; Example #305; Example #306; Example #313; Example #314; Example #339; Example #340; Example #344; Example #348; Example #352; Example #353; Example #363;

IC50 between 100 nM and 1000 nM:
Example #3; Example #13; Example #15; Example #34; Example #37; Example #38; Example #39; Example #40; Example #43; Example #45; Example #46; Example #48; Example #49; Example #50; Example #52; Example #53; Example #55; Example #57; Example #59; Example #61; Example #66; Example #67; Example #71; Example #73; Example #78; Example #81; Example #84; Example #86; Example #92; Example #98; Example #100; Example #101; Example #102; Example #103; Example #104; Example #105; Example #106; Example #107; Example #108; Example #112; Example #113; Example #114; Example #115; Example #117; Example #119; Example #121; Example #122; Example #124; Example #125; Example #126; Example #127; Example #128; Example #133; Example #134; Example #135; Example #136; Example #138; Example #142; Example #144; Example #145; Example #148; Example #151; Example #152; Example #160; Example #162; Example #163; Example #166; Example #167; Example #168; Example #170; Example #171; Example #172; Example #173; Example #175; Example #177; Example #179; Example #181; Example #184; Example #185; Example #189; Example #193; Example #195; Example #196; Example #200; Example #201; Example #206; Example #207; Example #208; Example #215; Example #216; Example #221; Example #222; Example #223; Example #224; Example #225; Example #228; Example #229; Example #230; Example #232; Example #236; Example #238; Example #239; Example #241; Example #242; Example #243; Example #244; Example #245; Example #246; Example #247; Example #248; Example #250; Example #251; Example #252; Example #253; Example #254; Example #255; Example #256; Example #257; Example #258; Example #259; Example #262; Example #264; Example #268; Example #270; Example #273; Example #274; Example #279; Example #280; Example #282; Example #283; Example #284; Example #285; Example #290; Example #294; Example #296; Example #304; Example #307; Example #308; Example #310; Example #312; Example #317; Example #319; Example #320; Example #321; Example #323; Example #324; Example #325; Example #328; Example #333; Example #338; Example #343; Example #346; Example #351; Example #355; Example #356; Example #357; Example #361; Example #362; Example #364;

MYLK Activites:

IC50 lower than 5000 nM:

Example #13; Example #34; Example #38; Example #39; Example #41; Example #42; Example #43; Example #44; Example #49; Example #52; Example #53; Example #55; Example #56; Example #57; Example #58; Example #67; Example #71; Example #73; Example #84; Example #86; Example #87; Example #98; Example #102; Example #111; Example #112; Example #116; Example #118; Example #120; Example #121; Example #122; Example #126; Example #127; Example #128; Example #131; Example #132; Example #133; Example #134; Example #136; Example #139; Example #142; Example #147; Example #148; Example #150; Example #152; Example #160; Example #162; Example #163; Example #164; Example #165; Example #166; Example #167; Example #169; Example #171; Example #172; Example #179; Example #183; Example #184; Example #185; Example #187; Example #188; Example #192; Example #193; Example #194; Example #195; Example #199; Example #201; Example #202; Example #203; Example #206; Example #208; Example #209; Example #221; Example #222; Example #223; Example #228; Example #229; Example #230; Example #232; Example #233; Example #234; Example #235; Example #236; Example #237; Example #238; Example #239; Example #240; Example #241; Example #242; Example #243; Example #245; Example #246; Example #248; Example #251; Example #252; Example #253; Example #254; Example #255; Example #257; Example #258; Example #259; Example #261; Example #262; Example #263; Example #264; Example #266; Example #268; Example #269; Example #270; Example #271; Example #272; Example #273; Example #276; Example #277; Example #278; Example #280; Example #281; Example #282; Example #283; Example #284; Example #286; Example #287; Example #290; Example #291; Example #292; Example #294; Example #295; Example #296; Example #300; Example #301; Example #303; Example #304; Example #305; Example #306; Example #307; Example #308; Example #320; Example #322; Example #323; Example #324; Example #326; Example #327; Example #333; Example #337; Example #338; Example #339; Example #340; Example #341; Example #346; Example #348; Example #349; Example #350; Example #352; Example #353; Example #354; Example #360;

FIG. 1 shows the LAD2-SYK Correlation

The invention claimed is:

1. A compound of formula (I)

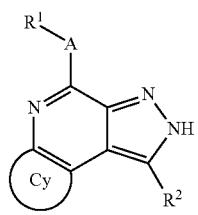

(I)

wherein

A is NH, O, S, C=O, $NR^3$ or $CR^4R^5$;

Cy is an optionally substituted phenylene group or an optionally substituted heteroarylene group having 6 ring atoms and 1, 2 or 3 heteroatoms selected from O, S and N, or Cy is an optionally substituted oxazole, thiazole, isoxazole, 1,2,5-thiadiazole, furan, thiophene, 1,2,3-thiadiazole, 1,2,5-oxadiazole, 1,2,3-oxadiazole, 1H-imidazole, 1H-1,2,4-triazole, 1H-1,2,3-triazole, 1H-tetrazole, 4H-1,2,4-triazole, 1H-pyrazole, 1,2,5-selenadiazole, 1,3-selenazole, selenophene, 2H-1,2,3-triazole, 1,3-dithiol-1-ium, 1,4-dithiine or a regioisomer thereof;

$R^1$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

$R^2$ is a hydrogen atom or methyl group;

$R^3$ is an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

$R^4$ is a hydrogen atom, $NO_2$, $N_3$, OH, SH, $NH_2$ or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group; and $R^5$ is a hydrogen atom, $NO_2$, $N_3$, OH, SH, $NH_2$ or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

or a pharmaceutically acceptable salt, ester, solvate or hydrate or a pharmaceutically acceptable formulation thereof.

2. A compound according to claim 1, wherein A is NH.

3. A compound according to claim 1, wherein $R^1$ is an optionally substituted aryl, heteroaryl, cycloalkyl, heterocycloalkyl, alkylcycloalkyl, heteroalkylcycloalkyl, aralkyl or heteroaralkyl group.

4. A compound according to claim 1, wherein $R^1$ is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings and 9 to 20 ring atoms; or wherein $R^1$ is a group of formula —$CH_2$—Ar wherein Ar is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings and 9 to 20 ring atoms.

5. A compound according to claim 1, wherein $R^1$ is a group of formula $X^1$-$L^1$-$Y^1$ or a group of formula $X^1$-$L^1$-$Y^1$-$L^2$-$Z^1$ wherein $X^1$ is an optionally substituted phenyl group or an optionally substituted heteroaryl group containing 5 or 6 ring atoms and 1, 2, 3 or 4 heteroatoms selected from O, S and N;

$L^1$ is a bond or a group of formula —$CH_2$—, —C(=O)—, —SO—, —$SO_2$—, —NH—C(=O)—, —C(=O)—NH—; —C(=O)—O—, —O—C(=O)—, —NH—C(=O)—O—, —O—C(=O)—NH—, —NH—$SO_2$—NH—, —$CH_2$—NH—$CH_2$—, —NH—$SO_2$—, —$SO_2$—NH— or —NH—C(=O)—NH—;

$Y^1$ is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N;

$L^2$ is a bond or a group of formula —$CH_2$—, —C(=O)—, —SO—, —$SO_2$—, —NH—C(=O)—, —C(=O)—

NH—; —C(═O)—O—, —O—C(═O)—, —NH—C(═O)—O—, —O—C(═O)—NH—, —NH—SO$_2$—NH—, —CH$_2$—NH—CH$_2$—, —NH—SO$_2$—, —SO$_2$—NH— or —NH—C(═O)—NH—; and $Z^1$ is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N.

6. A compound according to claim 1, wherein $R^1$ is selected from the following groups:

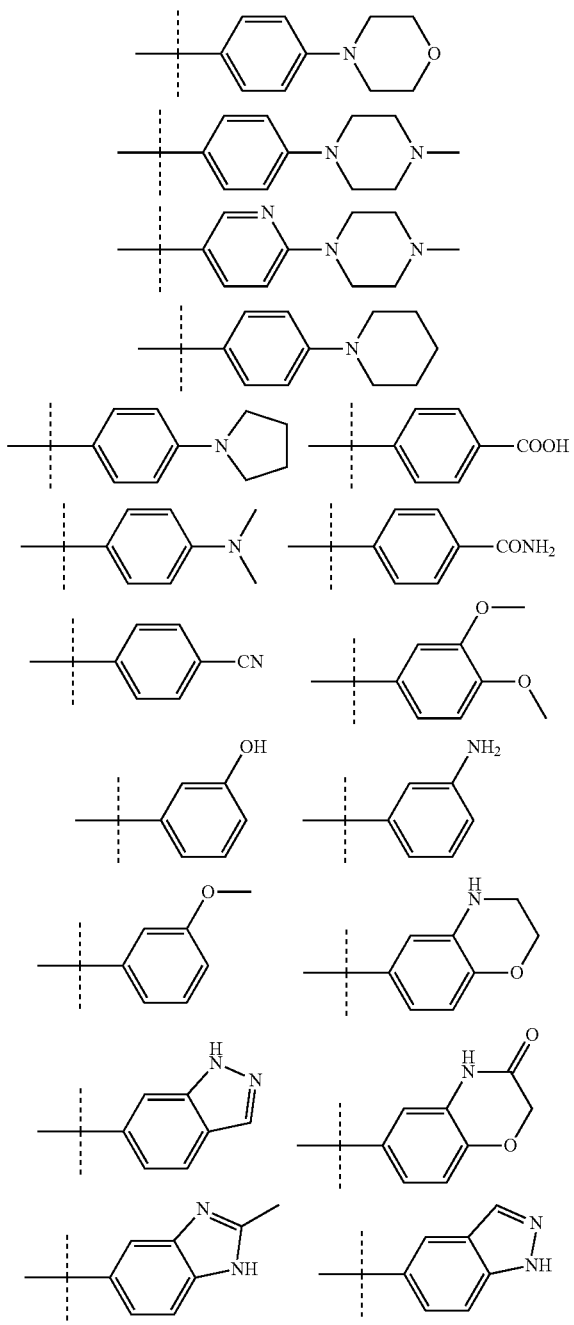
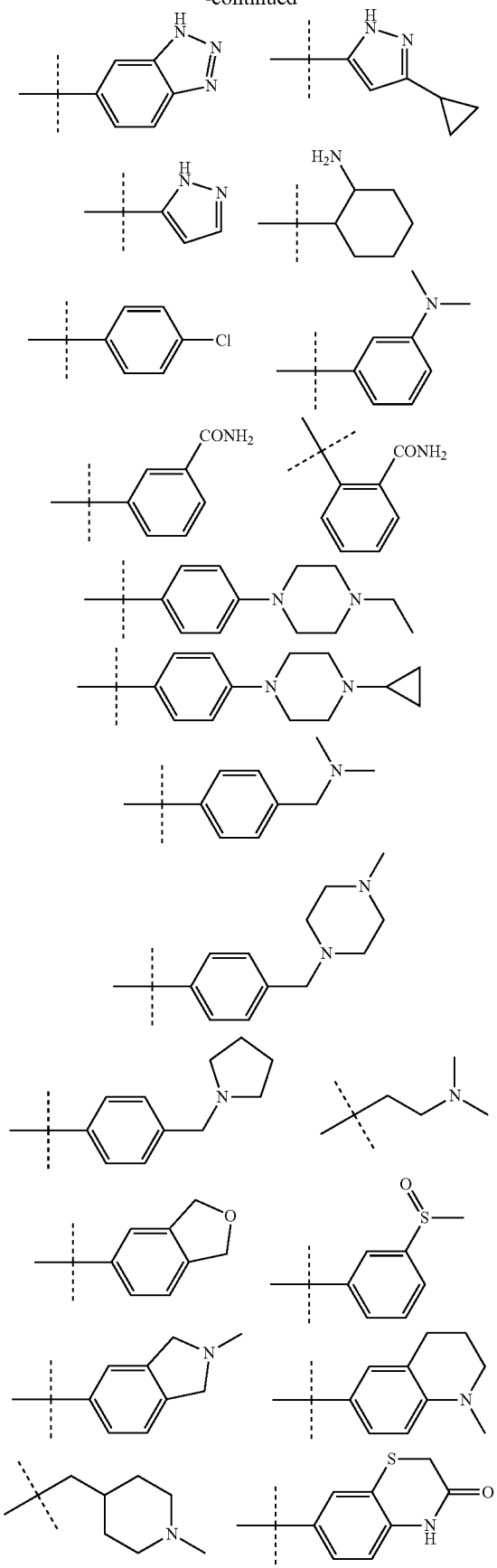

-continued

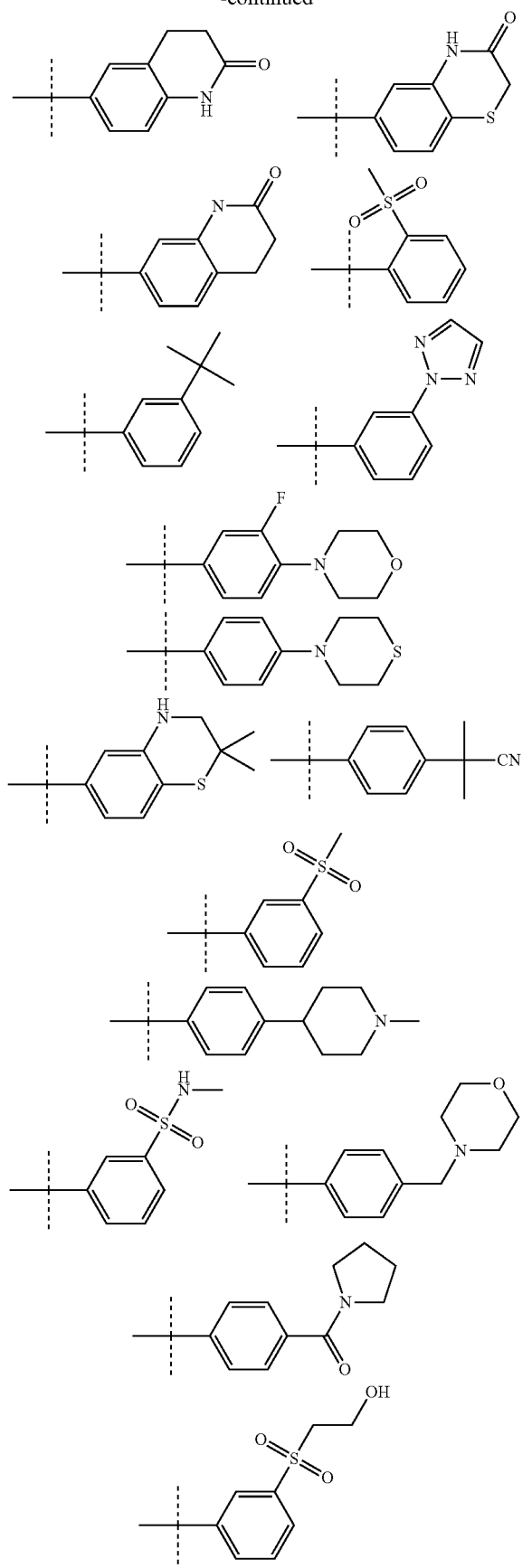
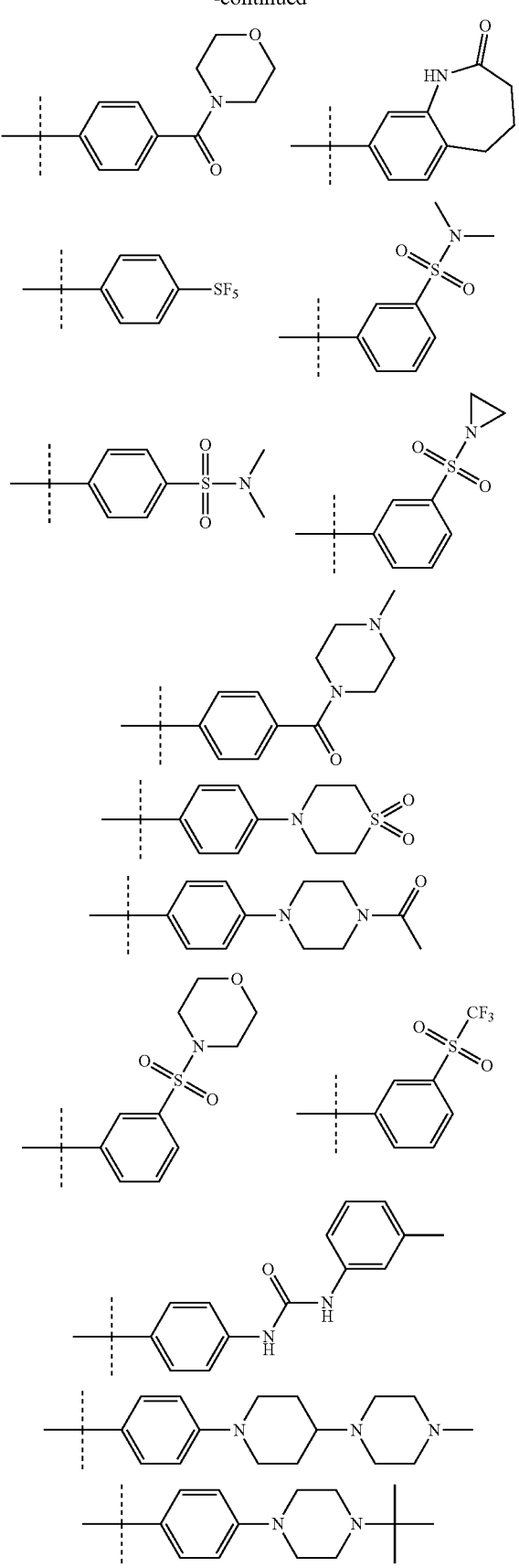

-continued

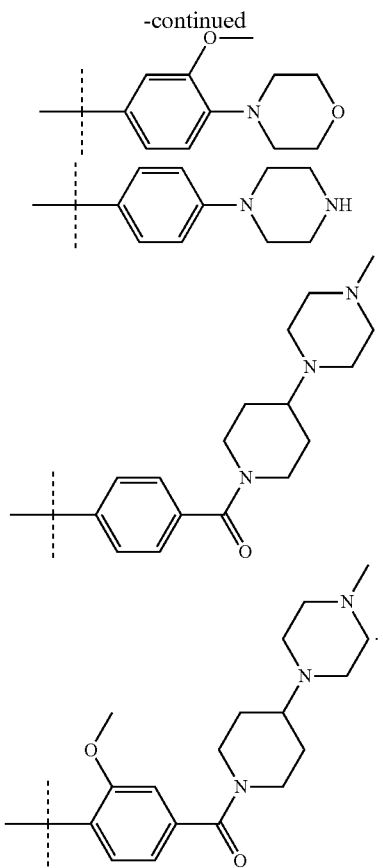

7. A compound according to claim 1, wherein Cy is an optionally substituted phenylene group or an optionally substituted pyridylene group, an optionally substituted thiophenylene group or an optionally substituted isothiazole group.

8. A compound according to claim 1 exemplified as follows:

N-(m-tolyl)-2H-pyrazolo[3,4-c]quinolin-4-amine; N-(3-(trifluoromethyl)phenyl)-2H-pyrazolo[3,4-c]quinolin-4-amine; N-(3,4,5-trimethoxyphenyl)-2H-pyrazolo[3,4-c]quinolin-4-amine; N-(1H-indazol-5-yl)-2H-pyrazolo[3,4-c]quinolin-4-amine; N-phenyl-2H-pyrazolo[3,4-c]quinolin-4-amine; N-(1H-indazol-6-yl)-2H-pyrazolo[3,4-c]quinolin-4-amine; N-(3-chlorophenyl)-2H-pyrazolo[3,4-c]quinolin-4-amine; N-(7-methyl-1H-indazol-5-yl)-2H-pyrazolo[3,4-c]quinolin-4-amine; N-(2-methoxyethyl)-2H-pyrazolo[3,4-c]quinolin-4-amine; 8-methoxy-N-(7-methyl-1H-indazol-5-yl)-2H-pyrazolo[3,4-c]quinolin-4-amine; N-(thiophen-2-ylmethyl)-2H-pyrazolo[3,4-c]quinolin-4-amine; N-(6-methyl-1H-indazol-5-yl)-2H-pyrazolo[3,4-c]quinolin-4-amine; 8-methoxy-N-phenyl-2H-pyrazolo[3,4-c]quinolin-4-amine; 8-methoxy-N-(2-methoxyethyl)-2H-pyrazolo[3,4-c]quinolin-4-amine; N-(2H-indazol-6-yl)-8-methoxy-2H-pyrazolo[3,4-c]quinolin-4-amine; methyl 4-((2H-pyrazolo[3,4-c]quinolin-4-yl)amino)benzoate; N-(1H-benzo[d]imidazol-5-yl)-2H-pyrazolo[3,4-c]quinolin-4-amine; N-(2H-indazol-7-yl)-2H-pyrazolo[3,4-c]quinolin-4-amine; 8-methoxy-N-((1-methyl-1H-pyrrol-2-yl)methyl)-2H-pyrazolo[3,4-c]quinolin-4-amine; N-(2H-indazol-7-yl)-8-methoxy-2H-pyrazolo[3,4-c]quinolin-4-amine; N-(benzo[d][1,3]dioxol-5-yl)-2H-pyrazolo[3,4-c]quinolin-4-amine; N-(pyridin-3-yl)-3H-pyrazolo[3,4-c]quinolin-4-amine; N-(1-methyl-1H-indazol-6-yl)-2H-pyrazolo[3,4-c]quinolin-4-amine; N-(6-methoxypyridin-3-yl)-2H-pyrazolo[3,4-c]quinolin-4-amine; N-(4-(4-methylpiperazin-1-yl)phenyl)-2H-pyrazolo[3,4-c]quinolin-4-amine; N-(4-(4-methyl-1,4-diazepan-1-yl)phenyl)-2H-pyrazolo[3,4-c]quinolin-4-amine; N-(pyridin-2-yl)-3H-pyrazolo[3,4-c]quinolin-4-amine; N-(5-bromopyridin-2-yl)-3H-pyrazolo[3,4-c]quinolin-4-amine; N-(isoquinolin-3-yl)-3H-pyrazolo[3,4-c]quinolin-4-amine; N-(4-methylpyridin-2-yl)-3H-pyrazolo[3,4-c]quinolin-4-amine; N-(4,6-dimethylpyridin-2-yl)-3H-pyrazolo[3,4-c]quinolin-4-amine; 8-bromo-N-(1H-indazol-6-yl)-2H-pyrazolo[3,4-c]quinolin-4-amine; N-(1H-benzo[d]imidazol-5-yl)-8-bromo-2H-pyrazolo[3,4-c]quinolin-4-amine; 8-bromo-N-(1-methyl-1H-indazol-6-yl)-2H-pyrazolo[3,4-c]quinolin-4-amine; 8-bromo-N-(1H-indazol-7-yl)-2H-pyrazolo[3,4-c]quinolin-4-amine; 8-methoxy-N-(m-tolyl)-2H-pyrazolo[3,4-c]quinolin-4-amine; N-(1H-indazol-5-yl)-8-methoxy-2H-pyrazolo[3,4-c]quinolin-4-amine; N-(1H-benzo[d]imidazol-5-yl)-8-methoxy-2H-pyrazolo[3,4-c]quinolin-4-amine; 8-methoxy-N-(1-methyl-1H-indazol-6-yl)-2H-pyrazolo[3,4-c]quinolin-4-amine; 8-bromo-N-(7-methyl-1H-indazol-5-yl)-2H-pyrazolo[3,4-c]quinolin-4-amine; 8-methoxy-N-(4-(4-methylpiperazin-1-yl)phenyl)-2H-pyrazolo[3,4-c]quinolin-4-amine; 8-bromo-N-(4-(4-methylpiperazin-1-yl)phenyl)-2H-pyrazolo[3,4-c]quinolin-4-amine; N1-(8-methoxy-2H-pyrazolo[3,4-c]quinolin-4-yl)benzene-1,3-diamine; 8-bromo-N-(1H-indazol-5-yl)-2H-pyrazolo[3,4-c]quinolin-4-amine; 6-((3H-pyrazolo[3,4-c]quinolin-4-yl)amino)-2H-benzo[b][1,4]oxazin-3(4H)-one; 6-((8-methoxy-3H-pyrazolo[3,4-c]quinolin-4-yl)amino)-2H-benzo[b][1,4]oxazin-3(4H)-one; N-(1H-benzo[d][1,2,3]triazol-5-yl)-8-methoxy-2H-pyrazolo[3,4-c]quinolin-4-amine; 3-((8-methoxy-2H-pyrazolo[3,4-c]quinolin-4-yl)amino)benzimidamide; 8-methoxy-N-(4-(piperidin-1-yl)phenyl)-2H-pyrazolo[3,4-c]quinolin-4-amine; N1-(8-methoxy-2H-pyrazolo[3,4-c]quinolin-4-yl)-N4,N4-dimethylbenzene-1,4-diamine; 3-((8-methoxy-2H-pyrazolo[3,4-c]quinolin-4-yl)amino)benzamide; N-(3,4-dimethoxyphenyl)-8-methoxy-2H-pyrazolo[3,4-c]quinolin-4-amine; 8-methoxy-N-(4-morpholinophenyl)-2H-pyrazolo[3,4-c]quinolin-4-amine; 8-methoxy-N-(2-methyl-1H-benzo[d]imidazol-6-yl)-2H-pyrazolo[3,4-c]quinolin-4-amine; N-(1H-indazol-5-yl)-8H-pyrazolo[3,4-c][1,5]naphthyridin-6-amine; 4-((8-methoxy-2H-pyrazolo[3,4-c]quinolin-4-yl)amino)benzoic acid; 4-((8-methoxy-2H-pyrazolo[3,4-c]quinolin-4-yl)amino)benzamide; 4-((8-methoxy-2H-pyrazolo[3,4-c]quinolin-4-yl)amino)benzonitrile; 8-methoxy-N-(3-methoxyphenyl)-2H-pyrazolo[3,4-c]quinolin-4-amine; 8-methoxy-N-(4-methoxyphenyl)-2H-pyrazolo[3,4-c]quinolin-4-amine; 3-((8-methoxy-2H-pyrazolo[3,4-c]quinolin-4-yl)amino)benzonitrile; N-(8-methoxy-2H-pyrazolo[3,4-c]quinolin-4-yl)benzo[c][1,2,5]thiadiazol-5-amine; 3-((8-methoxy-2H-pyrazolo[3,4-c]quinolin-4-yl)amino)pyridin-2(1H)-one; N-(2-ethoxyphenyl)-8-methoxy-2H-pyrazolo[3,4-c]quinolin-4-amine; 8-methoxy-N-(1H-pyrazol-3-yl)-2H-pyrazolo[3,4-c]quinolin-4-amine; 8-methoxy-N-(3,4,5-trimethoxyphenyl)-2H-pyrazolo[3,4-c]quinolin-4-amine; 5-((8-methoxy-2H-pyrazolo[3,4-c]quinolin-4-yl)amino)-1H-pyrazole-4-carboxamide; 8-methoxy-N-

(2-phenoxyphenyl)-2H-pyrazolo[3,4-c]quinolin-4-amine; 8-methoxy-N-(3-phenoxyphenyl)-2H-pyrazolo[3,4-c]quinolin-4-amine; 5-((8-methoxy-2H-pyrazolo[3,4-c]quinolin-4-yl)amino)-1H-benzo[d]imidazol-2(3H)-one; N-(1H-indol-5-yl)-8-methoxy-2H-pyrazolo[3,4-c]quinolin-4-amine; N-(4-(aminomethyl)phenyl)-8-methoxy-3H-pyrazolo[3,4-c]quinolin-4-amine; N-(1H-indazol-6-yl)-8-methoxy-2H-pyrazolo[3,4-c]quinolin-4-amine; N-(1H-indol-6-yl)-8-methoxy-3H-pyrazolo[3,4-c]quinolin-4-amine; N1-(8-methoxy-2H-pyrazolo[3,4-c]quinolin-4-yl)-N3,N3-dimethylbenzene-1,3-diamine; 8-methoxy-N-(3-phenyl-1H-pyrazol-5-yl)-2H-pyrazolo[3,4-c]quinolin-4-amine; N1,N1-diethyl-N4-(8-methoxy-2H-pyrazolo[3,4-c]quinolin-4-yl)benzene-1,4-diamine; 8-methoxy-N-(4-(pyrrolidin-1-yl)phenyl)-2H-pyrazolo[3,4-c]quinolin-4-amine; N3-(8-methoxy-3H-pyrazolo[3,4-c]quinolin-4-yl)-4H-1,2,4-triazole-3,5-diamine; 8-methoxy-N-(3-morpholinophenyl)-3H-pyrazolo[3,4-c]quinolin-4-amine; N-(1H-indol-5-yl)-2H-pyrazolo[3,4-c]quinolin-4-amine; 8-bromo-N-(4-(piperidin-1-yl)phenyl)-2H-pyrazolo[3,4-c]quinolin-4-amine; N1-(8-bromo-2H-pyrazolo[3,4-c]quinolin-4-yl)-N4,N4-dimethylbenzene-1,4-diamine; N-(3-cyclobutyl-1H-pyrazol-5-yl)-8-methoxy-2H-pyrazolo[3,4-c]quinolin-4-amine; N-(4-(4,5-dihydro-1H-imidazol-2-yl)phenyl)-8-methoxy-2H-pyrazolo[3,4-c]quinolin-4-amine; 4-(4-((8-methoxy-2H-pyrazolo[3,4-c]quinolin-4-yl)amino)phenyl)morpholin-3-one; N-(8-methoxy-2H-pyrazolo[3,4-c]quinolin-4-yl)-2,2-dimethyl-3,4-dihydro-2H-benzo[b][1,4]thiazin-6-amine; N-(4-morpholinophenyl)-8H-pyrazolo[3,4-c][1,5]naphthyridin-6-amine; N-(1H-indazol-5-yl)-2-methoxy-8H-pyrazolo[3,4-c][1,5]naphthyridin-6-amine; N-(1H-indazol-6-yl)-2H-pyrazolo[3,4-c][1,7]naphthyridin-4-amine; 7,8-diethoxy-N-(1H-indazol-6-yl)-2H-pyrazolo[3,4-c]quinolin-4-amine; 7-((8-methoxy-2H-pyrazolo[3,4-c]quinolin-4-yl)amino)-3,4-dihydroquinolin-2(1H)-one; 6-((8-methoxy-3H-pyrazolo[3,4-c]quinolin-4-yl)amino)-2H-benzo[b][1,4]thiazin-3(4H)-one; N-(5-(tert-butyl)-1H-pyrazol-3-yl)-8-methoxy-3H-pyrazolo[3,4-c]quinolin-4-amine; 8-methoxy-N-(3-methyl-1H-pyrazol-5-yl)-3H-pyrazolo[3,4-c]quinolin-4-amine; N-(5-cyclopropyl-1H-pyrazol-3-yl)-8-methoxy-3H-pyrazolo[3,4-c]quinolin-4-amine; N-(4-(1H-tetrazol-5-yl)phenyl)-8-methoxy-3H-pyrazolo[3,4-c]quinolin-4-amine; 8-bromo-N-(1H-indol-5-yl)-2H-pyrazolo[3,4-c]quinolin-4-amine; N-(benzo[d][1,3]dioxol-5-yl)-8-methoxy-2H-pyrazolo[3,4-c]quinolin-4-amine; N-(2,3-dihydrobenzo[b][1,4]dioxin-6-yl)-8-methoxy-2H-pyrazolo[3,4-c]quinolin-4-amine; 8-methoxy-N-(4-(1-methylpiperidin-4-yl)phenyl)-2H-pyrazolo[3,4-c]quinolin-4-amine; 8-methoxy-N-(6-morpholinopyridin-3-yl)-3H-pyrazolo[3,4-c]quinolin-4-amine; 8-methoxy-N-(4-(2-methoxyethoxy)phenyl)-3H-pyrazolo[3,4-c]quinolin-4-amine; N-(4-ethoxy-3-methoxyphenyl)-8-methoxy-3H-pyrazolo[3,4-c]quinolin-4-amine; 1-(4-((8-methoxy-3H-pyrazolo[3,4-c]quinolin-4-yl)amino)phenyl)pyrrolidin-2-one; 8-methoxy-N-(4-thiomorpholinophenyl)-3H-pyrazolo[3,4-c]quinolin-4-amine; 5-((8-methoxy-3H-pyrazolo[3,4-c]quinolin-4-yl)amino)benzo[d]oxazol-2(3H)-one; N-(8-methoxy-3H-pyrazolo[3,4-c]quinolin-4-yl)-3,4-dihydro-2H-benzo[b][1,4]oxazin-6-amine; 7-((8-methoxy-3H-pyrazolo[3,4-c]quinolin-4-yl)amino)quinazolin-4-ol; 4-(4-((8-methoxy-3H-pyrazolo[3,4-c]quinolin-4-yl)amino)phenyl)thiomorpholine 1,1-dioxide; 2-(4-((8-methoxy-3H-pyrazolo[3,4-c]quinolin-4-yl)amino)phenyl)acetamide; 3-((8-methoxy-3H-pyrazolo[3,4-c]quinolin-4-yl)amino)phenol; N-(3,4-diethoxyphenyl)-8-methoxy-3H-pyrazolo[3,4-c]quinolin-4-amine; 8-bromo-N-(4-morpholinophenyl)-2H-pyrazolo[3,4-c]quinolin-4-amine; 6-((8-bromo-2H-pyrazolo[3,4-c]quinolin-4-yl)amino)-2H-benzo[b][1,4]oxazin-3(4H)-one; 6-((8-methoxy-2H-pyrazolo[3,4-c]quinolin-4-yl)amino)-1H-benzo[d][1,3]oxazine-2,4-dione; 2-methoxy-5-((8-methoxy-2H-pyrazolo[3,4-c]quinolin-4-yl)amino)phenol; 8-bromo-N-(1H-pyrazol-3-yl)-2H-pyrazolo[3,4-c]quinolin-4-amine; 8-methoxy-N-(3-methoxyphenyl)-N-methyl-3H-pyrazolo[3,4-c]quinolin-4-amine; N-(3-((8-methoxy-3H-pyrazolo[3,4-c]quinolin-4-yl)amino)phenyl)acetamide; 8-methoxy-N-(1H-pyrazol-4-yl)-3H-pyrazolo[3,4-c]quinolin-4-amine; N-(3,4-dimethoxyphenyl)-7,8-dimethoxy-2H-pyrazolo[3,4-c]quinolin-4-amine; N-(3,4-dimethoxyphenyl)-8H-pyrazolo[3,4-c][1,5]naphthyridin-6-amine; N-(4-fluoro-3-methoxyphenyl)-8-methoxy-2H-pyrazolo[3,4-c]quinolin-4-amine; N-(3-fluoro-4-methoxyphenyl)-8-methoxy-2H-pyrazolo[3,4-c]quinolin-4-amine; 8-methoxy-N-(1-methyl-1H-benzo[d]imidazol-5-yl)-2H-pyrazolo[3,4-c]quinolin-4-amine; 1-(3-((8-methoxy-2H-pyrazolo[3,4-c]quinolin-4-yl)amino)phenyl)ethan-1-one; N-(4-((8-methoxy-2H-pyrazolo[3,4-c]quinolin-4-yl)amino)phenyl)acetamide; 8-methoxy-N-(pyridin-2-yl)-2H-pyrazolo[3,4-c]quinolin-4-amine; 8-methoxy-N-(1H-pyrrolo[2,3-b]pyridin-6-yl)-2H-pyrazolo[3,4-c]quinolin-4-amine; 3-((8-methoxy-2H-pyrazolo[3,4-c]quinolin-4-yl)amino)benzenesulfonamide; 4-((8-methoxy-2H-pyrazolo[3,4-c]quinolin-4-yl)amino)benzenesulfonamide; 7,8-dimethoxy-N-(4-morpholinophenyl)-2H-pyrazolo[3,4-c]quinolin-4-amine; 7,8-dimethoxy-N-(4-(4-methylpiperazin-1-yl)phenyl)-2H-pyrazolo[3,4-c]quinolin-4-amine; N1-(7,8-dimethoxy-2H-pyrazolo[3,4-c]quinolin-4-yl)-N4,N4-dimethylbenzene-1,4-diamine; N-(1H-indazol-6-yl)-7,8-dimethoxy-2H-pyrazolo[3,4-c]quinolin-4-amine; N2-(8-methoxy-2H-pyrazolo[3,4-c]quinolin-4-yl)pyridine-2,6-diamine; 8-methoxy-N-(1,2,3-trimethyl-1H-indol-5-yl)-2H-pyrazolo[3,4-c]quinolin-4-amine; N2-(8-methoxy-2H-pyrazolo[3,4-c]quinolin-4-yl)pyrimidine-2,4-diamine; 8-methoxy-N-(5-(methylthio)-4H-1,2,4-triazol-3-yl)-2H-pyrazolo[3,4-c]quinolin-4-amine; N-(5-cyclopropyl-4H-1,2,4-triazol-3-yl)-8-methoxy-2H-pyrazolo[3,4-c]quinolin-4-amine; N-(2-methoxy-5-((8-methoxy-2H-pyrazolo[3,4-c]quinolin-4-yl)amino)phenyl)acetamide; N-(1H-benzo[d]imidazol-2-yl)-8-methoxy-2H-pyrazolo[3,4-c]quinolin-4-amine; N-(1H-imidazol-2-yl)-8-methoxy-2H-pyrazolo[3,4-c]quinolin-4-amine; 1-(4-((8-methoxy-2H-pyrazolo[3,4-c]quinolin-4-yl)amino)phenyl)ethan-1-one; N-(4H-benzo[d][1,3]dioxin-6-yl)-8-methoxy-2H-pyrazolo[3,4-c]quinolin-4-amine; N-(1,3-dihydroisobenzofuran-5-yl)-8-methoxy-2H-pyrazolo[3,4-c]quinolin-4-amine; 8-methoxy-N-(1-methyl-1H-benzo[d]imidazol-6-yl)-2H-pyrazolo[3,4-c]quinolin-4-amine; N-(8-methoxy-2H-pyrazolo[3,4-c]quinolin-4-yl)-4,5-dimethylthiazol-2-amine; N-(5-cyclopropyl-1H-pyrazol-3-yl)-7,8-dimethoxy-2H-pyrazolo[3,4-c]quinolin-4-amine; N-(7,8-dimethoxy-2H-pyrazolo[3,4-c]quinolin-4-yl)-3,4-dihydro-2H-benzo[b][1,4]oxazin-6-amine; 5-((7,8-dimethoxy-2H-pyrazolo[3,4-c]quinolin-4-yl)amino)-2-methoxyphenol; 8-methoxy- N-(2-methyl-4-(4-methylpiperazin-1-yl)phenyl)-2H-pyrazolo[3,4-c]quinolin-4-amine; 8-methoxy-N-(4-methylpyridin-2-yl)-2H-pyrazolo[3,4-c]quinolin-4-amine; 8-methoxy-N-(6-methylpyridin-2-yl)-2H-pyrazolo[3,4-c]quinolin-4-amine; N-(4,6-dimethylpyridin-2-yl)-8-methoxy-2H-pyrazolo[3,4-c]quinolin-4-amine; N-(8-methoxy-2H-pyrazolo[3,4-c]quinolin-4-yl)-4-methylthiazol-2-amine; N-(8-methoxy-2H-pyrazolo[3,4-c]quinolin-4-yl)-4,5,6,7-tetrahydrobenzo[d]thiazol-2-amine; 8-methoxy-N-(4-phenoxyphenyl)-2H-pyrazolo[3,4-c]quinolin-4-amine; 8-methoxy-N-(2-methyl-1,2,3,4-tetrahydrobenzo[4,5]imidazo[1,2-a]pyrazin-8-yl)-2H-pyrazolo[3,4-c]quinolin-4-amine; 8-methoxy-N-(4-(pyridin-4-ylmethyl)phenyl)-2H-pyrazolo[3,4-c]quinolin-4-amine; 4-((8-methoxy-2H-pyrazolo[3,4-c]quinolin-4-yl)amino)benzene-1,2-diol; 8-methoxy-N-(4-((1-methylpiperidin-4-yl)oxy)phenyl)-2H-pyrazolo[3,4-c]quinolin-4-amine; 1-(4-(4-((8-methoxy-2H-pyrazolo[3,4-c]quinolin-4-yl)amino)phenyl)piperazin-1-yl)ethan-1-one; 8-methoxy-N-(6-(4-methylpiperazin-1-yl)pyridin-3-yl)-2H-pyrazolo[3,4-c]quinolin-4-amine; 6-methoxy-N-(4-(4-methylpiperazin-1-yl)phenyl)-2H-pyrazolo[3,4-c]quinolin-4-amine; N-(3,4-dimethoxyphenyl)-6-methoxy-2H-pyrazolo[3,4-c]quinolin-4-amine; N-(6-methoxy-2H-pyrazolo[3,4-c]quinolin-4-yl)-3,4-dihydro-2H-benzo[b][1,4]oxazin-6-amine; N-(5-cyclopropyl-1H-pyrazol-3-yl)-6-methoxy-2H-pyrazolo[3,4-c]quinolin-4-amine; 6-methoxy-N-(4-morpholinophenyl)-2H-pyrazolo[3,4-c]quinolin-4-amine; N-(1H-indazol-6-yl)-6-methoxy-2H-pyrazolo[3,4-c]quinolin-4-amine; N-(1H-indazol-6-yl)-7-methoxy-2H-pyrazolo[3,4-c]quinolin-4-amine; N-(7-methoxy-2H-pyrazolo[3,4-c]quinolin-4-yl)-3,4-dihydro-2H-benzo[b][1,4]oxazin-6-amine; N-(3,4-dimethoxyphenyl)-7-methoxy-2H-pyrazolo[3,4-c]quinolin-4-amine; 7-methoxy-N-(4-(4-methylpiperazin-1-yl)phenyl)-2H-pyrazolo[3,4-c]quinolin-4-amine; 7-methoxy-N-(4-morpholinophenyl)-2H-pyrazolo[3,4-c]quinolin-4-amine; N4-(8-methoxy-2H-pyrazolo[3,4-c]quinolin-4-yl)-N1,N1,2-trimethylbenzene-1,4-diamine; N-(4-(4-cyclopropylpiperazin-1-yl)phenyl)-8-methoxy-2H-pyrazolo[3,4-c]quinolin-4-amine; 8-methoxy-pyrazolo[3,4-c]quinolin-4-amine; N-(3-fluoro-4-morpholinophenyl)-8-methoxy-2H-pyrazolo[3,4-c]quinolin-4-amine; 7-((8-methoxy-2H-pyrazolo[3,4-c]quinolin-4-yl)amino)quinoxalin-2(1H)-one; 8-methoxy-N-(3-methyl-4-(4-methylpiperazin-1-yl)phenyl)-2H-pyrazolo[3,4-c]quinolin-4-amine; 8-methoxy-N-(4-(piperazin-1-yl)phenyl)-2H-pyrazolo[3,4-c]quinolin-4-amine; N-(4-((dimethylamino)methyl)phenyl)-8-methoxy-2H-pyrazolo[3,4-c]quinolin-4-amine; N-(2-fluoro-4-morpholinophenyl)-8-methoxy-2H-pyrazolo[3,4-c]quinolin-4-amine; N-(4-(4-ethylpiperazin-1-yl)phenyl)-8-methoxy-2H-pyrazolo[3,4-c]quinolin-4-amine; 8-((8-methoxy-2H-pyrazolo[3,4-c]quinolin-4-yl)amino)-4,5-dihydro-1H-benzo[b]azepin-2(3H)-one; 5-((8-methoxy-2H-pyrazolo[3,4-c]quinolin-4-yl)amino)-1,3-dimethyl-1H-benzo[d]imidazol-2(3H)-one; N-(4-benzylphenyl)-8-methoxy-2H-pyrazolo[3,4-c]quinolin-4-amine; 8-methoxy-N-(2-methyl-4-morpholinophenyl)-2H-pyrazolo[3,4-c]quinolin-4-amine; N1-(8-methoxy-2H-pyrazolo[3,4-c]quinolin-4-yl)-N4-methyl-N4-(1-methylpiperidin-4-yl)benzene-1,4-diamine; 8-methoxy-N-(4-(2-morpholinoethyl)phenyl)-2H-pyrazolo[3,4-c]quinolin-4-amine; N-(3-chloro-4-(4-methylpiperazin-1-yl)phenyl)-8-methoxy-2H-pyrazolo[3,4-c]quinolin-4-amine; 8-methoxy-N-(1,2,3,4-tetrahydroquinolin-7-yl)-2H-pyrazolo[3,4-c]quinolin-4-amine; 4-((1H-indazol-6-yl)amino)-2H-pyrazolo[3,4-c]quinoline-8-carbonitrile; N-(9-methoxy-2H-pyrazolo[3,4-c]quinolin-4-yl)-3,4-dihydro-2H-benzo[b][1,4]oxazin-6-amine; N-(5-cyclopropyl-1H-pyrazol-3-yl)-9-methoxy-2H-pyrazolo[3,4-c]quinolin-4-amine; N-(3,4-dimethoxyphenyl)-9-methoxy-2H-pyrazolo[3,4-c]quinolin-4-amine; 9-methoxy-N-(4-(4-methylpiperazin-1-yl)phenyl)-2H-pyrazolo[3,4-c]quinolin-4-amine; 9-methoxy-N-(4-morpholinophenyl)-2H-pyrazolo[3,4-c]quinolin-4-amine; N-(1H-indazol-6-yl)-9-methoxy-2H-pyrazolo[3,4-c]quinolin-4-amine; N1-(8-methoxy-2H-pyrazolo[3,4-c]quinolin-4-yl)cyclohexane-1,2-diamine; 8-methoxy-N-(pyridin-4-yl)-2H-pyrazolo[3,4-c]quinolin-4-amine; 8-methoxy-N-(6-methoxypyridin-3-yl)-2H-pyrazolo[3,4-c]quinolin-4-amine; N-(3,4-dimethoxyphenyl)-1-methyl-2H-pyrazolo[3,4-c]quinolin-4-amine; 1-methyl-N-(4-(4-methylpiperazin-1-yl)phenyl)-2H-pyrazolo[3,4-c]quinolin-4-amine; N-(1H-indazol-6-yl)-1-methyl-2H-pyrazolo[3,4-c]quinolin-4-amine; N-(3,4-dimethoxyphenyl)-1-(trifluoromethyl)-2H-pyrazolo[3,4-c]quinolin-4-amine; N-(4-(4-methylpiperazin-1-yl)phenyl)-1-(trifluoromethyl)-2H-pyrazolo[3,4-c]quinolin-4-amine; N-(1H-indazol-6-yl)-1-(trifluoromethyl)-2H-pyrazolo[3,4-c]quinolin-4-amine; N-(3,4-dimethoxyphenyl)-1-nitro-2H-pyrazolo[3,4-c]quinolin-4-amine; N-(4-(4-methylpiperazin-1-yl)phenyl)-1-nitro-2H-pyrazolo[3,4-c]quinolin-4-amine; 2-(4-((8-methoxy-2H-pyrazolo[3,4-c]quinolin-4-yl)amino)phenyl)-N-(4-methoxyphenethyl)acetamide; 4-((3,4-dimethoxyphenyl)amino)-2H-pyrazolo[3,4-c]quinoline-8-carbonitrile; 4-((4-morpholinophenyl)amino)-2H-pyrazolo[3,4-c]quinoline-8-carbonitrile; N-(3,4-dimethoxyphenyl)-1-methyl-7H-isothiazolo[5,4-b]pyrazolo[4,3-d]pyridin-5-amine; N-(1H-indazol-6-yl)-1-methyl-7H-isothiazolo[5,4-b]pyrazolo[4,3-d]pyridin-5-amine; 1-methyl-N-(4-(4-methylpiperazin-1-yl)phenyl)-7H-isothiazolo[5,4-b]pyrazolo[4,3-d]pyridin-5-amine; 8-methoxy-N-(3-(piperazin-1-yl)phenyl)-2H-pyrazolo[3,4-c]quinolin-4-amine; N-(2-(diethylamino)ethyl)-4-((8-methoxy-2H-pyrazolo[3,4-c]quinolin-4-yl)amino)benzamide; 8-methoxy-N-(2-(4-methylpiperazin-1-yl)pyrimidin-5-yl)-2H-pyrazolo[3,4-c]quinolin-4-amine; 7-((8-methoxy-3H-pyrazolo[3,4-c]quinolin-4-yl)amino)-2H-benzo[b][1,4]oxazin-3(4H)-one; N-(8-methoxy-3H-pyrazolo[3,4-c]quinolin-4-yl)-3,4-dihydro-2H-benzo[b][1,4]oxazin-7-amine; 4-((3,4-dimethoxyphenyl)amino)-1-methyl-2H-pyrazolo[3,4-c]quinoline-7-carbonitrile; 4-((1H-indazol-6-yl)amino)-1-methyl-2H-pyrazolo[3,4-c]quinoline-7-carbonitrile; 8-methoxy-N-(3-(4-methylpiperazin-1-yl)phenyl)-2H-pyrazolo[3,4-c]quinolin-4-amine; 8-methoxy-N-(3-(2-(piperazin-1-yl)ethoxy)phenyl)-2H-pyrazolo[3,4-c]quinolin-4-amine; 8-methoxy-N-(6-methyl-5,6,7,8-tetrahydro-1,6-naphthyridin-3-yl)-2H-pyrazolo[3,4-c]quinolin-4-amine; (4-((8-methoxy-2H-pyrazolo[3,4-c]quinolin-4-yl)amino)phenyl)(pyrrolidin-1-yl)methanone; (4-((8-methoxy-2H-pyrazolo[3,4-c]quinolin-4-yl)amino)phenyl)(morpholino)methanone; N-(4-((dimethylamino)methyl)phenyl)-6-methoxy-2H-pyrazolo[3,4-c]quinolin-4-amine; 8-methoxy-N-(4-(pyrrolidin-1- ylmethyl)phenyl)-2H-pyrazolo[3,4-c]quinolin-4-amine; (4-((8-methoxy-2H-pyrazolo[3,4-c]quinolin-4-yl)amino)phenyl)(4-methylpiperazin-1-yl)methanone; N2-(2-(dimethylamino)ethyl)-N5-(8-methoxy-2H-pyrazolo[3,4-c]quinolin-4-yl)pyrimidine-2,5-diamine; 8-methoxy-N-(4-(morpholinomethyl)phenyl)-2H-pyrazolo[3,4-c]quinolin-4-amine; 8-methoxy-N-(4-((4-methylpiperazin-1-yl)methyl)phenyl)-2H-pyrazolo[3,4-c]quinolin-4-amine; N-(4-(4-ethylpiperazin-1-yl)phenyl)-6-methoxy-2H-pyrazolo[3,4-c]quinolin-4-amine; N-(4-(4-ethylpiperazin-1-yl)-3-fluorophenyl)-8-methoxy-2H-pyrazolo[3,4-c]quinolin-4-amine; N-(4-(2-(4-benzylpiperidin-1-yl)ethyl)phenyl)-8-methoxy-2H-pyrazolo[3,4-c]quinolin-4-amine; N-(4-((4-benzylpiperidin-1-yl)methyl)phenyl)-8-methoxy-2H-pyrazolo[3,4-c]quinolin-4-amine; 8-((6-methoxy-2H-pyrazolo[3,4-c]quinolin-4-yl)amino)-4,5-dihydro-1H-benzo[b]azepin-2(3H)-one; N-(1H-benzo[d]imidazol-5-yl)-6-methoxy-2H-pyrazolo[3,4-c]quinolin-4-amine; N-(4-(4-cyclopropylpiperazin-1-yl)phenyl)-9-methoxy-2H-pyrazolo[3,4-c]quinolin-4-amine; 8-methoxy-N-(p-tolyl)-2H-pyrazolo[3,4-c]quinolin-4-amine; N-(6-(2-(dimethylamino)ethoxy)pyridin-3-yl)-8-methoxy-2H-pyrazolo[3,4-c]quinolin-4-amine; N-(3-fluoro-4-morpholinophenyl)-6-methoxy-2H-pyrazolo[3,4-c]quinolin-4-amine; 6-methoxy-N-(4-thiomorpholinophenyl)-2H-pyrazolo[3,4-c]quinolin-4-amine; 6-methoxy-N-(2-methyl-1H-benzo[d]imidazol-5-yl)-2H-pyrazolo[3,4-c]quinolin-4-amine; N-(benzo[d][1,3]dioxol-5-yl)-6-methoxy-2H-pyrazolo[3,4-c]quinolin-4-amine; 6-((6-methoxy-2H-pyrazolo[3,4-c]quinolin-4-yl)amino)-2H-benzo[b][1,4]oxazin-3(4H)-one; N-(3,4-dimethoxyphenyl)-6,8-dimethoxy-2H-pyrazolo[3,4-c]quinolin-4-amine; N-(4-(4-cyclopropylpiperazin-1-yl)phenyl)-6,8-dimethoxy-2H-pyrazolo[3,4-c]quinolin-4-amine; N2-(3-(dimethylamino)propyl)-N5-(8-methoxy-2H-pyrazolo[3,4-c]quinolin-4-yl)pyridine-2,5-diamine; N2-(2-(dimethylamino)ethyl)-N5-(8-methoxy-2H-pyrazolo[3,4-c]quinolin-4-yl)pyridine-2,5-diamine; 8-methoxy-N-(6-((1-methylpiperidin-4-yl)oxy)pyridin-3-yl)-2H-pyrazolo[3,4-c]quinolin-4-amine; N-(1H-indazol-5-yl)-7-methoxy-2H-pyrazolo[3,4-c]quinolin-4-amine; 8-((7-methoxy-2H-pyrazolo[3,4-c]quinolin-4-yl)amino)-4,5-dihydro-1H-benzo[b]azepin-2(3H)-one; N-(2,3-dihydrobenzo[b][1,4]dioxin-6-yl)-6-methoxy-2H-pyrazolo[3,4-c]quinolin-4-amine; N-(4-((dimethylamino)methyl)phenyl)-7-methoxy-2H-pyrazolo[3,4-c]quinolin-4-amine; N-(4-(4-ethylpiperazin-1-yl)phenyl)-7-methoxy-2H-pyrazolo[3,4-c]quinolin-4-amine; 6-methoxy-N-phenyl-2H-pyrazolo[3,4-c]quinolin-4-amine; N-(4-(4-cyclopropylpiperazin-1-yl)phenyl)-7-methoxy-2H-pyrazolo[3,4-c]quinolin-4-amine; N-(1H-benzo[d]imidazol-5-yl)-7-methoxy-2H-pyrazolo[3,4-c]quinolin-4-amine; 7-methoxy-N-(2-methyl-1H-benzo[d]imidazol-5-yl)-2H-pyrazolo[3,4-c]quinolin-4-amine; N-(2,3-dihydrobenzo[b][1,4]dioxin-6-yl)-7-methoxy-2H-pyrazolo[3,4-c]quinolin-4-amine; 6-((7-methoxy-2H-pyrazolo[3,4-c]quinolin-4-yl)amino)-2H-benzo[b][1,4]oxazin-3(4H)-one; N-(benzo[d][1,3]dioxol-5-yl)-7-methoxy-2H-pyrazolo[3,4-c]quinolin-4-amine; N-(1H-indazol-5-yl)-6-methoxy-2H-pyrazolo[3,4-c]quinolin-4-amine; N-(4-(4-cyclopentylpiperazin-1-yl)phenyl)-8-methoxy-2H-pyrazolo[3,4-c]quinolin-4-amine; N-(4-(4-isobutylpiperazin-1-yl)phenyl)-8-methoxy-2H-pyrazolo[3,4-c]quinolin-4-amine; N-(4-(4-isopropylpiperazin-1-yl)phenyl)-8-methoxy-2H-pyrazolo[3,4-c]quinolin-4-amine; N-(4-(4-(cyclopropylmethyl)piperazin-1-yl)phenyl)-8-methoxy-2H-pyrazolo[3,4-c]quinolin-4-amine; N-(4-(4-(tert-butyl)piperazin-1-yl)phenyl)-8-methoxy-2H-pyrazolo[3,4-c]quinolin-4-amine; 6-methoxy-N-(p-tolyl)-2H-pyrazolo[3,4-c]quinolin-4-amine; methyl 4-((3,4-dimethoxyphenyl)amino)-2H-pyrazolo[4,3-d]thieno[3,4-b]pyridine-6-carboxylate; methyl 4-((4-(4-cyclopropylpiperazin-1-yl)phenyl)amino)-2H-pyrazolo[4,3-d]thieno[3,4-b]pyridine-6-carboxylate; 2-(4-(4-((8-methoxy-2H-pyrazolo[3,4-c]quinolin-4-yl)amino)phenyl)piperazin-1-yl)acetic acid; 6-methoxy-N-(4-((4-methylpiperazin-1-yl)methyl)phenyl)-2H-pyrazolo[3,4-c]quinolin-4-amine; 2-(2-methoxy-4-((8-methoxy-2H-pyrazolo[3,4-c]quinolin-4-yl)amino)phenoxy)acetic acid; (4-((8-methoxy-2H-pyrazolo[3,4-c]quinolin-4-yl)amino)phenyl)methanol; N-(4-(4-(2-(dimethylamino)ethyl)piperazin-1-yl)phenyl)-8-methoxy-2H-pyrazolo[3,4-c]quinolin-4-amine; 6,8-dimethoxy-N-(4-((4-methylpiperazin-1-yl)methyl)phenyl)-2H-pyrazolo[3,4-c]quinolin-4-amine; (4-((6,8-dimethoxy-2H-pyrazolo[3,4-c]quinolin-4-yl)amino)phenyl)(4-methylpiperazin-1-yl)methanone; N-(4-((dimethylamino)methyl)phenyl)-6,8-dimethoxy-2H-pyrazolo[3,4-c]quinolin-4-amine; 2-(4-((8-methoxy-2H-pyrazolo[3,4-c]quinolin-4-yl)amino)phenyl)acetic acid; 6-((8-methoxy-2H-pyrazolo[3,4-c]quinolin-4-yl)amino)-2-naphthoic acid; 3-((8-methoxy-2H-pyrazolo[3,4-c]quinolin-4-yl)amino)benzoic acid; 4'-((8-methoxy-2H-pyrazolo[3,4-c]quinolin-4-yl)amino)-[1,1'-biphenyl]-4-carboxylic acid; 1-(4-((8-methoxy-2H-pyrazolo[3,4-c]quinolin-4-yl)amino)phenyl)-3-(m-tolyl)urea; 2-(4-((8-methoxy-2H-pyrazolo[3,4-c]quinolin-4-yl)amino)phenoxy)acetic acid; 6-((8-methoxy-2H-pyrazolo[3,4-c]quinolin-4-yl)amino)-2H-benzo[b][1,4]oxazin-3(4H)-one; 4-(4-((8-methoxy-2H-pyrazolo[3,4-c]quinolin-4-yl)amino)phenyl)thiomorpholine 1,1-dioxide; 8-methoxy-N-(4-thiomorpholinophenyl)-2H-pyrazolo[3,4-c]quinolin-4-amine; 8-methoxy-N-(2-methylisoindolin-5-yl)-2H-pyrazolo[3,4-c]quinolin-4-amine; (3-methoxy-4-((8-methoxy-2H-pyrazolo[3,4-c]quinolin-4-yl)amino)phenyl)(4-(4-methylpiperazin-1-yl)piperidin-1-yl)methanone; 3-((8-hydroxy-2H-pyrazolo[3,4-c]quinolin-4-yl)amino)benzoic acid; 1-(4-((6,8-dimethoxy-2H-pyrazolo[3,4-c]quinolin-4-yl)amino)phenyl)-3-(m-tolyl)urea; 1-(4-((7-methoxy-2H-pyrazolo[3,4-c]quinolin-4-yl)amino)phenyl)-3-(m-tolyl)urea; 1-(4-((7,8-dimethoxy-2H-pyrazolo[3,4-c]quinolin-4-yl)amino)phenyl)-3-(m-tolyl)urea; N-(2-(dimethylamino)ethyl)-4-((8-methoxy-2H-pyrazolo[3,4-c]quinolin-4-yl)amino)-N-methylbenzamide; (4-((8-methoxy-2H-pyrazolo[3,4-c]quinolin-4-yl)amino)phenyl)(2-(methoxymethyl)pyrrolidin-1-yl)methanone; azetidin-1-yl(4-((8-methoxy-2H-pyrazolo[3,4-c]quinolin-4-yl)amino)phenyl)methanone; 4-((8-methoxy-2H-pyrazolo[3,4-c]quinolin-4-yl)amino)-N,N-dimethylbenzamide; (4-((8-methoxy-2H-pyrazolo[3,4-c]quinolin-4-yl)amino)phenyl)(4-methyl-1,4-diazepan-1-yl)methanone; 1-(4-((8-methoxy-2H-pyrazolo[3,4-c]quinolin-4-yl)amino)benzoyl)piperidin-4-one; (4-((8-methoxy-2H-pyrazolo[3,4-c]quinolin-4-yl)amino)phenyl)(1,4-dioxa-8-azaspiro[4.5]decan-8-yl)methanone; (3-(dimethylamino)pyrrolidin-1-yl)(4-((8-methoxy-2H-pyrazolo[3,4-c]quinolin-4-yl)amino)phenyl)methanone; 8-methoxy- N-(1-methyl-1,2,3,4-tetrahydroquinolin-6-yl)-2H-pyrazolo[3,4-c]quinolin-4-amine; 8-methoxy-N-(3-(pentafluorosulfanyl)phenyl)-2H-pyrazolo[3,4-c]quinolin-4-amine; N-(4-fluorophenyl)-8-methoxy-2H-pyrazolo[3,4-c]quinolin-4-amine; N-(3,4-difluorophenyl)-8-methoxy-2H-pyrazolo[3,4-c]quinolin-4-amine; 2,2,2-trifluoro-N-(4-((8-methoxy-2H-pyrazolo[3,4-c]quinolin-4-yl)amino)phenyl)acetamide; 3-((6-((8-methoxy-2H-pyrazolo[3,4-c]quinolin-4-yl)amino)-2H-benzo[b][1,4]oxazin-3-yl)amino)propan-1-ol; N6-(8-methoxy-2H-pyrazolo[3,4-c]quinolin-4-yl)-N3-phenethyl-2H-benzo[b][1,4]oxazine-3,6-diamine; N-(3,5-difluorophenyl)-8-methoxy-2H-pyrazolo[3,4-c]quinolin-4-amine; N-(3-fluoro-4-methylphenyl)-8-methoxy-2H-pyrazolo[3,4-c]quinolin-4-amine; 8-methoxy-N-(3,4,5-trifluorophenyl)-2H-pyrazolo[3,4-c]quinolin-4-amine; 8-methoxy-N-(4-nitrophenyl)-2H-pyrazolo[3,4-c]quinolin-4-amine; 8-methoxy-N-(3-methoxy-4-morpholinophenyl)-2H-pyrazolo[3,4-c]quinolin-4-amine; 8-methoxy-N-(3-(methylsulfonyl)phenyl)-2H-pyrazolo[3,4-c]quinolin-4-amine; 1,1,1,3,3,3-hexafluoro-2-(4-((8-methoxy-2H-pyrazolo[3,4-c]quinolin-4-yl)amino)phenyl)propan-2-ol; (4-((8-fluoro-3H-pyrazolo[3,4-c]quinolin-4-yl)amino)phenyl)(pyrrolidin-1-yl)methanone; 1-(4-(4-((8-fluoro-3H-pyrazolo[3,4-c]quinolin-4-yl)amino)phenyl)piperazin-1-yl)ethan-1-one; 6-((8-fluoro-3H-pyrazolo[3,4-c]quinolin-4-yl)amino)-2H-benzo[b][1,4]oxazin-3(4H)-one; 8-fluoro-N-(4-morpholinophenyl)-3H-pyrazolo[3,4-c]quinolin-4-amine; 8-fluoro-N-(4-(4-methylpiperazin-1-yl)phenyl)-3H-pyrazolo[3,4-c]quinolin-4-amine; N-(3,4-dimethoxyphenyl)-8-fluoro-3H-pyrazolo[3,4-c]quinolin-4-amine; N-(4-(difluoromethoxy)-3-methoxyphenyl)-8-methoxy-2H-pyrazolo[3,4-c]quinolin-4-amine; N-(3-fluoro-4-(trifluoromethyl)phenyl)-8-methoxy-2H-pyrazolo[3,4-c]quinolin-4-amine; N-(3-fluoro-4-(trifluoromethoxy)phenyl)-8-methoxy-2H-pyrazolo[3,4-c]quinolin-4-amine; N-(2,3-dimethoxyphenyl)-8-methoxy-2H-pyrazolo[3,4-c]quinolin-4-amine; N-(2,4-dimethoxyphenyl)-8-methoxy-2H-pyrazolo[3,4-c]quinolin-4-amine; 8-iodo-N-(4-(4-methylpiperazin-1-yl)phenyl)-3H-pyrazolo[3,4-c]quinolin-4-amine; 6-((7-fluoro-3H-pyrazolo[3,4-c]quinolin-4-yl)amino)-2H-benzo[b][1,4]oxazin-3(4H)-one; 7-fluoro-N-(4-morpholinophenyl)-3H-pyrazolo[3,4-c]quinolin-4-amine; N-(3,4-dimethoxyphenyl)-7-fluoro-3H-pyrazolo[3,4-c]quinolin-4-amine; 7-fluoro-N-(4-(4-methylpiperazin-1-yl)phenyl)-3H-pyrazolo[3,4-c]quinolin-4-amine; 9-methoxy-N-(3-(methylsulfonyl)phenyl)-3H-pyrazolo[3,4-c]quinolin-4-amine; 7-((9-methoxy-3H-pyrazolo[3,4-c]quinolin-4-yl)amino)-3,4-dihydroquinolin-2(1H)-one; 1-(4-(4-((9-methoxy-3H-pyrazolo[3,4-c]quinolin-4-yl)amino)phenyl)piperazin-1-yl)ethan-1-one; N-(3,5-dimethoxyphenyl)-8-methoxy-2H-pyrazolo[3,4-c]quinolin-4-amine; (4-((7-fluoro-3H-pyrazolo[3,4-c]quinolin-4-yl)amino)phenyl)(pyrrolidin-1-yl)methanone; 4-((8-methoxy-2H-pyrazolo[3,4-c]quinolin-4-yl)amino)-N,N-dimethylbenzenesulfonamide; N-cyclopropyl-3-((8-methoxy-2H-pyrazolo[3,4-c]quinolin-4-yl)amino)benzenesulfonamide; N-(4-(2H-1,2,3-triazol-2-yl)phenyl)-8-methoxy-2H-pyrazolo[3,4-c]quinolin-4-amine; 8-methoxy-N-(3-(methylsulfinyl)phenyl)-2H-pyrazolo[3,4-c]quinolin-4-amine; N-(3-(2H-1,2,3-triazol-2-yl)phenyl)-8-methoxy-2H-pyrazolo[3,4-c]quinolin-4-amine; 3-((8-methoxy-2H-pyrazolo[3,4-c]quinolin-4-yl)amino)-N-methylbenzenesulfonamide; 8-methoxy-N-(3-(morpholinosulfonyl)phenyl)-2H-pyrazolo[3,4-c]quinolin-4-amine; 8-methoxy-N-(3-((trifluoromethyl)sulfonyl)phenyl)-2H-pyrazolo[3,4-c]quinolin-4-amine; 2-((3-((8-methoxy-2H-pyrazolo[3,4-c]quinolin-4-yl)amino)phenyl)sulfonyl)ethan-1-ol; 9-methoxy-N-(2-methylisoindolin-5-yl)-3H-pyrazolo[3,4-c]quinolin-4-amine; N-(4-((dimethylamino)methyl)phenyl)-9-methoxy-3H-pyrazolo[3,4-c]quinolin-4-amine; N-(3,4-dimethoxyphenyl)-8-iodo-3H-pyrazolo[3,4-c]quinolin-4-amine; 8-iodo-N-(4-morpholinophenyl)-3H-pyrazolo[3,4-c]quinolin-4-amine; (4-((8-iodo-3H-pyrazolo[3,4-c]quinolin-4-yl)amino)phenyl)(pyrrolidin-1-yl)methanone; 1-(4-(4-((8-iodo-3H-pyrazolo[3,4-c]quinolin-4-yl)amino)phenyl)piperazin-1-yl)ethan-1-one; 4-fluoro-N-(4-((8-methoxy-2H-pyrazolo[3,4-c]quinolin-4-yl)amino)phenyl)benzamide; 8-methoxy-N-(4-morpholino-3-nitrophenyl)-2H-pyrazolo[3,4-c]quinolin-4-amine; N-(2,4-difluorophenyl)-8-methoxy-2H-pyrazolo[3,4-c]quinolin-4-amine; N-(3,4-dimethoxyphenyl)-9-fluoro-3H-pyrazolo[3,4-c]quinolin-4-amine; 9-fluoro-N-(3-(methylsulfonyl)phenyl)-3H-pyrazolo[3,4-c]quinolin-4-amine; 9-fluoro-N-(4-(4-(4-methylpiperazin-1-yl)piperidin-1-yl)phenyl)-3H-pyrazolo[3,4-c]quinolin-4-amine; 9-fluoro-N-(3-fluoro-4-morpholinophenyl)-3H-pyrazolo[3,4-c]quinolin-4-amine.

9. A pharmaceutical composition comprising a compound of claim 1 or a pharmaceutically acceptable ester, prodrug, hydrate, solvate or salt thereof, optionally in combination with a pharmaceutically acceptable carrier.

10. A method of treatment of a disease mediated by kinase-activity comprising the administration, to a patient in need thereof, of a therapeutically effective amount of a compound according to claim 1, wherein the kinase is selected from SYK (Spleen Tyrosine Kinase), LRRK2 (Leucine-rich repeat kinase 2) and/or Myosin light chain kinase (MYLK or MLCK) or mutants thereof and wherein the disease is selected from the group consisting of pruritus, eczema, asthma, rhinitis, dry eye, ocular inflammation, allergic conjunctivitis, vernal conjunctivitis, vernal keratoconjunctivitis, giant papillary conjunctivitis, fungal keratitis and uveitis.

11. A compound of formula (II), (IIIa) or (IIIb) wherein $R^2$ and Cy are defined as in claim 1 and PG is a protecting group selected from a 4-methoxy benzyl group or a carboxybenzyl group:

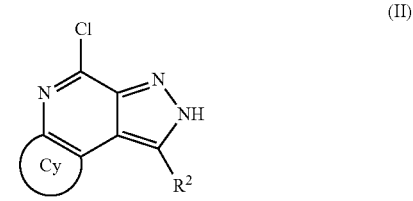

(II)

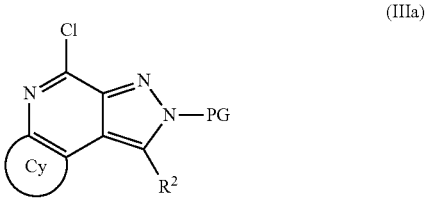

(IIIa)

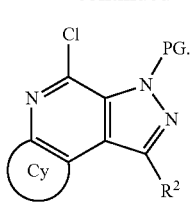

(IIIb)

12. A compound according to claim 11 wherein PG is a 4-methoxy benzyl group or a carboxybenzyl group.

13. A compound according to claim 11 which is selected from the following compounds:
4-chloro-2H-pyrazolo[3,4-c]quinoline; 4-chloro-8-methoxy-2H-pyrazolo[3,4-c]quinoline; 8-bromo-4-chloro-2H-pyrazolo[3,4-c]quinoline; 6-chloro-8H-pyrazolo[3,4-c][1,5]naphthyridine; 6-chloro-2-methoxy-8H-pyrazolo[3,4-c][1,5]naphthyridine; 4-chloro-2H-pyrazolo[3,4-c][1,7]naphthyridine; 4-chloro-7,8-diethoxy-2H-pyrazolo[3,4-c]quinoline; 4-chloro-7,8-dimethoxy-2H-pyrazolo[3,4-c]quinoline; 4-chloro-6-methoxy-2H-pyrazolo[3,4-c]quinoline; 4-chloro-7-methoxy-2H-pyrazolo[3,4-c]quinoline; 4-chloro-2H-pyrazolo[3,4-c]quinoline-8-carbonitrile; 4-chloro-9-methoxy-2H-pyrazolo[3,4-c]quinoline; 4-chloro-1-methyl-2H-pyrazolo[3,4-c]quinoline; 4-chloro-1-(trifluoromethyl)-2H-pyrazolo[3,4-c]quinoline; 4-chloro-1-nitro-2H-pyrazolo[3,4-c]quinoline; 5-chloro-1-methyl-7H-isothiazolo[5,4-b]pyrazolo[4,3-d]pyridine; 4-chloro-1-methyl-2H-pyrazolo[3,4-c]quinoline-7-carbonitrile; 4-chloro-6,8-dimethoxy-2H-pyrazolo[3,4-c]quinoline; methyl 4-chloro-2H-pyrazolo[4,3-d]thieno[3,4-b]pyridine-6-carboxylate; 4-chloro-2H-pyrazolo[3,4-c]quinolin-8-ol; 4-chloro-8-fluoro-2H-pyrazolo[3,4-c]quinoline; 4-chloro-8-iodo-2H-pyrazolo[3,4-c]quinoline; 4-chloro-7-fluoro-2H-pyrazolo[3,4-c]quinoline; 4-chloro-9-fluoro-2H-pyrazolo[3,4-c]quinoline; 4-chloro-2-(4-methoxybenzyl)-2H-pyrazolo[3,4-c]quinoline; 4-chloro-8-methoxy-2-(4-methoxybenzyl)-2H-pyrazolo[3,4-c]quinoline; 8-bromo-4-chloro-2-(4-methoxybenzyl)-2H-pyrazolo[3,4-c]quinoline; 6-chloro-8-(4-methoxybenzyl)-8H-pyrazolo[3,4-c][1,5]naphthyridine; 6-chloro-2-methoxy-8-(4-methoxybenzyl)-8H-pyrazolo[3,4-c][1,5]naphthyridine; 4-chloro-2-(4-methoxybenzyl)-2H-pyrazolo[3,4-c][1,7]naphthyridine; 4-chloro-7,8-diethoxy-2-(4-methoxybenzyl)-2H-pyrazolo[3,4-c]quinoline; 4-chloro-7,8-dimethoxy-2-(4-methoxybenzyl)-2H-pyrazolo[3,4-c]quinoline; 4-chloro-6-methoxy-2-(4-methoxybenzyl)-2H-pyrazolo[3,4-c]quinoline; 4-chloro-7-methoxy-2-(4-methoxybenzyl)-2H-pyrazolo[3,4-c]quinoline; 4-chloro-2-(4-methoxybenzyl)-2H-pyrazolo[3,4-c]quinoline-8-carbonitrile; 4-chloro-9-methoxy-2-(4-methoxybenzyl)-2H-pyrazolo[3,4-c]quinoline; 4-chloro-2-(4-methoxybenzyl)-1-methyl-2H-pyrazolo[3,4-c]quinoline; 4-chloro-2-(4-methoxybenzyl)-1-(trifluoromethyl)-2H-pyrazolo[3,4-c]quinoline; 4-chloro-2-(4-methoxybenzyl)-1-nitro-2H-pyrazolo[3,4-c]quinoline; 5-chloro-7-(4-methoxybenzyl)-1-methyl-7H-isothiazolo[5,4-b]pyrazolo[4,3-d]pyridine; 4-chloro-2-(4-methoxybenzyl)-1-methyl-2H-pyrazolo[3,4-c]quinoline-7-carbonitrile; 4-chloro-6,8-dimethoxy-2-(4-methoxybenzyl)-2H-pyrazolo[3,4-c]quinoline; methyl 4-chloro-2-(4-methoxybenzyl)-2H-pyrazolo[4,3-d]thieno[3,4-b]pyridine-6-carboxylate; 4-chloro-2-(4-methoxybenzyl)-2H-pyrazolo[3,4-c]quinolin-8-ol; 4-chloro-8-fluoro-2-(4-methoxybenzyl)-2H-pyrazolo[3,4-c]quinoline; 4-chloro-8-iodo-2-(4-methoxybenzyl)-2H-pyrazolo[3,4-c]quinoline; 4-chloro-7-fluoro-2-(4-methoxybenzyl)-2H-pyrazolo[3,4-c]quinoline; 4-chloro-9-fluoro-2-(4-methoxybenzyl)-2H-pyrazolo[3,4-c]quinoline.

14. A method of treatment of a disease mediated by kinase-activity comprising the administration, to a patient in need thereof, of a therapeutically effective amount of a pharmaceutical composition of claim 9, wherein the kinase is selected from SYK (Spleen Tyrosine Kinase), LRRK2 (Leucine-rich repeat kinase 2) and/or Myosin light chain kinase (MYLK or MLCK) or mutants thereof and wherein the disease is selected from the group consisting of pruritus, eczema, asthma, rhinitis, dry eye, ocular inflammation, allergic conjunctivitis, vernal conjunctivitis, vernal keratoconjunctivitis, giant papillary conjunctivitis, fungal keratitis and uveitis.

* * * * *